(12) United States Patent
Verano et al.

(10) Patent No.: US 12,227,488 B2
(45) Date of Patent: Feb. 18, 2025

(54) SMALL MOLECULE DEGRADERS OF HELIOS AND METHODS OF USE

(71) Applicant: DANA-FARBER CANCER INSTITUTE, INC., Boston, MA (US)

(72) Inventors: Alyssa Verano, Allston, MA (US); Eric Wang, Brookline, MA (US); Radoslaw Nowak, Boston, MA (US); Jing Ting Christine Yuan, Brookline, MA (US); Nathanael Gray, Boston, MA (US); Eric Fischer, Chestnut Hill, MA (US); Tinghu Zhang, Brookline, MA (US); Hu Liu, Newton, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 847 days.

(21) Appl. No.: 17/298,823

(22) PCT Filed: Dec. 3, 2019

(86) PCT No.: PCT/US2019/064169
§ 371 (c)(1),
(2) Date: Jun. 1, 2021

(87) PCT Pub. No.: WO2020/117759
PCT Pub. Date: Jun. 11, 2020

(65) Prior Publication Data
US 2022/0177443 A1     Jun. 9, 2022

Related U.S. Application Data

(60) Provisional application No. 62/938,410, filed on Nov. 21, 2019, provisional application No. 62/774,482, filed on Dec. 3, 2018.

(51) Int. Cl.
*C07D 401/04* (2006.01)
*A61P 35/00* (2006.01)
*C07D 401/14* (2006.01)
*C07D 417/14* (2006.01)

(52) U.S. Cl.
CPC ........... *C07D 401/04* (2013.01); *A61P 35/00* (2018.01); *C07D 401/14* (2013.01); *C07D 417/14* (2013.01)

(58) Field of Classification Search
CPC .................................................. A61P 35/00
See application file for complete search history.

(56) References Cited

U.S. PATENT DOCUMENTS

| | | | |
|---|---|---|---|
| 8,716,315 B2 | 5/2014 | Figg et al. | |
| 2010/0204227 A1 | 8/2010 | Muller et al. | |
| 2012/0142734 A1 | 6/2012 | D'Amato | |
| 2016/0356778 A1 | 12/2016 | Hidekatsu et al. | |
| 2018/0215731 A1* | 8/2018 | Crew | A61P 35/02 |
| 2019/0062309 A1 | 2/2019 | Beckwith et al. | |
| 2023/0192644 A1* | 6/2023 | Gray | C07D 401/14 |
| | | | 514/210.2 |

FOREIGN PATENT DOCUMENTS

| | | |
|---|---|---|
| WO | 2017197051 A1 | 11/2017 |
| WO | 2018144649 A1 | 8/2018 |
| WO | 2019043214 A1 | 3/2019 |
| WO | 2019079701 A1 | 4/2019 |
| WO | 2019140387 A1 | 7/2019 |
| WO | 2020012334 A1 | 1/2020 |
| WO | 2020165833 A1 | 8/2020 |
| WO | 2020165834 A1 | 8/2020 |

OTHER PUBLICATIONS

Jiang, L., et al. Disease Markers. Hindawi. vol. 2017. (Year: 2017).*
Hansen, J. D., et al. J. Med. Chem. 2018, 61, 492-503. (Year: 2018).*
Lee, D. H., et al. Curr. Treat. Options Cardio. Med. (2018) 20:19. (Year: 2018).*
CAS No. 1333622-73-3.
CAS No. 1489856-35-0.
El-Zanfally, S., et al., "Derivatives of Glutarimide Likely to Possess Therapeutic Activity", Journal of Pharmaceutical Sciences, 1965, vol. 54, No. 3, pp. 467-469.
"Pubchem CID 134482", create date: Aug. 8, 2008 (Aug. 8, 2008) p. 2 formula.
Hansen, J. D. et al. "Protein Degradation via CRL4 Crbn Ubiquitin Ligase: Discovery and Structure-Activity Relationships of Novel Glutarimide Analogs That Promote Degradation of Aiolos and/or GSPT1", J. Med. Chem., 2018, vol. 61, No. 2, pp. 492-503.
Matyskiela, M. E. et al. "A Novel Cereblon Modulator Recruits GSPT1 to the CRL4 CRBN Ubiquitin Ligase", Nature, 2016, vol. 535, No. 7611, p. 252-257.
Rana, S., et al., "Inhibitors, PROTACs, and Molecular Glues as Diverse Therapeutic Modalities to Target Cyclin-Dependent Kinase", Cancers, 2021, vol. 13, No. 5506, 21 pages.
Zhao, L., et al., "Targeted protein degradation: mechanisms, strategies, and application", Signal Transduction and Targeted Therapy, 2022, vol. 7, No. 113, 13 pages.

* cited by examiner

*Primary Examiner* — Eric Olson
*Assistant Examiner* — Samuel L Galster
(74) *Attorney, Agent, or Firm* — ArentFox Schiff LLP; Daniel W. Clarke; Shawn P. Foley

(57) ABSTRACT

Disclosed are compounds and pharmaceutically acceptable salts and stereoisomers thereof that may cause degradation of various proteins e.g., IKZF2 (Helios). Also disclosed are pharmaceutical compositions containing same, and methods of making and using the compounds to treat diseases and disorders characterized or mediated by aberrant protein activity.

47 Claims, 21 Drawing Sheets

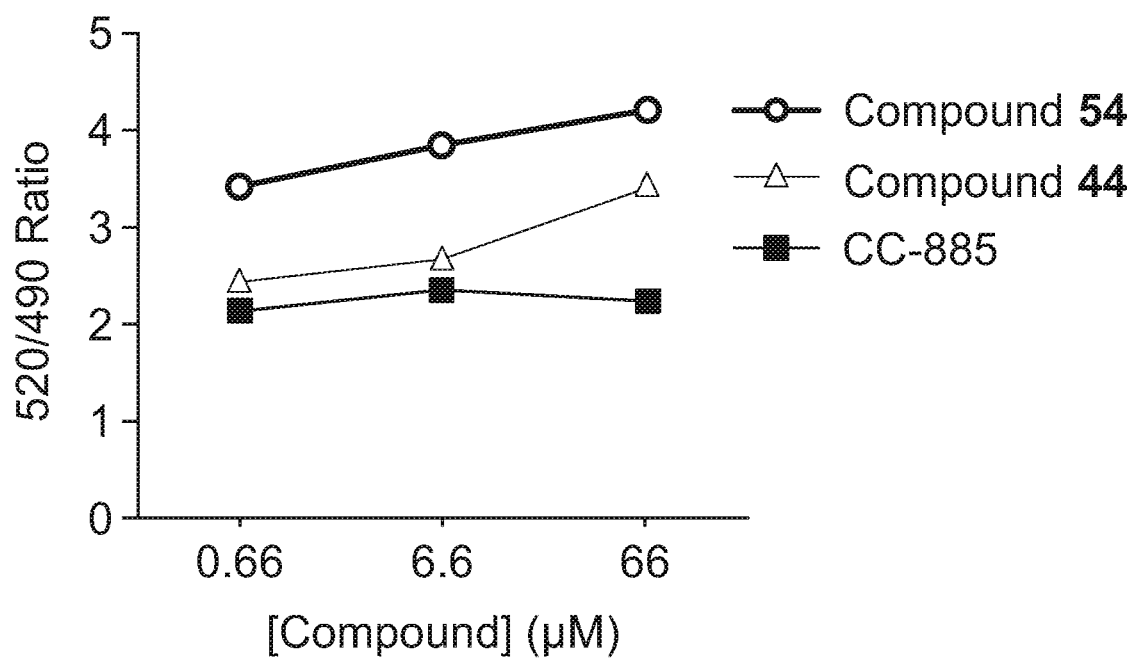

SMALL MOLECULE DEGRADERS OF HELIOS AND METHODS OF USE

RELATED APPLICATIONS

This application is a national stage application, filed under 35 U.S.C. § 371, of International Application No. PCT/US2019/064169, filed Dec. 3, 2019, which claims the benefit of priority under 35 U.S.C. § 119 (e) to U.S. Provisional Application No. 62/774,482, filed Dec. 3, 2018 and U.S. Provisional Application No. 62/938,410, filed Nov. 21, 2019, each of which are incorporated herein by reference in their entireties.

GOVERNMENT LICENSE RIGHTS

This invention was made with government support under grant number R01 CA214608 awarded by the National Institutes of Health. The government has certain rights in the invention.

BACKGROUND OF THE INVENTION

The discovery of immune checkpoint receptors, such as cytotoxic T-lymphocyte-associated protein-4 (CTLA-4) and programmed cell death protein-1 (PD-1) (Leach et al., Science 271:1734-1736 (1996); Phan et al., Proc. Natl. Acad. Sci. 100:8372-8377 (2003); Nishimura et al., Immunity 11:141-151 (1999); Dong et al., Nat. Med. 8:793-800 (2002); Brahmer et al., J. Clin. Oncol. 28:3167-3175 (2010)), that repress the activity of anti-tumor T cells, has led to the development of blocking antibodies directed against these receptors or their ligands, including ipilimumab (anti-CTLA-4), pembrolizumab (anti-PD-1), and nivolumab (anti-PD-1). Strikingly, some patients treated with checkpoint inhibitors have experienced durable tumor regression, in contrast to targeted small molecule therapies where tumor relapse is common (Sharma et al., Cell 161: 205-214 (2015)). This remarkable response has led to the rapid approval of these therapies for patients and tremendous optimism in the field. However, checkpoint blockade therapies have only been successful in a subset of patients; certain tumor types have responded more favorably than others (Mahoney et al., Nat. Rev. Drug Discov. 14:561-584 (2015)). Thus, it is crucial to more fully understand the mechanisms behind tumor-induced immune dysfunction and to develop complementary treatments that will broaden the types of treatable tumors and increase the anti-tumor activity of existing approaches while reducing autoimmune side effects.

One such approach is to target regulatory T cells (Tregs). These T cells are a specialized subset of Foxp3-expressing cluster of differentiation 4+ T (CD4+ T) cells which have important function in maintaining normal immune tolerance and homeostasis (Sakaguchi et al., Cell 133:775-787 (2008)) but which also play a detrimental role in that they repress the anti-tumor immune response (Tanaka et al., Cell Res. 27:109-118 (2017)). The observed accumulation of Tregs within the tumor microenvironment may be due to efficient Treg recruitment and expansion. Furthermore, the majority of Tregs develop in the thymus as an alternative to elimination due to negative selection of CD4+ T cells that express self-reactive T cell receptors (TCRs) (Hogquist et al., Nat. Rev. Immunol. 5:772-782 (2005)); thus, accumulation of Tregs in tumors may also reflect increased autoreactivity of Tregs, including recognition of tumor-associated antigens (Scanlan et al., Immunol. Rev. 188:22-32 (2002); Nishikawa et al., Curr. Opin. Immunol. 27:1-7 (2014)). Due to the prevalence of self-reactive TCRs, mechanisms to ensure stability of the suppressive phenotype of Tregs appear critical to prevent the development of autoimmunity.

The zinc finger transcription factor Helios (also known as Ikaros family zinc finger protein 2 (IKZF2)) has been identified as a critical regulator of Treg suppressive activity. While not all Tregs express Helios, higher expression of Helios has been shown to correlate with increased suppressive function, in both murine (Sugita et al., Exp. Dermatol. 24:554-556 (2015); Zabransky et al., PLoS One 7:e34547 (2012)) and human (Bin Dhuban et al., J. Immunol. 194: 3687-3696 (2015)) Tregs. Consistent therewith, Helios has been recently identified as a critical factor for maintaining stable Treg phenotypes in the inflammatory tumor microenvironment (Nakagawa et al., Proc. Natl. Acad. Sci. 113: 6248-6253 (2016); Kim et al., Science 350:334-339 (2015); Yates et al., Proc. Natl. Acad. Sci. 115:2162-2167 (2018)). Genetic deletion of Helios in Tregs resulted in the loss of suppressive activity as well as acquisition of effector T cell functions (i.e., secretion of type II interferon (IFNγ) and tumor necrosis factor-α (TNFα)), indicating that Helios loss permitted the conversion of Tregs into effector-like T cells (Nakagawa et al., Proc. Natl. Acad. Sci. 113:6248-6253 (2016); Kim et al., Science 350:334-339 (2015)).

Although targeting transcription factors with small molecules is challenging, protein degradation strategies have expanded the range of druggable targets. Notably, recent work uncovered that immunomodulatory imide (IMiD) molecules such as thalidomide and its analogs bind Cereblon (CRBN), a substrate adaptor for the ubiquitously-expressed E3 ubiquitin ligase CUL4-RBX1-DDB1-CRBN ($CRL4^{CRBN}$) (Ito et al., Science 327:1345-1350 (2010)). Rather than inhibiting the activity of $CRL4^{CRBN}$, binding of these imide molecules to CRBN generates a novel surface that results in neo-interactions between CRBN and other proteins, notably Ikaros (IKZF1) and Aiolos (IKZF3). Treatment with thalidomide or its analogs was found to result in the CRBN-dependent ubiquitination and subsequent proteasomal degradation of Ikaros and Aiolos (Kronke et al., Science 343:301-305 (2014); Lu et al., Science 343:305-309 (2014)).

SUMMARY OF THE INVENTION

A first aspect of the present invention is directed to a compound represented by a structure of formula (I):

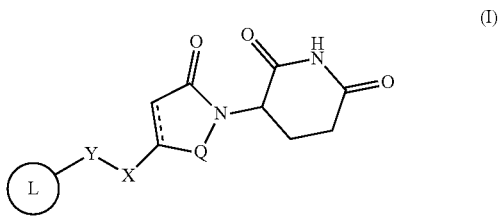

wherein Q, X, Y and

are as defined herein, or a pharmaceutically acceptable salt or stereoisomer thereof.

A second aspect of the present invention is directed to a compound represented by a structure of formula (II):

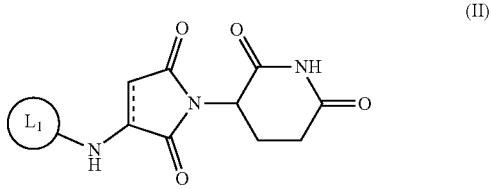

wherein

is as defined herein, or a pharmaceutically acceptable salt or stereoisomer thereof.

A third aspect of the present invention is directed to a compound represented by a structure of formula (III):

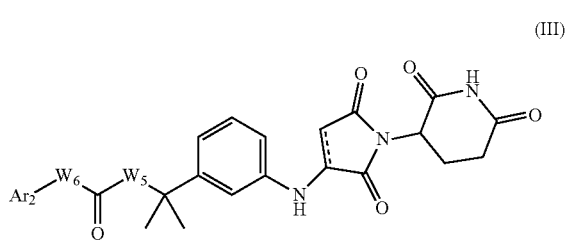

wherein $Ar_2$, $W_5$, and $W_6$ are as defined herein, or a pharmaceutically acceptable salt or stereoisomer thereof.

Another aspect of the present invention is directed to a pharmaceutical composition that includes a therapeutically effective amount of a compound of formula (I, II, or III) or a pharmaceutically acceptable salt or stereoisomer thereof, and a pharmaceutically acceptable carrier.

Another aspect of the present invention is directed to methods of treating diseases or disorders characterized or mediated by aberrant (e.g., dysregulated) activity of a protein that is a substrate for a complex between cereblon (CRBN) and an inventive compound, that entails the administration of a therapeutically effective amount of a compound of formula (I, II, or III) or a pharmaceutically acceptable salt or a stereoisomer thereof, to a subject in need thereof.

Such protein substrates may include, for example, family with sequence similarity 83 member F (FAM83F), DTW domain containing 1 (DTWD1), zinc finger protein 62 (ZFP62), ZFP91, ring finger protein 166 (RNF166), Ikaros family zinc finger protein 1 (IKZF1), IKZF2 (Helios), IKZF3, IKZF4, IKZF5, casein kinase 1 isoform alpha (CKla), zinc finger protein 653 (ZN653), ZN654, ZN827, ZN692, zinc finger and BTB domain-containing protein 2 (ZBTB2), ZBTB39, RAB28, glutathione S-transferase P1 (GSTP1), ZFP36 ring finger protein-like 2 (ZFP36L2), glial cell line-derived neurotrophic factor (GDNF) inducible zinc finger protein 1 (GZF1), G1 to S phase transition 2 protein (GSPT2), early growth response protein 1 (EGR1), hyper- methylated in cancer 1 protein (HIC1), HIC2, insulinoma-associated protein 2 (INSM2), odd-skipped-related 1 protein (OSR1), OSR2, positive regulatory domain zinc finger protein 15 (PRD15), Sal-like protein 1 (SALL1), SALL3, SALL4, widely-interspaced zinc finger-containing protein (WIZ), zinc finger protein 324B (Z324B), zinc finger and BTB domain-containing protein 17 (ZBT17), ZBT41, ZBT49, ZBT7A, ZBT7B, zinc finger protein interacting with K protein 1 (ZIK1), zinc finger protein 3 (ZNF3), ZNF217, ZNF276, ZNF316, ZNF335, ZNF397, ZNF407, ZNF408, ZNF462, ZNF483, ZNF517, ZNF526, ZNF581, ZNF582, ZNF587, ZNF589, ZNF618, ZNF644, ZNF646, ZNF653, ZNF654, ZNF692, ZNF724, ZNF771, ZNF782, ZNF784, ZNF787, ZNF814, ZNF827, zinc finger and SCAN domain containing protein 10 (ZSC10), ZSC22, zinc finger with UFM1-specific peptidase domain protein (ZUFSP), E4F1, B-cell lymphoma 6 protein (BCL6), BCL6B, POZ/BTB and AT hook containing zinc finger 1 (PATZ1), and zinc finger protein with Krueppel-associated box (KRAB) and SCAN domains 5 (ZKSC5).

In some embodiments, the disease or disorder is characterized or mediated by aberrant IKZF2 (Helios) activity, e.g., coronary heart disease. In some embodiments, the disease or disorder is cancer. In some embodiments, the cancer is T cell leukemia, T cell lymphoma, Hodgkin's lymphoma, non-Hodgkin's lymphoma, myeloid leukemia, non-small cell lung cancer (NSCLC), melanoma, triple-negative breast cancer (TNBC), or nasopharyngeal cancer (NPC).

In some embodiments, the aberrant protein contains one or more sequence motifs, such as, the CxxCG motif, which is present in ZFP62, GZF1, EGR1, HIC1, HIC2, INSM2, Z324B, ZBT17, ZBT41, ZBT49, ZBT7A, ZBT7B, ZIK1, ZNF3, ZNF217, ZNF316, ZNF335, ZNF407, ZNF408, ZNF462, ZNF483, ZNF526, ZNF581, ZNF587, ZNF589, ZNF618, ZNF644, ZNF646, ZNF724, ZNF771, ZNF782, ZNF784, ZNF814, ZSC10, ZSC22, ZN654 and ZUFSP.

A further aspect of the present invention is directed to methods of treating a disease or disorder that is affected by the reduction of TXNIP protein levels. The methods entail administering, to a subject in need thereof, a therapeutically effective amount of a compound of formula (I, II, or III), or a pharmaceutically acceptable salt or stereoisomer thereof.

As demonstrated in the working examples, compounds of the present invention exhibit potent and selective degradation of IKZF1 (Ikaros) and IKZF2 (Helios).

BRIEF DESCRIPTION OF THE DRAWINGS

FIG. 2A is a graph of 520/490 TR-FRET ratios.

FIG. 4A displays H9 human embryonic stem cells (hESC) that were treated with 10 μM thalidomide or DMSO control. FIG. 4B shows H9 hESC that were treated with 5 μM lenalidormide or DMSO control. FIG. 4C depicts H9 hESC that were treated with 1 μM pomalidomide or DMSO control. Protein abundance was analyzed using tandem mass tags (TMT) quantification mass spectrometry. Significant changes were assessed by a moderated t-test as implemented in the limma package, with the log 2 fold change (log 2 FC) shown on the y-axis, and negative logic p values on the x-axis (two independent biological replicates for each of the IMiDs, or three independent biological replicates for DMSO).

FIG. 8A shows FACS plots of murine splenocytes stained for TCRβ, CD4, CD8, and FoxP3. FIG. 8B depicts levels of Ikaros and Helios of splenic T cell subpopulations from Crbn$^{I391V/I391V}$ mice that were treated with 1 μM of indicated compounds for 16 h.

FIG. 9A shows the FACS plots for IFNγ. FIG. 9B is a bar graph showing the percent increase of IFNγ with treatment of compound 69. FIG. 9C shows levels of Helios in Tregs treated with DMSO or compound 69.

DETAILED DESCRIPTION OF THE INVENTION

Figure 1A:
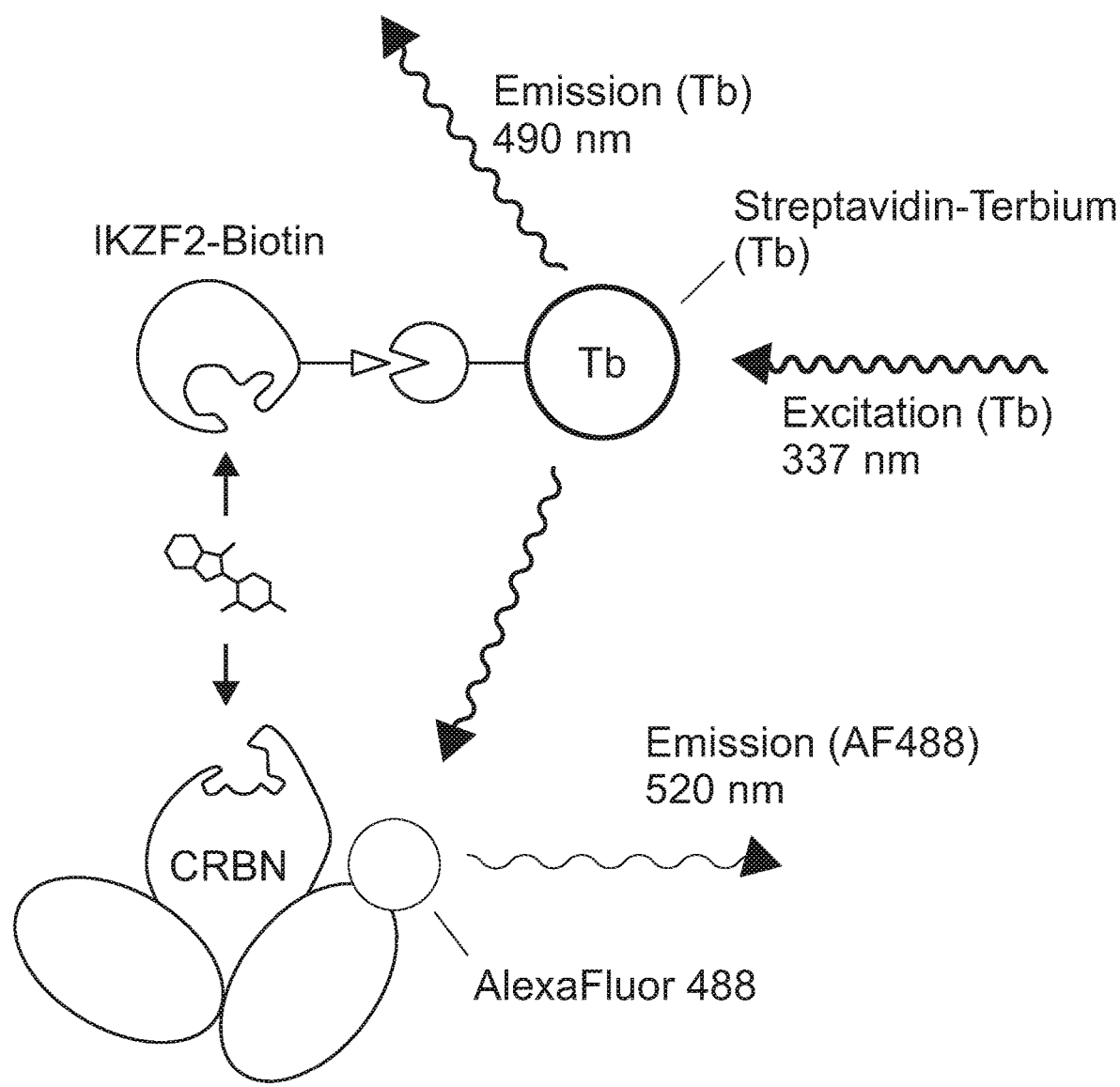
FIG. 1A is a cartoon of time-resolved fluorescence resonance energy transfer (TR-FRET) dimerization assay.

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2%, or 1%) of the particular value modified by the term "about."

The transitional term "comprising," which is synonymous with "including," "containing," or "characterized by," is inclusive or open-ended and does not exclude additional, unrecited elements, or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

With respect to compounds of the present invention, and to the extent the following terms are used herein to further describe them, the following definitions apply.

As used herein, the term "aliphatic" refers to a non-cyclic hydrocarbon group and includes branched and unbranched, alkyl, alkenyl, or alkynyl groups.

As used herein, the term "alkyl" refers to a saturated linear or branched-chain monovalent hydrocarbon radical. In one embodiment, the alkyl radical is a $C_1$-$C_{15}$ group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group.

In some embodiments, an alkyl group is a $C_1$-$C_2$ alkyl group.

As used herein, the term "alkylene" refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

As used herein, the term "haloalkyl" refers to an alkyl group as defined herein that is substituted with one or more (e.g., 1, 2, 3, or 4) halo groups.

As used herein, the term "alkenyl" refers to a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is a $C_2$-$C_{18}$ group. In other embodiments, the alkenyl radical is a $C_2$-$C_{12}$, $C_2$-$C_{10}$, $C_2$-$C_8$, $C_2$-$C_6$ or $C_2$-$C_3$ group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term "halogen" (or "halo" or "halide") refers to fluorine, chlorine, bromine, or iodine.

As used herein, the term "carbamate" is represented by the formula —O—C(O)NH$_2$.

As used herein, the term "carbamide" is represented by the formula —NH—C(O)NH$_2$.

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. Cyclic groups may have one or more (e.g., fused) ring systems. Thus, for example, a cyclic group can contain one or more carbocyclic, heterocyclic, aryl or heteroaryl groups.

As used herein, the term "carbocyclic" (also "carbocyclyl") refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula —R$^c$-carbocyclyl where R$^c$ is an alkylene chain.

The term carbocyclic also embraces carbocyclylalkoxy groups which as used herein refer to a group bonded through an oxygen atom of the formula —O—R$^c$-carbocyclyl where R$^c$ is an alkylene chain.

As used herein, the term "aryl" used alone or as part of a larger moiety (e.g., "aralkyl", wherein the terminal carbon atom on the alkyl group is the point of attachment, e.g., a benzyl group, "aralkoxy" wherein the oxygen atom is the point of attachment, or "aroxyalkyl" wherein the point of attachment is on the alkyl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups (e.g., benzyl) which as disclosed above refer to a group of the formula —R$^c$-aryl where R$^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—R$^c$-aryl where R$^c$ is an alkylene chain such as methylene or ethylene.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or S(O)$_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, thiophenyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$-heterocyclyl where $R^c$ is an alkylene chain.

The term heterocyclic also embraces heterocyclylalkoxy groups which as used herein refer to a radical bonded through an oxygen atom of the formula —O—$R^c$-heterocyclyl where $R^c$ is an alkylene chain.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, imidazopyridyl, pyrazinyl, pyridazinyl, triazinyl, tetrazinyl, tetrazolo[1,5-b]pyridazinyl, purinyl, deazapurinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, indolizinyl, isoindolyl, benzothienyl, benzothiophenyl, methylenedioxyphenyl, benzofuranyl, dibenzofuranyl, indazolyl, benzimidazolyl, benzodioxazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tricyclic. In some embodiments, a heteroaryl group includes a heteroaryl ring fused to one or more (e.g., 1, 2, or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring. Thus, the term heteroaryl embraces N-heteroaryl groups which as used herein refer to a heteroaryl group as defined above containing at least one nitrogen and where the point of attachment of the heteroaryl group to the rest of the molecule is through a nitrogen atom in the heteroaryl group.

The term heteroaryl also embraces C-heteroaryl groups which as used herein refer to a heteroaryl group as defined above and where the point of attachment of the heteroaryl group to the rest of the molecule is through a carbon atom in the heteroaryl group. The term heteroaryl also embraces heteroarylalkyl groups which as disclosed above refer to a group of the formula —R$^c$-heteroaryl, wherein R$^c$ is an alkylene chain as defined above. The term heteroaryl also embraces heteroaralkoxy (or heteroarylalkoxy) groups which as used herein refer to a group bonded through an oxygen atom of the formula —O—R$^c$-heteroaryl, where R$^c$ is an alkylene group as defined above.

Any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1, 2, 3, or 4) heteroatoms such as oxygen, sulfur, and nitrogen grouped in a linear, branched, or cyclic structural format.

Representative examples of substituents may thus include alkyl, substituted alkyl (e.g., C1-C6, C1-5, C1-4, C1-3, C1-2, C1), alkoxy (e.g., C1-C6, C1-5, C1-4, C1-3, C1-2, C1), substituted alkoxy (e.g., C1-C6, C1-5, C1-4, C1-3, C1-2, C1), haloalkyl (e.g., CF$_3$), alkenyl (e.g., C2-C6, C2-5, C2-4, C2-3, C2), substituted alkenyl (e.g., C2-C6, C2-5, C2-4, C2-3, C2), alkynyl (e.g., C2-C6, C2-5, C2-4, C2-3, C2), substituted alkynyl (e.g., C2-C6, C2-5, C2-4, C2-3, C2), cyclic (e.g., C3-C12, C5-C6), substituted cyclic (e.g., C3-C12, C5-C6), carbocyclic (e.g., C3-C12, C5-C6), substituted carbocyclic (e.g., C3-C12, C5-C6), heterocyclic (e.g., C3-C12, C5-C6), substituted heterocyclic (e.g., C3-C12, C5-C6), aryl (e.g., benzyl and phenyl), substituted aryl (e.g., substituted benzyl or phenyl), heteroaryl (e.g., pyridyl or pyrimidyl), substituted heteroaryl (e.g., substituted pyridyl or pyrimidyl), aralkyl (e.g., benzyl), substituted aralkyl (e.g., substituted benzyl), halo, hydroxyl, aryloxy (e.g., C6-C12, C6), substituted aryloxy (e.g., C6-C12, C6), alkylthio (e.g., C1-C6), substituted alkylthio (e.g., C1-C6), arylthio (e.g., C6-C12, C6), substituted arylthio (e.g., C6-C12, C6), cyano, carbonyl, substituted carbonyl, carboxyl, substituted carboxyl, amino, substituted amino, amido, substituted amido, thio, substituted thio, sulfinyl, substituted sulfinyl, sulfonyl, substituted sulfonyl, sulfinamide, substituted sulfinamide, sulfonamide, substituted sulfonamide, urea, substituted urea, carbamate, substituted carbamate, amino acid, and peptide groups.

In one aspect, compounds of the invention are represented by formula (I):

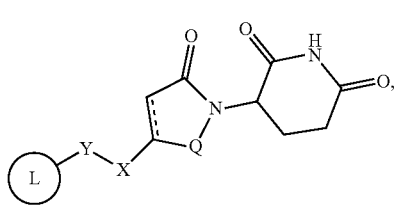

(I)

wherein:
Q represents CH$_2$ or C=O;
X represents NR, O, or S, wherein R is H or Me;
Y is absent or represents optionally substituted C1-C5 alkyl, optionally substituted aryl, or optionally substituted heteroaryl;

is absent or represents

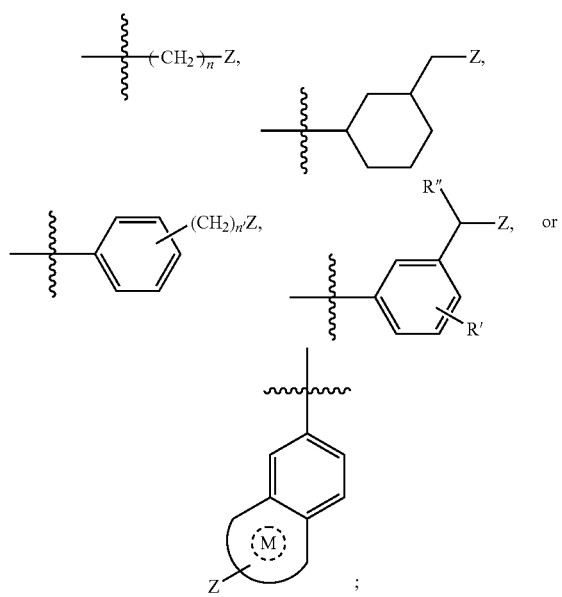

wherein n is 2 or 3; n' is 0 or 1; R' is halo, optionally substituted C1-C2 alkyl, optionally substituted aryl, or optionally substituted heteroaryl; wherein R" represents optionally substituted C1-C2 alkyl; wherein Z represents

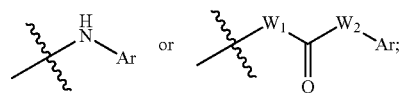

W$_1$ and W$_2$ are independently absent or independently represent CH, CH$_2$, O, O—CH$_2$, NH—CH$_2$ or optionally substituted amino;
M represents a 5- or 6-membered cyclic group; and
Ar represents optionally substituted phenyl or benzyl; wherein

or Y is absent;
or a pharmaceutically acceptable salt or stereoisomer thereof.
In some embodiments, Q is C=O.
In some embodiments, Q is CH$_2$.

In some embodiments, X is NH.
In some embodiments, X is NMe.
In some embodiments, X is O.
In some embodiments, X is S.
In some embodiments, M is cyclopentyl, cyclohexyl, pyrrolidinyl, piperidinyl, and benzene.
In some embodiments,

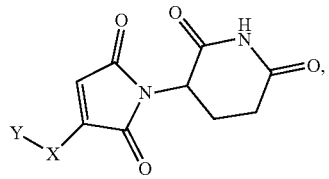

is absent and Q is C=O, and the compounds of the invention have a structure represented by formula (Ia):

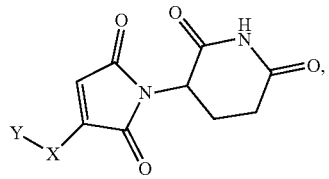

(Ia)

or a pharmaceutically acceptable salt or stereoisomer thereof.

In some embodiments, Y represents optionally substituted N-aryl including, for example, optionally substituted pyridinyl, optionally substituted imidazolyl, optionally substituted pyrazolyl, optionally substituted triazolyl, optionally substituted tetrazolyl, optionally substituted thiazolyl, optionally substituted quinolinyl, optionally substituted indolyl, or optionally substituted indazolyl.

In some embodiments, Y represents optionally substituted C1-C5 alkyl.

In some embodiments, Y represents optionally substituted phenyl or optionally substituted benzyl.

In some embodiments, wherein the compound is represented by formula Ia, Y is phenyl, benzyl,

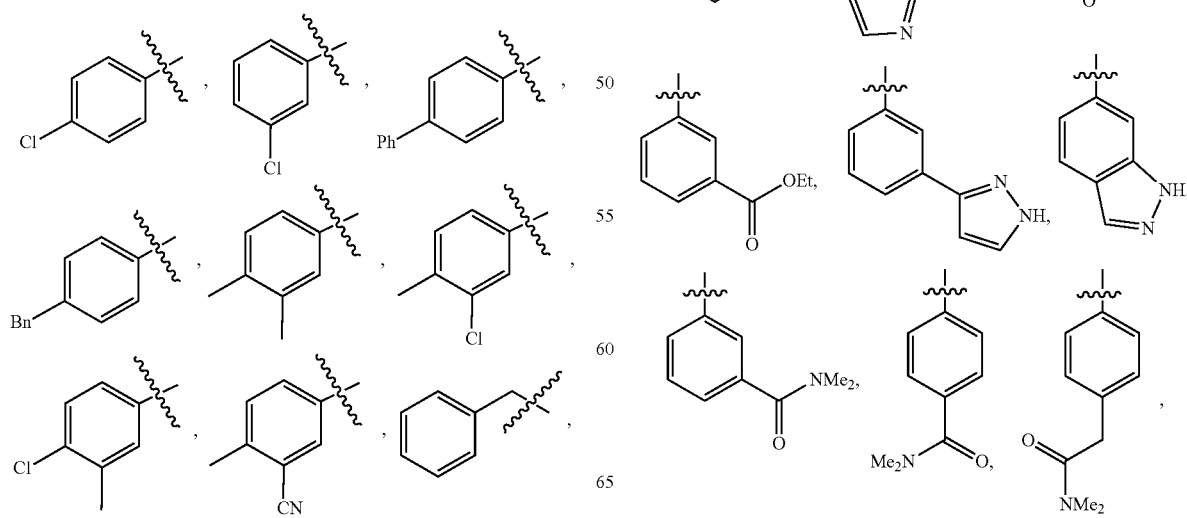

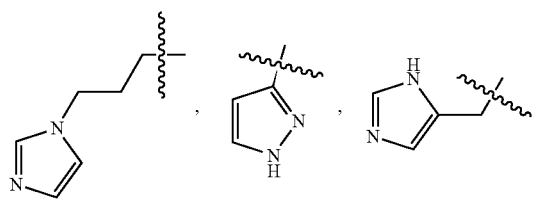

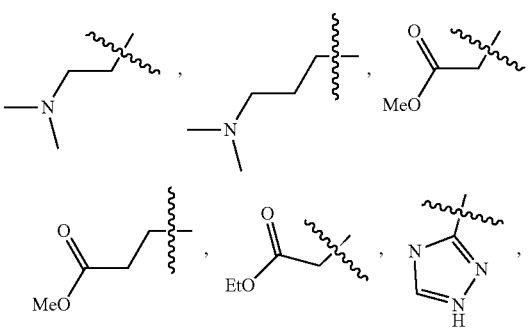

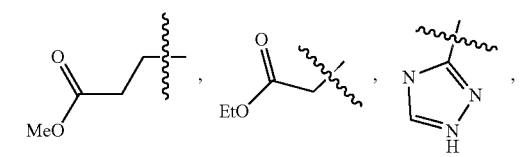

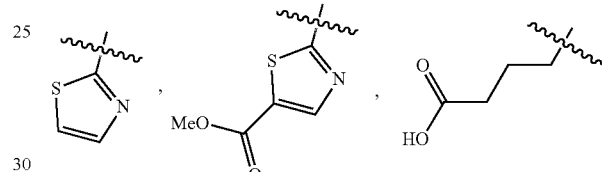

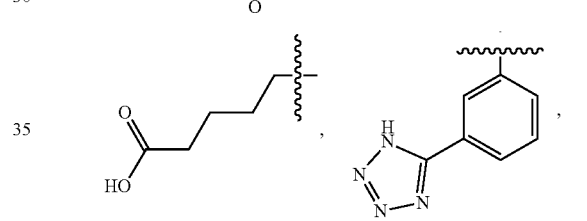

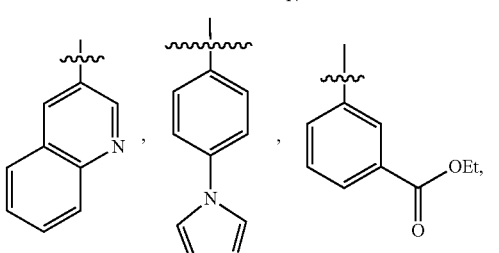

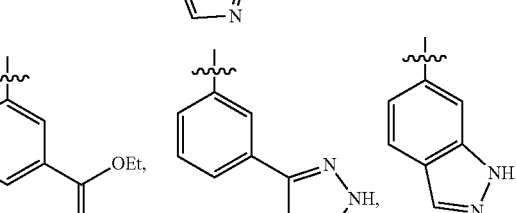

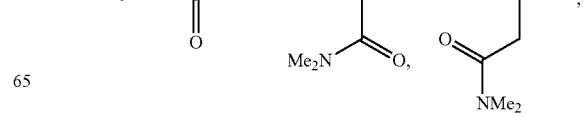
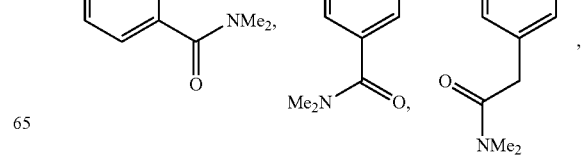
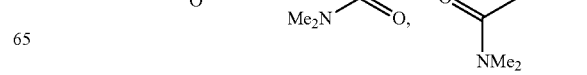

-continued

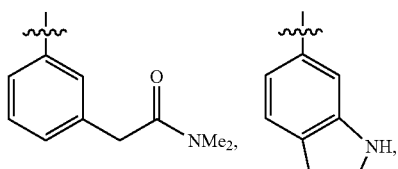

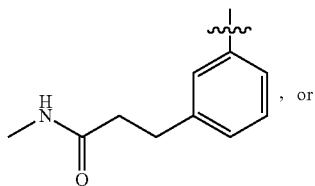, or

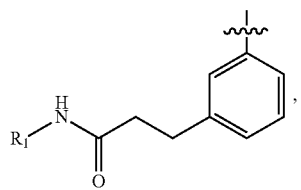, and R₁ represents alkyl, aryl, or heteroaryl.

In some embodiments, R₁ is ethyl, isopropyl, tert-butyl, phenyl, benzyl, pyrazolyl, imidazolyl, tetrazolyl, pyridinyl, or pyrimidinyl.

In some embodiments, the optional substituents of any of the groups in the compounds of formula Ia may include methyl, chloro, fluoro, phenyl, benzyl,

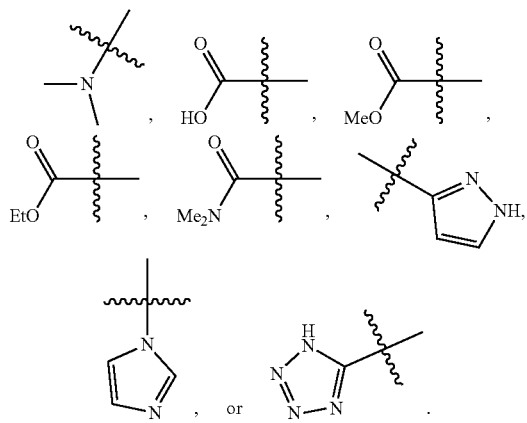

In some embodiments, Y is absent and the compounds of the invention have a structure represented by formula (Ib):

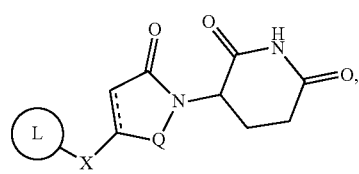

(Ib)

or a pharmaceutically acceptable salt or stereoisomer thereof.

In some embodiments,

is a substituted alkyl or cyclic group.

In some embodiments,

is selected from

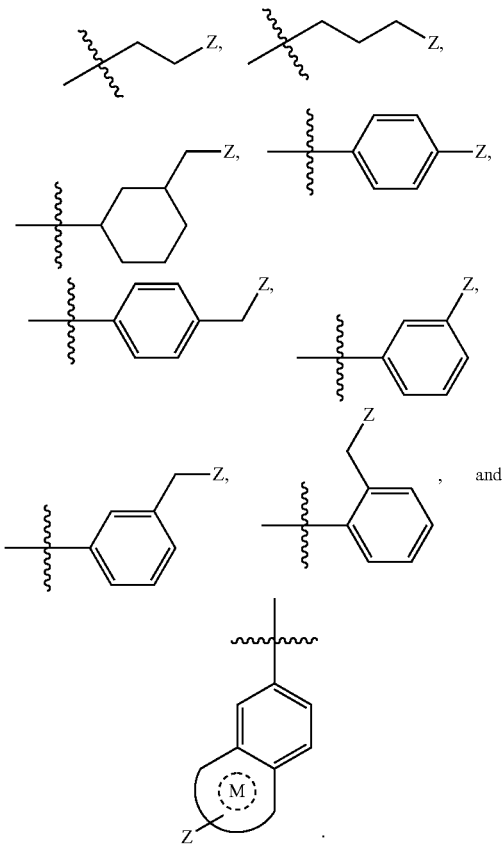

In some embodiments,

is an optionally substituted fused-5,6 or -6,6 ring system.

In some embodiments,

is selected from

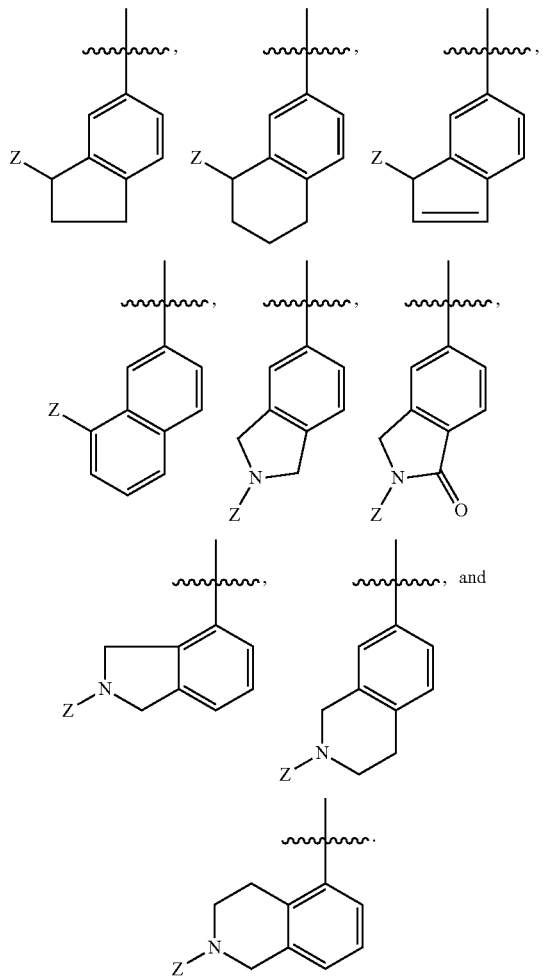

In some embodiments, Z represents

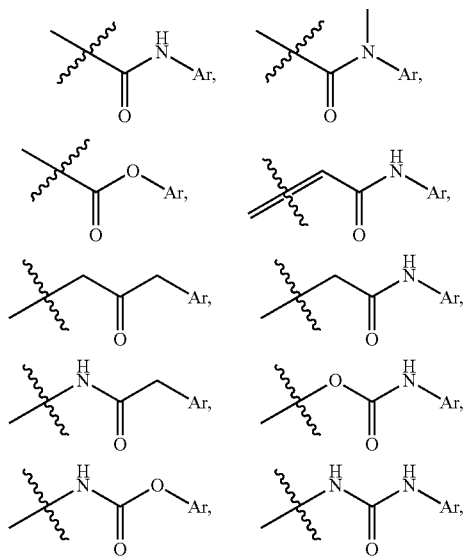

-continued

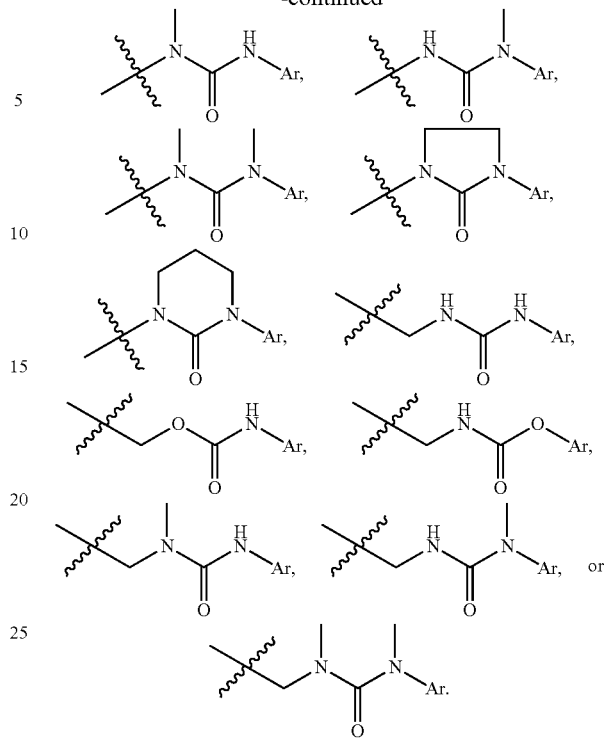

In some embodiments, Ar is optionally substituted phenyl, e.g.,

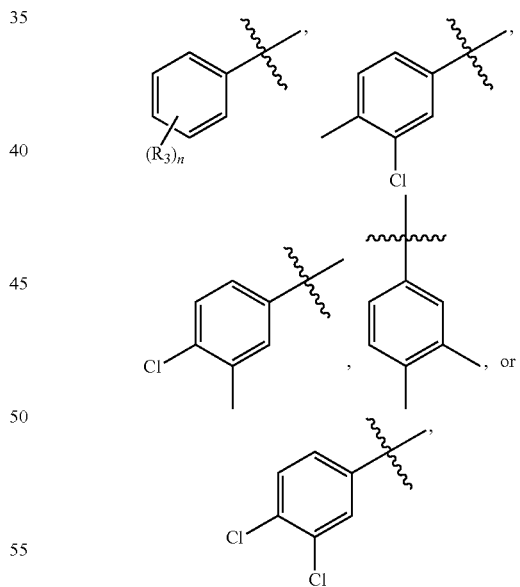

wherein $R_3$ is alkyl, halo, aryl, or heteroaryl, and n is 0, 1, or 2. In the event n is 2, each $R_3$ may represent the same or different substituents.

In some embodiments, $R_3$ independently represents methyl, ethyl, isopropyl, tert-butyl, trifluoromethyl, chloro, or fluoro.

In some embodiments, the optional substituents of any of the groups in the compounds of formula Ib may include methyl, chloro, fluoro, phenyl, benzyl,

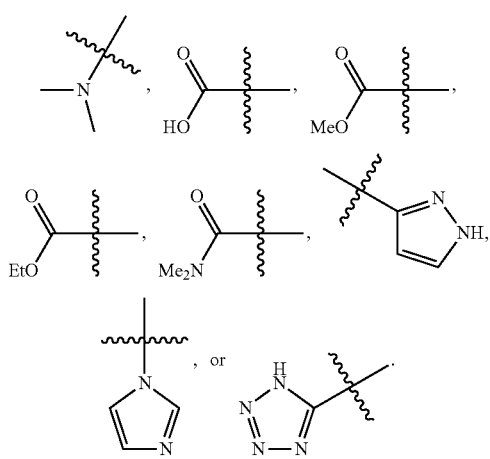
Representative embodiments of the compounds of formula (I) are as follows:
(1)
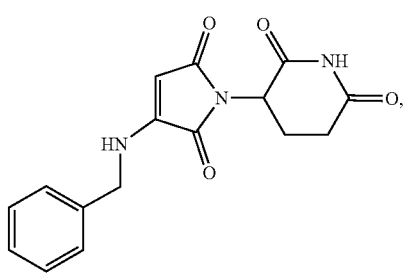
(2)
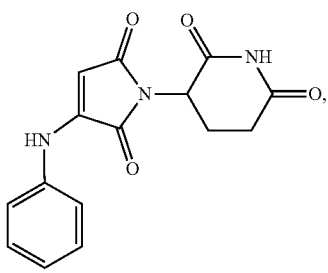
(3)
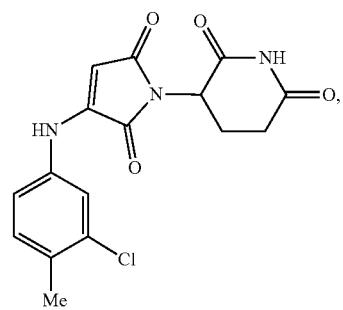
(4)
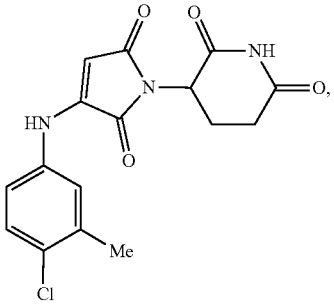
(5)
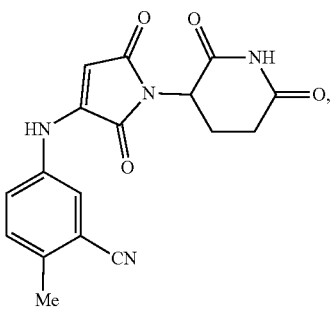
(6)
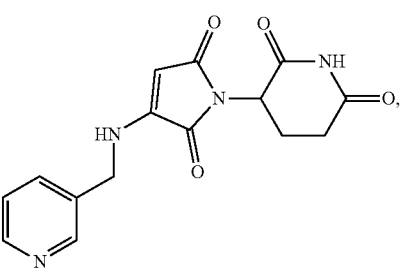
(7)
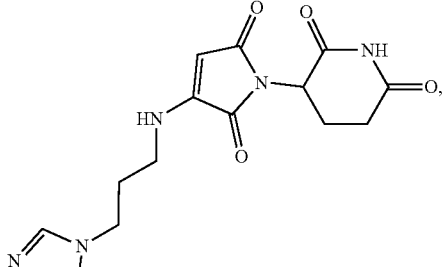
(8)
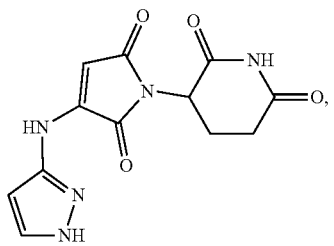

-continued
(9)
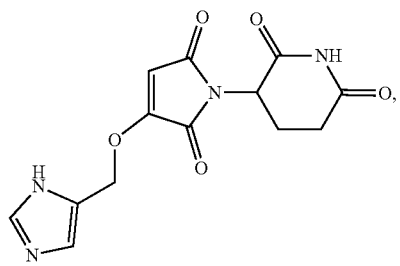
(10)
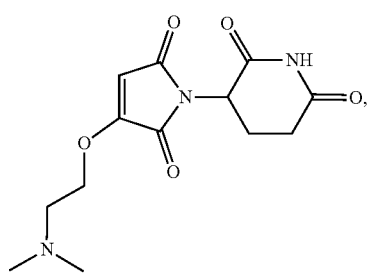
(11)
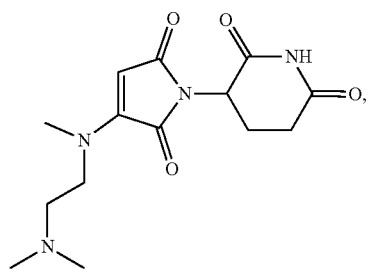
(12)
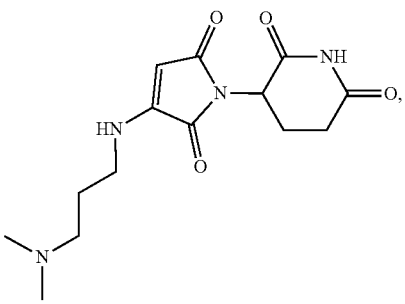
(13)
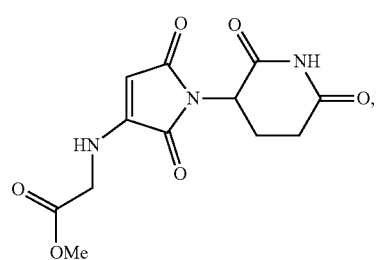
(14)
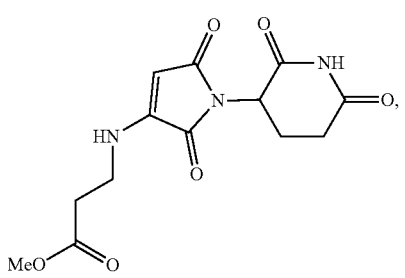
-continued
(15)
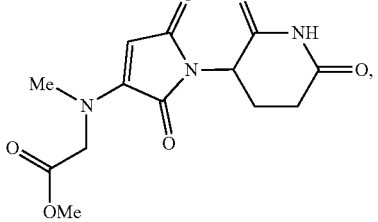
(16)
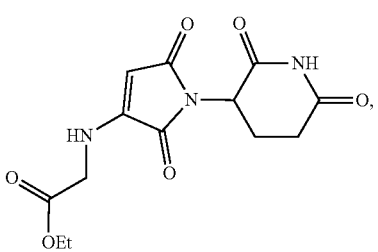
(17)
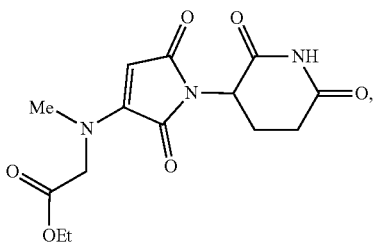
(18)
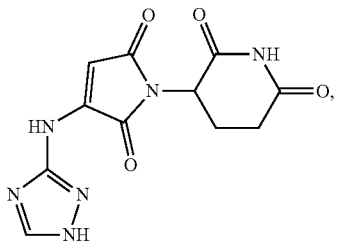
(19)
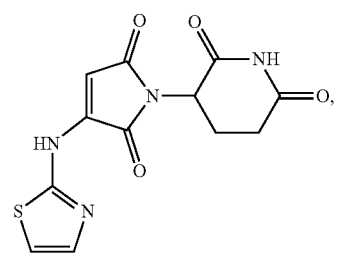
(20)
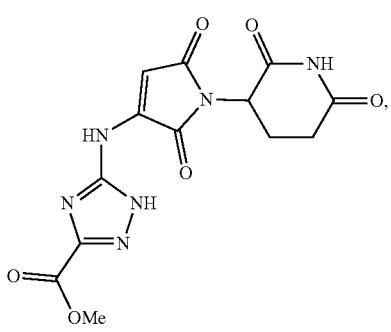

(21) 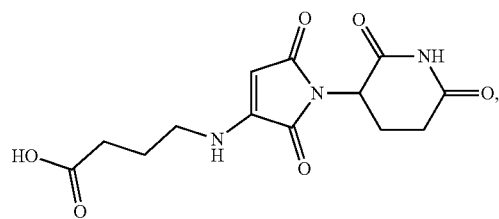
(22) 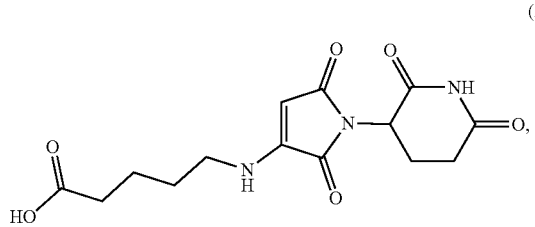
(23) 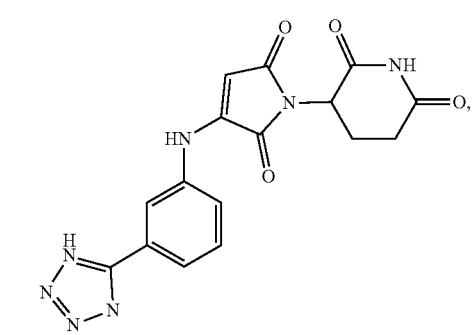
(24) 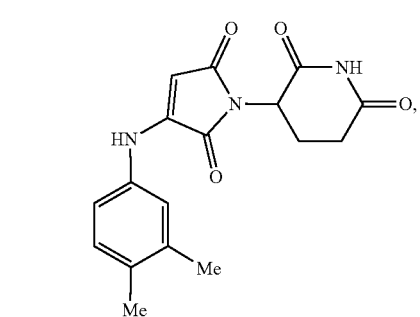
(25) 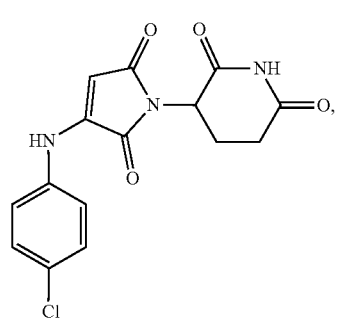
(26) 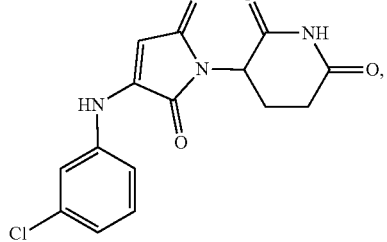
(27) 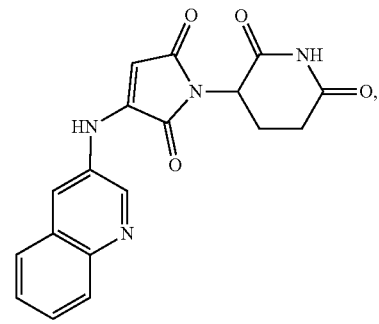
(28) 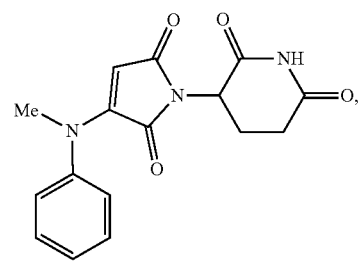
(29) 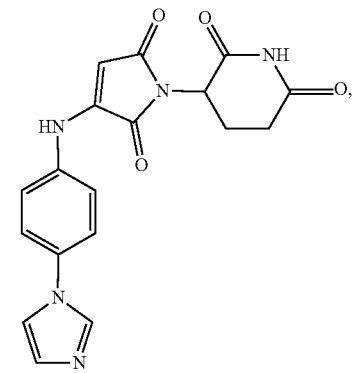
(30) 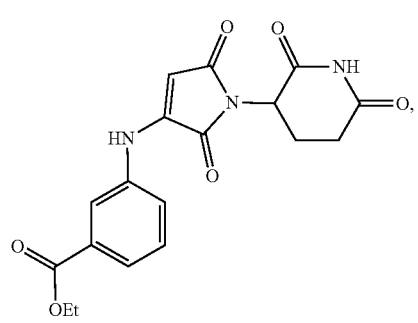

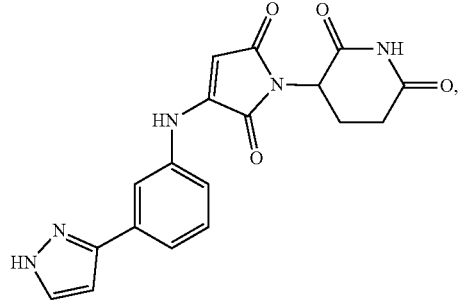
(31)
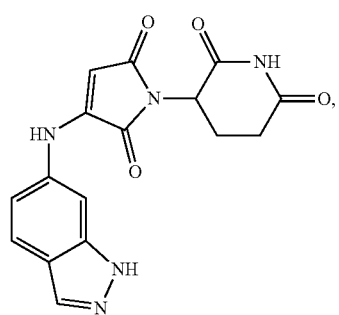
(32)
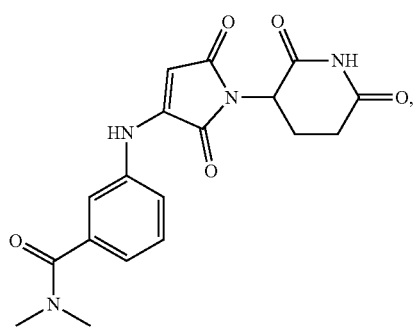
(33)
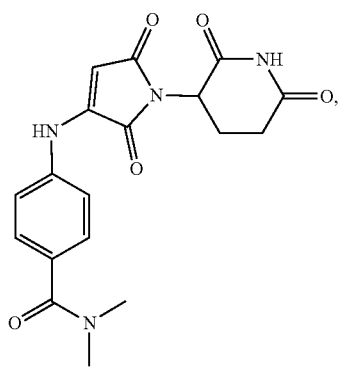
(34)
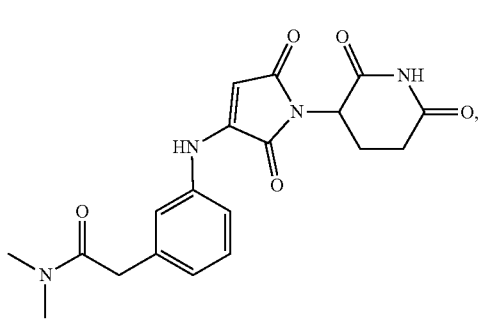
(35)
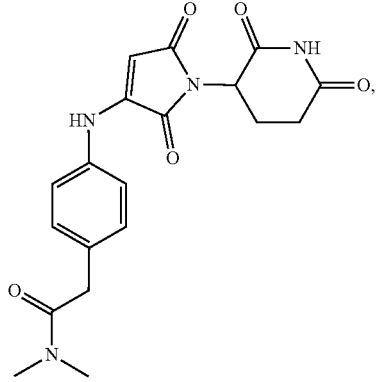
(36)
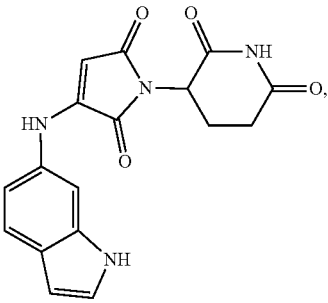
(37)
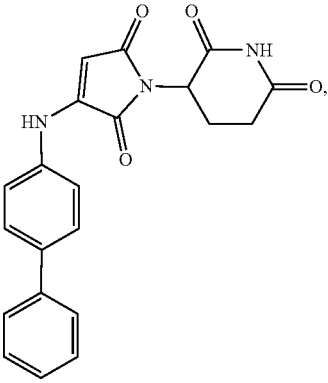
(38)
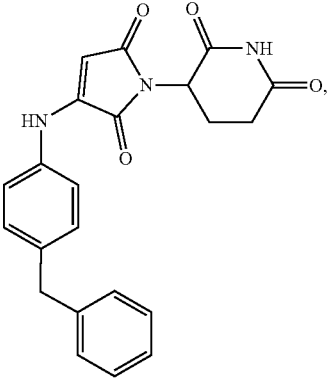
(39)

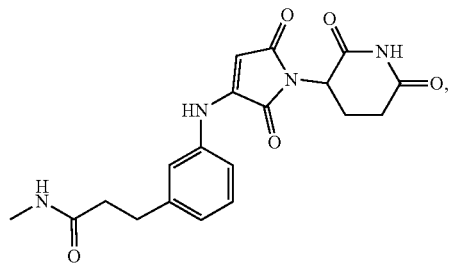
(40)
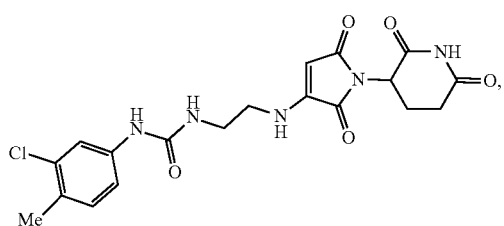
(41)
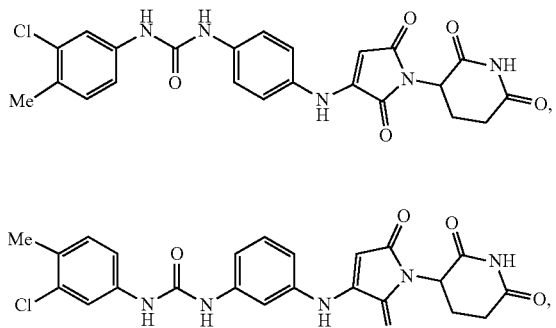
(42)
(43)
(44)
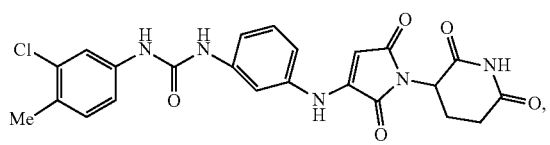
(45)
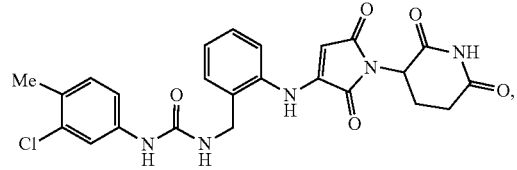
(46)
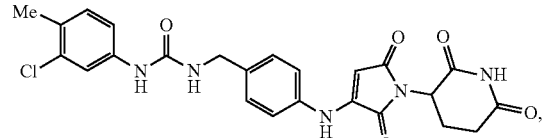
(47)
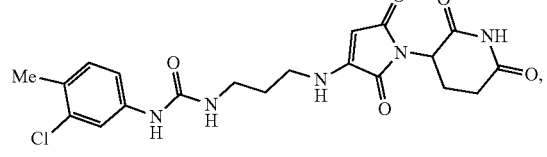
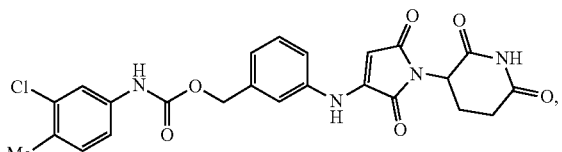
(48)
(49)
(51)
(50)
(51)
(52)
(53)
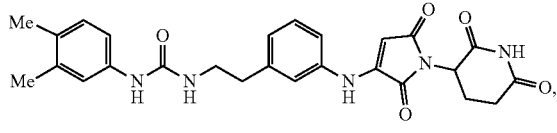
(55)

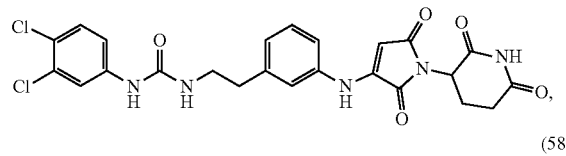
(56)
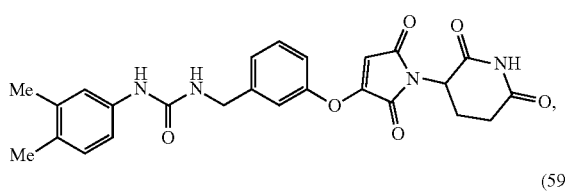
(58)
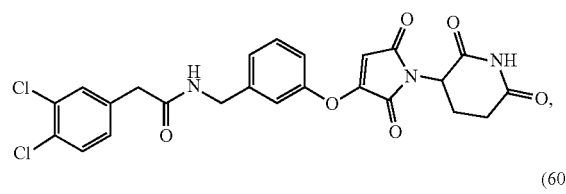
(59)
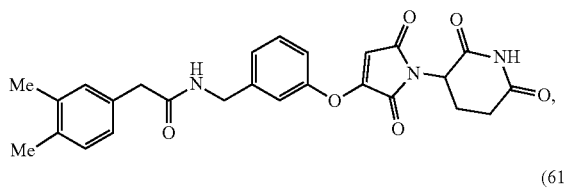
(60)
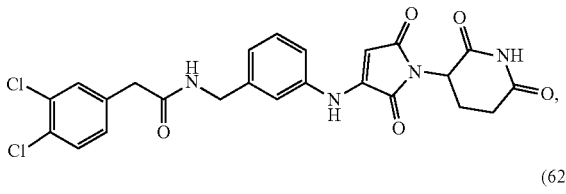
(61)
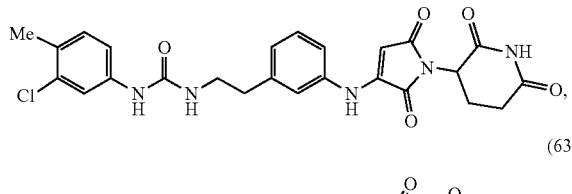
(62)
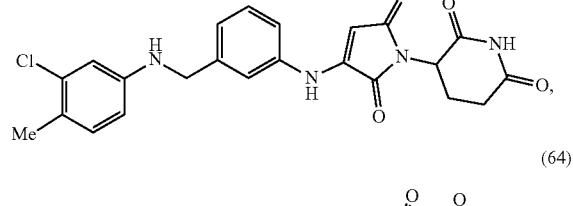
(63)
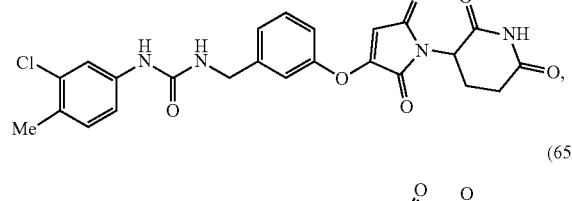
(64)
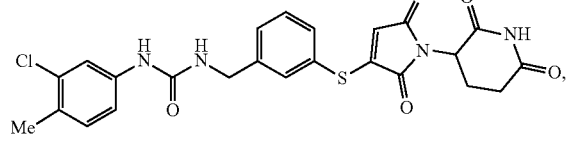
(65)
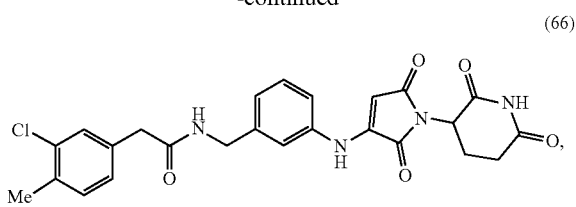
(66)
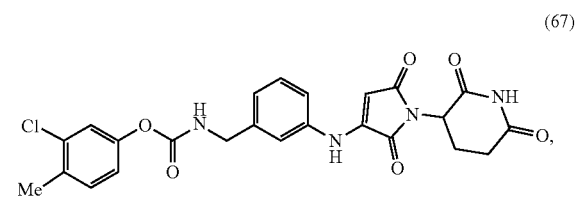
(67)
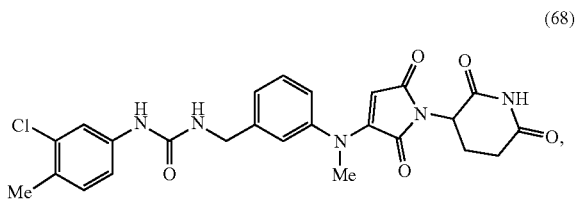
(68)
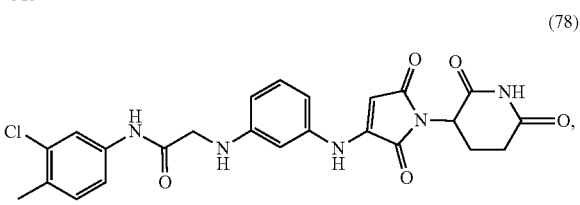
(78)
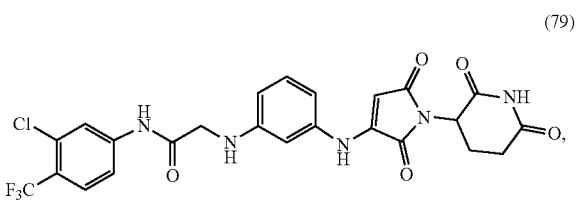
(79)
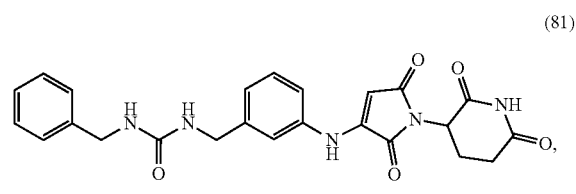
(81)
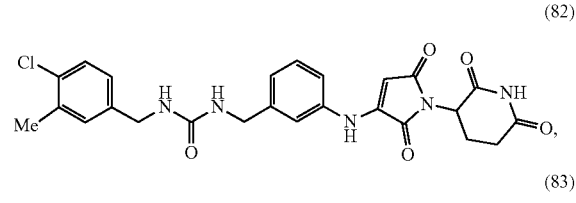
(82)
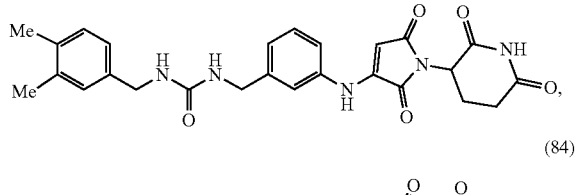
(83)
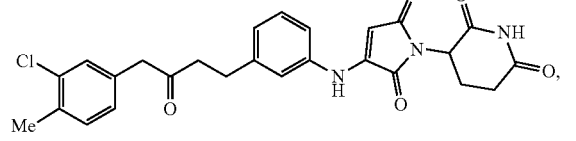
(84)

(85)
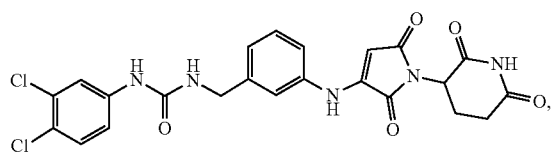
(88)
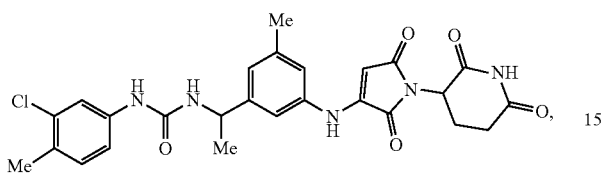
(90)
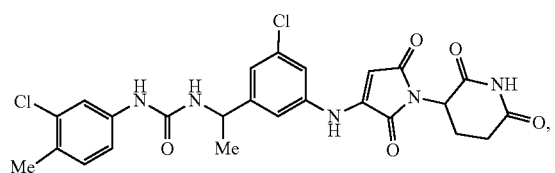
(97)
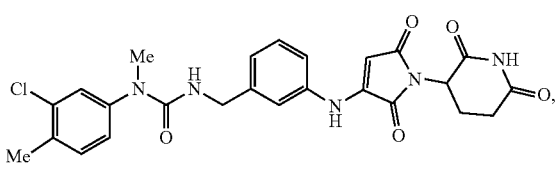
(98)
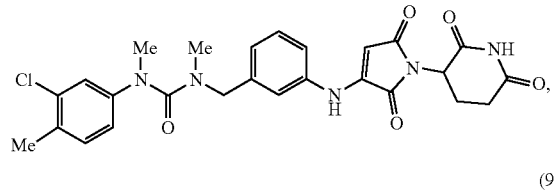
(99)
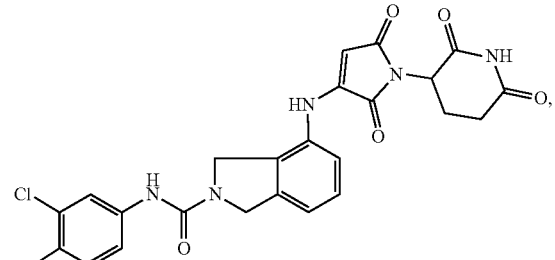
(100)
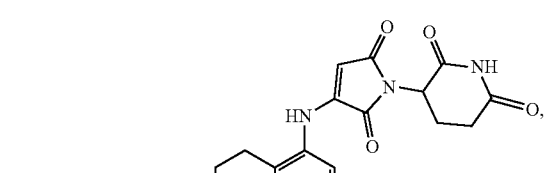
(101)
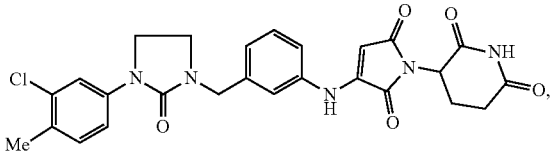
(102)
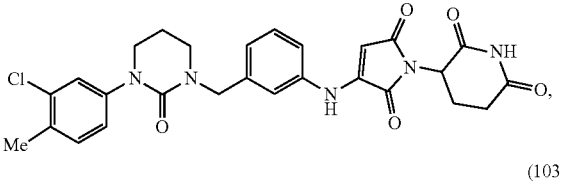
(103)
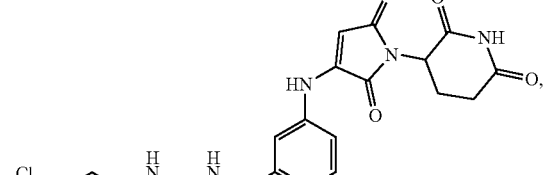
(105)
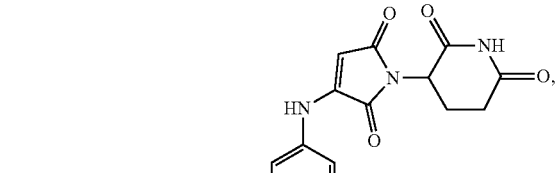
(106)
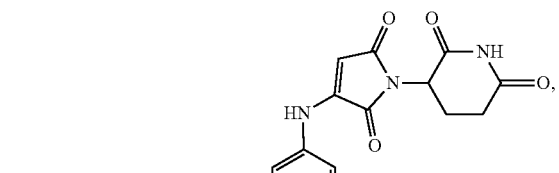
(107)
(108)

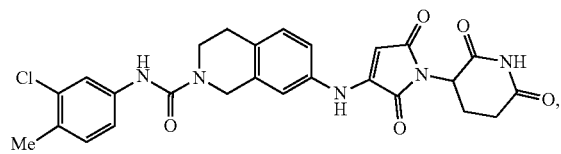
(109)
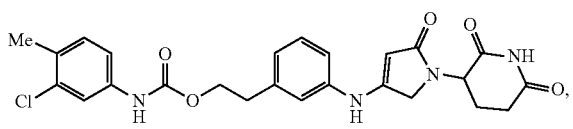
(110)
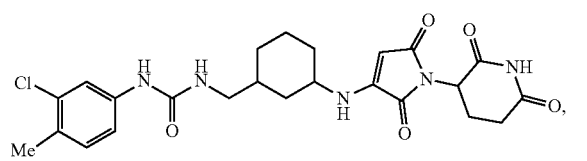
(113)
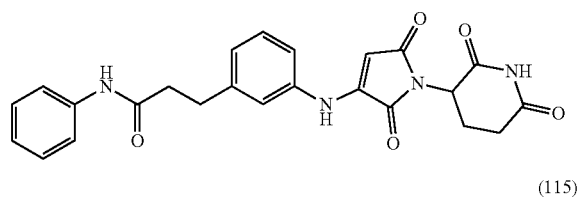
(114)
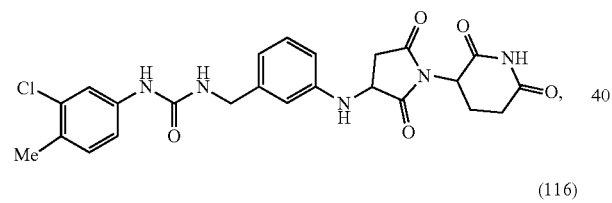
(115)
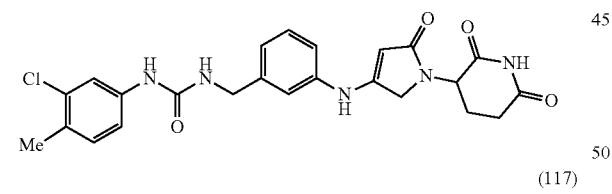
(116)
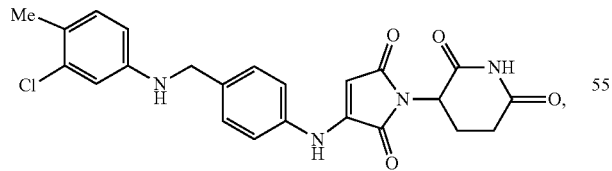
(117)
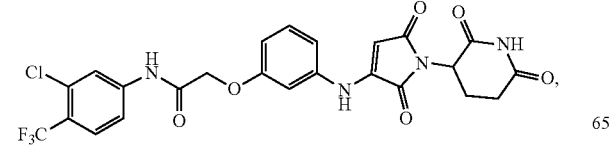
(118)
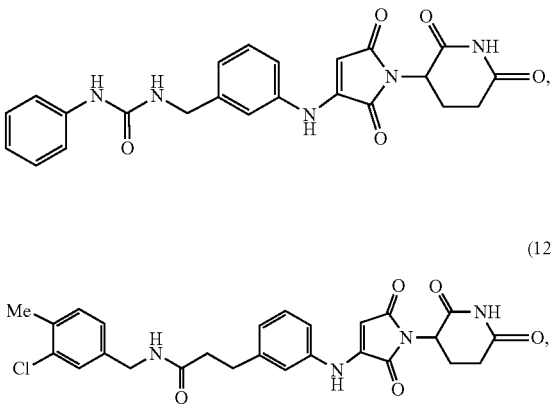
(119)
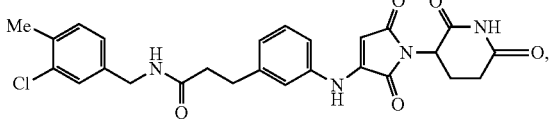
(121)
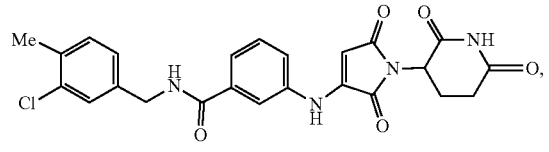
(122)
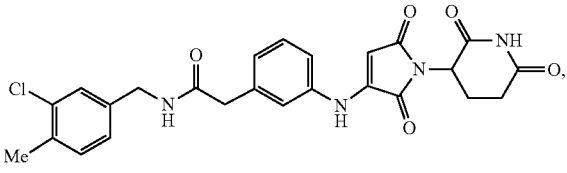
(123)
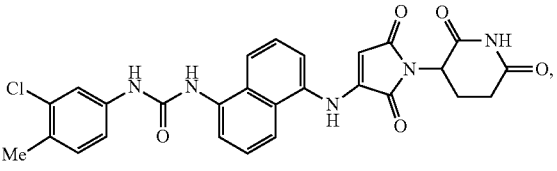
(124)
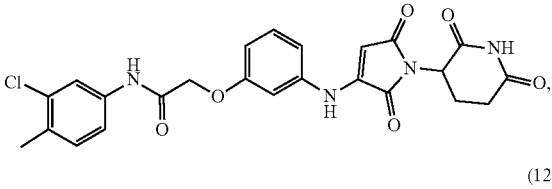
(125)
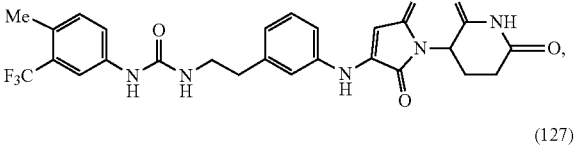
(126)
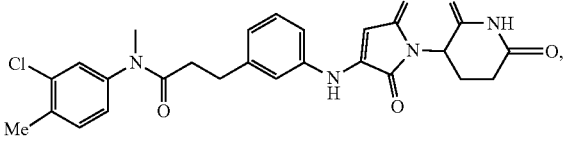
(127)

(128)

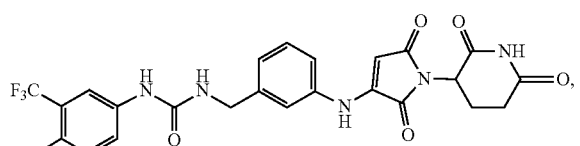

(129)

(130)

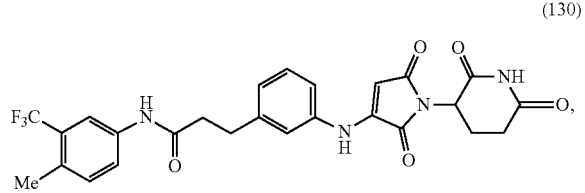

(148)

(149)

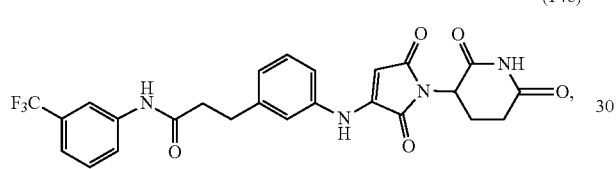

(150)

(151)

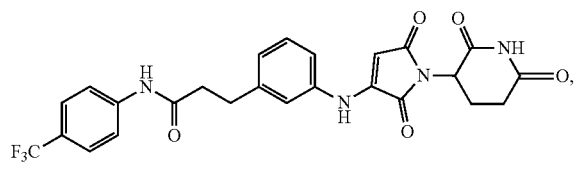

(153)

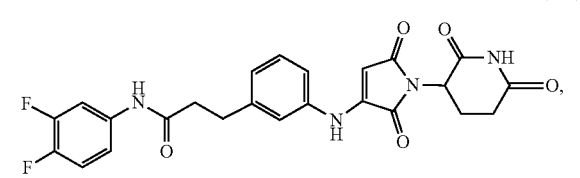

and (154)

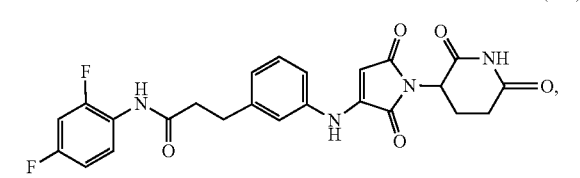

or a pharmaceutically acceptable salt or stereoisomer thereof.

A second aspect of the invention is directed to compounds that are represented by a structure of formula II:

(II)

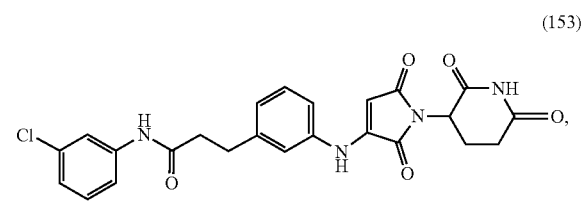

wherein:

L₁ represents

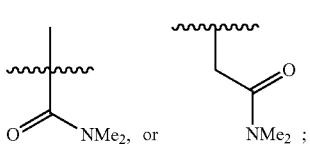

wherein R₄ is H or a substituent, e.g., alkyl, halo, hydroxyl, amino; R₅ represents H, -Me, -Et,

[structures with NMe₂]

W₃ and W₄ are independently absent or represent CH₂, NH, or NH—CH₂; and

Ar₁ is optionally substituted aryl or heteroaryl;

or a pharmaceutically acceptable salt or stereoisomer thereof.

In some embodiments, wherein
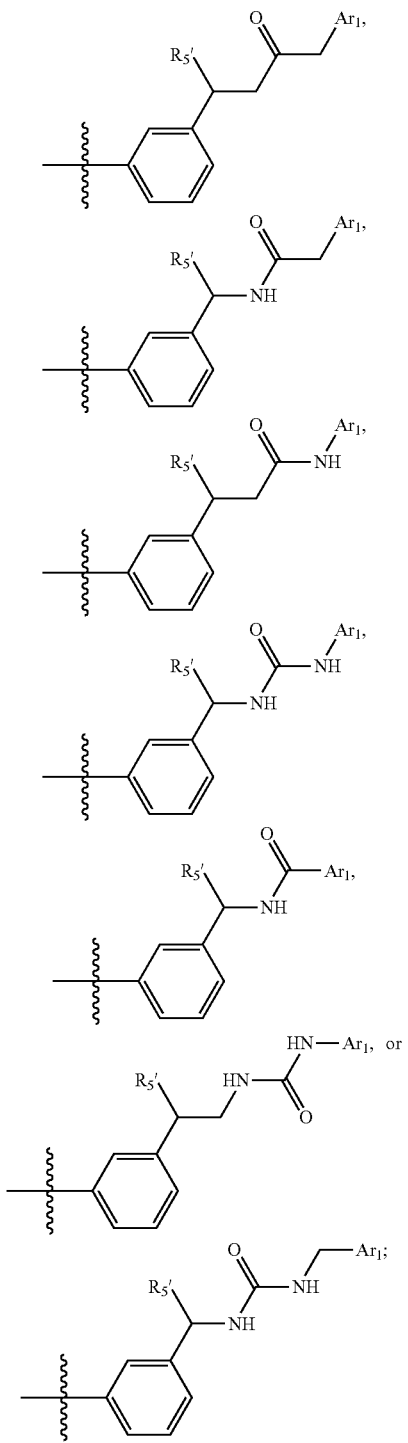
is
$R_5'$ is H, Me, or Et.
In some embodiments, $R_4$ is alkyl, halo, hydroxyl, amino, amido, substituted carbamate, or substituted carbamide.
In some embodiments, $Ar_1$ is optionally substituted phenyl.
Representative embodiments of the compounds of formula (II) are as follows:
(54)
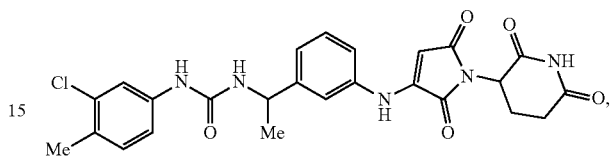
(57)
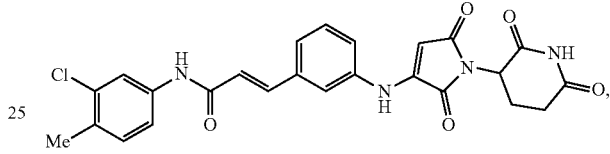
(70)
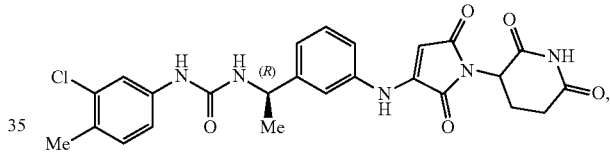
(71)
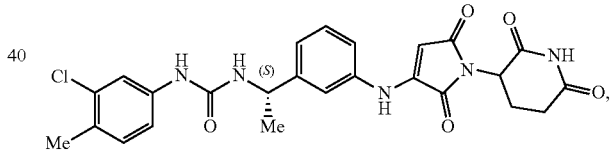
(72)
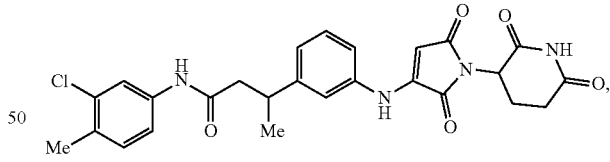
(73)
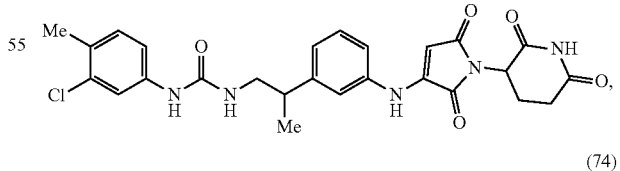
(74)
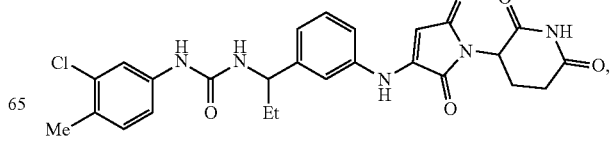

(75) 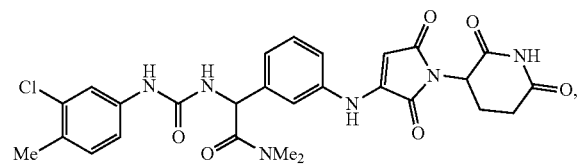
(76) 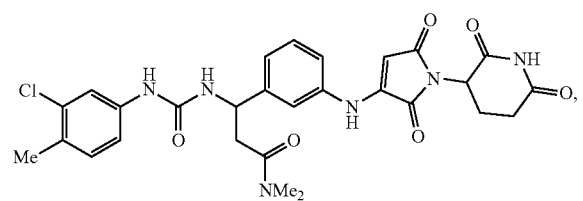
(77) 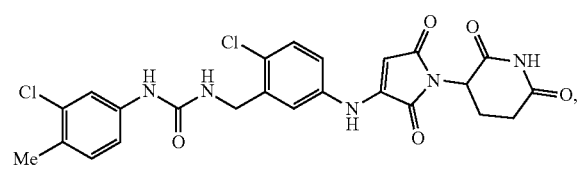
(80) 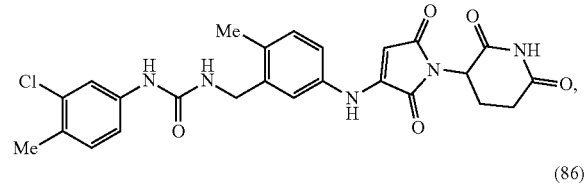
(86) 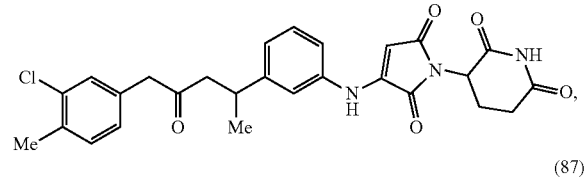
(87) 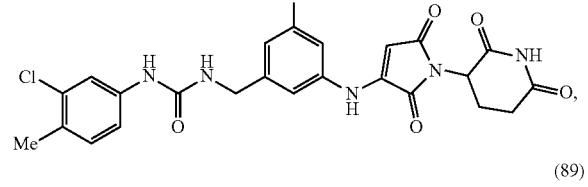
(89) 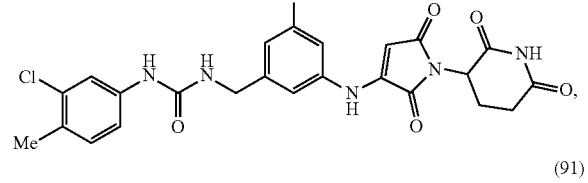
(91) 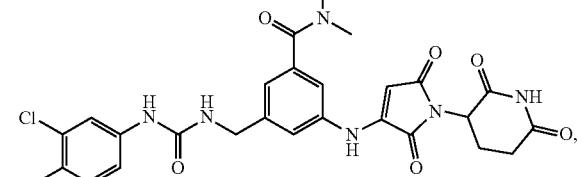
(92) 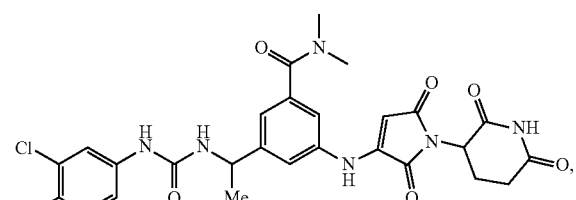
(93) 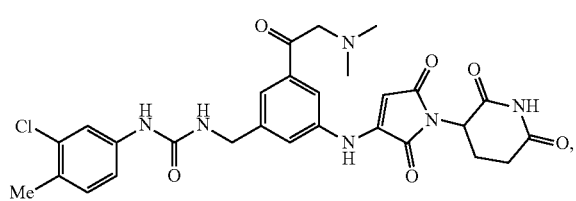
(94) 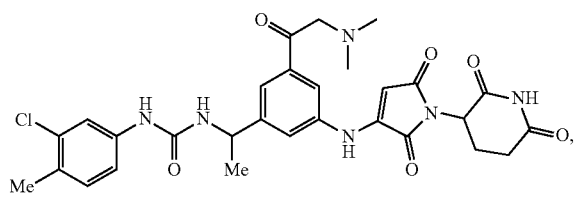
(95) 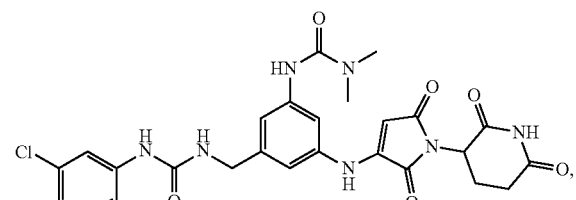
(96) 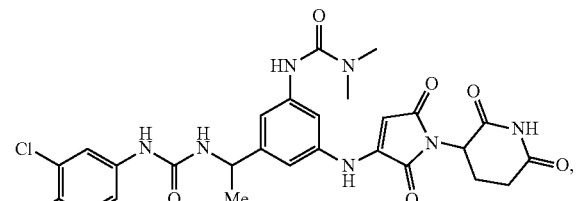
(111) 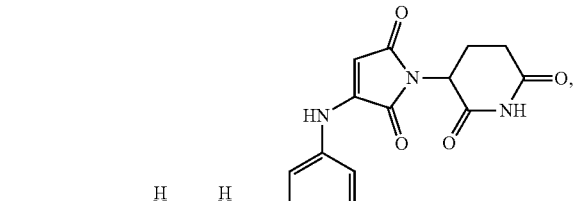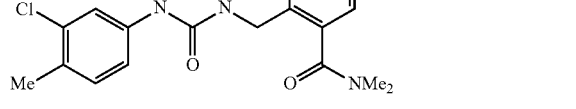

(112)
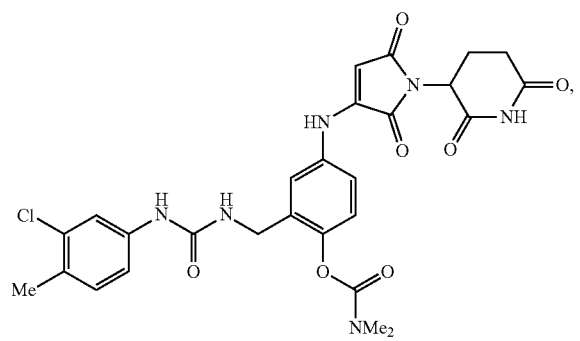
(120)
(137)
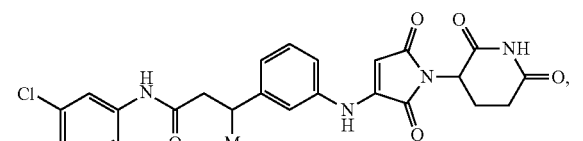
(131)
(138)
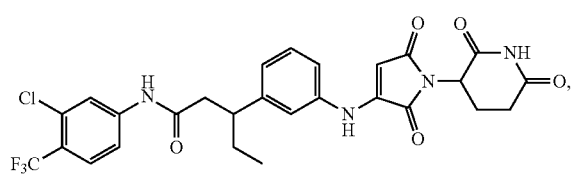
(132)
(140)
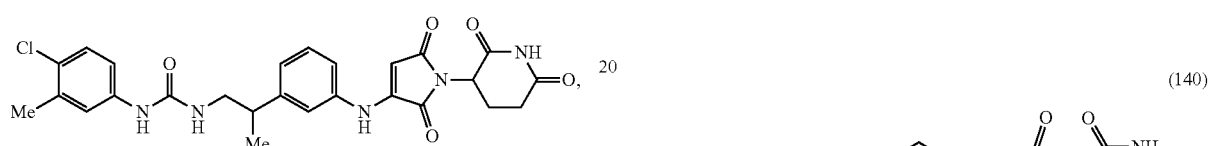
(133)
(141)
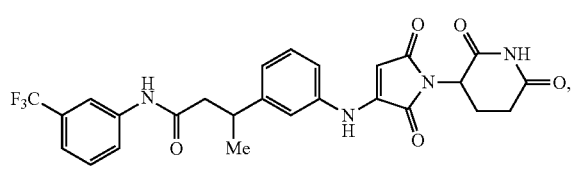
(134)
(142)
(135)
(143)
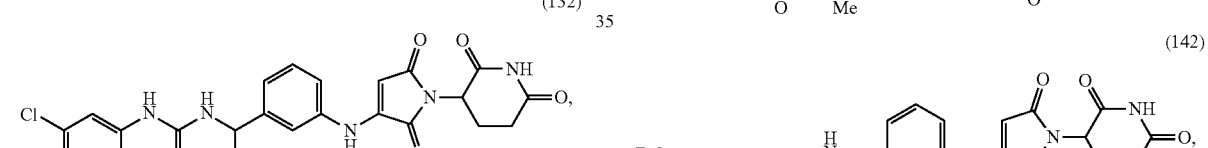
(144)
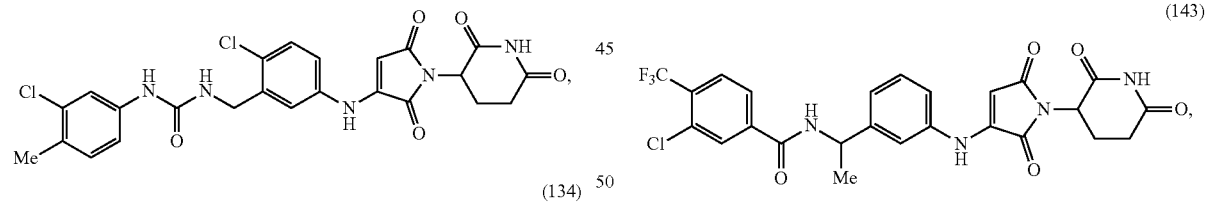
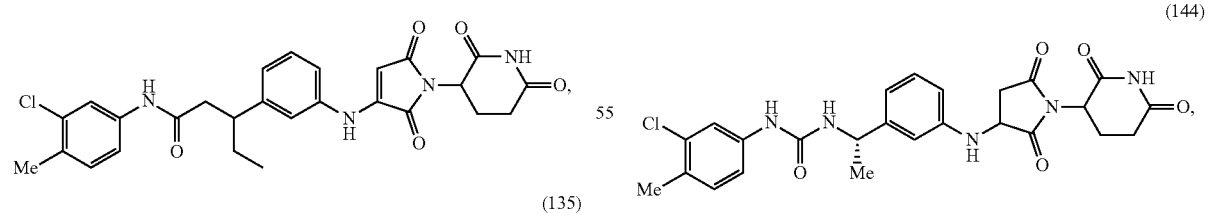
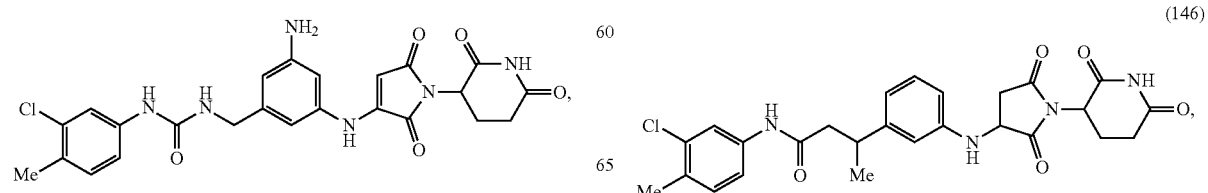
(146)
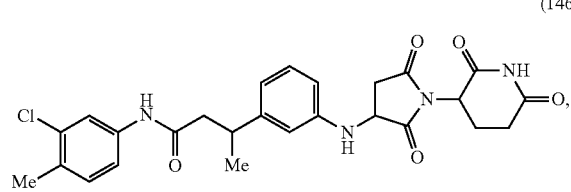

-continued (147)
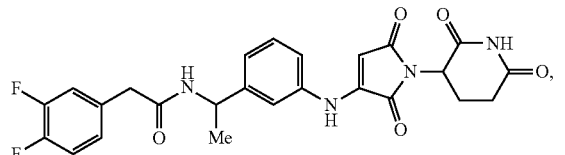

(152)
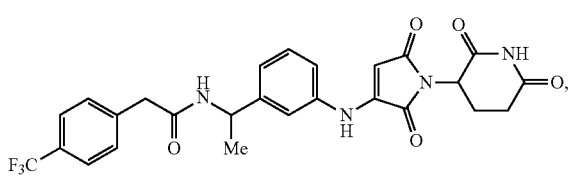

(155)
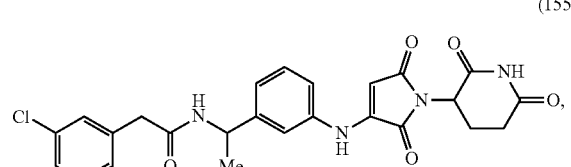

(156)
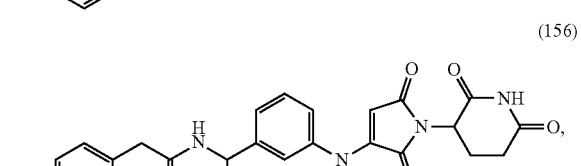

(157)
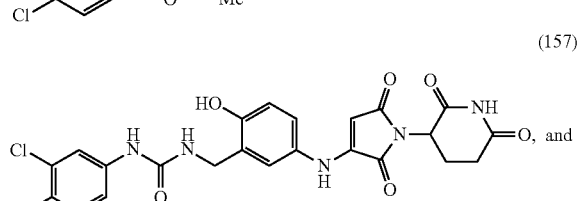

(158)
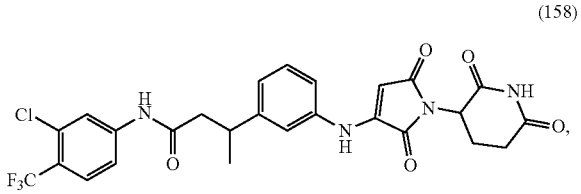

or a pharmaceutically acceptable salt or stereoisomer thereof.

A third aspect of the invention is directed to compounds that are represented by a structure of formula III:

(III)
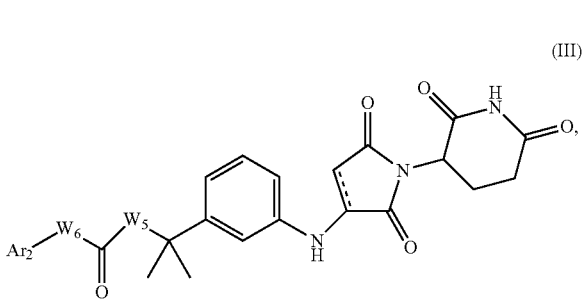

wherein
$W_5$ and $W_6$ each independently represents —$CH_2$— or —NH—, provided that one of $W_5$ and $W_6$ is —NH—; and
$Ar_2$ is optionally substituted aryl or heteroaryl;
or a pharmaceutically acceptable salt or stereoisomer thereof.

In some embodiments, $W_5$ and $W_6$ are both —NH—.

In some embodiments, $Ar_2$ is phenyl substituted with one or more groups selected from alkyl, halo, and haloalkyl.

Representative embodiments of the compounds of formula (III) are as follows:

(69)
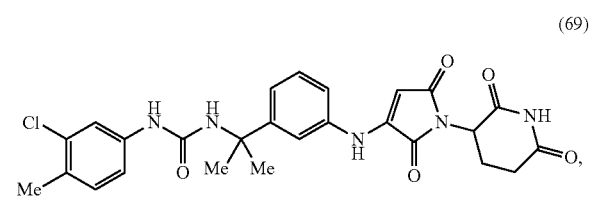

(136)
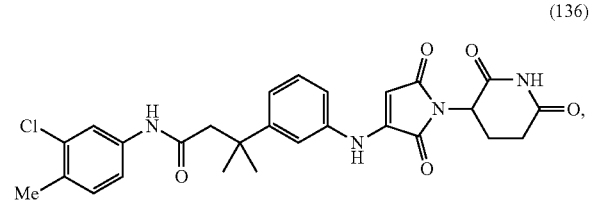

(139)
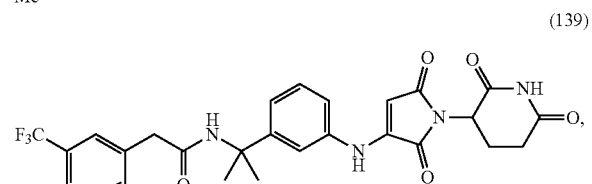

(145)
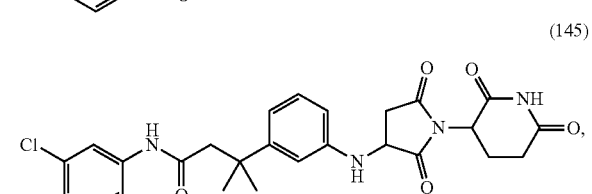

(159)
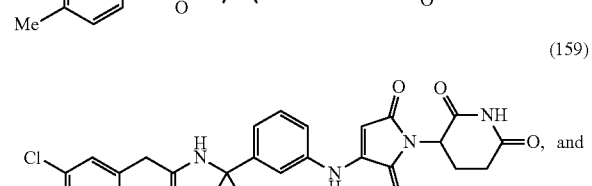

(160)
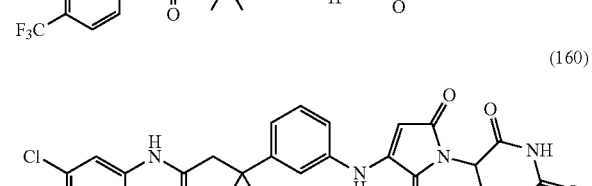

or a pharmaceutically acceptable salt or stereoisomer thereof.

Compounds of the present invention may be in the form of a free acid or free base, or a pharmaceutically acceptable salt. As used herein, the term "pharmaceutically acceptable" refers to a material, such as a carrier or diluent, which does not abrogate the biological activity or properties of the compound, and is relatively non-toxic, i.e., the material may be administered to a subject without causing undesirable biological effects (such as dizziness or gastric upset) or interacting in a deleterious manner with any of the components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

Compounds of the present invention may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R-) form is considered equivalent to administration of the compound in its (S-) form. Accordingly, the compounds of the present invention may be made and used in the form of individual isomers and substantially free of other isomers, or in the form of a mixture of various isomers, e.g., racemic mixtures of stereoisomers.

In some embodiments, the compound is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^2$H, may afford certain therapeutic advantages resulting from greater metabolic stability, for example, increased in vivo half-life or reduced dosage requirements, and thus may be advantageous in some circumstances.

The compounds of the present invention may be prepared by crystallization under different conditions and may exist as one or a combination of polymorphs of the compound. For example, different polymorphs may be identified and/or prepared using different solvents, or different mixtures of solvents for recrystallization, by performing crystallizations at different temperatures, or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other known techniques. Thus, the term "compound" embraces their isotopic derivatives, tautomeric forms, polymorphs, pharmaceutically acceptable solvates and hydrates, and pharmaceutically acceptable prodrugs.

In some embodiments, the pharmaceutical composition comprises a co-crystal of an inventive compound. The term "co-crystal", as used herein, refers to a stoichiometric multi-component system comprising a compound of the invention and a co-crystal former wherein the compound of the invention and the co-crystal former are connected by non-covalent interactions. The term "co-crystal former", as used herein, refers to compounds which can form intermolecular interactions with a compound of the invention and co-crystallize with it.

Representative examples of co-crystal formers include benzoic acid, succinic acid, fumaric acid, glutaric acid, trans-cinnamic acid, 2,5-dihydroxybenzoic acid, glycolic acid, trans-2-hexanoic acid, 2-hydroxycaproic acid, lactic acid, sorbic acid, tartaric acid, ferulic acid, suberic acid, picolinic acid, salicyclic acid, maleic acid, saccharin, 4,4'-bipyridine p-aminosalicyclic acid, nicotinamide, urea, isonicotinamide, methyl-4-hydroxybenzoate, adipic acid, terephthalic acid, resorcinol, pyrogallol, phloroglucinol, hydroxyquinol, isoniazid, theophylline, adenine, theobromine, phenacetin, phenazone, etofylline, and phenobarbital.

Methods of Synthesis

In another aspect, the present invention is directed to a method for making the inventive compounds, or a pharmaceutically acceptable salt or stereoisomer thereof. Broadly, the inventive compounds or pharmaceutically-acceptable salts or stereoisomers thereof may be prepared by any process known to be applicable to the preparation of chemically related compounds. The compounds of the present invention will be better understood in connection with the synthetic schemes that described in various working examples and which illustrate non-limiting methods by which the compounds of the invention may be prepared.

Pharmaceutical Compositions

Another aspect of the present invention is directed to a pharmaceutical composition that includes a therapeutically effective amount of an inventive compound of formula (I, II, or III) or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may further include one or more pharmaceutically acceptable excipients.

Broadly, compounds of the present invention and their pharmaceutically acceptable salts and stereoisomers may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the compounds are formulated for oral or intravenous administration (e.g., systemic intravenous injection).

Accordingly, compounds of the present invention may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, compounds of the present invention may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, compounds of the present invention may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The inventive compounds may be formulated for buccal or sublingual administration, examples of which include tablets, lozenges and gels.

The compounds may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Compounds of the present invention may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerine, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of an inventive compound or a pharmaceutically acceptable salt or a stereoisomer thereof that is effective in producing the desired therapeutic response in a particular patient suffering from a disease or disorder characterized or mediated by aberrant activity of a protein (e.g., IKZF2 (Helios)) that may be a substrate for a complex between an inventive compound and cereblon. The term "therapeutically effective amount" thus includes the amount of a compound of the invention or a pharmaceutically acceptable salt or a stereoisomer thereof, that when administered, induces a positive modification in the disease or disorder to be treated, or is sufficient to prevent development or progression of the disease or disorder, or alleviate to some extent, one or more of the symptoms of the disease or disorder being treated in a subject, or which simply kills or inhibits the growth of diseased (e.g., cancer) cells, or reduces the amounts of the aberrant protein in diseased cells.

The total daily dosage of compounds of the present invention and usage thereof may be decided in accordance with standard medical practice, e.g., by the attending physician using sound medical judgment. The specific therapeutically effective dose for any particular patient will depend upon any one or more of a variety of factors including the disease or disorder being treated and the severity thereof (e.g., its present status); the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's The Pharmacological Basis of Therapeutics, 10th Edition, A. Gilman, J. Hardman and L. Limbird, eds., McGraw-Hill Press, 155-173 (2001)).

Compounds of the present invention and their pharmaceutically acceptable salts and stereoisomers may be effective over a wide dosage range. In some embodiments, the total daily dosage (e.g., for adult humans) may range from about 0.001 to about 1600 mg, from 0.01 to about 1000 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, and in yet other embodiments from about 10 to about 30 mg per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, individual dosages may be formulated to contain the desired dosage amount depending upon the number of times the compound is administered per day.

Methods of Use

In another aspect, the compounds and pharmaceutically acceptable salts and stereoisomers of the present invention may be useful in the treatment of diseases and disorders characterized or mediated by aberrant (e.g., dysregulated) activity of a protein that is a substrate for a complex between CRBN and an inventive compound, and which participates in the inception, manifestation of one or more symptoms or markers, severity or progression of the disease or disorder, and where the degradation of the targeted protein may confer a therapeutic benefit. These proteins may include FAM83F, DTWD1, ZFP62, ZFP91, RNF166, IKZF1, IKZF2, IKZF3, IKZF4, IKZF5, CKla, ZN653, ZN654, ZN827, ZN692, ZBTB2, ZBTB39, RAB28, GSTP1, ZFP36L2, GZF1, GSPT1, GSPT2, EGR1, HIC1, HIC2, INSM2, OSR1, OSR2, PRD15, SALL1, SALL3, SALL4, WIZ, Z324B, ZBT17, ZBT41, ZBT49, ZBT7A, ZBT7B, ZIK1, ZNF3, ZNF217, ZNF276, ZNF316, ZNF335, ZNF397, ZNF407, ZNF408, ZNF462, ZNF483, ZNF517, ZNF526, ZNF581, ZNF582, ZNF587, ZNF589, ZNF618, ZNF644, ZNF646, ZNF653, ZNF654, ZNF692, ZNF724, ZNF771, ZNF782, ZNF784, ZNF787, ZNF814, ZNF827, ZSC10, ZSC22, ZUFSP, E4F1, BCL6, BCL6B, PATZ1, or ZKSC5. The methods entail the administration of a therapeutically effective amount of a compound of formula (I, II, or III) or a pharmaceutically acceptable salt or a stereoisomer thereof, to a subject in need thereof.

In some embodiments, the aberrantly functioning protein contains one or more sequence motifs, such as, the CxxCG motif, which is present in ZFP62, GZF1, EGR1, HIC1, HIC2, INSM2, Z324B, ZBT17, ZBT41, ZBT49, ZBT7A, ZBT7B, ZIK1, ZNF3, ZNF217, ZNF316, ZNF335, ZNF407, ZNF408, ZNF462, ZNF483, ZNF526, ZNF581, ZNF587, ZNF589, ZNF618, ZNF644, ZNF646, ZNF724, ZNF771, ZNF782, ZNF784, ZNF814, ZSC10, ZSC22, ZN654 and ZUFSP.

The compounds of the present invention may also be useful in the treatment of a disease or disorder that is affected by the reduction of TXNIP protein levels. The methods entail administering, to a subject in need thereof, a therapeutically effective amount of a compound of formula (I, II, or III), or a pharmaceutically acceptable salt or stereoisomer thereof.

A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

In some embodiments, compounds of the invention may be useful in the treatment of cell proliferative diseases and disorders (e.g., cancer or benign neoplasms). As used herein, the term "cell proliferative disease or disorder" refers to the conditions characterized by deregulated or abnormal cell growth, or both, including noncancerous conditions such as neoplasms, precancerous conditions, benign tumors, and cancer.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present invention may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

Exemplary types of non-cancerous (e.g., cell proliferative) diseases or disorders that may be amenable to treatment with the compounds of the present invention include inflammatory diseases and conditions, autoimmune diseases, neurodegenerative diseases, heart diseases, viral diseases, chronic and acute kidney diseases or injuries, metabolic diseases, and allergic and genetic diseases.

Representative examples of specific non-cancerous diseases and disorders include rheumatoid arthritis, alopecia areata, lymphoproliferative conditions, autoimmune hematological disorders (e.g. hemolytic anemia, aplastic anemia, anhidrotic ectodermal dysplasia, pure red cell anemia and idiopathic thrombocytopenia), cholecystitis, acromegaly, rheumatoid spondylitis, osteoarthritis, gout, scleroderma, sepsis, septic shock, dacryoadenitis, cryopyrin associated periodic syndrome (CAPS), endotoxic shock, endometritis, gram-negative sepsis, keratoconjunctivitis sicca, toxic shock syndrome, asthma, adult respiratory distress syndrome, chronic obstructive pulmonary disease, chronic pulmonary inflammation, chronic graft rejection, hidradenitis suppurativa, inflammatory bowel disease, Crohn's disease, Behcet's syndrome, systemic lupus erythematosus, glomerulonephritis, multiple sclerosis, juvenile-onset diabetes, autoimmune uveoretinitis, autoimmune vasculitis, thyroiditis, Addison's disease, lichen planus, appendicitis, bullous pemphigus, pemphigus vulgaris, pemphigus foliaceus, paraneoplastic pemphigus, myasthenia gravis, immunoglobulin A nephropathy, Hashimoto's disease, Sjogren's syndrome, vitiligo, Wegener granulomatosis, granulomatous orchitis, autoimmune oophoritis, sarcoidosis, rheumatic carditis, ankylosing spondylitis, Grave's disease, autoimmune thrombocytopenic purpura, psoriasis, psoriatic arthritis, eczema, dermatitis herpetiformis, ulcerative colitis, pancreatic fibrosis, hepatitis, hepatic fibrosis, CD14 mediated sepsis, non-CD14 mediated sepsis, acute and chronic renal disease, irritable bowel syndrome, pyresis, restenosis, cervicitis, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniasis, Lyme disease, Reiter's syndrome, acute synovitis, muscle degeneration, bursitis, tendonitis, tenosynovitis, herniated, ruptured, or prolapsed intervertebral disk syndrome, osteopetrosis, rhinosinusitis, thrombosis, silicosis, pulmonary sarcosis, bone resorption diseases, such as osteoporosis, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q11.2 deletion syndrome, Angelman syndrome, Canavan disease, celiac disease, Charcot-Marie-Tooth disease, color blindness, Cri du chat, Down syndrome, cystic fibrosis, Duchenne muscular dystrophy, haemophilia, Klinefleter's syndrome, neurofibromatosis, phenylketonuria, Prader-Willi syndrome, sickle cell disease, Tay-Sachs disease, Turner syndrome, urea cycle disorders, thalassemia, otitis, pancreatitis, parotitis, pericarditis, peritonitis, pharyngitis, pleuritis, phlebitis, pneumonitis, uveitis, polymyositis, proctitis, interstitial lung fibrosis, dermatomyositis, atherosclerosis, arteriosclerosis, amyotrophic lateral sclerosis, asociality, varicosis, vaginitis, depression, and Sudden Infant Death Syndrome.

In some embodiments, a compound of the present invention may be used to treat gout, idiopathic pulmonary fibrosis, silicosis, asbestosis, nonalcoholic steatohepatitis, atherosclerosis, diabetes, diabetic nephropathy, diabetic retinopathy, or diabetic cardiomyopathy.

In other embodiments, the methods are directed to treating subjects having cancer. Broadly, the compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) such as leukemia, lymphoma and multiple myeloma. Adult tumors/cancers and pediatric tumors/cancers are included. The cancers may be vascularized, or not yet substantially vascularized, or non-vascularized tumors.

Representative examples of cancers includes adrenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, gestational trophoblastic tumor glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), germ cell tumor, ovarian germ cell tumor, head and neck cancer, Hodgkin's lymphoma, leukemia, lymphoma, multiple myeloma, hypopharyngeal cancer, intraocular melanoma, ocular cancer, islet cell tumors (endocrine pancreas), renal cancer (e.g., Wilm's Tumor, clear cell renal cell carcinoma), liver cancer, lung cancer (e.g., non-small cell lung cancer and small cell lung cancer), Waldenstrom's macroglobulinema, melanoma, intraocular (eye) melanoma, merkel cell carcinoma, mesothelioma, metastatic squamous neck cancer with occult primary, multiple endocrine neoplasia (MEN), myelodysplastic syndromes, myelodyplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, pituitary tumor, plasma cell neoplasm/multiple myeloma, pleuropulmonary blastoma, prostate cancer, retinoblastoma rhabdomyosarcoma, salivary gland cancer, uterine cancer (e.g., endometrial uterine cancer, uterine sarcoma, uterine corpus cancer), squamous cell carcinoma, thymoma, thymic carcinoma, thyroid cancer, transitional cell cancer of the renal pelvis and ureter and other urinary organs, urethral cancer, gestational trophoblastic tumor, vaginal cancer and vulvar cancer.

Sarcomas that may be treatable with compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue) and mesenchymous or mixed mesodermal tumor (mixed connective tissue types).

In some embodiments, methods of the present invention entail treatment of subjects having cell proliferative diseases or disorders of the hematological system, liver, brain, lung, colon, pancreas, prostate, ovary, breast, skin, and endometrium.

As used herein, "cell proliferative diseases or disorders of the hematological system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, metastatic pancreatic adenocarcinoma, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the liver may include hyperplasia, metaplasia, dysplasia of the liver, hepatocellular carcinoma, intrahepatic cholangiocarcinoma (bile duct cancer), angiosarcoma, hemangiosarcoma, hepatoblastoma, and secondary liver cancer (metastatic liver cancer). In some embodiments, the compounds of the present invention may be effective in the treatment of biliary tract cancer (BTC). In some embodiments, the BTC is intrahepatic cholangiocarcinoma (ICC) or extrahepatic cholangiocarcinoma (ECC).

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), squamous cell carcinoma, adenocarcinoma, small cell carcinoma, large cell carcinoma, squamous cell carcinoma, and mesothelioma. Lung cancer can include "scar carcinoma", bronchioveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types). In some embodiments, a compound of the present invention may be used to treat non-metastatic or metastatic lung cancer (e.g., NSCLC, ALK-positive NSCLC, NSCLC harboring ROS1 Rearrangement, Lung Adenocarcinoma, and Squamous Cell Lung Carcinoma). In some embodiments, compounds of the present invention may be used to treat non-metastatic or metastatic lung cancer (e.g., NSCLC, ALK-positive NSCLC, NSCLC harboring ROS1 Rearrangement, Lung Adenocarcinoma, and Squamous Cell Lung Carcinoma).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polyposis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell types).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting cells of the endometrium. Cell proliferative disorders of the endometrium may include a precancer or precancerous condition of the endometrium, benign growths or lesions of the endometrium, endometrial cancer, and metastatic lesions in tissue and organs in the body other than the endometrium. Cell proliferative disorders of the endometrium may include hyperplasia, metaplasia, and dysplasia of the endometrium.

In some embodiments, a compound of the present invention may be used to treat coronary heart disease.

In some embodiments, a compound of the present invention may be used to treat T cell leukemia or T cell lymphoma.

In some embodiments, a compound of the present invention may be used to treat Hodgkin's lymphoma or non-Hodgkin's lymphoma.

In some embodiments, a compound of the present invention may be used to treat myeloid leukemia.

In some embodiments, a compound of the present invention may be used to treat non-small cell lung cancer (NSCLC).

In some embodiments, a compound of the present invention may be used to treat melanoma.

In some embodiments, a compound of the present invention may be used to treat triple-negative breast cancer (TNBC).

In some embodiments, a compound of the present invention may be used to treat nasopharyngeal cancer (NPC).

In some embodiments, a compound of the present invention may be used to treat microsatellite stable colorectal cancer (mssCRC).

In some embodiments, a compound of the present invention may be used to treat thymoma.

In some embodiments, a compound of the present invention may be used to treat carcinoid.

In some embodiments, a compound of the present invention may be used to treat gastrointestinal stromal tumor (GIST).

The compounds of the present invention may be administered to a patient, e.g., a cancer patient, as a monotherapy or by way of combination therapy, and as a front-line or a follow-on therapy for patients who are unresponsive to front line therapy. Therapy may be "first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been partially successful but are intolerant to the particular treatment. Therapy may also be given as an adjuvant treatment, i.e., to prevent reoccurrence of cancer in patients with no currently detectable disease or after surgical removal of a tumor. Thus, in some embodiments, the compound may be administered to a patient who has received another therapy, such as chemotherapy, radioimmunotherapy, surgical therapy, immunotherapy, radiation therapy, targeted therapy or any combination thereof.

The methods of the present invention may entail administration of an inventive compound or a pharmaceutical composition thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails a 28-day cycle which includes daily administration for 3 weeks (21 days) followed by a 7-day off period. In other embodiments, the compound may be dosed twice a day (BID) over the course of two and a half days (for a total of 5 doses) or once a day (QD) over the course of two days (for a total of 2 doses). In other embodiments, the compound may be dosed once a day (QD) over the course of five days.

Combination Therapy

The compounds of the present invention and their pharmaceutically acceptable salts and stereoisomers may be used in combination or concurrently with at least one other active agent e.g., anti-cancer agent or regimen, in treating diseases and disorders. The terms "in combination" and "concurrently" in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically to provide an increased benefit than if they were administered otherwise). For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments involving cancer, the treatment regimen may include administration of a compound of the invention in combination with one or more additional anticancer therapeutics. The dosage of the additional anticancer therapeutic may be the same or even lower than known or recommended doses. See, Hardman et al., eds., *Goodman & Gilman's The Pharmacological Basis Of Therapeutics*, 10th ed., McGraw-Hill, New York, 2001; Physician's Desk Reference 60th ed., 2006. Anti-cancer agents that may be used in combination with the inventive compounds are known in the art. See, e.g., U.S. Pat. No. 9,101,622 (Section 5.2 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy.

In some embodiments, the compound of the invention and the additional anticancer therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more anticancer therapeutics may be administered within the same patient visit.

In some embodiments, the compound of formula (I, II, or III) and the additional agent or therapeutic (e.g., an anticancer therapeutic) are cyclically administered. By way of example in the context of cancer treatment, cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

In some embodiments, a compound of the present invention may be used in combination with other anti-cancer agents, examples of which include Paclitaxel (e.g., ovarian cancer, breast cancer, lung cancer, Kaposi sarcoma, cervical cancer, and pancreatic cancer), Topotecan (e.g., ovarian cancer and lung cancer), Irinotecan (e.g., colon cancer, and small cell lung cancer), Etoposide (e.g., testicular cancer, lung cancer, lymphomas, and nonlymphocytic leukemia), Vincristine (e.g., leukemia), Leucovorin (e.g., colon cancer), Altretamine (e.g., ovarian cancer), Daunorubicin (e.g., acute myeloid leukemia (AML), acute lymphocytic leukemia (ALL), chronic myelogenous leukemia (CML), and Kaposi's sarcoma), Trastuzumab (e.g., breast cancer, stomach cancer, and esophageal cancer), Rituximab (e.g., non-Hodgkin's lymphoma), Cetuximab (e.g., colorectal cancer, metastatic non-small cell lung cancer and head and neck cancer), Pertuzumab (e.g., metastatic HER2-positive breast cancer), Alemtuzumab (e.g., chronic lymphocytic leukemia (CLL), cutaneous T-cell lymphoma (CTCL) and T-cell lymphoma), Panitumumab (e.g., colon and rectum cancer), Tamoxifen (e.g., breast cancer), Fulvestrant (e.g., breast cancer), Letrazole (e.g., breast cancer), Exemestane (e.g., breast cancer), Azacytidine (e.g., myelodysplastic syndromes), Mitomycin C (e.g., gastro-intestinal cancers, anal cancers, and breast cancers), Dactinomycin (e.g., Wilms tumor, rhabdomyosarcoma, Ewing's sarcoma, trophoblastic neoplasm, testicular cancer, and ovarian cancer), Erlotinib (e.g., non-small cell lung cancer and pancreatic cancer), Sorafenib (e.g., kidney cancer and liver cancer), Temsirolimus (e.g., kidney cancer), Bortezomib (e.g., multiple myeloma and mantle cell lymphoma), Pegaspargase (e.g., acute lymphoblastic leukemia), Cabometyx (e.g., hepatocellular carcinoma, medullary thyroid cancer, and renal cell carcinoma), Keytruda (e.g., cervical cancer, gastric cancer, hepatocellular carcinoma, Hodgkin lymphoma, melanoma, Merkel cell carcinoma, non-small cell lung cancer, urothelial carcinoma, and squamous cell carcinoma of the head and neck), Nivolumab (e.g., colorectal cancer, hepatocellular carcinoma, melanoma, non-small cell lung cancer, renal cell carcinoma, small cell lung cancer, and urothelial carcinoma), and Regorafenib (e.g., colorectal cancer, gastrointestinal stromal tumor, and hepatocellular carcinoma).

Pharmaceutical Kits

The present compositions may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain a compound of formula (I, II, or III) of the present invention or a pharmaceutical composition. The kits or pharmaceutical systems of the invention may also include printed instructions for using the compounds and compositions.

These and other aspects of the present invention will be further appreciated upon consideration of the following Examples, which are intended to illustrate certain particular embodiments of the invention but are not intended to limit its scope, as defined by the claims.

EXAMPLES

These and other aspects of the present invention will be further appreciated upon consideration of the following Examples, which are intended to illustrate certain particular embodiments of the invention but are not intended to limit its scope, as defined by the claims.

Example 1: Synthesis of Key Bromomaleimide Intermediate

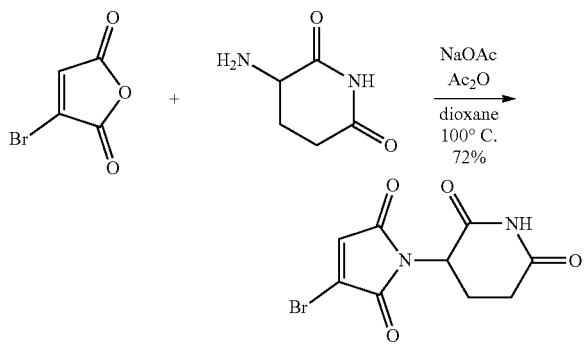

3-(3-bromo-2,5-dioxo-2,5-dihydro-1H-pyrrol-1-yl)piperidine-2,6-dione

In a 40-mL vial, 3-aminopiperidine-2,6-dione (1 g, 6.08 mmol, 1.0 equiv) was dissolved in dioxane (14 mL, 0.45 M).

Bromomaleic anhydride (621 µL, 6.68 mmol, 1.1 equiv) was added, and the reaction mixture was stirred at 80° C. for 1 h. Sodium acetate (550 mg, 6.68 mmol, 1.1 equiv) was added, and the reaction mixture was stirred at 80° C. for 5 h. Acetic anhydride (632 µL, 6.68 mmol, 1.1 equiv) was added dropwise, and the reaction mixture was stirred at 100° C. for 15 h. Upon cooling to room temperature (rt), the reaction mixture was concentrated. The crude product was dissolved in $CH_2Cl_2$ and washed with saturated aqueous $NaHCO_3$ 3× and water. The organic layers were collected, dried over $Na_2SO_4$, and filtered. Concentration in vacuo provided a crude oil, which was dissolved in water and acetonitrile, frozen, and lyophilized. The title compound (1.25 g, 72% yield) was obtained as a light brown solid, which was used without further purification.

Example 2: General Synthetic Procedures for Michael Addition of Amines with Bromomaleimide Method A: Base-Promoted Michael Addition

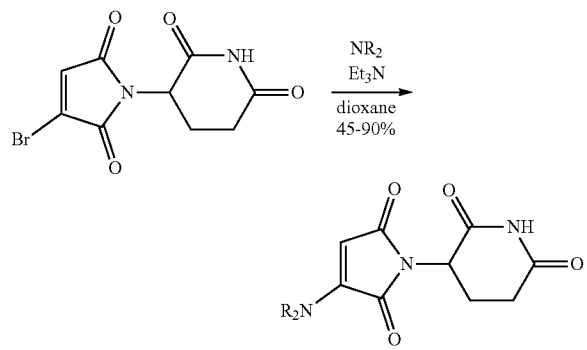

In an 8-mL vial, nucleophile $NR_2$ (0.348 mmol, 1.0 equiv), which was commercially available or prepared in advance as described below, was dissolved in dioxane (1 mL). A solution of 3-(3-bromo-2,5-dioxo-2,5-dihydro-1H-pyrrol-1-yl)piperidine-2,6-dione (50 mg, 0.348 mmol, 1.0 equiv) in dioxane (500 µL) was added to the reaction mixture, followed by triethylamine (60 L, 0.418 mmol, 1.2 equiv). The reaction mixture was stirred at 65° C. overnight, unless indicated otherwise. Upon cooling to rt, the reaction mixture was concentrated in vacuo. Purification by silica flash chromatography, and/or prep TLC afforded the Michael addition product.

In addition to amine nucleophiles, this synthetic procedure can be expanded towards use of alcohol (ROH) and thiol (RSH) nucleophiles.

Method B: Lewis-Acid Promoted Michael Addition

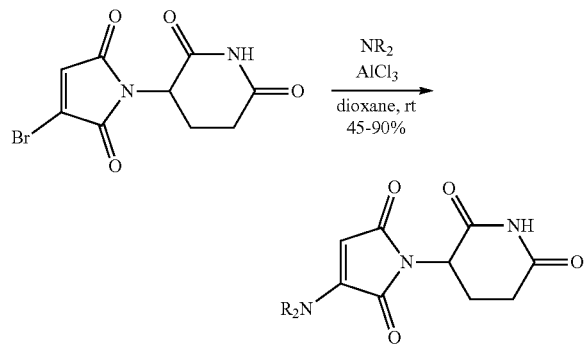

In an 8-mL vial, nucleophile $NR_2$ (0.383 mmol, 1.1 equiv), which is commercially available, was dissolved in dioxane (1 mL). A solution of 3-(3-bromo-2,5-dioxo-2,5-dihydro-1H-pyrrol-1-yl)piperidine-2,6-dione (50 mg, 0.348 mmol, 1.0 equiv) in dioxane (1 mL) was added to the reaction mixture, followed by $AlCl_3$ (17 mg, 0.070 mmol, 0.20 equiv). The reaction mixture was stirred at rt for 1 h, unless indicated otherwise. Upon cooling to rt, the reaction mixture was diluted with water and extracted with $CH_2Cl_2$ 3×. The organic layers were collected and dried over $Na_2SO_4$, filtered, and concentrated in vacuo. Purification by silica flash chromatography, and/or prep TLC afforded Lewis-acid promoted Michael addition product.

Example 3: General Synthetic Procedures Toward Amine ($NR_2$) Coupling Partners

Method C: Synthesis of Int-2

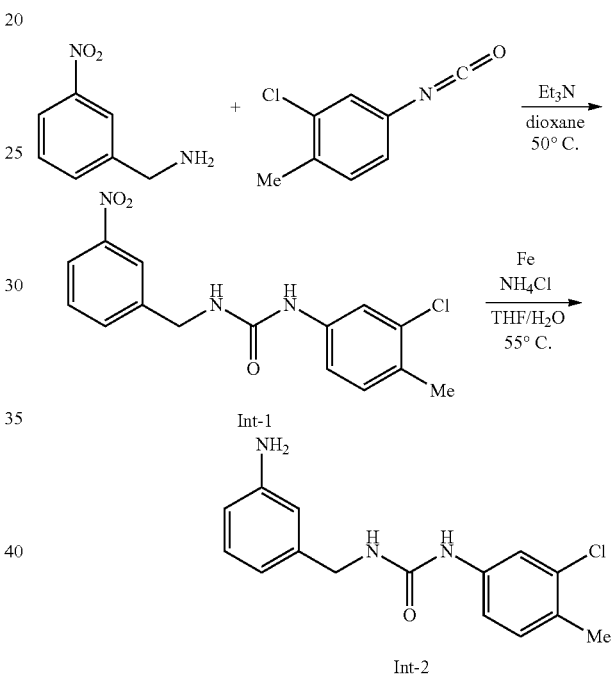

In an 8-mL vial, 3-nitrobenzylamine (250 mg, 1.33 mmol, 1.0 equiv) was dissolved in dioxane (2 mL, 0.67 M). A solution of 3-chloro-4-methylphenyl isocyanate (244 mg, 1.46 mmol, 1.1 equiv) in dioxane (1 mL) was added to the reaction mixture, followed by $Et_3N$ (203 µL, 1.46 mmol, 1.1 equiv). The reaction mixture was stirred at 50° C. for 1 h. Upon cooling to rt, the reaction mixture was diluted with water and extracted with $CH_2Cl_2$ 3×. The organic layers were collected, dried over $Na_2SO_4$, filtered, and concentrated in vacuo to provide crude Int-1 (72% yield), which was used without further purification.

In an 8-mL vial, Int-1 (307 mg, 0.96 mmol, 1.0 equiv) was dissolved in THE (4.5 mL, 0.21 M). Satd. aq. $NH_4Cl$ (2 mL) was added, followed by iron powder (1.1 g mg, 19 mmol, 20 equiv). The reaction mixture was stirred at 55° C. for 3 h. Upon cooling to rt, the reaction mixture was diluted with water and extracted with EtOAc 3×. The organic layers were collected, washed with brine, dried over $Na_2SO_4$, filtered over Celite®, and concentrated in vacuo to provide crude Int-2 (quantitative yield) as a light yellow solid, which was used without further purification.

Method D: Synthesis of Int-3

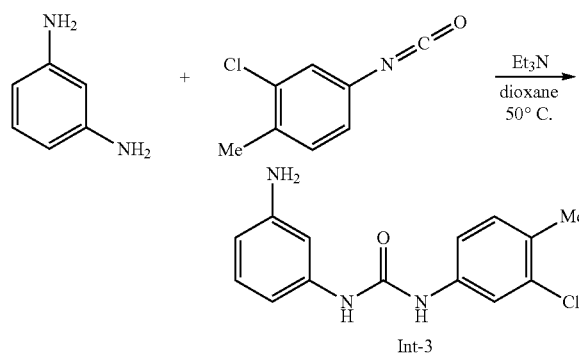

In an 8-mL vial, 1,3-phenylenediamine (150 mg, 1.39 mmol, 1.0 equiv) was dissolved in dioxane (2 mL, 0.7 M). A solution of 3-chloro-4-methylphenyl isocyanate (256 mg, 1.53 mmol, 1.1 equiv) in dioxane (1 mL) was added to the reaction mixture, followed by $Et_3N$ (213 µL, 1.53 mmol, 1.1 equiv). The reaction mixture was stirred at 50° C. for 1 h. Upon cooling to rt, the reaction mixture was concentrated in vacuo to provide crude Int-3 as a white solid, which was used without further purification.

Method E: Synthesis of Int-5

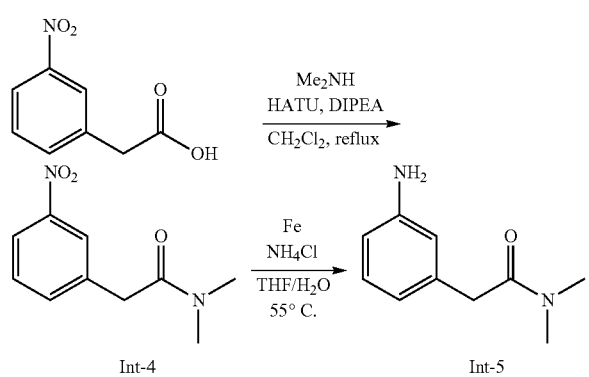

In an 8-mL vial, 3-nitrophenylacetic acid (200 mg, 1.1 mmol, 1.0 equiv) was dissolved in $CH_2Cl_2$ (2 mL, 0.55 M). Hexafluorophosphate azabenzotriazole tetramethyl uronium (HATU) (460 mg, 1.21 mmol, 1.1 equiv), N,N-diisopropylethylamine (422 µL, 2.42 mmol, 2.2 equiv), and dimethylamine (84 µL, 1.21 mmol, 1.1 equiv) were added sequentially. The reaction mixture was stirred at reflux for 4 h. Upon cooling to rt, the reaction mixture was diluted with water and extracted with $CH_2Cl_2$ 3×. The organic layers were collected, dried over $Na_2SO_4$, filtered, and concentrated in vacuo. Purification by silica flash chromatography (0-100% EtOAc/hexanes) provided Int-4 (55% yield).

In an 8-mL vial, Int-4 (127 mg, 0.61 mmol, 1.0 equiv) was dissolved in THF (2 mL, 0.3 M). Satd. aq. $NH_4Cl$ (1 mL) was added, followed by iron powder (681 mg, 12.2 mmol, 20 equiv). The reaction mixture was stirred at 55° C. for 15 h. Upon cooling to rt, the reaction mixture was diluted with water and extracted with $CH_2Cl_2$ 3×. The organic layers were collected, dried over $Na_2SO_4$, filtered over Celite®, and concentrated in vacuo to provide crude Int-5 (63% yield) as a yellow solid, which was used without further purification.

Method F: Synthesis of Int-7

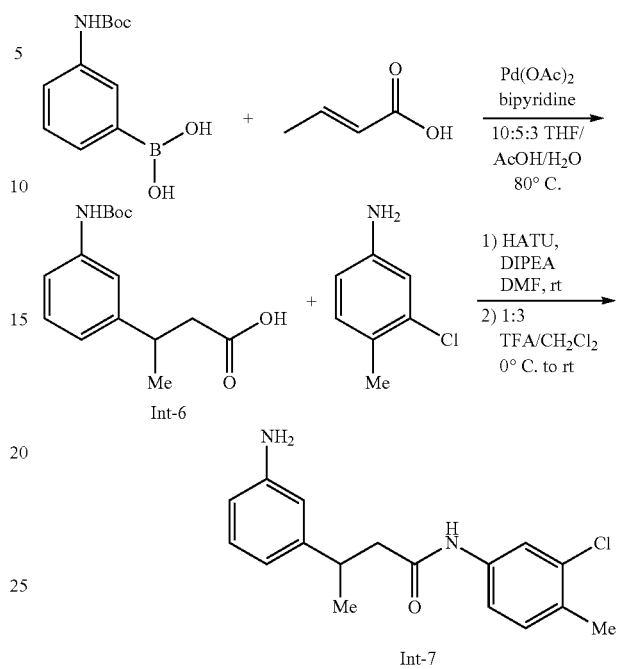

In a 20-mL vial, (3-((tert-butoxycarbonyl)amino)phenyl) boronic acid (993 mg, 4.19 mmol) was dissolved in THF (5.6 mL). Palladium acetate (24 mg, 0.105 mmol), bipyridine (33 mg, 0.209 mmol), and (E)-but-2-enoic acid (180 mg, 2.09 mmol) were added sequentially. Water (1.7 mL) and AcOH (2.8 mL) were added, and the reaction mixture was stirred at 80° C. for 14 h. Upon cooling to rt, the reaction mixture was extracted with $CH_2Cl_2$, washed with $H_2O$, dried over $Na_2SO_4$, filtered over Celite®, and concentrated by rotary evaporation. Purification by silica flash chromatography (0-80% EtOAc/$CH_2Cl_2$) provided Int-6 (426.2 mg, 73% yield) as an orange oil.

In an 8-mL vial, Int-6 (100 mg, 0.358 mmol) was dissolved in DMF (2 mL). HATU (150 mg, 0.394), DIPEA (190 µL, 1.07 mmol), and 3-chloro-4-methylaniline (50 µL, 0.394 mmol) were added sequentially. The reaction mixture was stirred at rt for 3 h. The reaction mixture was extracted with EtOAc, washed with water 2×, brine, dried over $Na_2SO_4$, filtered, and concentrated by rotary evaporation. The crude product was then dissolved in $CH_2Cl_2$ (3 mL) and cooled to 0° C. Trifluoroacetic acid (1 mL) was added dropwise at 0° C., then slowly warmed to rt over 1 h. The reaction mixture was concentrated by rotary evaporation to give Int-7 (78.6 mg, 55% yield), which was carried forward without purification.

Example 4: General Synthetic Procedure Toward Succinimide Scaffolds

Method G: Hydrogenation of Aminomaleimide

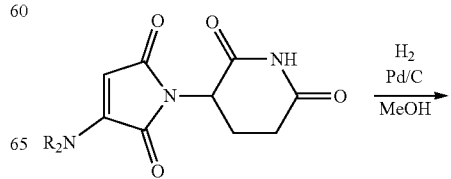

-continued

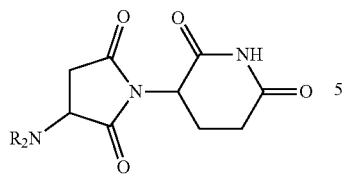

In an 8-mL vial, aminomaleimide was dissolved in 1:1 DMF/MeOH (3 mL). Palladium on carbon (Pd/C, 0.10 equiv) was added, and $H_2$ was bubbled through the reaction mixture with stirring overnight. The reaction mixture was filtered over Celite® to remove Pd-catalyst and washed with MeOH. The filtrate was collected and concentrated by rotary evaporation. Purification by prep TLC (5% 1.75 N $NH_3$ in MeOH/$CH_2Cl_2$) furnished the succinimide product.

Example 5: Synthesis of 3-(3-(benzylamino)-2,5-dioxo-2,5-dihydro-1H-pyrrol-1-yl)piperidine-2,6-dione (1)

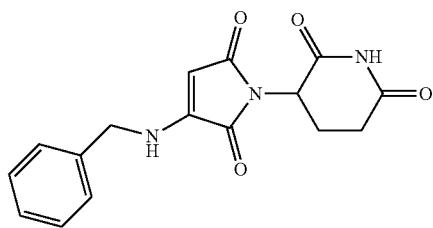 [SMILES: O=C1CCC(N2C(=O)C=C(NCc3ccccc3)C2=O)C(=O)N1]

Compound 1 was prepared according to Method B. $^1$H NMR (500 MHz, DMSO-$d_6$) δ 10.98 (s, 1H), 8.48 (t, J=6.2, 1H), 7.35 (d, J=4.3, 4H), 7.28 (h, J=4.3, 1H), 4.97 (s, 1H), 4.84 (dd, J=13.0, 5.4, 1H), 4.33 (d, J=6.3, 2H), 2.81 (ddd, J=17.0, 13.9, 5.4, 1H), 2.58-2.51 (m, 1H), 2.40 (qd, J=13.2, 4.3, 1H), 1.94-1.88 (m, 1H). LC-MS m/z: (pos) 314.0 ([M+H]$^+$).

Example 6: Synthesis of 3-(2,5-dioxo-3-(phenylamino)-2,5-dihydro-1H-pyrrol-1-yl)piperidine-2,6-dione (2)

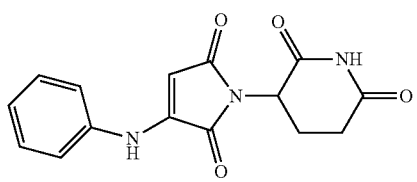 [SMILES: O=C1CCC(N2C(=O)C=C(Nc3ccccc3)C2=O)C(=O)N1]

Compound 2 was prepared according to Method B. $^1$H NMR (500 MHz, DMSO-$d_6$) δ 11.05 (s, 1H), 9.81 (s, 1H), 7.46-7.35 (m, 4H), 7.13 (t, J=7.2, 1H), 5.74 (s, 1H), 4.96 (dd, J=13.0, 5.4, 1H), 2.85 (ddd, 1H), 2.61-2.52 (m, 1H), 2.45 (qd, J=13.3, 4.4, 1H), 2.03-1.96 (m, 1H). LC-MS m/z: (pos) 300.0 ([M+H]$^+$).

Example 7: Synthesis of 3-(3-((3-chloro-4-methylphenyl)amino)-2,5-dioxo-2,5-dihydro-1H-pyrrol-1-yl)piperidine-2,6-dione (3)

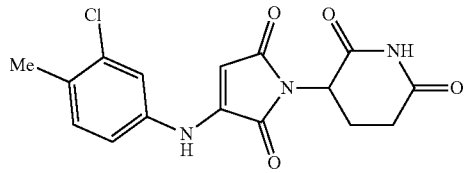 [SMILES: Cc1ccc(NC2=CC(=O)N(C3CCC(=O)NC3=O)C2=O)cc1Cl]

Compound 3 was prepared according to Method A. $^1$H NMR (500 MHz, DMSO-$d_6$) δ 11.05 (s, 1H), 9.83 (s, 1H), 7.47 (d, J=2.2, 1H), 7.35 (d, J=8.4, 1H), 7.31 (dd, J=8.2, 2.2, 1H), 5.76 (s, 1H), 4.96 (dd, J=13.0, 5.4, 1H), 2.86 (ddd, J=17.3, 13.9, 5.5, 1H), 2.60-2.54 (m, 1H), 2.48-2.41 (m, 1H), 2.30 (s, 3H), 2.02-1.96 (m, 1H). LC-MS m/z: (pos) 348.0 ([M+H]$^+$).

Example 8: Synthesis of 3-(3-((4-chloro-3-methylphenyl)amino)-2,5-dioxo-2,5-dihydro-1H-pyrrol-1-yl)piperidine-2,6-dione (4)

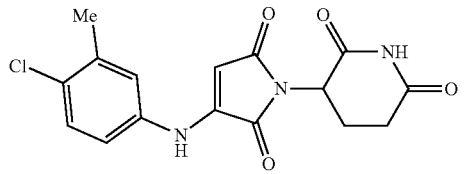 [SMILES: Cc1cc(NC2=CC(=O)N(C3CCC(=O)NC3=O)C2=O)ccc1Cl]

Compound 4 was prepared according to Method A. $^1$H NMR (500 MHz, DMSO-$d_6$) δ 11.05 (s, 1H), 9.82 (s, 1H), 7.46-7.32 (m, 2H), 7.29 (dd, J=8.7, 2.5, 1H), 5.84 (s, 1H), 4.96 (dd, J=13.0, 5.4, 1H), 2.86 (ddd, J=17.1, 13.9, 5.5, 1H), 2.60-2.54 (m, 1H), 2.49-2.42 (m, 1H), 2.34 (s, 3H), 2.02-1.97 (m, 1H). LC-MS m/z: (pos) 348.1 ([M+H]$^+$).

Example 9: Synthesis of 5-((1-(2,6-dioxopiperidin-3-yl)-2,5-dioxo-2,5-dihydro-1H-pyrrol-3-yl)amino)-2-methylbenzonitrile (5)

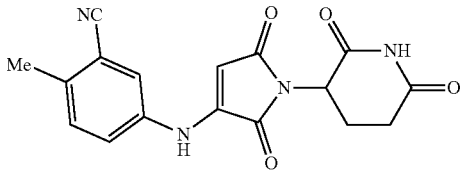 [SMILES: Cc1ccc(NC2=CC(=O)N(C3CCC(=O)NC3=O)C2=O)cc1C#N]

Compound 5 was prepared according to Method A. $^1$H NMR (500 MHz, DMSO-$d_6$) δ 11.06 (s, 1H), 9.93 (s, 1H), 7.74 (d, J=2.3, 1H), 7.65 (dd, J=8.5, 2.4, 1H), 7.46 (d, J=8.5, 1H), 5.94 (s, 1H), 4.97 (dd, J=13.0, 5.4, 1H), 2.86 (ddd, J=17.1, 13.9, 5.4, 1H), 2.61-2.54 (m, 1H, overlap), 2.47-2.40 (m, 1H) 2.45 (s, 3H), 2.00 (dtd, J=12.8, 5.5, 2.3, 1H). LC-MS m/z: (pos) 339.1 ([M+H]$^+$).

Example 10: Synthesis of 3-(2,5-dioxo-3-((pyridin-3-ylmethyl)amino)-2,5-dihydro-1H-pyrrol-1-yl)piperidine-2,6-dione (6)

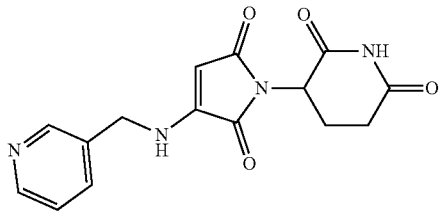 [SMILES: O=C1CCC(N2C(=O)C=C(NCc3cccnc3)C2=O)C(=O)N1]

Compound 6 was prepared according to Method B. LC-MS m/z: (pos) 314.0 ([M+H]$^+$).

Example 11: Synthesis of 3-(3-((3-(1H-imidazol-1-yl)propyl)amino)-2,5-dioxo-2,5-dihydro-1H-pyrrol-1-yl)piperidine-2,6-dione (7)

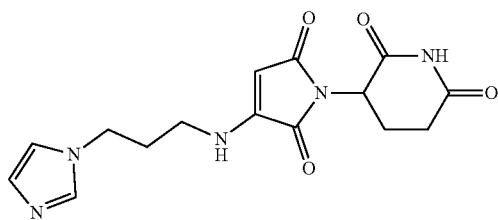 [SMILES: O=C1CCC(N2C(=O)C=C(NCCCn3ccnc3)C2=O)C(=O)N1]

Compound 7 was prepared according to Method B. LC-MS m/z: (pos) 331.3 ([M+H]$^+$).

Example 12: Synthesis of 3-(3-((1H-pyrazol-3-yl)amino)-2,5-dioxo-2,5-dihydro-1H-pyrrol-1-yl)piperidine-2,6-dione (8)

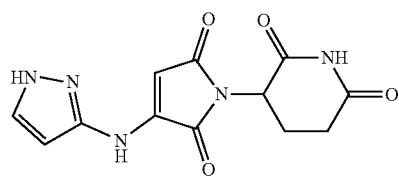 [SMILES: O=C1CCC(N2C(=O)C=C(Nc3cc[nH]n3)C2=O)C(=O)N1]

Compound 8 was prepared according to Method B. LC-MS m/z: (pos) 290.0 ([M+H]$^+$).

Example 13: Synthesis of 3-(3-((1H-imidazol-5-yl)methoxy)-2,5-dioxo-2,5-dihydro-1H-pyrrol-1-yl)piperidine-2,6-dione (9)

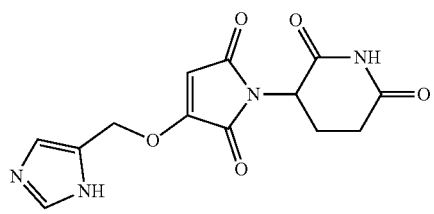 [SMILES: O=C1CCC(N2C(=O)C=C(OCc3cnc[nH]3)C2=O)C(=O)N1]

Compound 9 was prepared according to Method A at rt. LC-MS m/z: (pos) 305.0 ([M+H]$^+$).

Example 14: Synthesis of 3-(3-(2-(dimethylamino)ethoxy)-2,5-dioxo-2,5-dihydro-1H-pyrrol-1-yl)piperidine-2,6-dione (10)

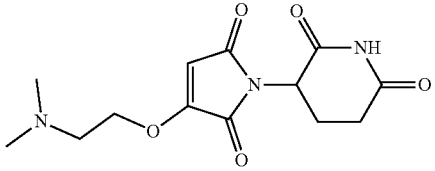 [SMILES: CN(C)CCOC1=CC(=O)N(C2CCC(=O)NC2=O)C1=O]

Compound 10 was prepared according to Method A at rt. $^1$H NMR (500 MHz, DMSO-d$_6$) δ 11.05 (s, 1H), 5.99 (s, 1H), 4.93 (dd, J=13.0, 5.3, 1H), 4.23 (t, J=5.3, 2H), 2.82 (ddd, J=17.2, 13.9, 5.5, 1H), 2.75-2.68 (m, 2H), 2.58-2.53 (m, 1H), 2.40 (qd, J=13.2, 4.3, 1H), 2.25 (s, 6H), 1.99-1.94 (m, 1H). LC-MS m/z: (pos) 296.0 ([M+H]$^+$).

Example 15: Synthesis of 3-(3-((2-(dimethylamino)ethyl)(methyl)amino)-2,5-dioxo-2,5-dihydro-1H-pyrrol-1-yl)piperidine-2,6-dione (11)

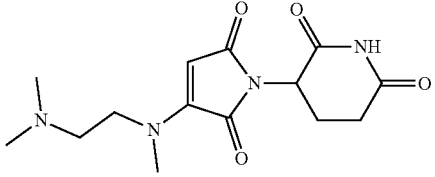 [SMILES: CN(C)CCN(C)C1=CC(=O)N(C2CCC(=O)NC2=O)C1=O]

Compound 11 was prepared according to Method A at rt. LC-MS m/z: (pos) 309.1 ([M+H]$^+$).

Example 16: Synthesis of 3-(3-((3-(dimethylamino)propyl)amino)-2,5-dioxo-2,5-dihydro-1H-pyrrol-1-yl)piperidine-2,6-dione (12)

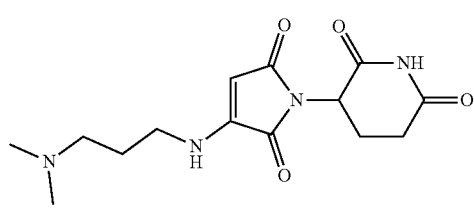 [SMILES: CN(C)CCCNC1=CC(=O)N(C2CCC(=O)NC2=O)C1=O]

Compound 12 was prepared according to Method A at rt. $^1$H NMR (500 MHz, DMSO-d$_6$) δ 10.99 (s, 1H), 7.98 (t, J=5.9, 1H), 4.93 (s, 1H), 4.84 (dd, J=13.0, 5.4, 1H), 3.14 (q, J=6.6, 2H), 2.82 (ddd, J=17.0, 13.9, 5.4, 1H), 2.58-2.51 (m, 1H), 2.42 (qd, J=13.2, 4.4, 1H), 2.24 (t, J=6.8, 2H), 2.12 (s, 6H), 1.92 (dtd, J=13.1, 5.4, 2.3, 1H), 1.67 (p, J=6.9, 2H). LC-MS m/z: (pos) 309.1 ([M+H]$^+$).

Example 17: Synthesis of Methyl (1-(2,6-dioxopiperidin-3-yl)-2,5-dioxo-2,5-dihydro-1H-pyrrol-3-yl)glycinate (13)

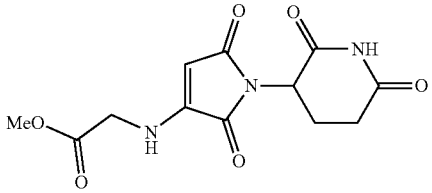 [SMILES: COC(=O)CNC1=CC(=O)N(C2CCC(=O)NC2=O)C1=O]

Compound 13 was prepared according to Method A at rt. $^1$H NMR (500 MHz, DMSO-d$_6$) δ 11.01 (s, 1H), 7.98 (t, J=6.0, 1H), 5.05 (s, 1H), 4.87 (dd, J=13.0, 5.3, 1H), 4.03 (d, J=6.0, 2H), 3.68 (s, 3H), 2.82 (ddd, J=17.1, 13.9, 5.5, 1H), 2.57-2.52 (m, 1H), 2.42 (qd, J=13.2, 4.4, 1H), 1.97-1.91 (m, 1H). LC-MS m/z: (pos) 296.0 ([M+H]$^+$).

Example 18: Synthesis of Methyl 3-((1-(2,6-dioxopiperidin-3-yl)-2,5-dioxo-2,5-dihydro-1H-pyrrol-3-yl)amino)propanoate (14)

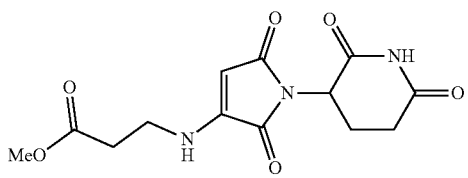 [SMILES: COC(=O)CCNC1=CC(=O)N(C2CCC(=O)NC2=O)C1=O]

Compound 14 was prepared according to Method A at rt. $^1$H NMR (500 MHz, DMSO-d$_6$) δ 10.99 (s, 1H), 7.89 (t, J=5.6, 1H), 5.02 (s, 1H), 4.85 (dd, J=13.0, 5.3, 1H), 3.61 (s, 3H), 3.36 (q, J=6.5, 2H), 2.82 (ddd, J=17.1, 14.0, 5.5, 1H), 2.65 (t, J=6.8, 2H), 2.56-2.52 (m, 1H), 2.46-2.38 (m, 1H), 1.95-1.88 (m, 1H). LC-MS m/z: (pos) 310.1 ([M+H]$^+$).

Example 19: Synthesis of Methyl N-(1-(2,6-dioxopiperidin-3-yl)-2,5-dioxo-2,5-dihydro-1H-pyrrol-3-yl)-N-methylglycinate (15)

Compound 15 was prepared according to Method A at rt. $^1$H NMR (500 MHz, DMSO-d$_6$) δ 10.99 (s, 1H), 5.19 (s, 1H), 4.84 (dd, J=12.9, 5.3, 1H), 4.61 (s, 2H), 3.67 (s, 3H), 3.01 (s, 3H), 2.85-2.77 (m, 1H), 2.59-2.51 (m, 1H), 2.39 (qd, J=13.2, 4.7, 1H), 1.93-1.87 (m, 1H). LC-MS m/z: (pos) 310.0 ([M+H]$^+$).

Example 20: Synthesis of Ethyl (1-(2,6-dioxopiperidin-3-yl)-2,5-dioxo-2,5-dihydro-1H-pyrrol-3-yl)glycinate (16)

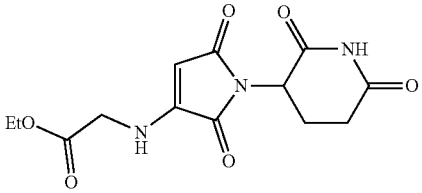 [SMILES: CCOC(=O)CNC1=CC(=O)N(C2CCC(=O)NC2=O)C1=O]

Compound 16 was prepared according to Method A at rt. $^1$H NMR (500 MHz, DMSO-d$_6$) δ 11.01 (s, 1H), 7.97 (t, J=6.3, 1H), 5.03 (s, 1H), 4.87 (dd, J=13.0, 5.4, 1H), 4.14 (q, J=7.1, 2H), 4.01 (d, J=6.2, 2H), 2.83 (ddd, J=17.1, 13.9, 5.4, 1H), 2.58-2.52 (m, 1H), 2.42 (qd, J=13.5, 4.7, 1H), 1.97-1.90 (m, 1H), 1.21 (t, J=7.1, 3H). LC-MS m/z: (pos) 310.1 ([M+H]$^+$).

Example 21: Synthesis of Ethyl N-(1-(2,6-dioxopiperidin-3-yl)-2,5-dioxo-2,5-dihydro-1H-pyrrol-3-yl)-N-methylglycinate (17)

Compound 17 was prepared according to Method A at rt. $^1$H NMR (500 MHz, DMSO-d$_6$) δ 10.99 (s, 1H), 5.19 (s, 1H), 4.84 (dd, J=12.9, 5.3, 1H), 4.59 (s, 2H), 4.13 (q, J=5.3, 2H), 3.01 (s, 3H), 2.80 (ddd, J=13.9, 10.2, 6.9, 1H), 2.58-2.51 (m, 1H), 2.39 (qd, J=13.1, 5.0, 1H), 1.92-1.86 (m, 1H), 1.20 (t, J=7.1, 3H). LC-MS m/z: (pos) 324.1 ([M+H]$^+$).

Example 22: Synthesis of 3-(3-((1H-1,2,4-triazol-3-yl)amino)-2,5-dioxo-2,5-dihydro-1H-pyrrol-1-yl)piperidine-2,6-dione (18)

Compound 18 was prepared according to Method A. $^1$H NMR (500 MHz, DMSO-d$_6$) δ 11.12 (s, 1H), 7.48 (s, 1H), 6.41 (s, 1H), 5.10-5.01 (m, 1H), 2.86 (ddd, J=17.3, 13.9, 5.5, 1H), 2.62-2.56 (m, 1H), 2.47-2.39 (m, 1H), 2.06-1.99 (m, 1H). LC-MS m/z: (pos) 291.0 ([M+H]$^+$).

Example 23: Synthesis of 3-(2,5-dioxo-3-(thiazol-2-ylamino)-2,5-dihydro-1H-pyrrol-1-yl)piperidine-2,6-dione (19)

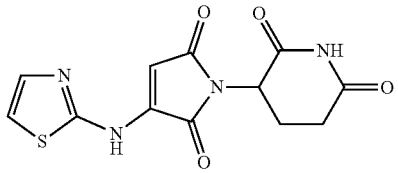 [SMILES: O=C1CCC(N2C(=O)C=C(Nc3nccs3)C2=O)C(=O)N1]

Compound 19 was prepared according to Method A. $^1$H NMR (500 MHz, DMSO-$d_6$) δ 11.09 (s, 1H), 10.00 (s, 1H), 7.93 (d, J=5.4, 1H), 7.29 (s, 1H), 6.54 (d, J=5.4, 1H), 5.02 (dd, J=13.0, 5.3, 1H), 2.85 (ddd, J=17.1, 13.9, 5.5, 1H), 2.60-2.55 (m, 1H), 2.47-2.40 (m, 1H), 2.02-1.97 (m, 1H). LC-MS m/z: (pos) 306.9 ([M+H]$^+$).

Example 24: Synthesis of Methyl 5-((1-(2,6-dioxopiperidin-3-yl)-2,5-dioxo-2,5-dihydro-1H-pyrrol-3-yl)amino)-1H-1,2,4-triazole-3-carboxylate (20)

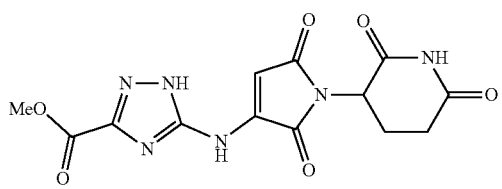 [SMILES: COC(=O)c1n[nH]c(NC2=CC(=O)N(C3CCC(=O)NC3=O)C2=O)n1]

Compound 20 was prepared according to Method A. $^1$H NMR (500 MHz, DMSO-$d_6$) δ 11.13 (s, 1H), 7.57 (s, 2H), 7.03 (s, 1H), 5.08 (dd, J=12.9, 5.4, 1H), 3.83 (s, 3H), 2.86 (ddd, J=17.2, 13.9, 5.5, 1H), 2.62-2.57 (m, 1H), 2.46-2.39 (m, 1H), 2.05-2.01 (m, 1H). LC-MS m/z: (pos) 349.0 ([M+H]$^+$).

Example 25: Synthesis of 4-((1-(2,6-dioxopiperidin-3-yl)-2,5-dioxo-2,5-dihydro-1H-pyrrol-3-yl)amino)butanoic acid (21)

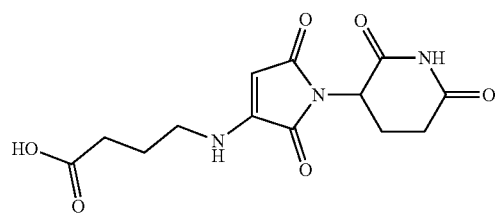 [SMILES: O=C(O)CCCNC1=CC(=O)N(C2CCC(=O)NC2=O)C1=O]

Compound 21 was prepared according to Method A at 75° C. $^1$H NMR (500 MHz, DMSO-$d_6$) δ 8.03 (s, 1H), 4.96 (s, 1H), 4.85 (dd, J=12.9, 5.4, 1H), 3.12 (t, J=6.9, 2H), 2.82 (ddd, J=17.0, 13.9, 5.4, 1H), 2.56-2.54 (m, 1H), 2.42 (qd, J=13.4, 4.4, 1H), 2.26 (t, J=7.2, 2H), 1.97-1.90 (m, 1H), 1.75 (p, J=7.2, 6.7, 2H). LC-MS m/z: (pos) 332.0 ([M+Na]$^+$).

Example 26: Synthesis of 5-((1-(2,6-dioxopiperidin-3-yl)-2,5-dioxo-2,5-dihydro-1H-pyrrol-3-yl)amino)pentanoic acid (22)

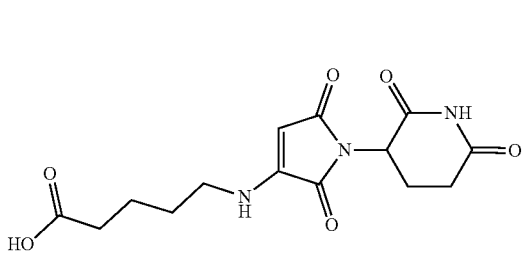 [SMILES: O=C(O)CCCCNC1=CC(=O)N(C2CCC(=O)NC2=O)C1=O]

Compound 22 was prepared according to Method A at 75° C. $^1$H NMR (500 MHz, DMSO-$d_6$) δ 8.00 (s, 1H), 4.95 (s, 1H), 4.84 (dd, J=13.0, 5.4, 1H), 3.11 (t, J=6.3, 2H), 2.82 (ddd, J=17.0, 13.9, 5.5, 1H), 2.58-2.51 (m, 1H), 2.42 (qd, J=13.2, 4.5, 1H), 2.19 (t, J=6.9, 2H), 1.95-1.88 (m, 1H), 1.57-1.48 (m, 4H). LC-MS m/z: (pos) 346.0 ([M+Na]$^+$).

Example 27: Synthesis of 3-(3-((3-(1H-tetrazol-5-yl)phenyl)amino)-2,5-dioxo-2,5-dihydro-1H-pyrrol-1-yl)piperidine-2,6-dione (23)

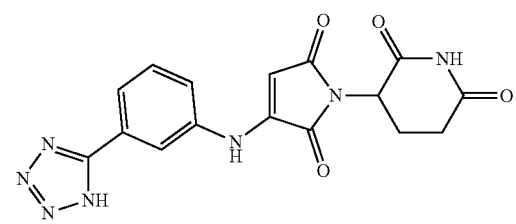 [SMILES: O=C1CCC(N2C(=O)C=C(Nc3cccc(-c4nnn[nH]4)c3)C2=O)C(=O)N1]

Compound 23 was prepared according to Method A at 50° C. $^1$H NMR (500 MHz, DMSO-$d_6$) δ 11.06 (s, 1H), 9.90 (s, 1H), 8.02 (s, 1H), 7.74 (d, J=7.6, 1H), 7.40 (t, J=7.8, 1H), 7.35-7.30 (m, 1H), 5.64 (s, 1H), 4.98 (dd, J=13.0, 5.4, 1H), 2.87 (ddd, J=5.3, 1H), 2.60 (m, 1H), 2.54-2.43 (m, 1H, overlap), 2.06-1.97 (m, 1H). LC-MS m/z: (pos) 368.0 ([M+Na]$^+$).

Example 28: Synthesis of 3-(3-((3,4-dimethylphenyl)amino)-2,5-dioxo-2,5-dihydro-1H-pyrrol-1-yl)piperidine-2,6-dione (24)

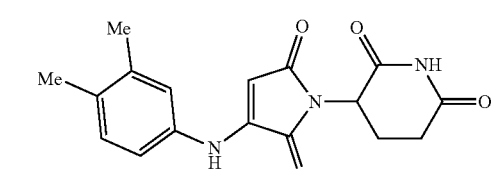

Compound 24 was prepared according to Method A at 50° C. LC-MS m/z: (pos) 328.0 ([M+H]$^+$).

Example 29: Synthesis of 3-(3-((4-chlorophenyl)amino)-2,5-dioxo-2,5-dihydro-1H-pyrrol-1-yl)piperidine-2,6-dione (25)

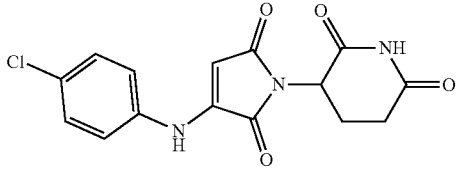 [SMILES: O=C1CCC(N2C(=O)C=C(Nc3ccc(Cl)cc3)C2=O)C(=O)N1]

Compound 25 was prepared according to Method A at 50° C. ¹H NMR (500 MHz, DMSO-d$_6$) δ 11.06 (s, 1H), 9.91 (s, 1H), 7.55-7.39 (m, 4H), 5.79 (s, 1H), 4.96 (dd, J=13.0, 5.4, 1H), 2.86 (ddd, J=17.2, 13.9, 5.5, 1H), 2.60-2.55 (m, 1H), 2.48-2.42 (m, 1H), 2.02-1.97 (m, 1H). LC-MS m/z: (pos) 334.0 ([M+H]$^+$).

Example 30: Synthesis of 3-(3-((3-chlorophenyl)amino)-2,5-dioxo-2,5-dihydro-1H-pyrrol-1-yl)piperidine-2,6-dione (26)

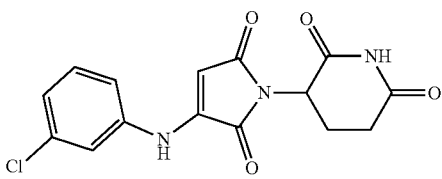 [SMILES: O=C1CCC(N2C(=O)C=C(Nc3cccc(Cl)c3)C2=O)C(=O)N1]

Compound 26 was prepared according to Method A at 55° C. ¹H NMR (500 MHz, DMSO-d$_6$) δ 11.05 (s, 1H), 9.82 (s, 1H), 7.48 (s, 1H), 7.46-7.36 (m, 2H), 7.18-7.16 (m, 1H), 5.85 (s, 1H), 4.97 (dd, J=13.0, 5.4, 1H), 2.86 (ddd, J=17.1, 13.9, 5.5, 1H), 2.58 (ddd, J=17.1, 4.4, 2.4, 1H), 2.49-2.41 (m, 1H), 2.00 (dtd, J=12.9, 5.4, 2.4, 1H). LC-MS m/z: (pos) 334.0 ([M+H]$^+$).

Example 31: Synthesis of 3-(2,5-dioxo-3-(quinolin-3-ylamino)-2,5-dihydro-1H-pyrrol-1-yl)piperidine-2,6-dione (27)

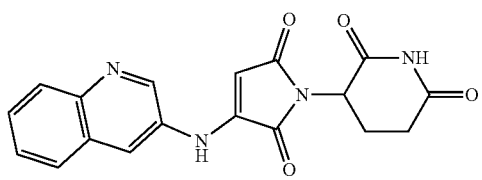 [SMILES: O=C1CCC(N2C(=O)C=C(Nc3cnc4ccccc4c3)C2=O)C(=O)N1]

Compound 27 was prepared according to Method A. LC-MS m/z: (pos) 351.0 ([M+H]$^+$).

Example 32: Synthesis of 3-(3-(methyl(phenyl)amino)-2,5-dioxo-2,5-dihydro-1H-pyrrol-1-yl)piperidine-2,6-dione (28)

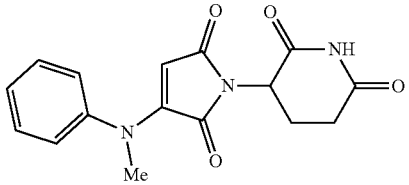 [SMILES: CN(C1=CC(=O)N(C2CCC(=O)NC2=O)C1=O)c1ccccc1]

Compound 28 was prepared according to Method A. ¹H NMR (500 MHz, DMSO-d$_6$) δ 10.97 (s, 1H), 7.41 (t, J=7.7, 2H), 7.34-7.28 (m, 3H), 5.26 (s, 1H), 4.82 (dd, J=12.9, 5.4, 1H), 3.42 (s, 3H), 2.80 (ddd, J=17.1, 13.9, 5.5, 1H), 2.57-2.51 (m, 1H), 2.37 (qd, J=13.2, 4.4, 1H), 1.91 (dtd, J=13.0, 5.4, 2.3, 1H). LC-MS m/z: (pos) 314.0 ([M+H]$^+$).

Example 33: Synthesis of 3-(3-((4-(1H-imidazol-1-yl)phenyl)amino)-2,5-dioxo-2,5-dihydro-1H-pyrrol-1-yl)piperidine-2,6-dione (29)

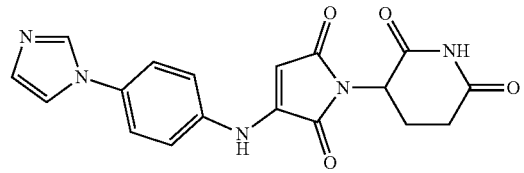 [SMILES: O=C1CCC(N2C(=O)C=C(Nc3ccc(-n4ccnc4)cc3)C2=O)C(=O)N1]

Compound 29 was prepared according to Method A. ¹H NMR (500 MHz, DMSO-d$_6$) δ 11.05 (s, 1H), 9.97 (s, 1H), 8.22 (s, 1H), 7.74-7.70 (m, 1H), 7.68-7.62 (m, 2H), 7.58-7.52 (m, 2H), 7.09 (d, J=10.2, 1H), 5.78 (s, 1H), 4.97 (dd, J=13.0, 5.4, 1H), 2.86 (ddd, J=17.0, 13.9, 5.5, 1H), 2.58 (ddd, J=17.2, 4.5, 2.5, 1H), 2.49-2.43 (m, 1H), 2.00 (dtd, J=12.9, 5.4, 2.4, 1H). LC-MS m/z: (pos) 366.1 ([M+H]$^+$).

Example 34: Synthesis of Ethyl 3-((1-(2,6-dioxopiperidin-3-yl)-2,5-dioxo-2,5-dihydro-1H-pyrrol-3-yl)amino)benzoate (30)

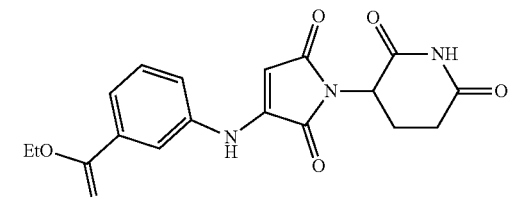

Compound 30 was prepared according to Method A. ¹H NMR (500 MHz, DMSO-d$_6$) δ 11.07 (s, 1H), 10.03 (s, 1H), 8.03 (s, 1H), 7.77-7.62 (m, 2H), 7.54 (t, J=7.9, 1H), 5.76 (s, 1H), 4.98 (dd, J=13.0, 5.4, 1H), 4.33 (q, J=7.1, 2H), 2.86 (ddd, J=17.0, 13.9, 5.5, 1H), 2.66-2.55 (m, 1H), 2.48-2.41 (m, 1H), 2.04-1.97 (m, 1H), 1.33 (t, J=7.1, 3H). LC-MS m/z: (pos) 372.1 ([M+H]$^+$).

Example 35: Synthesis of 3-(3-((3-(1H-pyrazol-3-yl)phenyl)amino)-2,5-dioxo-2,5-dihydro-1H-pyrrol-1-yl)piperidine-2,6-dione (31)

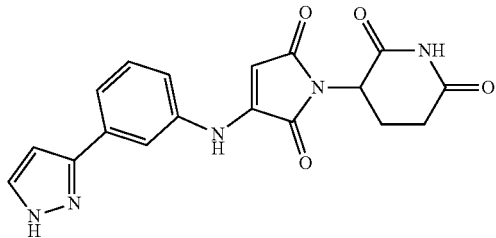 [SMILES: O=C1CCC(N2C(=O)C=C(Nc3cccc(-c4cc[nH]n4)c3)C2=O)C(=O)N1]

Compound 31 was prepared according to Method A at 50° C. $^1$H NMR (500 MHz, DMSO-$d_6$) δ 11.06 (s, 1H), 9.85 (s, 1H), 7.88-7.64 (m, 2H), 7.55 (d, J=7.6, 1H), 7.42 (t, J=7.9, 1H), 7.35 (d, J=8.2, 1H), 6.71 (d, J=2.2, 1H), 5.75 (s, 1H), 4.97 (dd, J=13.0, 5.4, 1H), 2.86 (ddd, J=17.1, 13.9, 5.4, 1H), 2.64-2.55 (m, 1H), 2.49-2.43 (m, 1H), 2.00 (dtd, J=12.9, 5.4, 2.3, 1H). LC-MS m/z: (pos) 366.1 ([M+H]$^+$).

Example 36: Synthesis of 3-(3-((1H-indazol-6-yl)amino)-2,5-dioxo-2,5-dihydro-1H-pyrrol-1-yl)piperidine-2,6-dione (32)

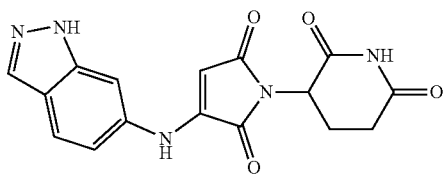 [SMILES: O=C1CCC(N2C(=O)C=C(Nc3ccc4cn[nH]c4c3)C2=O)C(=O)N1]

Compound 32 was prepared according to Method A at 50° C. $^1$H NMR (500 MHz, DMSO-$d_6$) δ 12.91 (s, 1H), 11.06 (s, 1H), 9.96 (s, 1H), 8.03 (s, 1H), 7.75 (d, J=8.7, 1H), 7.49 (s, 1H), 7.26 (dd, J=8.7, 1.9, 1H), 5.76 (s, 1H), 4.98 (dd, J=12.9, 5.4, 1H), 2.87 (ddd, J=17.1, 13.9, 5.5, 1H), 2.64-2.56 (m, 1H), 2.48-2.44 (m, 1H), 2.04-1.98 (m, 1H). LC-MS m/z: (pos) 340.1 ([M+H]$^+$).

Example 37: Synthesis of 3-((1-(2,6-dioxopiperidin-3-yl)-2,5-dioxo-2,5-dihydro-1H-pyrrol-3-yl)amino)-N,N-dimethylbenzamide (33)

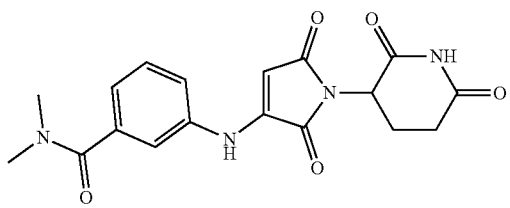 [SMILES: CN(C)C(=O)c1cccc(NC2=CC(=O)N(C3CCC(=O)NC3=O)C2=O)c1]

Compound 33 was prepared according to Method A. The aniline coupling partner was prepared according to Method E. $^1$H NMR (500 MHz, DMSO-$d_6$) δ 11.06 (s, 1H), 9.89 (s, 1H), 7.48 (d, J=8.2, 1H), 7.44 (t, J=7.8, 1H), 7.41 (s, 1H), 7.13 (d, J=7.3, 1H), 5.78 (s, 1H), 4.97 (dd, J=13.0, 5.4, 1H), 2.98 (s, 3H), 2.91 (s, 3H), 2.89-2.81 (m, 1H), 2.64-2.54 (m, 1H), 2.49-2.42 (m, 1H), 2.03-1.97 (m, 1H). LC-MS m/z: (pos) 371.1 ([M+H]$^+$).

Example 38: Synthesis of 4-((1-(2,6-dioxopiperidin-3-yl)-2,5-dioxo-2,5-dihydro-1H-pyrrol-3-yl)amino)-N,N-dimethylbenzamide (34)

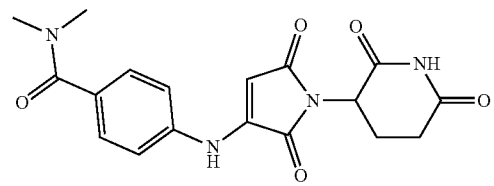 [SMILES: CN(C)C(=O)c1ccc(NC2=CC(=O)N(C3CCC(=O)NC3=O)C2=O)cc1]

Compound 34 was prepared according to Method A. The aniline coupling partner was prepared according to Method E. $^1$H NMR (500 MHz, DMSO-$d_6$) δ 11.05 (s, 1H), 9.90 (s, 1H), 7.47 (d, J=8.7, 2H), 7.43 (d, J=8.7, 2H), 5.86 (s, 1H), 4.97 (dd, J=13.0, 5.4, 1H), 2.95 (s, 6H), 2.86 (ddd, J=17.1, 13.9, 5.5, 1H), 2.58 (ddd, J=17.2, 4.6, 2.5, 1H), 2.49-2.42 (m, 1H), 2.04-1.99 (m, 1H). LC-MS m/z: (pos) 371.1 ([M+H]$^+$).

Example 39: Synthesis of 2-(3-((1-(2,6-dioxopiperidin-3-yl)-2,5-dioxo-2,5-dihydro-1H-pyrrol-3-yl)amino)phenyl)-N,N-dimethylacetamide (35)

Compound 35 was prepared according to Method A. The aniline coupling partner was prepared according to Method E. $^1$H NMR (500 MHz, DMSO-$d_6$) δ 11.05 (s, 1H), 9.81 (s, 1H), 7.34-7.25 (m, 3H), 6.97 (d, J=7.0, 1H), 5.72 (s, 1H), 4.96 (dd, J=13.0, 5.4, 1H), 3.72 (s, 2H), 3.01 (s, 3H), 2.91-2.80 (m, 1H), 2.85 (s, 3H), 2.62-2.54 (m, 1H), 2.49-2.43 (m, 1H), 2.03-1.97 (m, 1H). LC-MS m/z: (pos) 385.2 ([M+H]$^+$).

Example 40: Synthesis of 2-(4-((1-(2,6-dioxopiperidin-3-yl)-2,5-dioxo-2,5-dihydro-1H-pyrrol-3-yl)amino)phenyl)-N,N-dimethylacetamide (36)

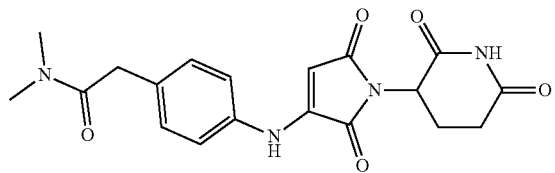 [SMILES: CN(C)C(=O)Cc1ccc(NC2=CC(=O)N(C3CCC(=O)NC3=O)C2=O)cc1]

Compound 36 was prepared according to Method A. The aniline coupling partner was prepared according to Method E. ¹H NMR (500 MHz, DMSO-d₆) δ 11.05 (s, 1H), 9.79 (s, 1H), 7.35 (d, J=8.2, 2H), 7.22 (d, J=8.2, 2H), 5.70 (s, 1H), 4.96 (dd, J=12.9, 5.4, 1H), 3.66 (s, 2H), 3.00 (s, 3H), 2.91-2.83 (m, 1H), 2.83 (s, 3H), 2.61-2.54 (m, 1H), 2.49-2.42 (m, 1H), 2.03-1.96 (m, 1H). LC-MS m/z: (pos) 385.2 ([M+H]⁺).

Example 41: Synthesis of 3-(3-((1H-indol-6-yl)amino)-2,5-dioxo-2,5-dihydro-1H-pyrrol-1-yl)piperidine-2,6-dione (37)

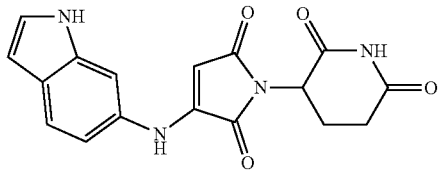 [SMILES: O=C1CCC(N2C(=O)C=C(Nc3ccc4cc[nH]c4c3)C2=O)C(=O)N1]

Compound 37 was prepared according to Method A. ¹H NMR (500 MHz, DMSO-d₆) δ 11.05 (s, 1H), 11.02 (s, 1H), 9.84 (s, 1H), 7.53 (d, J=8.5, 1H), 7.43 (s, 1H), 7.34 (t, J=2.6, 1H), 7.12 (dd, J=8.5, 1.6, 1H), 6.41 (t, J=2.5, 1H), 5.56 (s, 1H), 4.96 (dd, J=12.9, 5.4, 1H), 2.87 (ddd, J=17.2, 13.9, 5.4 Hz, 1H), 2.61-2.55 (m, 1H), 2.49-2.43 (m, 1H), 2.02-1.98 (m, 1H). LC-MS m/z: (pos) 339.0 ([M+H]⁺).

Example 42: Synthesis of 3-(3-([1,1'-biphenyl]-4-ylamino)-2,5-dioxo-2,5-dihydro-1H-pyrrol-1-yl)piperidine-2,6-dione (38)

Compound 38 was prepared according to Method A. ¹H NMR (500 MHz, DMSO-d₆) δ 11.07 (s, 1H), 9.94 (s, 1H), 7.69 (d, J=8.6, 2H), 7.67 (d, J=7.8, 3H), 7.53 (d, J=8, 2H), 7.46 (t, J=7.6, 2H), 7.35 (t, J=7.3, 1H), 5.82 (s, 1H), 4.98 (dd, J=13.0, 5.4, 1H), 2.87 (ddd, J=17.1, 13.8, 5.4, 1H), 2.61-2.56 (m, 1H), 2.49-2.44 (m, 1H), 2.04-1.99 (m, 1H). LC-MS m/z: (pos) 376.2 ([M+H]⁺).

Example 43: Synthesis of 3-(3-((4-benzylphenyl)amino)-2,5-dioxo-2,5-dihydro-1H-pyrrol-1-yl)piperidine-2,6-dione (39)

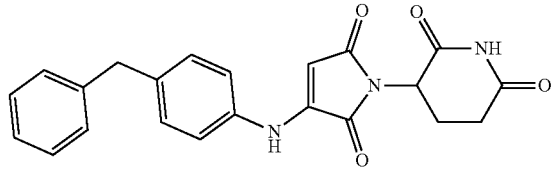 [SMILES: O=C1CCC(N2C(=O)C=C(Nc3ccc(Cc4ccccc4)cc3)C2=O)C(=O)N1]

Compound 39 was prepared according to Method A. ¹H NMR (500 MHz, DMSO-d₆) δ 11.04 (s, 1H), 9.77 (s, 1H), 7.34 (d, J=8.4, 2H), 7.29 (t, J=7.5, 2H), 7.23 (d, J=8.1, 4H), 7.19 (t, J=7.2, 1H), 5.67 (s, 1H), 4.95 (dd, J=13.0, 5.4, 1H), 3.92 (s, 2H), 2.85 (ddd, J=17.3, 13.9, 5.5, 1H), 2.57 (dt, J=17.2, 3.3, 1H), 2.49-2.42 (m, 1H), 2.01-1.96 (m, 1H). LC-MS m/z: (pos) 390.2 ([M+H]⁺).

Example 44: Synthesis of 1-(3-chloro-4-methylphenyl)-3-(2-((1-(2,6-dioxopiperidin-3-yl)-2,5-dioxo-2,5-dihydro-1H-pyrrol-3-yl)amino)ethyl)urea (41)

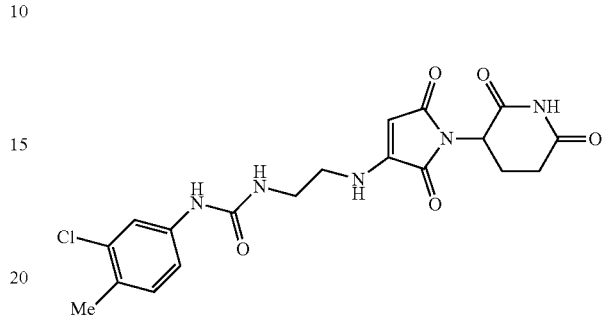

Compound 41 was prepared according to Method A. The amine coupling partner was prepared according to Method D. ¹H NMR (500 MHz, DMSO-d₆) δ 10.99 (s, 1H), 8.70 (s, 1H), 7.93 (t, J=5.5, 1H), 7.63 (d, J=1.9, 1H), 7.17 (d, J=8.3, 1H), 7.12 (dd, J=8.3, 1.9, 1H), 6.31 (t, J=5.7, 1H), 5.04 (s, 1H), 4.85 (dd, J=13.0, 5.4, 1H), 3.29 (q, J=6.1, 2H), 3.21 (q, J=6.0, 2H), 2.82 (ddd, J=17.1, 13.9, 5.5, 1H), 2.58-2.52 (m, 1H), 2.41 (qd, J=13.3, 4.4, 1H), 2.23 (s, 3H), 1.93-1.88 (m, 1H). LC-MS m/z: (pos) 434.2 ([M+H]⁺).

Example 45: Synthesis of 1-(3-chloro-4-methylphenyl)-3-(4-((1-(2,6-dioxopiperidin-3-yl)-2,5-dioxo-2,5-dihydro-1H-pyrrol-3-yl)amino)phenyl)urea (42)

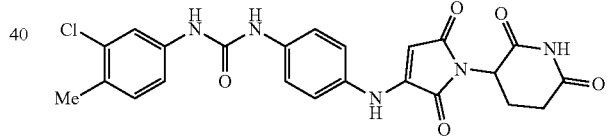

Compound 42 was prepared according to Method A. The aniline coupling partner was prepared according to Method D. ¹H NMR (500 MHz, DMSO-d₆) δ 11.05 (s, 1H), 9.77 (s, 1H), 8.76 (s, 2H), 7.68 (s, 1H), 7.46 (d, J=8.9, 2H), 7.35 (d, J=8.8, 2H), 7.24 (d, J=8.3, 1H), 7.18 (dd, J=8.2, 1.4, 1H), 5.64 (s, 1H), 4.95 (dd, J=12.9, 5.3, 1H), 2.90-2.82 (m, 1H), 2.60-2.55 (m, 1H), 2.48-2.41 (m, 1H), 2.26 (s, 3H), 2.01-1.97 (m, 1H). LC-MS m/z: (pos) 482.2 ([M+H]⁺).

Example 46: Synthesis of 1-(3-chloro-4-methylphenyl)-3-(3-((1-(2,6-dioxopiperidin-3-yl)-2,5-dioxo-2,5-dihydro-1H-pyrrol-3-yl)amino)phenyl)urea (43)

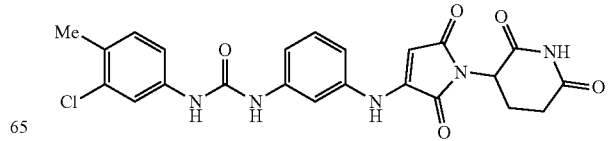

Compound 43 was prepared according to Method A. The aniline coupling partner was prepared according to Method D. $^1$H NMR (500 MHz, DMSO-d$_6$) δ 11.07 (s, 1H), 9.86 (s, 1H), 8.84 (s, 1H), 8.81 (s, 1H), 7.69 (d, J=2.3, 1H), 7.65 (t, J=2.1, 1H), 7.33-7.19 (m, 3H), 7.15 (dd, J=8.1, 2.0, 1H), 7.06 (dd, J=8.0, 2.2, 1H), 5.71 (s, 1H), 4.98 (dd, J=13.0, 5.4, 1H), 2.87 (ddd, J=17.0, 13.9, 5.4, 1H), 2.62-2.56 (m, 1H), 2.47 (qd, J=13.4, 4.5, 1H), 2.27 (s, 3H), 2.05-1.99 (m, 1H). LC-MS m/z: (pos) 482.2 ([M+H]$^+$).

Example 47: Synthesis of 1-(3-chloro-4-methylphenyl)-3-(3-((1-(2,6-dioxopiperidin-3-yl)-2,5-dioxo-2,5-dihydro-1H-pyrrol-3-yl)amino)benzyl)urea (44)

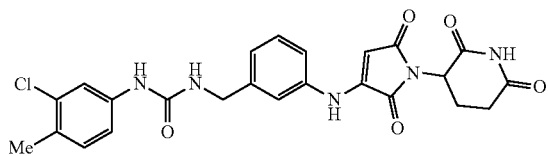 [SMILES: Cc1ccc(NC(=O)NCc2cccc(NC3=CC(=O)N(C4CCC(=O)NC4=O)C3=O)c2)cc1Cl]

Compound 44 was prepared according to Method A. The aniline coupling partner was prepared according to Method C. $^1$H NMR (500 MHz, DMSO-d$_6$) δ 11.05 (s, 1H), 9.84 (s, 1H), 8.70 (s, 1H), 7.69-7.61 (m, 1H), 7.36 (s, 1H), 7.33 (d, J=7.5, 1H), 7.30 (d, J=8.0, 1H), 7.17 (d, J=8.3, 1H), 7.13 (dd, J=8.4, 1.6, 1H), 7.05 (d, J=7.2, 1H), 6.70 (t, J=6.0, 1H), 5.77 (s, 1H), 4.96 (dd, J=13.0, 5.4, 1H), 4.30 (d, J=6.0, 2H), 2.86 (ddd, J=17.0, 13.9, 5.4, 1H), 2.60-2.55 (m, 1H), 2.45 (dd, J=13.4, 4.1, 1H), 2.23 (s, 3H), 2.01-1.97 (m, 1H). LC-MS m/z: (pos) 496.3 ([M+H]$^+$).

Example 48: Synthesis of 1-(3-chloro-4-methylphenyl)-3-(2-((1-(2,6-dioxopiperidin-3-yl)-2,5-dioxo-2,5-dihydro-1H-pyrrol-3-yl)amino)benzyl)urea (45)

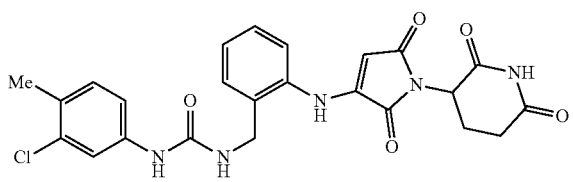 [SMILES: Cc1ccc(NC(=O)NCc2ccccc2NC2=CC(=O)N(C3CCC(=O)NC3=O)C2=O)cc1Cl]

Compound 45 was prepared according to Method A. The aniline coupling partner was prepared according to Method C. $^1$H NMR (500 MHz, DMSO-d$_6$) δ 11.05 (s, 1H), 9.76 (s, 1H), 8.77 (s, 1H), 7.62 (d, J=2.1, 1H), 7.44 (dd, J=7.7, 1.5, 1H), 7.41-7.30 (m, 2H), 7.25 (td, J=7.4, 1.6, 1H), 7.18 (d, J=8.3, 1H), 7.12 (dd, J=8.3, 2.2, 1H), 6.80 (t, J=6.0, 1H), 5.21 (s, 1H), 4.95 (dd, J=13.0, 5.4, 1H), 4.28 (d, J=6.1, 2H), 2.86 (ddd, J=17.0, 13.8, 5.4, 1H), 2.61-2.54 (m, 1H), 2.45 (qd, J=4.3, 1H), 2.23 (s, 3H), 2.00-1.93 (m, 1H). LC-MS m/z: (pos) 496.3 ([M+H]$^+$).

Example 49: Synthesis of 1-(3-chloro-4-methylphenyl)-3-(4-((1-(2,6-dioxopiperidin-3-yl)-2,5-dioxo-2,5-dihydro-1H-pyrrol-3-yl)amino)benzyl)urea (46)

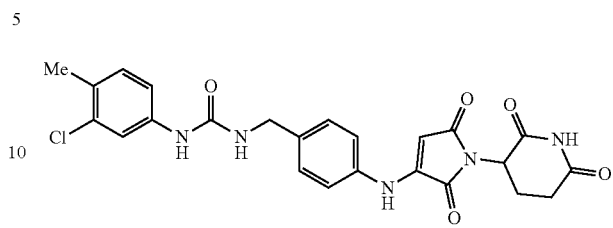

Compound 46 was prepared according to Method A. The aniline coupling partner was prepared according to Method C. $^1$H NMR (500 MHz, DMSO-d$_6$) δ 11.05 (s, 1H), 9.81 (s, 1H), 8.66 (s, 1H), 7.66 (s, 1H), 7.39 (d, J=8.1, 2H), 7.31 (d, J=8.1, 2H), 7.17 (d, J=8.3, 1H), 7.12 (d, J=7.7, 1H), 6.66 (t, J=5.6, 1H), 5.71 (s, 1H), 4.95 (dd, J=12.9, 5.4, 1H), 4.26 (d, J=5.5, 2H), 2.86 (ddd, J=17.8, 14.0, 5.4, 1H), 2.61-2.53 (m, 1H), 2.45 (qd, J=13.7, 4.3, 1H), 2.23 (s, 3H), 2.02-1.96 (m, 1H), 1.23 (s, 2H). LC-MS m/z: (pos) 496.2 ([M+H]$^+$).

Example 50: Synthesis of 1-(3-chloro-4-methylphenyl)-3-(3-((1-(2,6-dioxopiperidin-3-yl)-2,5-dioxo-2,5-dihydro-1H-pyrrol-3-yl)amino)propyl)urea (47)

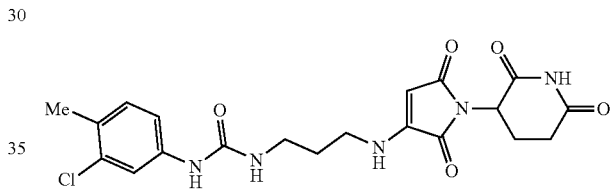

Compound 47 was prepared according to Method A. The alkylamine coupling partner was prepared according to Method D. $^1$H NMR (500 MHz, DMSO-d$_6$) δ 10.99 (s, 1H), 8.56 (s, 1H), 7.95 (t, J=5.8, 1H), 7.63 (d, J=1.6, 1H), 7.16 (d, J=8.3, 1H), 7.10 (dd, J=8.3, 1.7, 1H), 6.22 (t, J=5.6, 1H), 4.97 (s, 1H), 4.85 (dd, J=12.9, 5.4, 1H), 3.13 (dq, J=18.7, 6.4, 4H), 2.82 (ddd, J=17.4, 14.2, 5.4, 1H), 2.57-2.52 (m, 1H), 2.42 (ddd, J=13.2, 4.3, 1H), 2.22 (s, 3H), 1.95-1.88 (m, 1H), 1.71 (m, J=6.8, 2H). LC-MS m/z: (pos) 448.2 ([M+H]$^+$).

Example 51: Synthesis of 3-((1-(2,6-dioxopiperidin-3-yl)-2,5-dioxo-2,5-dihydro-1H-pyrrol-3-yl)amino)benzyl (3-chloro-4-methylphenyl)carbamate (48)

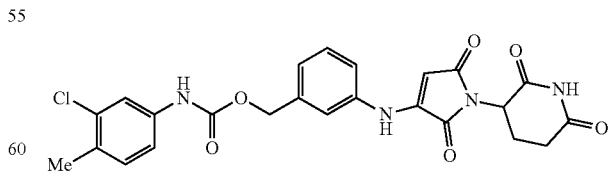

Compound 48 was prepared according to Method A. $^1$H NMR (500 MHz, DMSO-d$_6$) δ 11.05 (s, 1H), 8.87 (s, 1H), 8.83 (s, 1H), 7.69 (d, 1H), 7.61 (s, 1H), 7.44 (d, J=8.2, 1H), 7.34 (t, J=7.8, 1H), 7.24 (d, J=8.3, 1H), 7.19 (dd, 1H), 7.09 (d, J=7.5, 1H), 6.07 (s, 1H), 5.20 (s, 2H), 4.94 (dd, J=13.0, 5.3, 1H), 2.86-2.78 (m, 1H), 2.57-2.52 (m, 1H), 2.40 (qd, J=13.0, 4.2, 1H), 2.32-2.27 (m, 1H), 2.26 (s, 3H). LC-MS m/z: (pos) 497.2 ([M+H]$^+$).

Example 52: Synthesis of N-(3-chloro-4-methylphenyl)-3-((1-(2,6-dioxopiperidin-3-yl)-2,5-dioxo-2,5-dihydro-1H-pyrrol-3-yl)amino)benzamide (49)

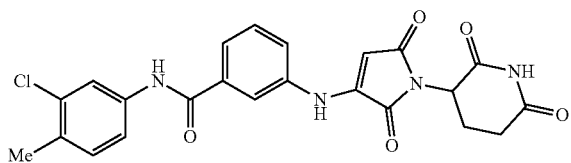

Compound 49 was prepared according to Method A. $^1$H NMR (500 MHz, DMSO-d$_6$) δ 11.07 (s, 1H), 10.36 (s, 1H), 9.98 (s, 1H), 7.94 (s, 1H), 7.89 (s, 1H), 7.68 (d, J=7.7, 1H), 7.66-7.57 (m, 2H), 7.54 (t, J=7.8, 1H), 7.33 (d, J=8.2, 1H), 5.87 (s, 1H), 4.98 (dd, J=13.0, 5.4, 1H), 2.87 (ddd, J=16.9, 13.9, 5.5, 1H), 2.61-2.55 (m, 1H), 2.49-2.43 (m, 1H), 2.30 (s, 3H), 2.03-1.98 (m, 1H). LC-MS m/z: (pos) 467.3 ([M+H]$^+$).

Example 53: Synthesis of N-(3-chloro-4-methylphenyl)-2-(3-((1-(2,6-dioxopiperidin-3-yl)-2,5-dioxo-2,5-dihydro-1H-pyrrol-3-yl)amino)phenyl)acetamide (50)

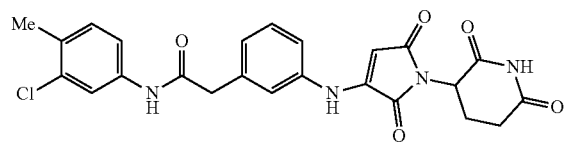 [SMILES: Cc1ccc(NC(=O)Cc2cccc(NC3=CC(=O)N(C4CCC(=O)NC4=O)C3=O)c2)cc1Cl]

Compound 50 was prepared according to Method A. $^1$H NMR (500 MHz, DMSO-d$_6$) δ 11.05 (s, 1H), 10.31 (s, 1H), 9.83 (s, 1H), 7.80 (d, J=2.2, 1H), 7.39 (s, 1H), 7.37 (dd, J=8.3, 2.2, 1H), 7.35-7.29 (m, 2H), 7.26 (d, J=8.3, 1H), 7.08 (d, J=6.7, 1H), 5.77 (s, 1H), 4.96 (dd, J=13.0, 5.4, 1H), 3.66 (s, 2H), 2.89-2.82 (m, 1H), 2.57 (ddd, J=17.2, 4.4, 2.4 1H), 2.48-2.41 (m, 1H), 2.26 (s, 3H), 2.03-1.97 (m, 1H). LC-MS m/z: (pos) 481.2 ([M+H]$^+$).

Example 54: Synthesis of 3-((1-(2,6-dioxopiperidin-3-yl)-2,5-dioxo-2,5-dihydro-1H-pyrrol-3-yl)amino)phenyl (3-chloro-4-methylphenyl)carbamate (51)

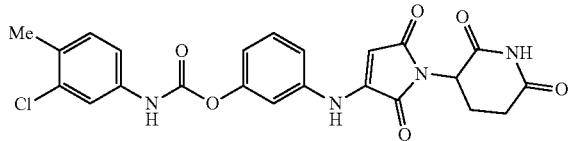 [SMILES: Cc1ccc(NC(=O)Oc2cccc(NC3=CC(=O)N(C4CCC(=O)NC4=O)C3=O)c2)cc1Cl]

Compound 51 was prepared according to Method A. $^1$H NMR (500 MHz, DMSO-d$_6$) δ 11.09 (s, 1H), 9.03 (s, 1H), 8.92 (s, 1H), 7.68 (s, 1H), 7.62 (s, 1H), 7.41 (t, J=8.1, 1H), 7.29 (d, J=8.0, 1H), 7.24 (d, J=8.2, 1H), 7.20 (dd, J=8.4, 2.1, 1H), 6.97 (dd, J=8.2, 2.4, 1H), 5.73 (s, 1H), 5.01 (dd, J=13.1, 5.3, 1H), 2.89-2.81 (m, 1H), 2.61-2.55 (m, 1H), 2.46-2.39 (m, 1H), 2.26 (s, 3H), 2.05-2.01 (m, 1H). LC-MS m/z: (pos) 483.2 ([M+H]$^+$).

Example 55: Synthesis of 3-(3-chloro-4-methylphenyl)-1-(3-((1-(2,6-dioxopiperidin-3-yl)-2,5-dioxo-2,5-dihydro-1H-pyrrol-3-yl)amino)benzyl)-1-methylurea (52)

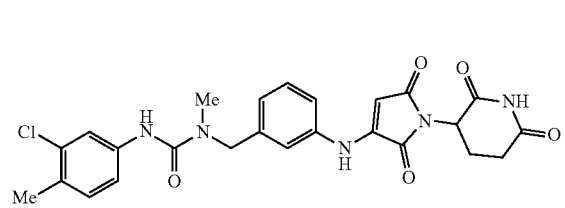 [SMILES: Cc1ccc(NC(=O)N(C)Cc2cccc(NC3=CC(=O)N(C4CCC(=O)NC4=O)C3=O)c2)cc1Cl]

Compound 52 was prepared according to Method A. $^1$H NMR (500 MHz, DMSO-d$_6$) δ 11.05 (s, 1H), 9.86 (s, 1H), 8.50 (s, 1H), 7.67 (d, 1H), 7.45-7.25 (m, 4H), 7.19 (d, J=8.3, 1H), 7.02 (d, J=7.2, 1H), 5.72 (s, 1H), 4.96 (dd, J=13.0, 5.3, 1H), 4.56 (s, 2H), 2.94 (s, 3H), 2.90-2.82 (m, 1H), 2.60-2.54 (m, 1H), 2.49-2.42 (m, 1H), 2.24 (s, 3H), 2.01-1.96 (m, 1H). LC-MS m/z: (pos) 510.3 ([M+H]$^+$).

Example 56: Synthesis of N-(3-chloro-4-methylphenyl)-3-(3-((1-(2,6-dioxopiperidin-3-yl)-2,5-dioxo-2,5-dihydro-1H-pyrrol-3-yl)amino)phenyl)propanamide (53)

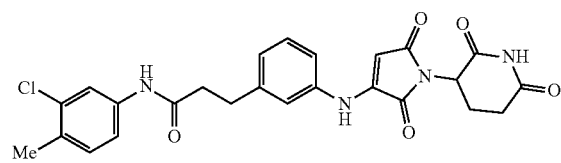 [SMILES: Cc1ccc(NC(=O)CCc2cccc(NC3=CC(=O)N(C4CCC(=O)NC4=O)C3=O)c2)cc1Cl]

Compound 53 was prepared according to Method A. $^1$H NMR (500 MHz, DMSO-d$_6$) δ 11.05 (s, 1H), 9.99 (s, 1H), 9.76 (s, 1H), 7.77 (d, 1H), 7.33 (dd, 1H), 7.32-7.19 (m, 4H), 7.01 (d, J=7.3, 1H), 5.76 (s, 1H), 4.96 (dd, J=13.0, 5.4, 1H), 2.92 (t, J=7.6, 2H), 2.86 (ddd, J=17.1, 14.0, 5.6, 1H), 2.63 (t, J=7.6, 2H), 2.60-2.55 (m, 1H), 2.49-2.41 (m, 1H), 2.25 (s, 3H), 1.99 (dtd, J=13.3, 5.6, 2.3, 1H). LC-MS m/z: (pos) 495.2 ([M+H]$^+$).

Example 57: Synthesis of 1-(3-chloro-4-methylphenyl)-3-(1-(3-((1-(2,6-dioxopiperidin-3-yl)-2,5-dioxo-2,5-dihydro-1H-pyrrol-3-yl)amino)phenyl)ethyl)urea (54)

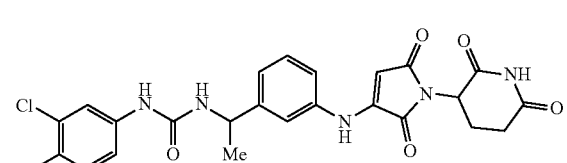

Compound 54 was prepared according to Method A. $^1$H NMR (500 MHz, DMSO-d$_6$) δ 11.05 (s, 1H), 9.82 (s, 1H), 8.48 (s, 1H), 7.62 (d, J=1.9, 1H), 7.37 (s, 1H), 7.35 (t, J=7.8, 1H), 7.31-7.26 (m, 1H), 7.16 (d, J=8.3, 1H), 7.12-7.06 (m, 2H), 6.72 (d, J=7.8, 1H), 5.75 (s, 1H), 4.96 (dd, J=12.9, 5.4, 1H), 4.82 (p, J=6.9, 1H), 2.86 (ddd, J=17.1, 13.9, 5.4, 1H), 2.57 (dt, J=17.2, 3.3, 1H), 2.49-2.43 (m, 1H), 2.22 (s, 3H), 2.02-1.96 (m, 1H), 1.39 (d, J=6.9, 3H). LC-MS m/z: (pos) 510.3 ([M+H]$^+$).

Example 58: Synthesis of 1-(3,4-dimethylphenyl)-3-(3-((1-(2,6-dioxopiperidin-3-yl)-2,5-dioxo-2,5-dihydro-1H-pyrrol-3-yl)amino)phenyl)urea (55)

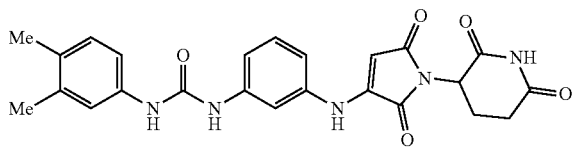 [SMILES: Cc1ccc(NC(=O)Nc2cccc(NC3=CC(=O)N(C4CCC(=O)NC4=O)C3=O)c2)cc1C]

Compound 55 was prepared according to Method A. LC-MS m/z: (pos) 462.3 ([M+H]$^+$).

Example 59: Synthesis of 1-(3,4-dichlorophenyl)-3-(3-((1-(2,6-dioxopiperidin-3-yl)-2,5-dioxo-2,5-dihydro-1H-pyrrol-3-yl)amino)phenyl)urea (56)

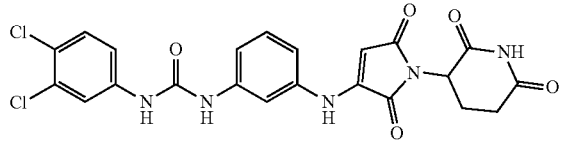 [SMILES: O=C1CCC(N2C(=O)C=C(Nc3cccc(NC(=O)Nc4ccc(Cl)c(Cl)c4)c3)C2=O)C(=O)N1]

Compound 56 was prepared according to Method A. $^1$H NMR (500 MHz, DMSO-d$_6$) δ 11.06 (s, 1H), 9.86 (s, 1H), 9.07 (s, 1H), 8.97 (s, 1H), 7.86 (d, J=2.5, 1H), 7.64 (t, J=2.1, 1H), 7.53 (d, J=8.8, 1H), 7.36 (dd, J=8.8, 2.5, 1H), 7.28 (t, J=8.2, 1H), 7.17-7.14 (m, 1H), 7.06 (dd, J=8.0, 1.5, 1H), 5.70 (s, 1H), 4.97 (dd, J=13.0, 5.4, 1H), 2.86 (ddd, J=17.1, 13.9, 5.5, 1H), 2.58 (dt, J=17.3, 3.4, 1H), 2.49-2.43 (m, 1H), 2.03-1.97 (m, 1H). LC-MS m/z: (pos) 502.2 ([M+H]$^+$).

Example 60: Synthesis of (E)-N-(3-chloro-4-methylphenyl)-3-(3-((1-(2,6-dioxopiperidin-3-yl)-2,5-dioxo-2,5-dihydro-1H-pyrrol-3-yl)amino)phenyl)acrylamide (57)

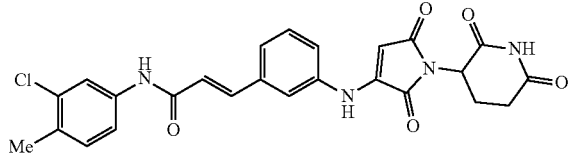 [SMILES: Cc1ccc(NC(=O)/C=C/c2cccc(NC3=CC(=O)N(C4CCC(=O)NC4=O)C3=O)c2)cc1Cl]

Compound 57 was prepared according to Method A. LC-MS m/z: (pos) 493.2 ([M+H]$^+$).

Example 61: Synthesis of 1-(3,4-dimethylphenyl)-3-(3-((1-(2,6-dioxopiperidin-3-yl)-2,5-dioxo-2,5-dihydro-1H-pyrrol-3-yl)amino)benzyl)urea (58)

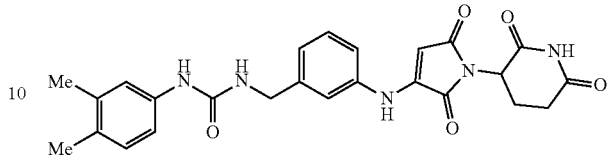

Compound 58 was prepared according to Method A. $^1$H NMR (500 MHz, DMSO-d$_6$) δ 11.05 (s, 1H), 9.84 (s, 1H), 8.37 (s, 1H), 7.36 (s, 1H), 7.35-7.31 (m, 1H), 7.29 (d, J=8.1, 1H), 7.18 (s, 1H), 7.10 (d, 1H), 7.05 (d, J=7.2, 1H), 6.96 (d, J=8.1, 1H), 6.57 (t, J=5.9, 1H), 5.77 (s, 1H), 4.96 (dd, J=13.0, 5.3, 1H), 4.29 (d, J=5.8, 2H), 2.86 (ddd, J=17.0, 13.9, 5.4, 1H), 2.57 (dt, J=17.0, 3.2, 1H), 2.49-2.42 (m, 1H), 2.15 (s, 3H), 2.12 (s, 3H), 2.02-1.96 (m, 1H). LC-MS m/z: (pos) 476.3 ([M+H]$^+$).

Example 62: Synthesis of 1-(3,4-dichlorophenyl)-3-(3-((1-(2,6-dioxopiperidin-3-yl)-2,5-dioxo-2,5-dihydro-1H-pyrrol-3-yl)amino)benzyl)urea (59)

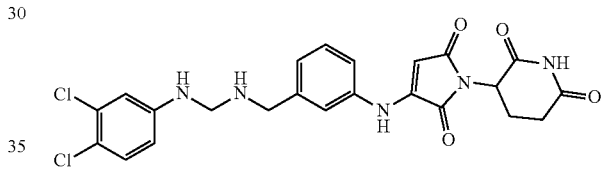

Compound 59 was prepared according to Method A. $^1$H NMR (500 MHz, DMSO-d$_6$) δ 11.05 (s, 1H), 9.84 (s, 1H), 8.96 (s, 1H), 7.85 (d, J=2.3, 1H), 7.45 (d, J=8.8, 1H), 7.37-7.26 (m, 4H), 7.05 (d, J=7.2, 1H), 6.84 (t, J=5.9, 1H), 5.76 (s, 1H), 4.96 (dd, J=13.0, 5.4, 1H), 4.31 (d, J=5.9, 2H), 2.86 (ddd, J=17.1, 13.9, 5.4, 1H), 2.57 (dt, J=17.3, 3.3, 1H), 2.49-2.42 (m, 1H), 1.99 (dtd, J=11.2, 5.7, 2.4, 1H). LC-MS m/z: (pos) 516.1 ([M+H]$^+$).

Example 63: Synthesis of 2-(3,4-dimethylphenyl)-N-(3-((1-(2,6-dioxopiperidin-3-yl)-2,5-dioxo-2,5-dihydro-1H-pyrrol-3-yl)amino)benzyl)acetamide (60)

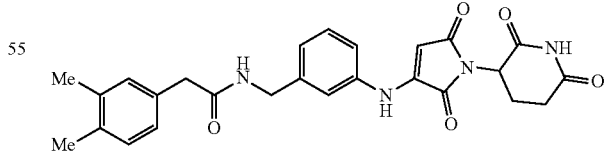

Compound 60 was prepared according to Method A. $^1$H NMR (500 MHz, DMSO-d$_6$) δ 11.06 (s, 1H), 9.81 (s, 1H), 8.51 (s, 1H), 7.38-7.21 (m, 3H), 7.06-7.00 (m, 2H), 7.00-6.94 (m, 2H), 5.73 (s, 1H), 4.97 (dd, J=12.9, 5.0, 1H), 4.27 (d, J=5.5, 2H), 3.39 (s, 2H), 2.87 (ddd, J=17.9, 13.9, 5.4, 1H), 2.61-2.55 (m, 1H), 2.48-2.43 (m, 1H), 2.16 (s, 6H), 2.03-1.99 (m, 1H). LC-MS m/z: (pos) 475.3 ([M+H]$^+$).

Example 64: Synthesis of 2-(3,4-dichlorophenyl)-N-(3-((1-(2,6-dioxopiperidin-3-yl)-2,5-dioxo-2,5-dihydro-1H-pyrrol-3-yl)amino)benzyl)acetamide (61)

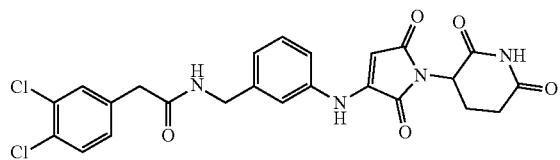 [SMILES: O=C(Cc1ccc(Cl)c(Cl)c1)NCc1cccc(NC2=CC(=O)N(C3CCC(=O)NC3=O)C2=O)c1]

Compound 61 was prepared according to Method A. $^1$H NMR (500 MHz, DMSO-d$_6$) δ 11.06 (s, 1H), 9.82 (s, 1H), 8.63 (t, J=5.9, 1H), 7.55 (d, J=8.2, 1H), 7.53 (d, J=1.6, 1H), 7.36-7.22 (m, 4H), 6.99 (d, J=6.8, 1H), 5.73 (s, 1H), 4.97 (dd, J=13.0, 5.4, 1H), 4.28 (d, J=5.9, 2H), 3.52 (s, 2H), 2.87 (ddd, J=17.2, 13.8, 5.4, 1H), 2.58 (dt, J=17.2, 3.3, 1H), 2.49-2.43 (m, 1H), 2.00 (ddd, J=12.7, 6.1, 3.7, 1H). LC-MS m/z: (pos) 515.1 ([M+H]$^+$).

Example 65: Synthesis of 1-(3-chloro-4-methylphenyl)-3-(3-((1-(2,6-dioxopiperidin-3-yl)-2,5-dioxo-2,5-dihydro-1H-pyrrol-3-yl)amino)phenethyl)urea (62)

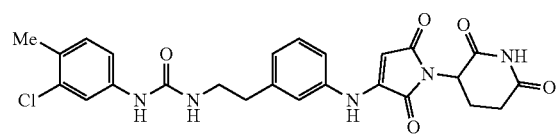

Compound 62 was prepared according to Method A. $^1$H NMR (500 MHz, DMSO-d$_6$) δ 11.05 (s, 1H), 9.77 (s, 1H), 8.56 (s, 1H), 7.64 (s, 1H), 7.41-7.19 (m, 3H), 7.15 (d, J=8.3, 1H), 7.08 (d, J=8.3, 1H), 7.00 (d, J=7.3, 1H), 6.15 (tz, J=5.3, 1H), 5.77 (s, 1H), 4.96 (dd, J=12.9, 5.2, 1H), 3.41-3.32 (m, 2H), 2.90-2.82 (m, 1H), 2.77 (t, J=6.8, 2H), 2.60-2.55 (m, 1H), 2.48-2.43 (m, 1H), 2.22 (s, 3H), 2.02-1.96 (m, 1H). LC-MS m/z: (pos) 510.2 ([M+H]$^+$).

Example 66: Synthesis of 3-(3-((3-(((3-chloro-4-methylphenyl)amino)methyl)-phenyl)amino)-2,5-dioxo-2,5-dihydro-1H-pyrrol-1-yl)piperidine-2,6-dione (63)

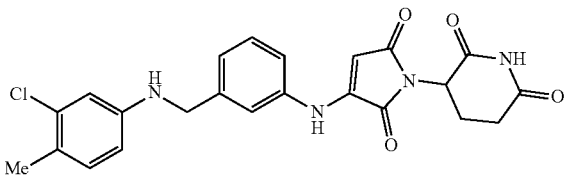 [SMILES: Cc1ccc(NCc2cccc(NC3=CC(=O)N(C4CCC(=O)NC4=O)C3=O)c2)cc1Cl]

Compound 63 was prepared according to Method A. $^1$H NMR (500 MHz, DMSO-d$_6$) δ 11.05 (s, 1H), 9.80 (s, 1H), 7.35 (s, 1H), 7.32 (t, J=7.7, 1H), 7.27 (d, J=8.4, 1.4, 1H), 7.10 (d, J=7.4, 1H), 6.98 (d, J=8.3, 1H), 6.59 (d, J=2.3, 1H), 6.47 (dd, J=8.3, 2.3, 1H), 6.41 (t, J=6.3, 1H), 5.66 (s, 1H), 4.95 (dd, J=13.0, 5.4, 1H), 4.28 (d, J=6.2, 2H), 2.85 (ddd, J=17.1, 13.8, 5.4, 1H), 2.57 (dt, J=16.9, 3.3, 1H), 2.48-2.42 (m, 1H), 2.13 (s, 3H), 1.99 (ddd, J=7.1, 5.6, 2.9, 1H). LC-MS m/z: (pos) 453.2 ([M+H]$^+$).

Example 67: Synthesis of 1-(3-chloro-4-methylphenyl)-3-(3-((1-(2,6-dioxopiperidin-3-yl)-2,5-dioxo-2,5-dihydro-1H-pyrrol-3-yl)oxy)benzyl)urea (64)

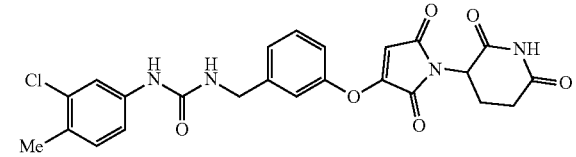 [SMILES: Cc1ccc(NC(=O)NCc2cccc(OC3=CC(=O)N(C4CCC(=O)NC4=O)C3=O)c2)cc1Cl]

Compound 64 was prepared according to Method A. $^1$H NMR (500 MHz, DMSO-d$_6$) δ 11.09 (s, 1H), 8.72 (s, 1H), 7.64 (d, J=2.1, 1H), 7.47 (t, J=8.1, 1H), 7.30-7.24 (m, 3H), 7.17 (d, J=8.4, 1H), 7.13 (dd, J=8.3, 2.1, 1H), 6.74 (t, J=6.0, 1H), 5.70 (s, 1H), 5.00 (dd, J=13.0, 5.4, 1H), 4.34 (d, J=5.9, 2H), 2.85 (ddd, J=17.2, 13.9, 5.5, 1H), 2.57 (ddd, J=17.3, 4.6, 2.6, 1H), 2.47-2.38 (m, 2H), 2.23 (s, 3H), 2.01 (dtd, J=12.9, 5.4, 2.5, 1H). LC-MS m/z: (pos) 497.15 ([M+H]$^+$).

Example 68: Synthesis of 1-(3-chloro-4-methylphenyl)-3-(2-(3-((1-(2,6-dioxopiperidin-3-yl)-2,5-dioxo-2,5-dihydro-1H-pyrrol-3-yl)amino)phenyl)propan-2-yl)urea (69)

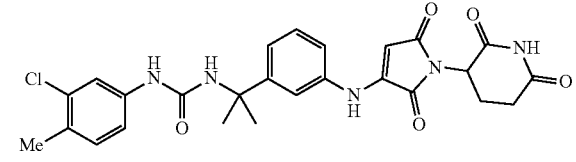 [SMILES: Cc1ccc(NC(=O)NC(C)(C)c2cccc(NC3=CC(=O)N(C4CCC(=O)NC4=O)C3=O)c2)cc1Cl]

Compound 69 was prepared according to Method A. $^1$H NMR (500 MHz, DMSO-d$_6$) δ 11.04 (s, 1H), 9.82 (s, 1H), 8.58 (s, 1H), 7.57 (d, J=2.1, 1H), 7.45 (s, 1H), 7.32 (t, J=7.9, 1H), 7.23 (dd, 1H), 7.15 (t, 2H), 7.01 (dd, J=8.3, 2.2, 1H), 6.73 (s, 1H), 5.62 (s, 1H), 4.95 (dd, J=13.0, 5.4, 1H), 2.89-2.81 (m, 1H), 2.57 (ddd, J=17.1, 4.5, 2.5, 1H), 2.49-2.42 (m, 1H), 2.21 (s, 3H), 1.98 (dtt, J=12.9, 5.5, 2.8, 1H), 1.59 (s, 6H). LC-MS m/z: (pos) 524.17 ([M+H]$^+$).

Example 69: Synthesis of 1-(3-chloro-4-methylphenyl)-3-((1R)-1-(3-((1-(2,6-dioxopiperidin-3-yl)-2,5-dioxo-2,5-dihydro-1H-pyrrol-3-yl)amino)phenyl)ethyl)urea (70)

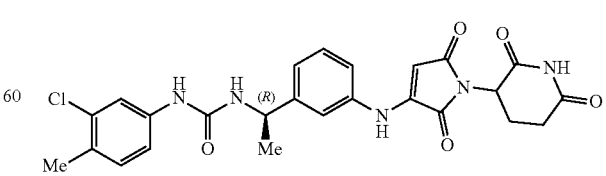

Compound 70 was prepared according to Method A. $^1$H NMR (500 MHz, DMSO-d$_6$) δ 11.05 (s, 1H), 9.82 (s, 1H), 8.48 (s, 1H), 7.62 (d, J=2.1, 1H), 7.37 (t, J=1.9, 1H), 7.34 (t, J=7.8, 1H), 7.31-7.26 (m, 1H), 7.16 (d, J=8.4, 1H), 7.12-7.05 (m, 2H), 6.72 (d, J=7.8, 1H), 5.75 (s, 1H), 4.96 (dd, J=13.0, 5.4, 1H), 4.82 (p, J=7.0, 1H), 2.86 (ddd, J=17.1, 13.9, 5.4, 1H), 2.57 (ddd, J=17.1, 4.5, 2.6, 1H), 2.49-2.42 (m, 1H), 2.22 (s, 3H), 2.02-1.97 (m, J=10.5, 5.4, 3.1, 1H), 1.39 (d, J=7.0, 3H). LC-MS m/z: (pos) 510.13 ([M+H]+).

Example 70: Synthesis of 1-(3-chloro-4-methylphenyl)-3-((1S)-1-(3-((1-(2,6-dioxopiperidin-3-yl)-2,5-dioxo-2,5-dihydro-1H-pyrrol-3-yl)amino)phenyl)ethyl)urea (71)

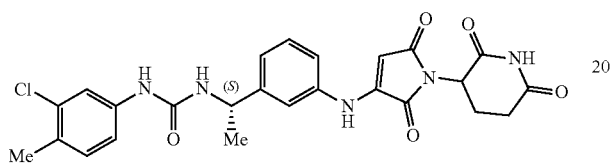

Compound 71 was prepared according to Method A. ¹H NMR (500 MHz, DMSO-d₆) δ 11.05 (s, 1H), 9.82 (s, 1H), 8.47 (s, 1H), 7.62 (d, J=2.1, 1H), 7.37 (t, J=1.9, 1H), 7.34 (t, J=7.8, 1H), 7.30-7.27 (m, 1H), 7.16 (d, J=8.4, 1H), 7.11-7.06 (m, 2H), 6.72 (d, J=7.8, 1H), 5.75 (s, 1H), 4.96 (dd, J=13.0, 5.4, 1H), 4.82 (p, J=7.0, 1H), 2.86 (ddd, J=17.1, 14.0, 5.4, 1H), 2.57 (dt, J=17.1, 3.4, 1H), 2.49-2.42 (m, 1H), 2.22 (s, 3H), 2.02-1.97 (m, J=10.5, 5.4, 3.1, 1H), 1.39 (d, J=7.0, 3H). LC-MS m/z: (pos) 510.07 ([M+H]+).

Example 71: Synthesis of 1-(3-chloro-4-methylphenyl)-3-(1-(3-((1-(2,6-dioxopiperidin-3-yl)-2,5-dioxo-2,5-dihydro-1H-pyrrol-3-yl)amino)phenyl)propyl)urea (74)

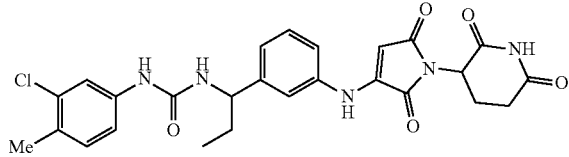 [SMILES: CCC(NC(=O)Nc1ccc(C)c(Cl)c1)c1cccc(NC2=CC(=O)N(C3CCC(=O)NC3=O)C2=O)c1]

Compound 74 was prepared according to Method A. ¹H NMR (500 MHz, DMSO-d₆) δ 11.05 (s, 1H), 9.82 (s, 1H), 8.46 (s, 1H), 7.62 (d, J=2.1, 1H), 7.37-7.31 (m, 2H), 7.31-7.26 (m, 1H), 7.16 (d, J=8.4, 1H), 7.07 (dd, J=8.4, 2.1, 2H), 6.74 (d, J=8.1, 1H), 5.74 (s, 1H), 4.96 (dd, J=13.0, 5.4, 1H), 4.61 (q, J=7.3, 1H), 2.86 (ddd, J=17.1, 13.9, 5.4, 1H), 2.57 (dt, J=17.0, 3.5, 1H), 2.49-2.41 (m, 1H), 2.21 (s, 3H), 2.00 (ddt, J=13.0, 5.5, 2.7, 1H), 1.73 (p, J=7.2, 2H), 0.87 (t, J=7.3, 3H). LC-MS m/z: (pos) 524.17 ([M+H]+).

Example 72: Synthesis of 3-(3-(3-chloro-4-methylphenyl)ureido)-3-(3-((1-(2,6-dioxopiperidin-3-yl)-2,5-dioxo-2,5-dihydro-1H-pyrrol-3-yl)amino)phenyl)-N,N-dimethylpropanamide (76)

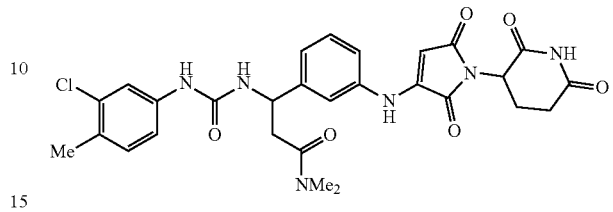

Compound 76 was prepared according to Method A. LC-MS m/z: (pos) 581.15 ([M+H]+).

Example 73: Synthesis of 1-(3-chloro-4-methylphenyl)-3-(2-chloro-5-((1-(2,6-dioxopiperidin-3-yl)-2,5-dioxo-2,5-dihydro-1H-pyrrol-3-yl)amino)benzyl)urea (77)

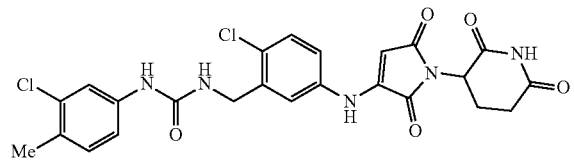 [SMILES: Cc1ccc(NC(=O)NCc2cc(NC3=CC(=O)N(C4CCC(=O)NC4=O)C3=O)ccc2Cl)cc1Cl]

Compound 77 was prepared according to Method A. LC-MS m/z: (pos) 530.12 ([M+H]+).

Example 74: Synthesis of N-(3-chloro-4-methylphenyl)-2-((3-((1-(2,6-dioxopiperidin-3-yl)-2,5-dioxo-2,5-dihydro-1H-pyrrol-3-yl)amino)phenyl)amino)acetamide (78)

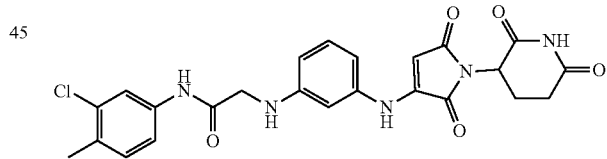

Compound 78 was prepared according to Method A. LC-MS m/z: (pos) 496.15 ([M+H]+).

Example 75: Synthesis of 1-benzyl-3-(3-((1-(2,6-dioxopiperidin-3-yl)-2,5-dioxo-2,5-dihydro-1H-pyrrol-3-yl)amino)benzyl)urea (81)

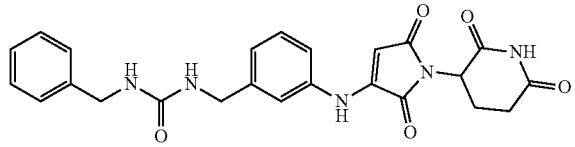 [SMILES: O=C1CCC(N2C(=O)C=C(Nc3cccc(CNC(=O)NCc4ccccc4)c3)C2=O)C(=O)N1]

Compound 81 was prepared according to Method A. ¹H NMR (500 MHz, DMSO-d₆) δ 11.06 (s, 1H), 9.83 (s, 1H), 7.38-7.16 (m, 11H), 5.74 (s, 1H), 4.97 (dd, J=12.5, 4.5, 1H), 4.26-4.21 (m, 4H), 2.92-2.80 (m, 1H), 2.62-2.55 (m, 1H), 2.48-2.39 (m, 1H, overlap with DMSO solvent peak), 2.02-1.96 (m, 1H). LC-MS m/z: (pos) 462.18 ([M+H]⁺).

Example 76: Synthesis of 1-(4-chloro-3-methylbenzyl)-3-(3-((1-(2,6-dioxopiperidin-3-yl)-2,5-dioxo-2,5-dihydro-1H-pyrrol-3-yl)amino)benzyl)urea (82)

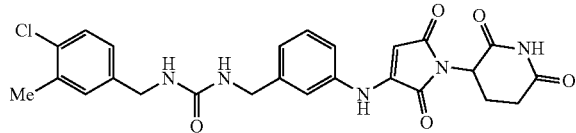 [SMILES: Cc1cc(CNC(=O)NCc2cccc(NC3=CC(=O)N(C4CCC(=O)NC4=O)C3=O)c2)ccc1Cl]

Compound 82 was prepared according to Method A. ¹H NMR (500 MHz, DMSO-d₆) δ 11.06 (s, 1H), 9.82 (s, 1H), 7.33-7.24 (m, 5H), 7.11 (dd, 1H), 7.01 (d, J=7.1, 1H), 6.54 (q, J=5.8, 2H), 5.74 (s, 1H), 4.97 (dd, J=12.9, 5.4, 1H), 4.24 (d, J=6.0, 2H), 4.19 (d, J=5.9, 2H), 2.91-2.82 (m, 1H), 2.61-2.55 (m, 1H), 2.49-2.43 (m, 1H), 2.28 (s, 3H), 2.03-1.98 (m, 1H). LC-MS m/z: (pos) 510.13 ([M+H]⁺).

Example 77: Synthesis of 2-((3-(3-chloro-4-methylphenyl)ureido)methyl)-4-((1-(2,6-dioxopiperidin-3-yl)-2,5-dioxo-2,5-dihydro-1H-pyrrol-3-yl)amino)phenyl Dimethylcarbamate (95)

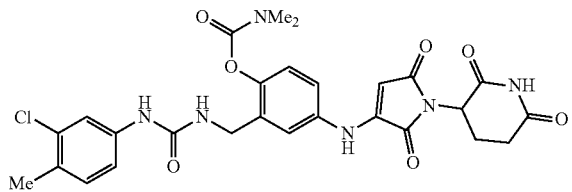 [SMILES: Cc1ccc(NC(=O)NCc2cc(NC3=CC(=O)N(C4CCC(=O)NC4=O)C3=O)ccc2OC(=O)N(C)C)cc1Cl]

Compound 95 was prepared according to Method A. ¹H NMR (500 MHz, DMSO-d₆) δ 11.05 (s, 1H), 9.90 (s, 1H), 8.75 (s, 1H), 7.65 (d, J=2.1, 1H), 7.39 (d, J=2.7, 1H), 7.32 (dd, J=8.7, 2.7, 1H), 7.17 (d, J=8.4, 1H), 7.15-7.07 (m, 2H), 6.52 (t, J=5.9, 1H), 5.72 (s, 1H), 4.95 (dd, J=13.0, 5.4, 1H), 4.24 (d, J=5.8, 2H), 3.07 (s, 3H), 2.90 (s, 3H), 2.86-2.81 (m, 1H), 2.57 (m, 1H), 2.48-2.42 (m, 1H), 2.23 (s, 3H), 1.99 (dtd, J=8.4, 5.4, 2.9, 1H). LC-MS m/z: (pos) 583.21 ([M+H]⁺).

Example 78: Synthesis of N-(3-chloro-4-methylphenyl)-5-((1-(2,6-dioxopiperidin-3-yl)-2,5-dioxo-2,5-dihydro-1H-pyrrol-3-yl)amino)isoindoline-2-carboxamide (107)

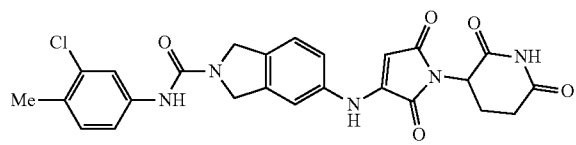 [SMILES: Cc1ccc(NC(=O)N2Cc3ccc(NC4=CC(=O)N(C5CCC(=O)NC5=O)C4=O)cc3C2)cc1Cl]

Compound 107 was prepared according to Method A. LC-MS m/z: (pos) 508.18 ([M+H]⁺).

Example 79: Synthesis of N-(3-chloro-4-methylphenyl)-7-((1-(2,6-dioxopiperidin-3-yl)-2,5-dioxo-2,5-dihydro-1H-pyrrol-3-yl)amino)-3,4-dihydroisoquinoline-2(1H)-carboxamide (109)

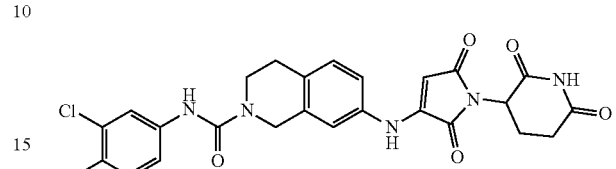

Compound 109 was prepared according to Method A. LC-MS m/z: (pos) 522.10 ([M+H]⁺).

Example 80: Synthesis of 3-((1-(2,6-dioxopiperidin-3-yl)-2,5-dioxo-2,5-dihydro-1H-pyrrol-3-yl)amino)phenethyl (3-chloro-4-methylphenyl)carbamate (110)

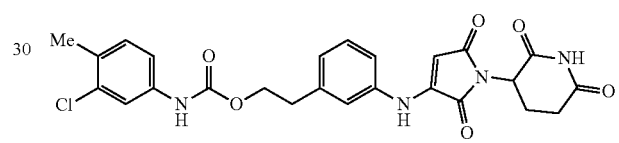

Compound 110 was prepared according to Method A. ¹H NMR (500 MHz, DMSO-d₆) δ 11.05 (s, 1H), 9.76 (s, 1H), 9.71 (s, 1H), 7.57 (s, 1H), 7.37-7.33 (m, 1H), 7.34-7.23 (m, 3H), 7.22 (d, J=8.3, 1H), 7.06 (dt, J=7.2, 1.5, 1H), 5.80 (s, 1H), 4.96 (dd, J=13.0, 5.4, 1H), 4.33 (t, J=6.7, 2H), 2.98 (t, J=6.7, 2H), 2.86 (ddd, J=17.1, 13.8, 5.3, 1H), 2.58 (dt, J=17.3, 3.4, 1H), 2.47-2.42 (m, 1H), 2.02-1.98 (m, 1H). LC-MS m/z: (pos) 511.07 ([M+H]⁺).

Example 81: Synthesis of 3-(3-((3-(3-chloro-4-methylphenyl)ureido)methyl)-5-((1-(2,6-dioxopiperidin-3-yl)-2,5-dioxo-2,5-dihydro-1H-pyrrol-3-yl)amino)phenyl)-1,1-dimethylurea (112)

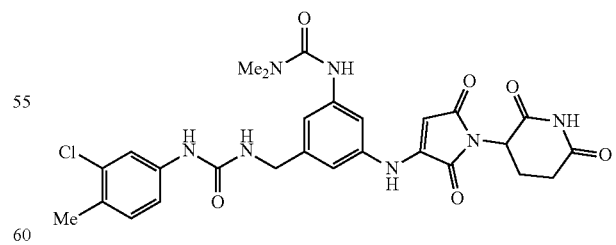

Compound 112 was prepared according to Method A. ¹H NMR (500 MHz, DMSO-d₆) δ 11.05 (s, 1H), 9.82 (s, 1H), 8.67 (s, 1H), 8.40 (s, 1H), 7.68 (d, J=2.0, 1H), 7.49 (s, 1H), 7.21 (s, 1H), 7.18 (d, J=8.4, 1H), 7.12 (dd, J=8.3, 2.1, 1H), 6.95 (s, 1H), 6.62 (t, J=5.9, 1H), 5.74 (s, 1H), 4.95 (dd, J=13.0, 5.4, 1H), 4.22 (d, J=5.9, 2H), 2.93 (s, 6H), 2.85 (ddd, 1H), 2.57 (dt, J=17.3, 3.4, 1H), 2.49-2.42 (m, 1H), 2.23 (s, 3H), 1.99 (dtt, J=10.7, 5.3, 2.2, 1H). LC-MS m/z: (pos) 582.15 ([M+H]⁺).

Example 82: Synthesis of 1-(3-((1-(2,6-dioxopiperidin-3-yl)-2,5-dioxo-2,5-dihydro-1H-pyrrol-3-yl)amino)benzyl)-3-phenylurea (119)

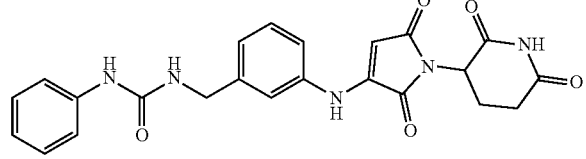

Compound 119 was prepared according to Method A. ¹H NMR (500 MHz, DMSO-d₆) δ 11.05 (s, 1H), 9.84 (s, 1H), 8.58 (s, 1H), 7.49-7.25 (m, 5H), 7.21 (t, J=7.8, 2H), 7.06 (d, J=7.2, 1H), 6.89 (t, J=7.3, 1H), 6.65 (t, J=5.9, 1H), 5.77 (s, 1H), 4.96 (dd, J=13.0, 5.3, 1H), 4.31 (d, J=5.9, 2H), 2.89-2.81 (m, 1H), 2.60-2.55 (m, 1H), 2.47-2.43 (m, 1H), 2.02-1.96 (m, 1H), 1.23 (s, 3H). LC-MS m/z: (pos) 448.20 ([M+H]⁺).

Example 83: Synthesis of 1-(4-chloro-3-methylbenzyl)-3-(1-(3-((1-(2,6-dioxopiperidin-3-yl)-2,5-dioxo-2,5-dihydro-1H-pyrrol-3-yl)amino)phenyl)ethyl)urea (120)

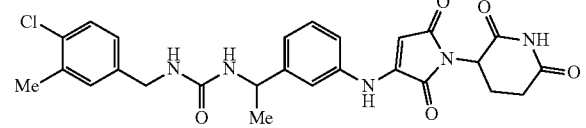

Compound 120 was prepared according to Method A. LC-MS m/z: (pos) 524.17 ([M+H]⁺).

Example 84: Synthesis of N-(3-chloro-4-methylbenzyl)-3-(3-((1-(2,6-dioxopiperidin-3-yl)-2,5-dioxo-2,5-dihydro-1H-pyrrol-3-yl)amino)phenyl)propanamide (121)

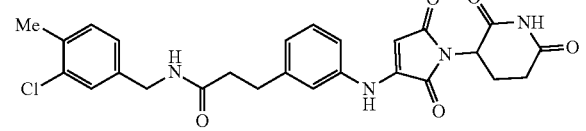

Compound 121 was prepared according to Method A. ¹H NMR (500 MHz, DMSO-d₆) δ 11.06 (s, 1H), 9.81 (s, 1H), 7.37-7.15 (m, 5H), 7.06 (t, J=6.8, 2H), 6.55 (d, J=8.1, 1H), 6.35 (t, J=6.1, 1H), 5.74 (s, 1H), 4.97 (dd, J=13.0, 5.4, 1H), 4.76 (p, J=7.2, 1H), 4.20-4.10 (m, 2H), 2.86 (ddd, J=17.2, 13.9, 5.5, 1H), 2.61-2.55 (m, 1H), 2.48-2.43 (m, 1H), 2.27 (s, 3H), 2.02-1.97 (m, 1H), 1.34 (d, J=7.0, 2H). LC-MS m/z: (pos) 509.13 ([M+H]⁺).

Example 85: Synthesis of N-(3-chloro-4-methylbenzyl)-3-((1-(2,6-dioxopiperidin-3-yl)-2,5-dioxo-2,5-dihydro-1H-pyrrol-3-yl)amino)benzamide (122)

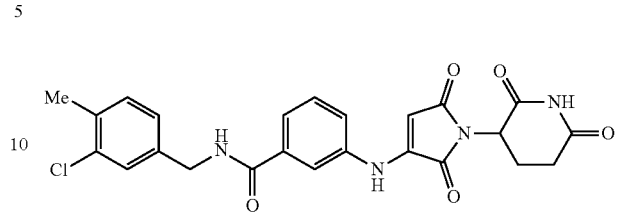

Compound 122 was prepared according to Method A. ¹H NMR (500 MHz, DMSO-d₆) δ 11.06 (s, 1H), 9.94 (s, 1H), 9.10 (t, J=6.0, 1H), 7.82 (t, J=2.0, 1H), 7.62 (dt, J=7.7, 1H), 7.58 (ddd, J=8.2, 2.5, 1.1, 1H), 7.49 (t, J=7.9, 1H), 7.35 (d, J=1.7, 1H), 7.31 (d, J=7.8, 1H), 7.20 (dd, J=7.8, 1.8, 1H), 5.85 (s, 1H), 4.97 (dd, J=13.0, 5.4, 1H), 4.45 (d, J=5.9, 2H), 2.86 (ddd, J=17.2, 13.9, 5.4, 1H), 2.58 (dt, J=17.3, 3.3, 1H), 2.48-2.43 (m, 1H), 2.30 (s, 3H), 2.00 (dtd, J=12.9, 5.4, 2.2, 1H). LC-MS m/z: (pos) 481.17 ([M+H]⁺).

Example 86: Synthesis of N-(3-chloro-4-methylbenzyl)-2-(3-((1-(2,6-dioxopiperidin-3-yl)-2,5-dioxo-2,5-dihydro-1H-pyrrol-3-yl)amino)phenyl)acetamide (123)

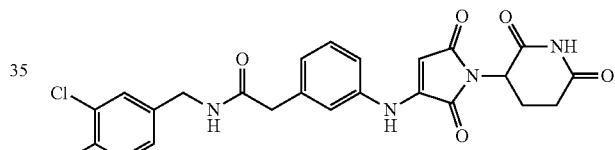

Compound 123 was prepared according to Method A. ¹H NMR (500 MHz, DMSO-d₆) δ 11.05 (s, 1H), 9.81 (s, 1H), 8.59 (t, J=5.9, 1H), 7.36-7.21 (m, 5H), 7.09 (dd, 1H), 7.05-6.99 (m, 1H), 5.74 (s, 1H), 4.97 (dd, J=13.0, 5.4, 1H), 4.23 (d, J=5.8, 2H), 3.50 (s, 2H), 2.86 (ddd, J=17.2, 13.9, 5.4, 1H), 2.61-2.55 (m, 1H), 2.48-2.43 (m, 1H), 2.27 (s, 3H), 1.99 (dtd, J=10.9, 5.3, 2.6, 1H). LC-MS m/z: (pos) 495.09 ([M+H]⁺).

Example 87: Synthesis of 1-(3-chloro-4-methylphenyl)-3-(5-((1-(2,6-dioxopiperidin-3-yl)-2,5-dioxo-2,5-dihydro-1H-pyrrol-3-yl)amino)naphthalen-1-yl)urea (124)

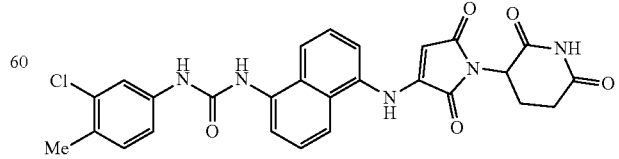

Compound 124 was prepared according to Method A. LC-MS m/z: (pos) 532.07 ([M+H]⁺).

Example 88: Synthesis of N-(3-chloro-4-methylphenyl)-2-(3-((1-(2,6-dioxopiperidin-3-yl)-2,5-dioxo-2,5-dihydro-1H-pyrrol-3-yl)amino)phenoxy)acetamide (125)

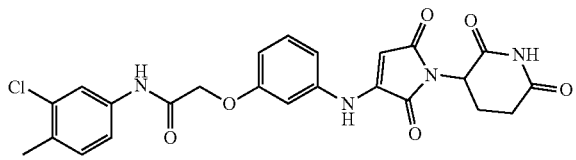 [SMILES: Cc1ccc(NC(=O)COc2cccc(NC3=CC(=O)N(C4CCC(=O)NC4=O)C3=O)c2)cc1Cl]

Compound 125 was prepared according to Method A. LC-MS m/z: (pos) 497.23 ([M+H]$^+$).

Example 89: Synthesis of 1-(3-((1-(2,6-dioxopiperidin-3-yl)-2,5-dioxo-2,5-dihydro-1H-pyrrol-3-yl)amino)phenethyl)-3-(4-methyl-3-(trifluoromethyl)phenyl)urea (126)

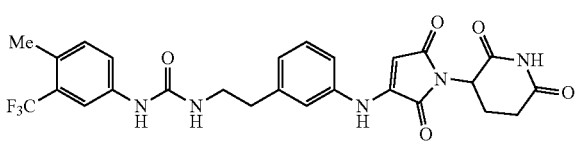 [SMILES: Cc1ccc(NC(=O)NCCc2cccc(NC3=CC(=O)N(C4CCC(=O)NC4=O)C3=O)c2)cc1C(F)(F)F]

Compound 126 was prepared according to Method A. $^1$H NMR (500 MHz, DMSO-d$_6$) δ 11.05 (s, 1H), 9.77 (s, 1H), 8.72 (s, 1H), 7.87 (d, J=2.0, 1H), 7.41 (dd, 1H), 7.36-7.15 (m, 4H), 7.00 (d, J=7.4, 1H), 6.18 (t, J=5.6, 1H), 5.77 (s, 1H), 4.96 (dd, J=13.0, 5.4, 1H), 3.35 (q, J=6.8, 2H), 2.86 (ddd, 1H), 2.77 (t, J=7.0, 2H), 2.58 (ddd, J=17.1, 4.4, 2.4, 1H), 2.47-2.43 (m, 1H), 2.33 (s, 3H), 1.99 (dtd, J=13.0, 5.5, 5.1, 2.1, 1H). LC-MS m/z: (pos) 544.16 ([M+H]$^+$).

Example 90: Synthesis of N-(3-chloro-4-methylphenyl)-3-(3-((1-(2,6-dioxopiperidin-3-yl)-2,5-dioxo-2,5-dihydro-1H-pyrrol-3-yl)amino)phenyl)-N-methylpropanamide (127)

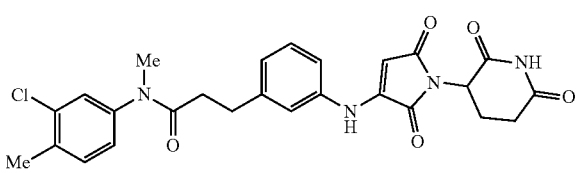 [SMILES: Cc1ccc(N(C)C(=O)CCc2cccc(NC3=CC(=O)N(C4CCC(=O)NC4=O)C3=O)c2)cc1Cl]

Compound 127 was prepared according to Method A. $^1$H NMR (500 MHz, DMSO-d$_6$) δ 11.05 (s, 1H), 9.73 (s, 1H), 7.36 (d, J=8.1, 1H), 7.27 (d, J=1.9, 1H), 7.26-7.20 (m, 2H), 7.18-7.04 (m, 2H), 6.85 (s, 1H), 5.66 (s, 1H), 4.97 (dd, 1H), 3.12 (s, 3H), 2.86 (ddd, J=17.4, 14.1, 5.5, 1H), 2.79 (t, J=7.5, 2H), 2.69 (s, 2H), 2.60-2.55 (m, 1H), 2.49-2.42 (m, 1H), 2.30 (s, 3H), 1.99 (dtt, J=11.1, 5.5, 2.3, 1H). LC-MS m/z: (pos) 509.13 ([M+H]$^+$).

Example 91: Synthesis of 1-(3-((1-(2,6-dioxopiperidin-3-yl)-2,5-dioxo-2,5-dihydro-1H-pyrrol-3-yl)amino)benzyl)-3-(4-methyl-3-(trifluoromethyl)phenyl)urea (128)

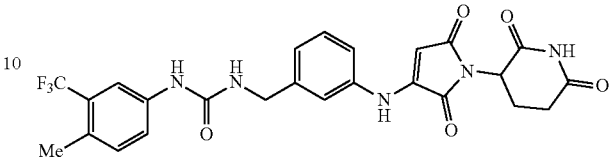

Compound 128 was prepared according to Method A. $^1$H NMR (500 MHz, DMSO-d6) δ 11.05 (s, 1H), 9.84 (s, 1H), 8.86 (s, 1H), 7.88 (s, 1H), 7.46 (d, J=8.1, 1H), 7.41-7.21 (m, 4H), 7.06 (d, J=7.2, 1H), 6.75 (t, J=5.8, 1H), 5.77 (s, 1H), 4.96 (dd, J=12.9, 5.3, 1H), 4.31 (d, J=5.8, 2H), 2.86 (ddd, J=17.1, 13.9, 5.5, 1H), 2.60-2.54 (m, 1H), 2.47-2.42 (m, 1H), 2.34 (s, 3H), 2.02-1.96 (m, 1H). LC-MS m/z: (pos) 530.12 ([M+H]$^+$).

Example 92: Synthesis of N-(3-chloro-4-(trifluoromethyl)phenyl)-3-(3-((1-(2,6-dioxopiperidin-3-yl)-2,5-dioxo-2,5-dihydro-1H-pyrrol-3-yl)amino)phenyl)propanamide (129)

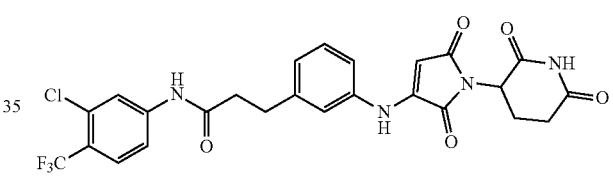

Compound 129 was prepared according to Method A. $^1$H NMR (500 MHz, DMSO-d$_6$) δ 11.05 (s, 1H), 10.44 (s, 1H), 9.77 (s, 1H), 8.01 (d, J=1.7, 1H), 7.78 (d, J=8.8, 1H), 7.63 (dd, 1H), 7.32-7.27 (m, 2H), 7.25 (dt, J=6.9, 1.2, 1H), 7.01 (d, J=7.5, 1H), 5.76 (s, 1H), 4.96 (dd, J=13.0, 5.4, 1H), 2.94 (t, J=7.5, 2H), 2.90-2.82 (m, 1H), 2.71 (t, J=7.6, 2H), 2.58 (ddd, J=17.1, 4.5, 2.5, 1H), 2.49-2.41 (m, 1H), 1.99 (dtd, J=12.8, 5.4, 2.4, 1H). LC-MS m/z: (pos) 549.07 ([M+H]$^+$).

Example 93: Synthesis of 3-(3-((1-(2,6-dioxopiperidin-3-yl)-2,5-dioxo-2,5-dihydro-1H-pyrrol-3-yl)amino)phenyl)-N-(4-methyl-3-(trifluoromethyl)phenyl)propanamide (130)

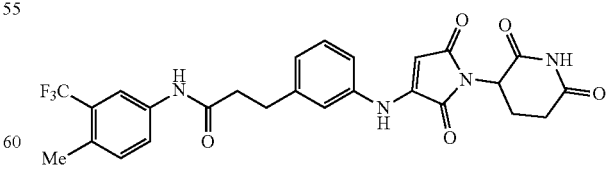

Compound 130 was prepared according to Method A. $^1$H NMR (500 MHz, DMSO-d$_6$) δ 11.05 (s, 1H), 10.13 (s, 1H), 9.76 (s, 1H), 7.98 (d, J=2.0, 1H), 7.68 (dd, J=8.3, 1.8, 1H), 7.34 (d, J=8.4, 1H), 7.31-7.27 (m, 2H), 7.25 (dt, J=7.1, 1.2, 1H), 7.01 (d, J=7.3, 1H), 5.76 (s, 1H), 4.96 (dd, J=13.0, 5.4, 1H), 2.93 (t, J=7.6, 2H), 2.86 (ddd, J=17.1, 13.9, 5.4, 1H), 2.65 (t, J=7.6, 2H), 2.60-2.55 (m, 1H), 2.49-2.42 (m, 1H), 2.36 (d, 3H), 1.99 (dtd, J=12.7, 5.3, 2.3, 1H). LC-MS m/z: (pos) 529.12 ([M+H]⁺).

Example 94: Synthesis of 1-(1-(3-((1-(2,6-dioxopiperidin-3-yl)-2,5-dioxo-2,5-dihydro-1H-pyrrol-3-yl)amino)phenyl)-ethyl)-3-(4-methyl-3-(trifluoromethyl)phenyl)urea (131)

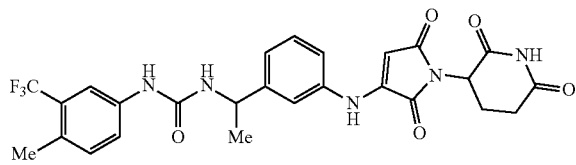

Compound 131 was prepared according to Method A. LC-MS m/z: (pos) 544.16 ([M+H]⁺).

Example 95: Synthesis of 1-(3-chloro-4-(trifluoromethyl)phenyl)-3-(1-(3-((1-(2,6-dioxopiperidin-3-yl)-2,5-dioxo-2,5-dihydro-1H-pyrrol-3-yl)amino)phenyl)ethyl)urea (132)

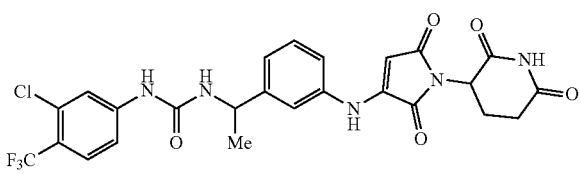 [SMILES: CC(NC(=O)Nc1ccc(C(F)(F)F)c(Cl)c1)c1cccc(NC2=CC(=O)N(C3CCC(=O)NC3=O)C2=O)c1]

Compound 132 was prepared according to Method A. LC-MS m/z: (pos) 564.10 ([M+H]⁺).

Example 96: Synthesis of N-(3-chloro-4-methylphenyl)-3-(3-((1-(2,6-dioxopiperidin-3-yl)-2,5-dioxo-2,5-dihydro-1H-pyrrol-3-yl)amino)phenyl)pentanamide (134)

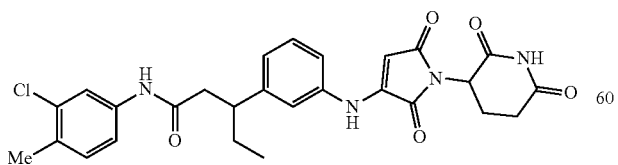

Compound 134 was prepared according to Method A. The aniline coupling partner was prepared according to Method F. LC-MS m/z: (pos) 523.16 ([M+H]⁺).

Example 97: Synthesis of N-(3-chloro-4-methylphenyl)-3-(3-((1-(2,6-dioxopiperidin-3-yl)-2,5-dioxo-2,5-dihydro-1H-pyrrol-3-yl)amino)phenyl)-3-methylbutanamide (136)

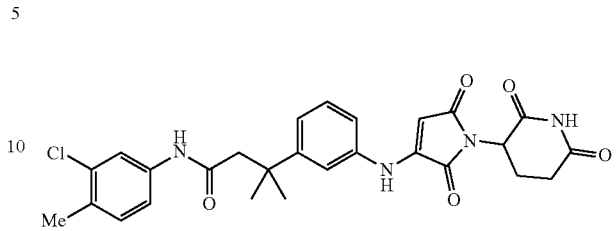

Compound 136 was prepared according to Method A. The aniline coupling partner was prepared according to Method F. LC-MS m/z: (pos) 523.16 ([M+H]⁺).

Example 98: Synthesis of N-(3-chloro-4-methylphenyl)-3-(3-((1-(2,6-dioxopiperidin-3-yl)-2,5-dioxo-2,5-dihydro-1H-pyrrol-3-yl)amino)phenyl)-3-methylbutanamide (137)

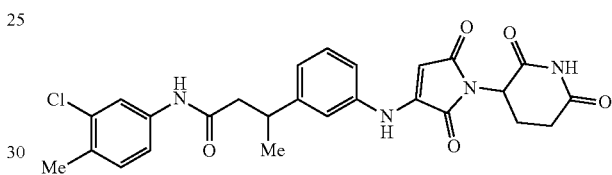

Compound 137 was prepared according to Method A. LC-MS m/z: (pos) 509.18 ([M+H]⁺).

Example 99: Synthesis of N-(3-chloro-4-(trifluoromethyl)phenyl)-3-(3-((1-(2,6-dioxopiperidin-3-yl)-2,5-dioxo-2,5-dihydro-1H-pyrrol-3-yl)amino)phenyl)pentanamide (138)

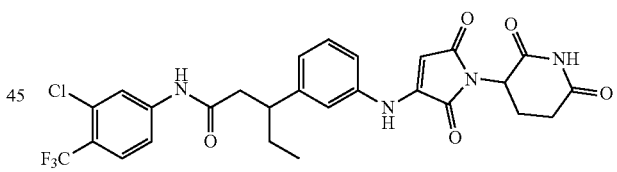

Compound 138 was prepared according to Method A. The aniline coupling partner was prepared according to Method F. LC-MS m/z: (pos) 577.19 ([M+H]⁺).

Example 100: Synthesis of N-(2-(3-((1-(2,6-dioxopiperidin-3-yl)-2,5-dioxo-2,5-dihydro-1H-pyrrol-3-yl)amino)phenyl)propan-2-yl)-2-(3-(trifluoromethyl)phenyl)acetamide (139)

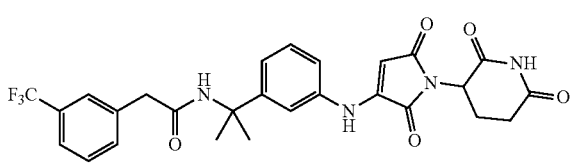 [SMILES: CC(C)(NC(=O)Cc1cccc(C(F)(F)F)c1)c1cccc(NC2=CC(=O)N(C3CCC(=O)NC3=O)C2=O)c1]

Compound 139 was prepared according to Method A. LC-MS m/z: (pos) 543.22 ([M+H]⁺).

Example 101: Synthesis of 3-(3-((1-(2,6-dioxopiperidin-3-yl)-2,5-dioxo-2,5-dihydro-1H-pyrrol-3-yl)amino)phenyl)-N-(3-(trifluoromethyl)phenyl)butanamide (140)

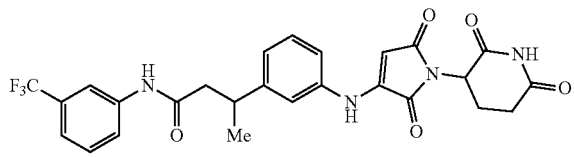 [SMILES: CC(CC(=O)Nc1cccc(C(F)(F)F)c1)c1cccc(NC2=CC(=O)N(C3CCC(=O)NC3=O)C2=O)c1]

Compound 140 was prepared according to Method A. The aniline coupling partner was prepared according to Method F. LC-MS m/z: (pos) 529.42 ([M+H]⁺).

Example 102: Synthesis of N-(1-(3-((1-(2,6-dioxopiperidin-3-yl)-2,5-dioxo-2,5-dihydro-1H-pyrrol-3-yl)amino)phenyl)-ethyl)-3-(trifluoromethyl)benzamide (141)

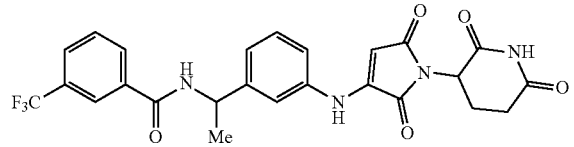 [SMILES: CC(NC(=O)c1cccc(C(F)(F)F)c1)c1cccc(NC2=CC(=O)N(C3CCC(=O)NC3=O)C2=O)c1]

Compound 141 was prepared according to Method A. LC-MS m/z: (pos) 515.44 ([M+H]⁺).

Example 103: Synthesis of N-(1-(3-((1-(2,6-dioxopiperidin-3-yl)-2,5-dioxo-2,5-dihydro-1H-pyrrol-3-yl)amino)phenyl)ethyl)-2-(3-(trifluoromethyl)phenyl)acetamide (142)

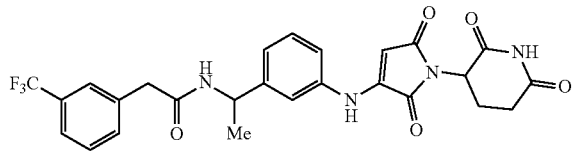 [SMILES: CC(NC(=O)Cc1cccc(C(F)(F)F)c1)c1cccc(NC2=CC(=O)N(C3CCC(=O)NC3=O)C2=O)c1]

Compound 142 was prepared according to Method A. LC-MS m/z: (pos) 529.42 ([M+H]⁺).

Example 104: Synthesis of 3-chloro-N-(1-(3-((1-(2,6-dioxopiperidin-3-yl)-2,5-dioxo-2,5-dihydro-1H-pyrrol-3-yl)amino)-phenyl)ethyl)-4-(trifluoromethyl)benzamide (143)

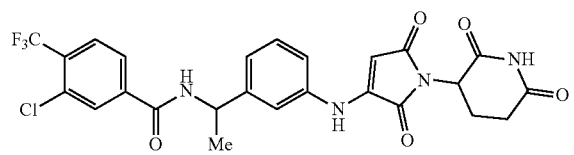 [SMILES: CC(NC(=O)c1ccc(C(F)(F)F)c(Cl)c1)c1cccc(NC2=CC(=O)N(C3CCC(=O)NC3=O)C2=O)c1]

Compound 143 was prepared according to Method A. LC-MS m/z: (pos) 549.41 ([M+H]⁺).

Example 105: Synthesis of 1-(3-chloro-4-methylphenyl)-3-((1S)-1-(3-((1-(2,6-dioxopiperidin-3-yl)-2,5-dioxopyrrolidin-3-yl)amino)phenyl)ethyl)urea (144)

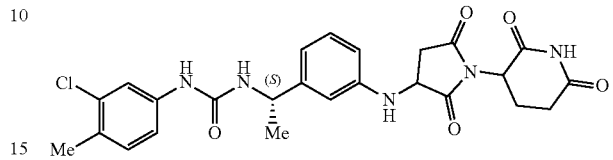

Compound 144 was prepared according to Method G. LC-MS m/z: (pos) 512.49 ([M+H]⁺).

Example 106: Synthesis of N-(3-chloro-4-methylphenyl)-3-(3-((1-(2,6-dioxopiperidin-3-yl)-2,5-dioxopyrrolidin-3-yl)-amino)phenyl)-3-methylbutanamide (145)

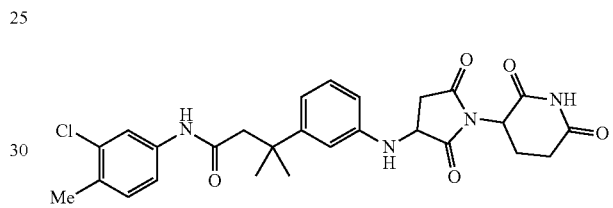

Compound 145 was prepared according to Method G. LC-MS m/z: (pos) 525.46 ([M+H]⁺).

Example 107: Synthesis of N-(3-chloro-4-methylphenyl)-3-(3-((1-(2,6-dioxopiperidin-3-yl)-2,5-dioxopyrrolidin-3-yl)amino)phenyl)butanamide (146)

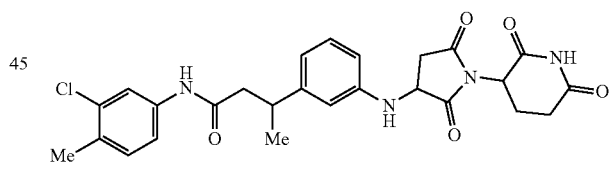

Compound 146 was prepared according to Method G. LC-MS m/z: (pos) 511.49 ([M+H]⁺).

Example 108: Synthesis of 2-(3,4-difluorophenyl)-N-(1-(3-((1-(2,6-dioxopiperidin-3-yl)-2,5-dioxo-2,5-dihydro-1H-pyrrol-3-yl)amino)phenyl)ethyl)acetamide (147)

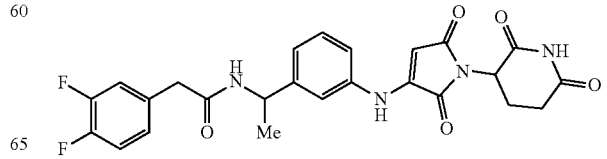

Compound 147 was prepared according to Method A. LC-MS m/z: (pos) 497.51 ([M+H]⁺).

Example 109: Synthesis of 3-(3-((1-(2,6-dioxopiperidin-3-yl)-2,5-dioxo-2,5-dihydro-1H-pyrrol-3-yl)amino)phenyl)-N-(3-(trifluoromethyl)phenyl)propanamide (148)

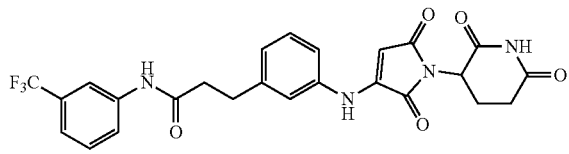 [SMILES: O=C1CCC(N2C(=O)C=C(Nc3cccc(CCC(=O)Nc4cccc(C(F)(F)F)c4)c3)C2=O)C(=O)N1]

Compound 148 was prepared according to Method A. LC-MS m/z: (pos) 515.44 ([M+H]⁺).

Example 110: Synthesis of 3-(3-((1-(2,6-dioxopiperidin-3-yl)-2,5-dioxo-2,5-dihydro-1H-pyrrol-3-yl)amino)phenyl)-N-(4-(trifluoromethyl)phenyl)propanamide (149)

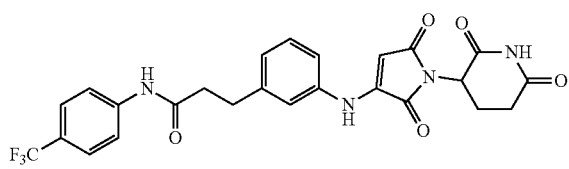 [SMILES: O=C1CCC(N2C(=O)C=C(Nc3cccc(CCC(=O)Nc4ccc(C(F)(F)F)cc4)c3)C2=O)C(=O)N1]

Compound 149 was prepared according to Method A. LC-MS m/z: (pos) 515.44 ([M+H]⁺).

Example 111: Synthesis of N-(3,4-difluorophenyl)-3-(3-((1-(2,6-dioxopiperidin-3-yl)-2,5-dioxo-2,5-dihydro-1H-pyrrol-3-yl)amino)phenyl)propanamide (150)

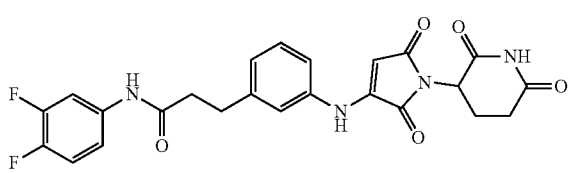 [SMILES: O=C1CCC(N2C(=O)C=C(Nc3cccc(CCC(=O)Nc4ccc(F)c(F)c4)c3)C2=O)C(=O)N1]

Compound 150 was prepared according to Method A. LC-MS m/z: (pos) 483.47 ([M+H]⁺).

Example 112: Synthesis of N-(2,4-difluorophenyl)-3-(3-((1-(2,6-dioxopiperidin-3-yl)-2,5-dioxo-2,5-dihydro-1H-pyrrol-3-yl)amino)phenyl)propanamide (151)

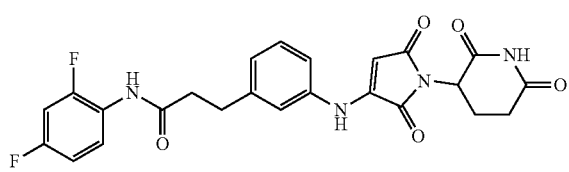 [SMILES: O=C1CCC(N2C(=O)C=C(Nc3cccc(CCC(=O)Nc4ccc(F)cc4F)c3)C2=O)C(=O)N1]

Compound 151 was prepared according to Method A. LC-MS m/z: (pos) 483.47 ([M+H]⁺).

Example 113: Synthesis of N-(1-(3-((1-(2,6-dioxopiperidin-3-yl)-2,5-dioxo-2,5-dihydro-1H-pyrrol-3-yl)amino)phenyl)-ethyl)-2-(4-(trifluoromethyl)phenyl)acetamide (152)

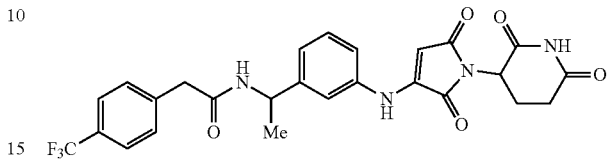

Compound 152 was prepared according to Method A. LC-MS m/z: (pos) 529.08 ([M+H]⁺).

Example 114: Synthesis of N-(3-chlorophenyl)-3-(3-((1-(2,6-dioxopiperidin-3-yl)-2,5-dioxo-2,5-dihydro-1H-pyrrol-3-yl)-amino)phenyl)propanamide (153)

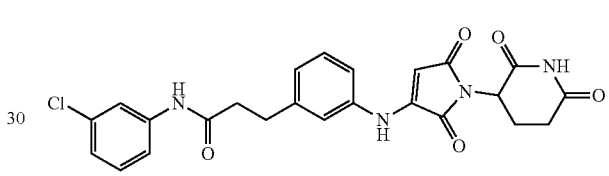

Compound 153 was prepared according to Method A. LC-MS m/z: (pos) 481.15 ([M+H]⁺).

Example 115: Synthesis of N-(4-chlorophenyl)-3-(3-((1-(2,6-dioxopiperidin-3-yl)-2,5-dioxo-2,5-dihydro-1H-pyrrol-3-yl)-amino)phenyl)propanamide (154)

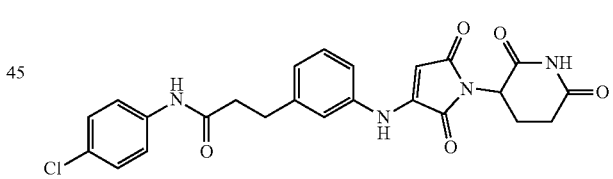

Compound 154 was prepared according to Method A. LC-MS m/z: (pos) 481.15 ([M+H]⁺).

Example 116: Synthesis of 2-(3-chlorophenyl)-N-(1-(3-((1-(2,6-dioxopiperidin-3-yl)-2,5-dioxo-2,5-dihydro-1H-pyrrol-3-yl)amino)phenyl)ethyl)acetamide (155)

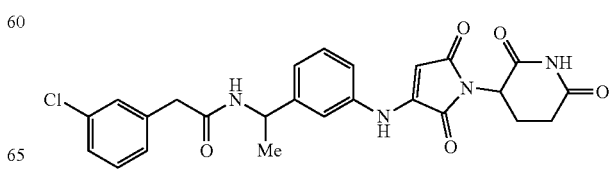

Compound 155 was prepared according to Method A. LC-MS m/z: (pos) 495.07 ([M+H]⁺).

Example 117: Synthesis of 2-(4-chlorophenyl)-N-(1-(3-((1-(2,6-dioxopiperidin-3-yl)-2,5-dioxo-2,5-dihydro-1H-pyrrol-3-yl)amino)phenyl)ethyl)acetamide (156)

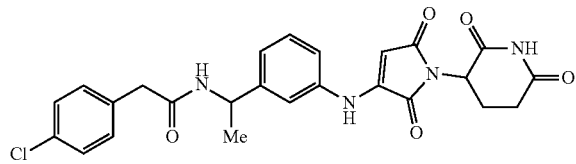 [SMILES: CC(NC(=O)Cc1ccc(Cl)cc1)c1cccc(NC2=CC(=O)N(C3CCC(=O)NC3=O)C2=O)c1]

Compound 156 was prepared according to Method A. LC-MS m/z: (pos) 495.12 ([M+H]⁺).

Example 118: Synthesis of 2-(3-chloro-4-(trifluoromethyl)phenyl)-N-(2-(3-((1-(2,6-dioxopiperidin-3-yl)-2,5-dioxo-2,5-dihydro-1H-pyrrol-3-yl)amino)phenyl)propan-2-yl)acetamide (159)

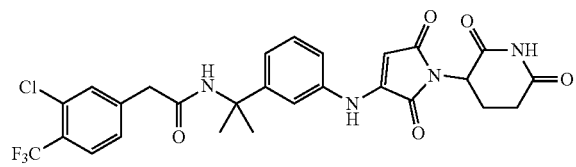 [SMILES: CC(C)(NC(=O)Cc1ccc(C(F)(F)F)c(Cl)c1)c1cccc(NC2=CC(=O)N(C3CCC(=O)NC3=O)C2=O)c1]

Compound 159 was prepared according to Method A. LC-MS m/z: (pos) 577.15 ([M+H]⁺).

Figure 1B:
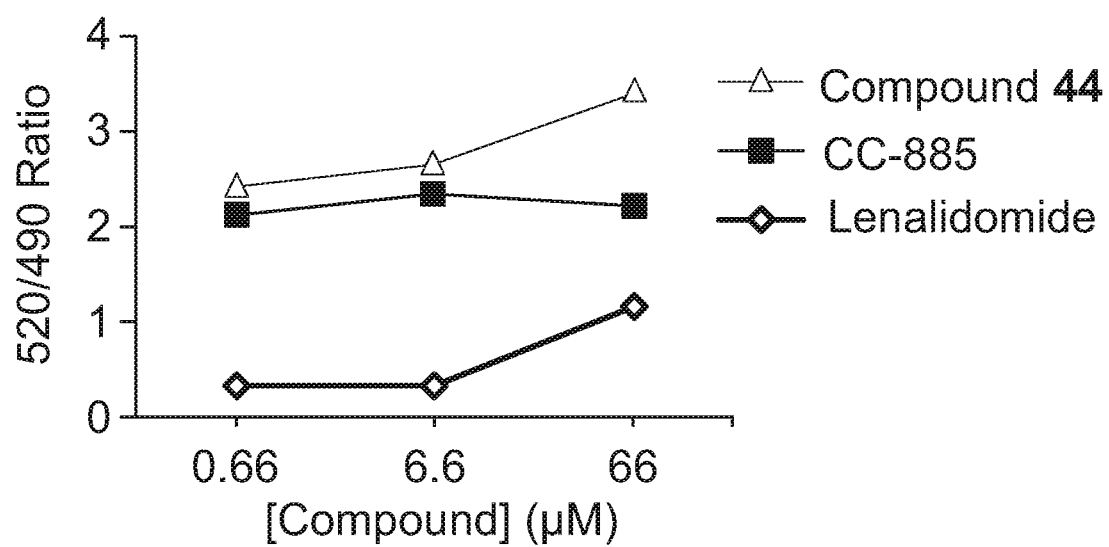
FIG. 1B is a graph of 520/490 TR-FRET ratios.
Figure 1C:
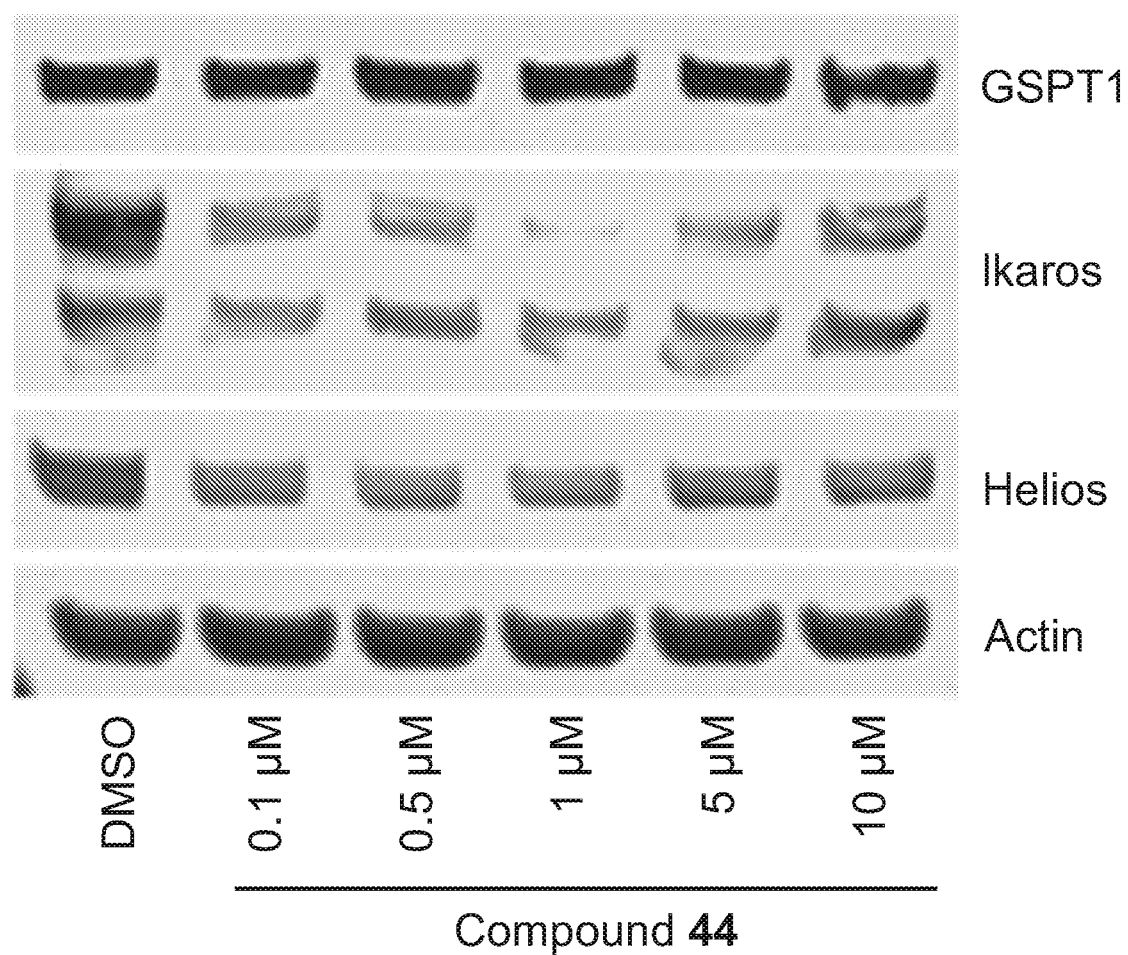
FIG. 1C shows immunoblots from Jurkat cells treated with compound 44 for 24 h with degradation of Ikaros and Helios.

Example 119: Optimization of Imide Analogs that Induce Potent and Selective Helios Degradation A focused library of imide analogs was synthesized and assessed for their ability to induce dimerization between CRBN and Helios in a time-resolved fluorescence energy transfer (TR-FRET) assay (FIG. 1A). Briefly, compounds were incubated with biotinylated Helios, streptavidin-labeled terbium, and GFP-tagged CRBN; compounds that were more potent dimerizers induced higher FRET signals (520/490 signal ratio). Consistent with previous reports, lenalidomide had minimal activity, while CC-885 had some activity (FIG. 1). Significantly, inventive compound 44 demonstrated increased activity over CC-885 at all tested concentrations, and treatment of Jurkat cells with compound 44 induced loss of both Ikaros and Helios after 24 h treatment, without affecting levels of GSPT1.

Figure 2B:
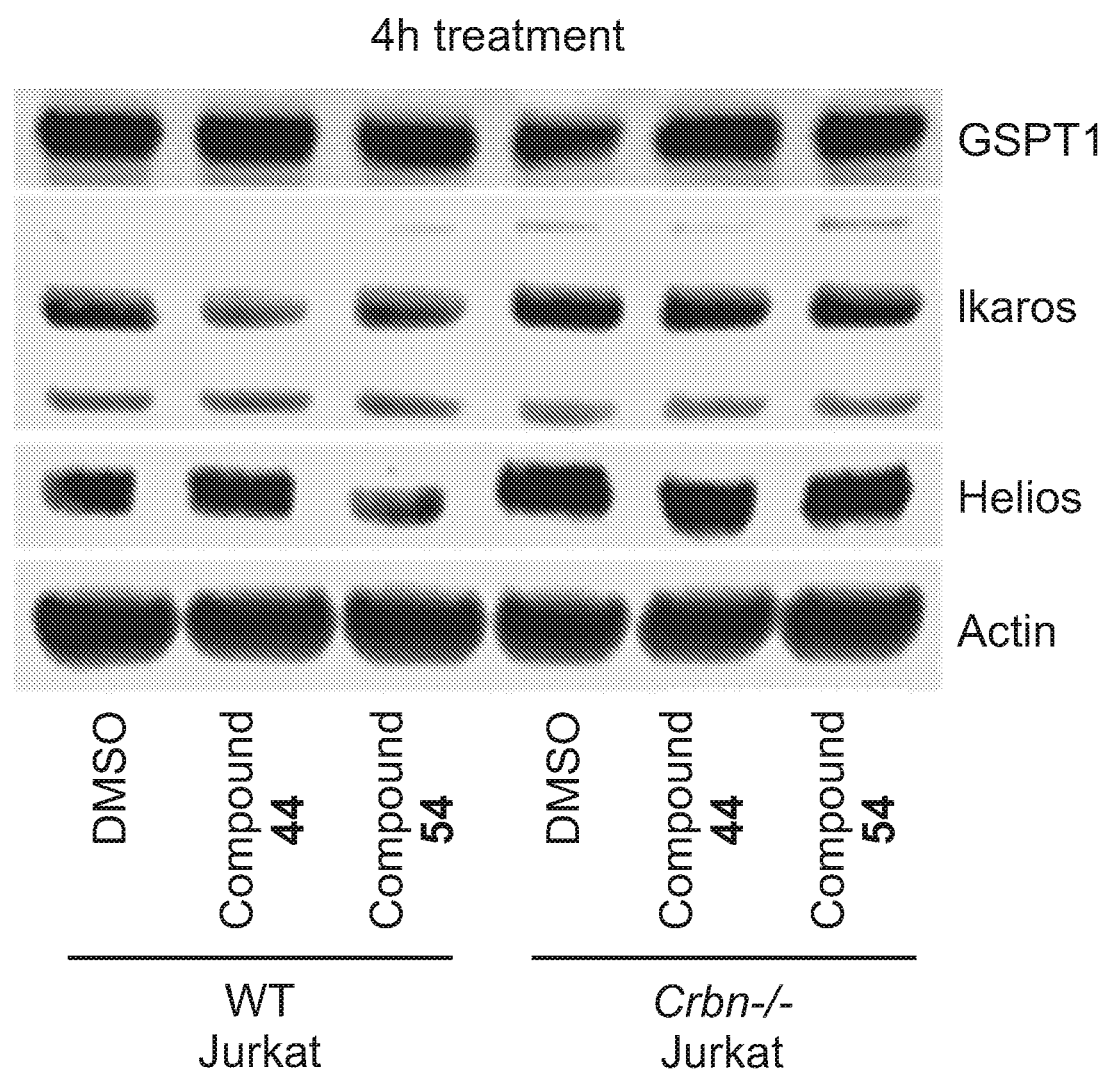
FIG. 2B shows immunoblots from Jurkat cells treated with compound 54 for 4 h.
Figure 2C:
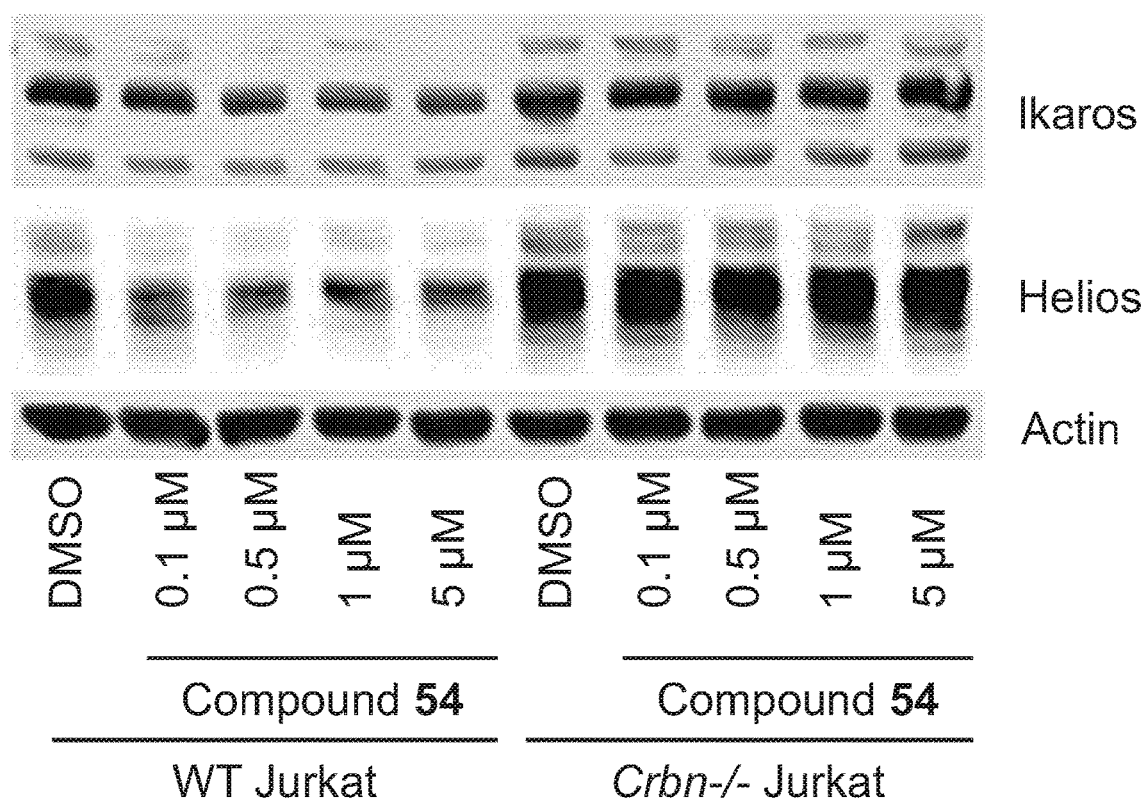
FIG. 2C is immunoblots from wildtype or Crbn−/− Jurkat cells treated with compound 54 for 4 h.
Figure 2D:
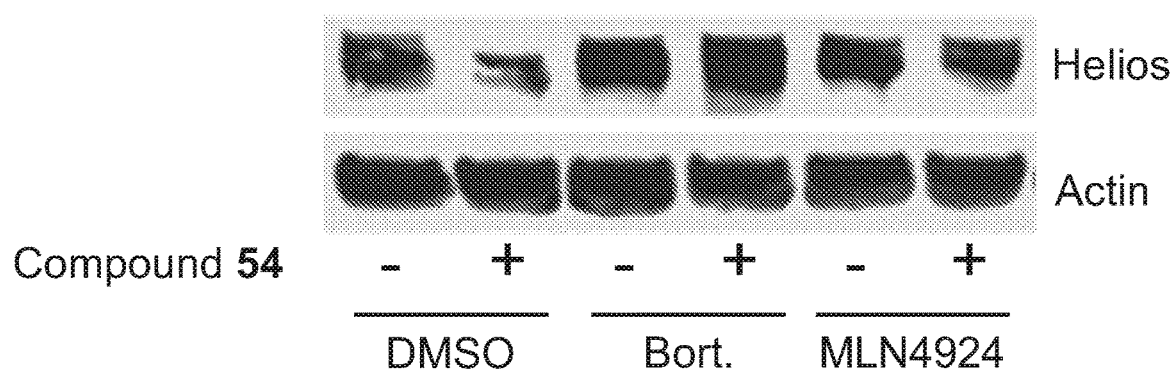
FIG. 2D is immunoblots from Jurkat cells co-treated with compound 54 (1 µM) and bortezomib (bort.; 1 µM) or MLN4924 (1 µM) for 4 h.
Figure 2E:
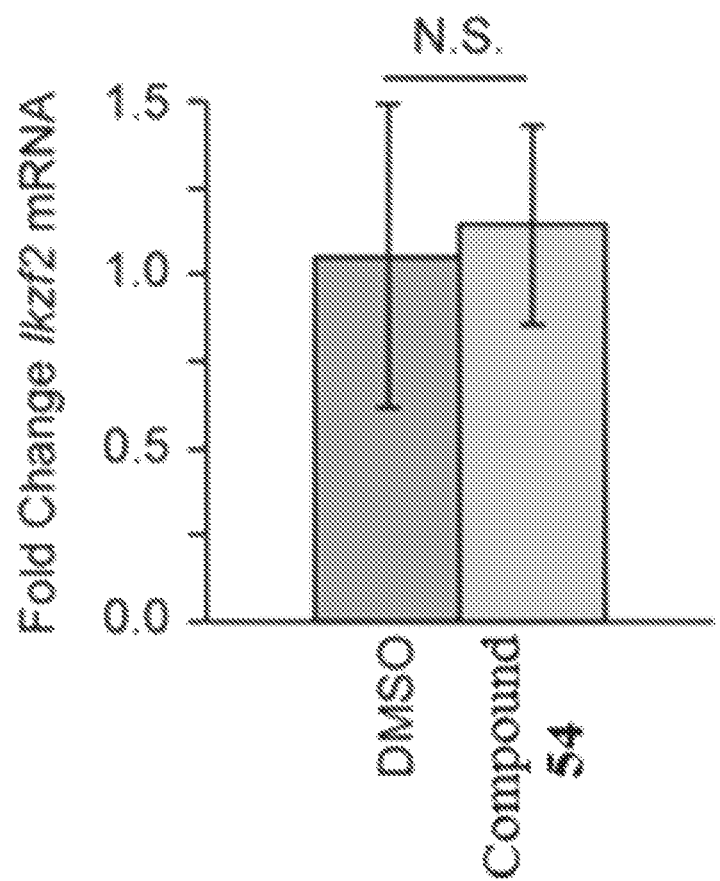
FIG. 2E is a bar graph showing quantitative polymerase chain reaction (qPCR) for Ikzf2 messenger ribonucleic acid (mRNA) from Jurkat cells treated for 4 h (n=3; N.S.=not significant).

Inventive compound 54 scored even higher than compound 44 in the TR-FRET assay at all concentrations tested (FIG. 2A). Compound 54 induced CRBN-dependent Helios degradation after just 4 h treatment, in contrast to compound 44, which required 24 h treatment (FIG. 2B and FIG. 2C). Moreover, compound 54 lost some degradation activity against Ikaros in comparison to compound 44 (FIG. 2B and FIG. 2C). Importantly, co-treatment with the proteasome inhibitor bortezomib or MLN4924, an inhibitor of NEDD8-activating enzyme (NAE) that is essential for the activation of Cullin-RING ubiquitin ligases such as CRL4$^{CRBN}$, both prevented Helios degradation, verifying that compound 54 induced proteasome-dependent degradation (FIG. 2D). Finally, treatment with compound 54 did not affect mRNA levels of IKZF2 (FIG. 2E). These results demonstrate that Helios is a degradable target.

Example 120: Helios Degradation Attenuates the Treg Suppressive Phenotype

Figure 3:
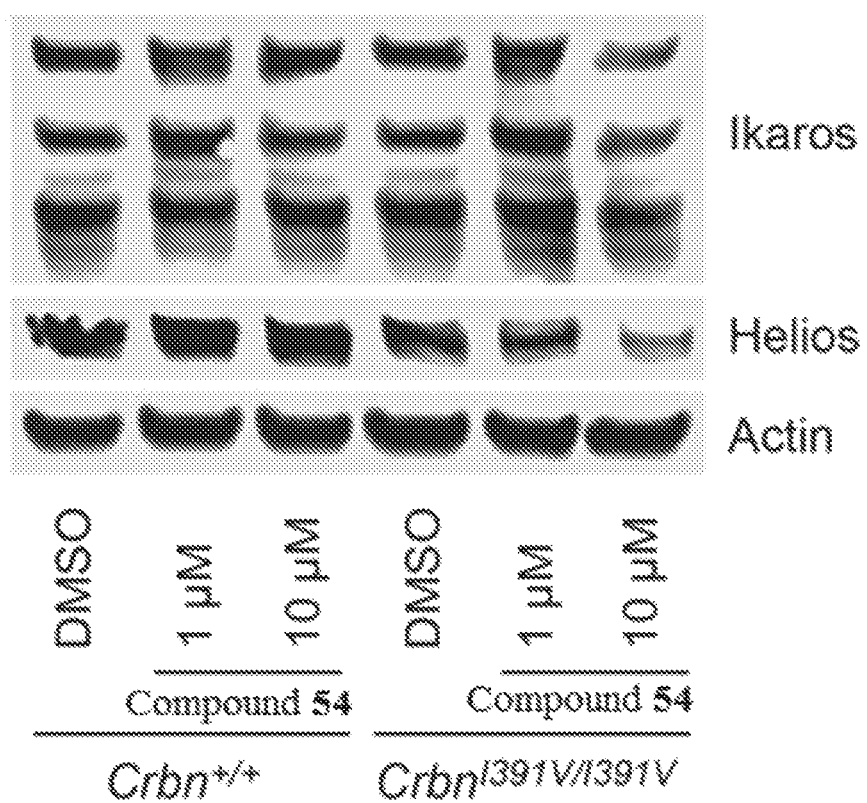
FIG. 3 shows immunoblots from murine Hoxb8-transformed myeloid progenitor cells treated with compound 54 for 18 h.
Figure 4A:
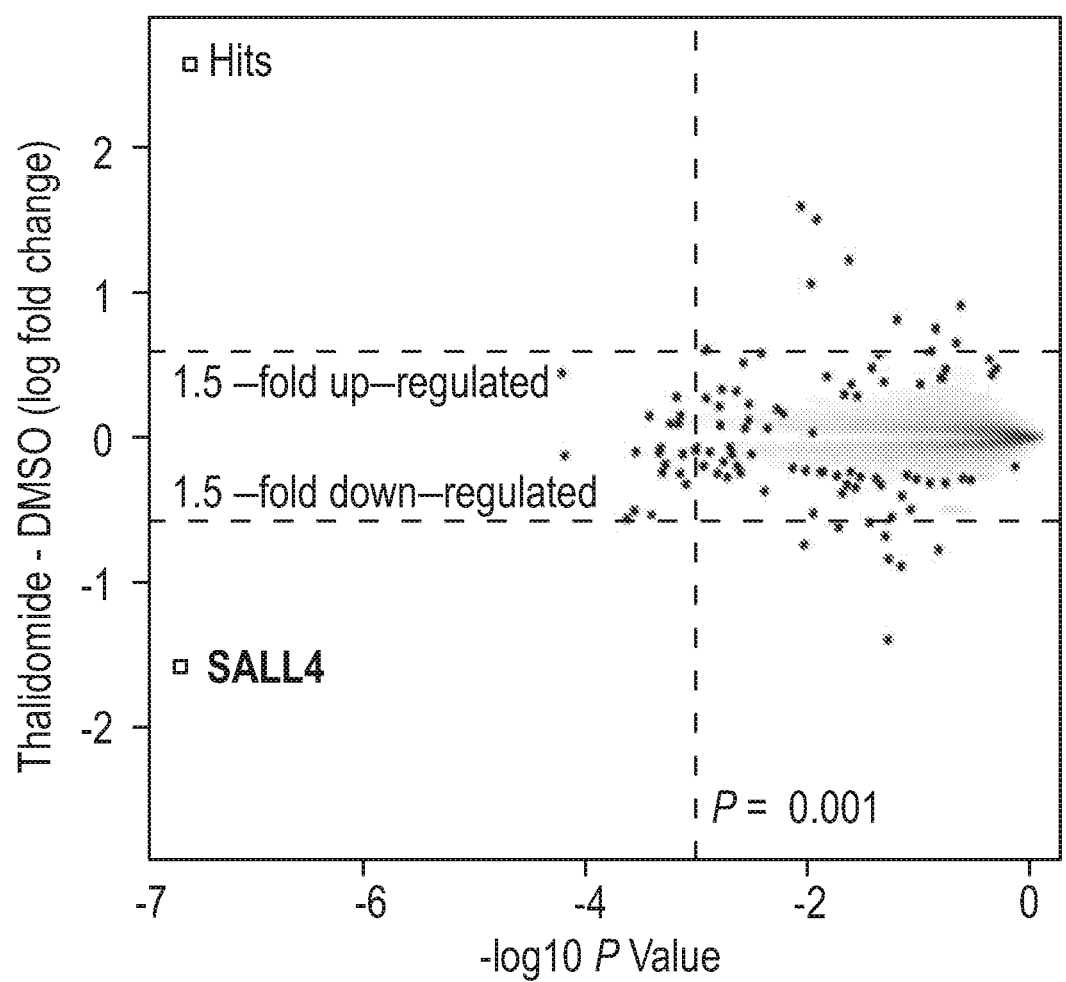
FIG. 4A-FIG. 4C are a series of scatter plots depicting the identification of IMiD-dependent substrate candidates.
Figure 4B:
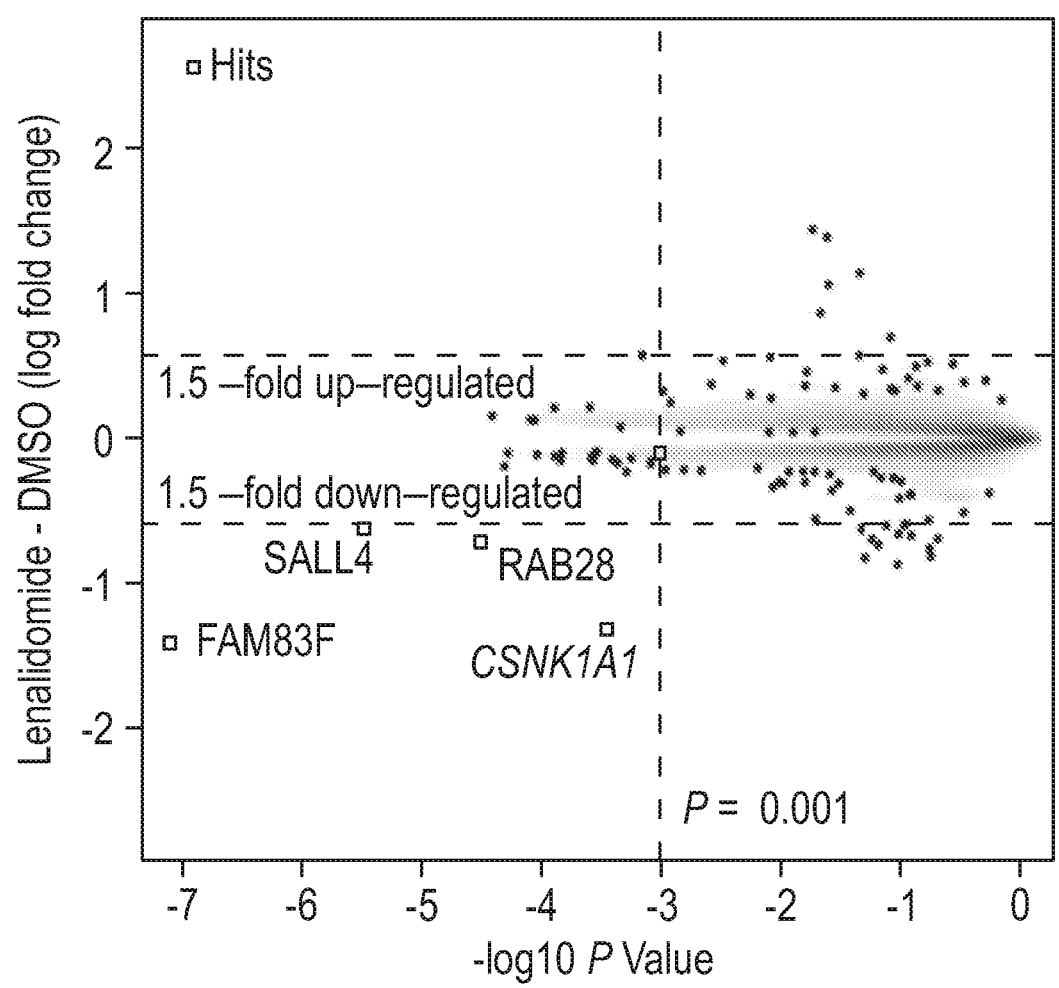
Figure 4C:
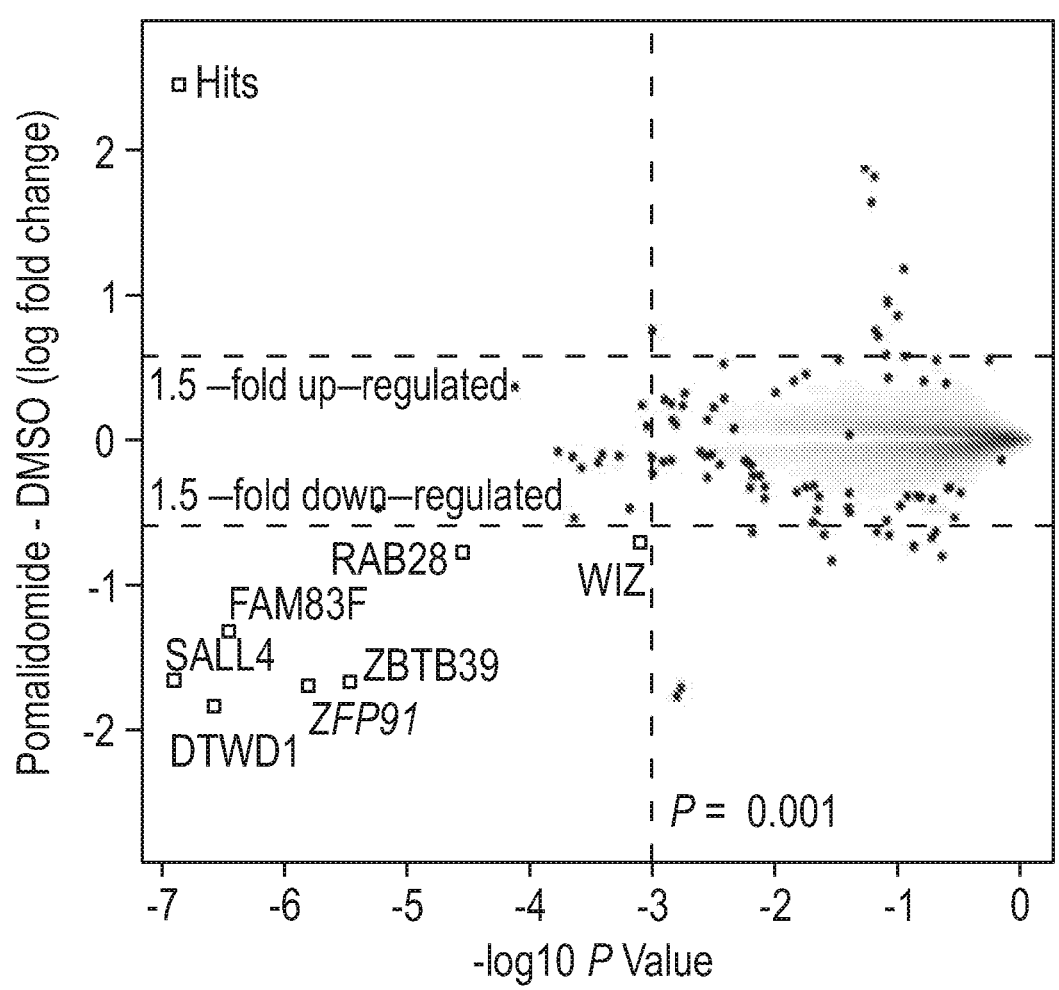
Figure 4D:
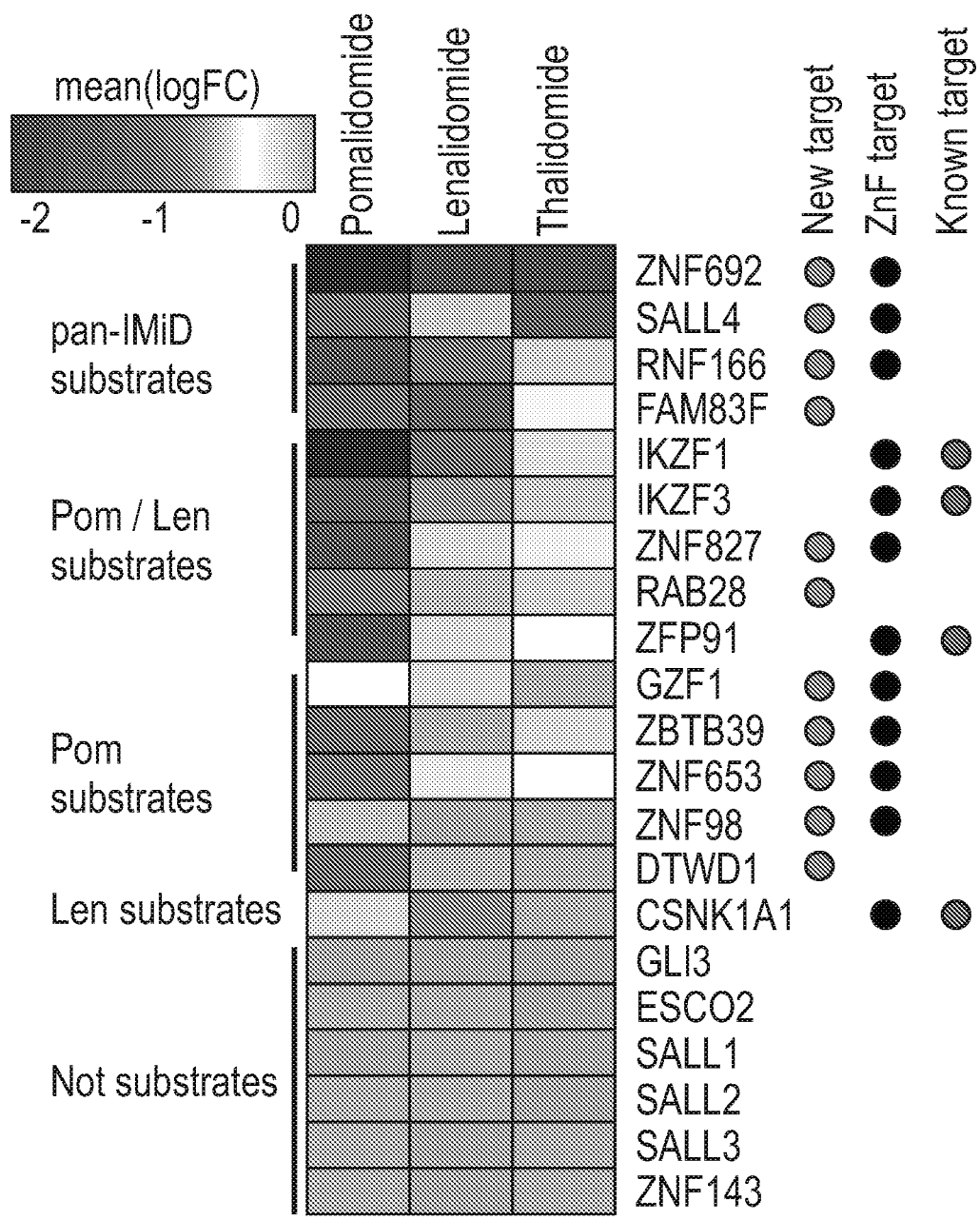
FIG. 4D is a heat map displaying the mean log 2 FC of the identified IMiD-dependent targets comparing treatment with thalidomide, lenalidornide, and pornalidomide. Mean log 2 FC values were derived from averaging across proteomics experiments in four different cell lines (hESC, MM is, Kelly, SK-N-DZ). The heat map colors are scaled with blue indicating a decrease in protein abundance (−2 log 2 FC) and red indicating no change (0 log 2 fC) in protein abundance. Targets newly identified in this study are marked with a green dot, ZnF containing targets with a cyan dot, and previously characterized targets with a gray dot. Substrates are grouped according to their apparent IMiD selectivity in the mass spectrometry-based proteomics. This does not refer to absolute selectivity but rather relative selectivity.

IKZF1/3 are not susceptible to IMiD-mediated degradation in murine cells, and this can be rescued by mutating a single amino acid on the surface of murine CRBN (Ile 391) to the analogous human residue (Val). To determine whether Helios follows a similar pattern, Hoxb8-immortalized myeloid progenitor cells derived from wildtype or Crbn$^{I391V/I391V}$ mice were treated with compound 54. The results showed that Helios was only degraded in Crbn$^{I391V/I391V}$ cells (FIG. 3). Thus, Helios is degradable in murine cells only if they express 'humanized' CRBN.

Example 121: Mass Spectrometry Method

Mass spectrometry profiling of IMiDs (e.g., thalidomide, lenalidomide, and pomalidomide) is illustrated in Donovan et al., eLife 7:e38430 (2018) and Sievers et al., Science 362:eaat0572 (2018).

Sample Preparation TMT LC-MS3 Mass Spectrometry

H9 hESC, Kelly, SK-N-DZ, and MM1s cells were treated with DMSO, 1 µM pomalidomide, 5 µM lenalidomide, or 10 µM thalidomide in biological triplicates (DMSO) or biological duplicates (pomalidomide, lenalidomide, thalidomide) for 5 h, and cells were harvested by centrifugation. Lysis buffer (8 M urea, 50 mM NaCl, 50 mM 4-(2-hydroxyethyl)-1-piperazineethanesulfonic acid (EPPS) pH 8.5, 1× Roche protease inhibitor, and 1× Roche PhosSTOP™) was added to the cell pellets and cells were homogenized by 20 passes through a 21 gauge (1.25 in. long) needle to achieve a cell lysate with a protein concentration between 0.5 and 4 mg mL$^{-1}$. The homogenized sample was clarified by centrifugation at 20,000×g for 10 min at 4° C. A micro-BCA assay (Pierce™) was used to determine the final protein concentration in the cell lysate. 200 µg protein for each sample were reduced and alkylated as previously described (An et al., Nat. Commun. 8:15398 (2017)) (FIG. 4).

Proteins were precipitated using methanol/chloroform. In brief, four volumes of methanol were added to the cell lysate, followed by one volume of chloroform, and finally three volumes of water. The mixture was vortexed and centrifuged at 14,000×g for 5 min to separate the chloroform phase from the aqueous phase. The precipitated protein was washed with three volumes of methanol, centrifuged at 14,000×g for 5 min, and the resulting washed precipitated protein was allowed to air dry.

Precipitated protein was resuspended in 4 M urea, 50 mM HEPES pH 7.4, followed by dilution to 1 M urea with the addition of 200 mM EPPS pH 8 for digestion with LysC (1:50; enzyme:protein) for 12 h at room temperature. The LysC digestion was diluted to 0.5 M urea, 200 mM EPPS pH 8, and then digested with trypsin (1:50; enzyme:protein) for 6 h at 37° C. Tandem mass tag (TMT) reagents (Thermo Fisher Scientific) were dissolved in anhydrous acetonitrile (ACN) according to manufacturer's instructions.

Anhydrous ACN was added to each peptide sample to a final concentration of 30% v/v, and labeling was induced with the addition of TMT reagent to each sample at a ratio of 1:4 peptide:TMT label. The 10-plex labeling reactions were performed for 1.5 h at room temperature and the reaction quenched by the addition of 0.3% hydroxylamine for 15 min at room temperature. The sample channels were combined in a 1:1:1:1:1:1:1:1:1:1 ratio, desalted using $C_{18}$ solid phase extraction cartridges (Waters) and analyzed by liquid chromatography-mass spectrometry (LC-MS) for channel ratio comparison. Samples were then combined using the adjusted volumes determined in the channel ratio analysis and dried down in a speed vacuum. The combined sample was then resuspended in 1% formic acid, and acidified (pH 2-3) before being subjected to desalting with C18 SPE (Sep-Pak®, Waters).

Samples were then offline fractionated into 96 fractions by high pH reverse-phase high performance liquid chromatography (HPLC) (Agilent LC1260) through an aeris peptide xb-c18 column (Phenomenex®) with mobile phase A containing 5% acetonitrile and 10 mM $NH_4HCO_3$ in LC-MS grade $H_2O$, and mobile phase B containing 90% acetonitrile and 10 mM $NH_4HCO_3$ in LC-MS grade $H_2O$ (both pH 8.0). The 96 resulting fractions were then pooled in a non-continuous manner into 24 fractions or 48 fractions and every fraction was used for subsequent mass spectrometry analysis.

Data were collected using an Orbitrap Fusion™ Lumos™ mass spectrometer (Thermo Fisher Scientific, San Jose, Calif., USA) coupled with a Proxeon EASY-nLC™ 1200 LC pump (Thermo Fisher Scientific). Peptides were separated on a 50 cm and 75 m inner diameter EASY-Spray™ column (ES803, Thermo Fisher Scientific). Peptides were separated using a 3 h gradient of 6-27% acetonitrile in 1.0% formic acid with a flow rate of 300 nL/min. Each analysis used an MS3-based TMT method as described previously (McAlister et al., Anal. Chem. 86:7150-7158 (2014)). The data were acquired using a mass range of m/z 350-1350, resolution 120,000, AGC target $1\times10^6$, maximum injection time 100 ms, dynamic exclusion of 90 s for the peptide measurements in the Orbitrap. Data-dependent MS2 spectra were acquired in the ion trap with a normalized collision energy (NCE) set at 35%, AGC target set to $1.8\times10^4$, and a maximum injection time of 120 ms. MS3 scans were acquired in the Orbitrap with a HCD collision energy set to 55%, AGC target set to $1.5\times10^5$, maximum injection time of 150 ms, resolution at 50,000, and with a maximum synchronous precursor selection (SPS) precursors set to 10.

LC-MS Data Analysis

Proteome Discoverer 2.2 (Thermo Fisher) was used for RAW file processing and controlling peptide and protein level false discovery rates, assembling proteins from peptides, and protein quantification from peptides. MS/MS spectra were searched against a Uniprot human database (September 2016) with both the forward and reverse sequences. Database search criteria are as follows: tryptic with two missed cleavages, a precursor mass tolerance of 20 ppm, fragment ion mass tolerance of 0.6 Da, static alkylation of cysteine (57.02146 Da), static TMT labeling of lysine residues and N-termini of peptides (229.16293 Da), and variable oxidation of methionine (15.99491 Da). TMT reporter ion intensities were measured using a 0.003 Da window around the theoretical m/z for each reporter ion in the MS3 scan. Peptide spectral matches with poor-quality MS3 spectra were excluded from quantitation (summed signal-to-noise across 10 channels >200 and precursor isolation specificity <0.5). Reporter ion intensities were normalized and scaled using in-house scripts and the R framework (R Core Team, R Foundation for Statistical Computing, Vienna, Austria (2013)). Statistical analysis was carried out using the limma package within the R framework (Ritchie et al., Nucleic Acids Res. 43:e47 (2015)).

Example 122: Biochemical TR-FRET and Degradation of IKZF2, GSPT1, and SALL4 ZNF1-2

A focused library of imide analogs was synthesized and assessed for their ability to induce dimerization between CRBN and Helios in a time-resolved fluorescence energy transfer (TR-FRET) assay as described above (Table 1) as well as in fluorescence mCherry reporter, GFP-tagged IKZF1, IKZF2, SALL4 and GSPT1 degradation assays both described below.

TR-FRET Dimerization Assay

Compounds in binding assays were dispensed into a 384-well microplate (Corning, 4514) using pin transfer to 1% DMSO and containing 100 nM biotinylated strep-avi-IKZF1 or strep-avi-IKZF2, 200 nM $His_6$-spy-DDB1ΔB-His-spy-CRBN$_{Bodipy-Spycatcher}$, and 2 nM terbium-coupled streptavidin (Invitrogen™) in a buffer containing 50 mM Tris pH 7.5, 100 mM NaCl, 1 mM TCEP, and 0.1% Pluronic F-68 solution (Sigma-Aldrich®). Prior to TR-FRET measurements being conducted, the reactions were incubated for 15 min at rt. After excitation of terbium fluorescence at 337 nm, emissions at 490 nm (terbium) and 520 nm (Bodipy) were recorded with a 70 μs delay over 600 μs to reduce background fluorescence, and the reaction was followed over 30×200 s cycles of each data point using a PHERAstar® FS microplate reader (BMG Labtech). The TR-FRET signal of each data point was extracted by calculating the 520/490 nm ratios. Data from single measurements (n=1), each calculated as an average of at least three technical replicates per well per experiment are presented in Table 1.

Cellular Degradation Assays

IKZF1Δ, IKZF2Δ, GSPT1 and SALL4 ZnF1-2 were subcloned into mammalian pcDNA5/FRT Vector (Ampicillin and Hygromycin B resistant) modified to contain MCS-eGFP-P2A-mCherry. Stable cell lines expressing eGFP-protein fusion and mCherry reporter were generated using Flp-In™ 293 system. Plasmid (0.3 μg) and pOG44 (4.7 μg) DNA were preincubated in 100 μL of Opti-MEM® I (Gibco®, Life Technologies™) media containing 0.05 mg/mL Lipofectamine® 2000 (Invitrogen™) for 20 min and added to Flp-In™ 293 cells containing 1.9 ml of DMEM media (Gibco®, Life Technologies™) per well in a 6-well plate format (Falcon, 353046). Cells were propagated after 48 h and transferred into a 10 cm² plate (Corning, 430165) in DMEM media containing 50 μg/mL of Hygromycin B (REF 10687010, Invitrogen™) as a selection marker. Following 2-3 passage cycle, FACS (FACSAria™ II, BD) was used to enrich for cells expressing eGFP and mCherry. Cells stably expressing the IKZF1Δ, IKZF2Δ, GSPT1 or SALL4 Znf1-2 GFP fusions with mCherry reporter were seeded at 30-50% confluency in 384-well plates with 50 μL Fluoro-Brite™ DMEM media (Thermo Fisher Scientific, A18967) containing 10% FBS per well a day before compound treatment. Compound titrations were dispensed using a D300e Digital Dispenser (HP), normalized to 0.5% DMSO, and incubated with cells for 5 hours. The assay plate was imaged immediately using an Acumen® High Content Imager (TTP Labtech) with 488 nm and 561 nm lasers in 2 m×1 m grid per well format.

The resulting images were analyzed using CellProfiler™. A series of image analysis steps ('image analysis pipeline') was constructed. First, the red and green channels were aligned and cropped to target the middle of each well (to avoid analysis of heavily clumped cells at the edges), and a background illumination function was calculated for both red and green channels of each well individually and subtracted to correct for illumination variations across the 384-well plate from various sources of error. An additional step was then applied to the green channel to suppress the analysis of large auto fluorescent artifacts and enhance the analysis of cell specific fluorescence by way of selecting for objects under a given size, 30 A.U., and with a given shape, speckles. mCherry-positive cells were then identified in the red channel filtering for objects between 8-60 pixels in diameter and using intensity to distinguish between clumped objects. The green channel was then segmented into GFP positive and negative areas and objects were labeled as GFP positive if at least 40% of it overlapped with a GFP positive area. The fraction of GFP-positive cells/mCherry-positive cells in each well was then calculated, and the green and red images were rescaled for visualization. The representative data from n=1 measurement at 3 concentrations of ligands after 5 h incubation are shown in Table 1 and Table 2.

TABLE 1

Biochemical TR-FRET and Degradation of IKZF2.

| Compounds | TR-FRET-IKZF2 (Normalized to CC-885) | | | IKZF2 GFP/RFP Relative Abundance | | |
|---|---|---|---|---|---|---|
| | 6.6667E−05 | 6.6667E−06 | 6.6667E−07 | 2.00E−05 | 2.00E−06 | 2.00E−07 |
| CC-885 | 1.065 | 0.982 | 0.953 | 0.277 | 0.281 | 0.289 |
| DMSO | 0.006 | 0.003 | 0.004 | 1.003 | 1.002 | 0.991 |
| 13 | 0.032 | 0.028 | 0.019 | 1.040 | 1.005 | 1.070 |
| 14 | 0.046 | 0.040 | 0.022 | 1.022 | 0.982 | 1.040 |
| 15 | 0.050 | 0.039 | 0.025 | 1.024 | 1.036 | 1.028 |
| 16 | 0.032 | 0.028 | 0.018 | 0.987 | 1.015 | 1.006 |
| 17 | 0.043 | 0.032 | 0.015 | 1.006 | 0.996 | 1.037 |
| 18 | 0.062 | 0.018 | 0.024 | 1.055 | 0.992 | 0.990 |
| 19 | 0.217 | 0.041 | 0.057 | 0.653 | 0.980 | 0.991 |
| 20 | 0.050 | 0.017 | 0.014 | 0.952 | 0.987 | 1.025 |
| 21 | 0.047 | 0.019 | 0.012 | 0.996 | 0.951 | 0.946 |
| 22 | 0.055 | 0.032 | 0.018 | 1.001 | 0.982 | 0.935 |
| 23 | 0.326 | 0.259 | 0.196 | 1.013 | 1.016 | 1.015 |
| 24 | 0.391 | 0.344 | 0.282 | 0.959 | 0.954 | 1.038 |
| 25 | 0.339 | 0.282 | 0.230 | 0.966 | 0.978 | 0.955 |
| 26 | 0.365 | 0.293 | 0.228 | 0.913 | 0.929 | 0.981 |
| 27 | 0.137 | 0.105 | 0.084 | 1.004 | 0.990 | 0.931 |
| 28 | 0.072 | 0.050 | 0.053 | 1.006 | 1.011 | 1.064 |
| 29 | 0.347 | 0.297 | 0.270 | 0.982 | 1.005 | 0.942 |
| 2 | 0.386 | 0.306 | 0.286 | 0.878 | 0.920 | 0.864 |
| 30 | 0.386 | 0.324 | 0.228 | 0.916 | 0.928 | 0.979 |
| 31 | 0.628 | 0.521 | 0.434 | 0.494 | 0.638 | 0.766 |
| 32 | 0.274 | 0.213 | 0.210 | 1.008 | 0.941 | 0.958 |
| 33 | 0.584 | 0.491 | 0.452 | 0.372 | 0.521 | 0.570 |
| 34 | 0.077 | 0.064 | 0.059 | 0.981 | 1.018 | 0.950 |
| 35 | 0.520 | 0.447 | 0.402 | 0.667 | 0.709 | 0.806 |
| 36 | 0.183 | 0.148 | 0.115 | 0.943 | 1.027 | 1.049 |
| 41 | 0.170 | 0.126 | 0.104 | 0.969 | 1.027 | 1.040 |
| 42 | 0.407 | 0.318 | 0.209 | 1.056 | 1.050 | 0.999 |
| 43 | 0.443 | 0.353 | 0.278 | 1.054 | 1.007 | 0.980 |
| 44 | 1.223 | 1.191 | 1.119 | 0.042 | 0.079 | 0.085 |
| 45 | 0.079 | 0.059 | 0.051 | 1.015 | 1.022 | 1.022 |
| 46 | 0.787 | 0.828 | 0.701 | 0.242 | 0.361 | 0.510 |
| 3 | 0.357 | 0.267 | 0.253 | 1.032 | 0.973 | 0.979 |
| 4 | 0.485 | 0.411 | 0.270 | 0.925 | 1.028 | 1.002 |
| 5 | 0.376 | 0.296 | 0.187 | 0.930 | 1.000 | 1.020 |
| 47 | 0.288 | 0.230 | 0.191 | 1.019 | 1.051 | 0.995 |
| 37 | 0.620 | 0.422 | 0.355 | 0.938 | 1.004 | 0.988 |
| 38 | 0.328 | 0.266 | 0.210 | 0.885 | 1.002 | 0.977 |
| 39 | 0.271 | 0.230 | 0.174 | 1.070 | 1.008 | 1.047 |
| 48 | 0.140 | 0.079 | 0.044 | 1.053 | 1.076 | 1.057 |
| 49 | 0.801 | 0.690 | 0.472 | 0.665 | 0.612 | 0.830 |
| 50 | 1.011 | 0.889 | 0.848 | 0.188 | 0.195 | 0.267 |
| 51 | 0.037 | 0.032 | 0.017 | 1.083 | 1.044 | 1.024 |
| 52 | 1.559 | 1.367 | 1.205 | 0.058 | 0.059 | 0.062 |
| 53 | 1.708 | 1.574 | 1.455 | 0.030 | 0.022 | 0.029 |
| 54 | 1.729 | 1.629 | 1.382 | 0.030 | 0.024 | 0.027 |
| 55 | 0.523 | 0.430 | 0.321 | 1.029 | 0.936 | 0.938 |
| 56 | 0.383 | 0.282 | 0.187 | 1.092 | 1.025 | 0.983 |
| 57 | 0.530 | 0.365 | 0.282 | 0.843 | 0.622 | 0.656 |
| 58 | 1.184 | 1.061 | 0.927 | 0.064 | 0.077 | 0.122 |
| 59 | 1.224 | 1.165 | 1.035 | 0.099 | 0.072 | 0.108 |
| 60 | 1.082 | 0.945 | 0.833 | 0.087 | 0.151 | 0.185 |
| 61 | 1.465 | 1.248 | 1.201 | 0.044 | 0.045 | 0.050 |
| 62 | 1.642 | 1.563 | 1.483 | 0.040 | 0.015 | 0.036 |
| 63 | 0.703 | 0.649 | 0.625 | 0.428 | 0.339 | 0.470 |
| 82 | 0.999 | 0.975 | 0.838 | 0.158 | 0.220 | 0.293 |
| 110 | 1.017 | 1.086 | 0.853 | 0.048 | 0.048 | 0.038 |
| 119 | 0.817 | 0.671 | 0.629 | 0.392 | 0.516 | 0.544 |
| 81 | 0.703 | 0.585 | 0.519 | 0.587 | 0.660 | 0.737 |

TABLE 1-continued

Biochemical TR-FRET and Degradation of IKZF2.

| Compounds | TR-FRET-IKZF2 (Normalized to CC-885) | | | IKZF2 GFP/RFP Relative Abundance | | |
|---|---|---|---|---|---|---|
| | 6.6667E−05 | 6.6667E−06 | 6.6667E−07 | 2.00E−05 | 2.00E−06 | 2.00E−07 |
| 120 | 1.263 | 1.011 | 0.860 | 0.077 | 0.117 | 0.157 |
| 121 | 1.521 | 1.376 | 1.357 | 0.071 | 0.087 | 0.051 |
| 122 | 0.715 | 0.628 | 0.469 | 0.738 | 0.789 | 0.833 |
| 123 | 1.234 | 1.087 | 0.960 | 0.065 | 0.093 | 0.078 |
| 107 | 0.086 | 0.066 | 0.066 | 0.225 | 1.034 | 1.048 |
| 69 | 2.037 | 1.970 | 1.737 | 0.032 | 0.013 | 0.028 |
| 124 | 0.159 | 0.130 | 0.077 | 0.829 | 1.015 | 0.985 |
| 112 | 0.048 | 0.035 | 0.035 | 1.081 | 1.047 | 1.034 |
| 95 | 0.124 | 0.109 | 0.094 | 1.070 | 1.058 | 1.029 |
| 74 | 2.010 | 1.914 | 1.817 | 0.021 | 0.033 | 0.032 |
| 71 | 1.811 | 1.675 | 1.657 | 0.016 | 0.018 | 0.019 |
| 70 | 1.531 | 1.409 | 1.271 | 0.021 | 0.057 | 0.031 |
| 109 | 0.463 | 0.640 | 0.506 | 0.563 | 0.313 | 0.539 |
| 76 | 1.961 | 1.657 | 1.577 | 0.027 | 0.036 | 0.032 |
| 126 | 1.762 | 1.603 | 1.420 | 0.059 | 0.033 | 0.047 |
| 64 | 0.030 | 0.025 | 0.021 | 1.087 | 1.038 | 1.061 |
| 127 | 1.390 | 1.362 | 1.195 | 0.266 | 0.047 | 0.060 |
| 129 | 1.626 | 1.551 | 1.583 | 0.063 | 0.013 | 0.027 |
| 137 | 1.665 | 1.677 | 1.665 | 0.023 | 0.009 | 0.011 |
| 140 | 2.291 | 1.72 | 1.626 | 0.174 | 0.017 | 0.013 |

TABLE 2

Degradation of IKZF1, GSPT1, and SALL4 ZNF1-2.

| Compounds | IKZF1 GFP/RFP Relative Abundance | | | GSPT1 GFP/RFP Relative Abundance | | | SALL4 ZNF1-2 GFP/RFP Relative Abundance | | |
|---|---|---|---|---|---|---|---|---|---|
| | 2.00E−05 | 2.00E−06 | 2.00E−07 | 2.00E−05 | 2.00E−06 | 2.00E−07 | 2.00E−05 | 2.00E−06 | 2.00E−07 |
| CC-885 | 0.133 | 0.071 | 0.077 | 0.240 | 0.041 | 0.012 | 1.000 | 0.876 | 0.852 |
| DMSO | 1.011 | 1.012 | 0.985 | 1.054 | 0.900 | 0.929 | 1.019 | 1.003 | 0.972 |
| 13 | 1.069 | 1.076 | 1.058 | 1.172 | 1.162 | 1.004 | 0.962 | 1.017 | 1.017 |
| 14 | 1.033 | 1.031 | 1.043 | 1.058 | 1.018 | 0.915 | 0.955 | 0.944 | 0.983 |
| 15 | 1.041 | 1.032 | 0.996 | 1.009 | 1.036 | 1.043 | 0.912 | 0.910 | 1.047 |
| 16 | 1.070 | 1.011 | 1.053 | 0.978 | 0.876 | 1.006 | 1.001 | 1.007 | 1.013 |
| 17 | 1.020 | 1.018 | 1.025 | 0.942 | 1.001 | 0.795 | 0.897 | 0.912 | 0.895 |
| 18 | 0.943 | 0.833 | 0.847 | 0.880 | 0.650 | 0.498 | 0.967 | 0.999 | 0.904 |
| 19 | 0.216 | 0.818 | 0.110 | 1.023 | 0.946 | 0.953 | 1.010 | 1.012 | 0.597 |
| 20 | 0.721 | 0.895 | 0.342 | 0.901 | 1.036 | 1.069 | 0.894 | 0.908 | 0.892 |
| 21 | 0.842 | 0.975 | 0.998 | 0.693 | 0.938 | 0.909 | 0.937 | 0.921 | 0.957 |
| 22 | 0.984 | 1.028 | 0.939 | 1.058 | 0.883 | 0.745 | 0.953 | 0.962 | 1.044 |
| 23 | 0.866 | 1.044 | 0.756 | 0.976 | 0.936 | 0.953 | 0.922 | 0.979 | 0.981 |
| 24 | 0.236 | 0.342 | 0.369 | 1.153 | 1.221 | 1.218 | 0.937 | 0.941 | 0.942 |
| 25 | 0.258 | 0.298 | 0.341 | 1.019 | 1.233 | 1.201 | 0.831 | 0.897 | 0.887 |
| 26 | 0.290 | 0.381 | 0.478 | 0.952 | 1.036 | 1.107 | 0.855 | 0.869 | 0.787 |
| 27 | 0.701 | 0.776 | 0.801 | 0.881 | 1.083 | 0.987 | 1.026 | 1.005 | 0.913 |
| 28 | 0.978 | 0.996 | 1.029 | 1.001 | 0.917 | 0.805 | 0.969 | 0.936 | 0.946 |
| 29 | 0.495 | 0.516 | 0.602 | 0.790 | 0.913 | 0.729 | 0.958 | 0.913 | 0.908 |
| 2 | 0.143 | 0.143 | 0.147 | 0.763 | 0.903 | 0.930 | 0.724 | 0.762 | 0.774 |
| 30 | 0.388 | 0.437 | 0.631 | 1.100 | 1.129 | 1.192 | 0.815 | 0.786 | 0.896 |
| 31 | 0.254 | 0.290 | 0.399 | 0.666 | 1.197 | 1.240 | 0.755 | 0.626 | 0.713 |
| 32 | 0.748 | 0.795 | 0.832 | 0.646 | 0.855 | 0.970 | 1.008 | 0.889 | 0.901 |
| 33 | 0.339 | 0.413 | 0.445 | 0.944 | 0.952 | 0.956 | 0.783 | 0.813 | 0.860 |
| 34 | 1.042 | 0.984 | 0.904 | 0.867 | 0.821 | 0.878 | 0.940 | 0.944 | 0.943 |
| 35 | 0.154 | 0.181 | 0.182 | 0.975 | 1.074 | 0.938 | 0.928 | 0.903 | 0.888 |
| 36 | 0.687 | 0.796 | 0.860 | 1.112 | 1.009 | 1.006 | 1.000 | 1.033 | 0.974 |
| 41 | 0.638 | 0.909 | 1.003 | 0.038 | 0.062 | 0.077 | 1.020 | 0.994 | 1.004 |
| 42 | 0.775 | 0.536 | 0.577 | 0.118 | 0.182 | 0.215 | 1.122 | 0.997 | 1.018 |
| 43 | 0.996 | 0.240 | 0.301 | 0.083 | 0.072 | 0.087 | 1.072 | 0.897 | 0.888 |
| 44 | 0.059 | 0.071 | 0.072 | 0.399 | 0.504 | 0.744 | 0.888 | 0.742 | 0.702 |
| 45 | 0.957 | 1.027 | 1.060 | 0.476 | 0.921 | 1.093 | 1.059 | 0.993 | 0.948 |
| 46 | 0.045 | 0.087 | 0.112 | 0.048 | 0.089 | 0.076 | 0.950 | 0.906 | 0.854 |
| 3 | 0.242 | 0.370 | 0.349 | 1.204 | 1.006 | 1.190 | 0.914 | 0.884 | 0.879 |
| 4 | 0.314 | 0.433 | 0.550 | 0.922 | 0.904 | 0.750 | 0.862 | 0.850 | 0.903 |
| 5 | 0.395 | 0.478 | 0.650 | 0.714 | 0.843 | 1.050 | 1.008 | 0.946 | 0.992 |
| 47 | 0.312 | 0.298 | 0.326 | 0.034 | 0.041 | 0.036 | 1.060 | 1.039 | 1.010 |
| 37 | 0.315 | 0.349 | 0.344 | 0.787 | 1.111 | 1.010 | 0.939 | 0.865 | 0.891 |
| 38 | 0.728 | 0.663 | 0.621 | 1.174 | 1.216 | 0.870 | 1.005 | 0.887 | 0.742 |
| 39 | 0.705 | 0.691 | 0.677 | 0.743 | 0.813 | 0.830 | 1.110 | 1.006 | 1.043 |
| 48 | 1.041 | 0.903 | 1.000 | 1.591 | 0.365 | 0.579 | | | |
| 49 | 0.268 | 0.187 | 0.314 | 0.125 | 0.055 | 0.069 | | | |

TABLE 2-continued

Degradation of IKZF1, GSPT1, and SALL4 ZNF1-2.

| | IKZF1 GFP/RFP Relative Abundance | | | GSPT1 GFP/RFP Relative Abundance | | | SALL4 ZNF1-2 GFP/RFP Relative Abundance | | |
|---|---|---|---|---|---|---|---|---|---|
| Compounds | 2.00E−05 | 2.00E−06 | 2.00E−07 | 2.00E−05 | 2.00E−06 | 2.00E−07 | 2.00E−05 | 2.00E−06 | 2.00E−07 |
| 50 | 0.073 | 0.068 | 0.093 | 0.645 | 0.702 | 0.643 | | | |
| 51 | 0.861 | 1.001 | 1.026 | 1.680 | 0.829 | 0.775 | | | |
| 52 | 0.103 | 0.092 | 0.080 | 0.308 | 0.815 | 0.787 | | | |
| 53 | 0.110 | 0.077 | 0.078 | 0.232 | 0.982 | 0.931 | | | |
| 54 | 0.119 | 0.106 | 0.102 | 0.420 | 0.638 | 0.567 | | | |
| 55 | 0.471 | 0.212 | 0.251 | 0.096 | 0.153 | 0.180 | | | |
| 56 | 1.190 | 0.319 | 0.403 | 1.572 | 0.074 | 0.112 | | | |
| 57 | 0.502 | 0.214 | 0.305 | 0.385 | 0.559 | 0.779 | | | |
| 58 | 0.075 | 0.070 | 0.074 | 0.421 | 0.603 | 0.594 | | | |
| 59 | 0.144 | 0.097 | 0.066 | 0.247 | 0.734 | 0.952 | | | |
| 60 | 0.132 | 0.078 | 0.091 | 0.387 | 0.558 | 0.528 | | | |
| 61 | 0.111 | 0.104 | 0.103 | 0.190 | 0.466 | 0.737 | | | |
| 62 | 0.133 | 0.098 | 0.109 | 0.353 | 1.021 | 1.208 | | | |
| 63 | 0.081 | 0.068 | 0.086 | 0.274 | 0.722 | 0.844 | | | |
| 82 | 0.085 | 0.085 | 0.069 | | | | | | |
| 110 | 0.096 | 0.066 | 0.086 | | | | | | |
| 119 | 0.055 | 0.079 | 0.101 | | | | | | |
| 81 | 0.063 | 0.056 | 0.094 | | | | | | |
| 120 | 0.094 | 0.110 | 0.092 | | | | | | |
| 121 | 0.125 | 0.093 | 0.120 | | | | | | |
| 122 | 0.076 | 0.088 | 0.096 | | | | | | |
| 123 | 0.083 | 0.057 | 0.092 | | | | | | |
| 107 | 0.245 | 1.043 | 0.997 | | | | | | |
| 69 | 0.086 | 0.140 | 0.132 | | | | | | |
| 124 | 0.689 | 0.978 | 1.005 | | | | | | |
| 112 | 0.726 | 0.949 | 1.002 | | | | | | |
| 95 | 0.944 | 0.904 | 0.960 | | | | | | |
| 74 | 0.096 | 0.090 | 0.114 | | | | | | |
| 71 | 0.088 | 0.086 | 0.076 | | | | | | |
| 70 | 0.076 | 0.080 | 0.103 | | | | | | |
| 109 | 0.189 | 0.101 | 0.142 | | | | | | |
| 76 | 0.103 | 0.069 | 0.107 | | | | | | |
| 126 | 0.177 | 0.072 | 0.100 | | | | | | |
| 64 | 1.154 | 1.077 | 1.122 | | | | | | |
| 127 | 0.313 | 0.079 | 0.079 | | | | | | |

There was a correlation between high TR-FRET ternary complex formation (CRBN-IKZF2) and IKZF2 degradation, where CC-885 was able to recruit IKZF2 to CRBN in TR-FRET dimerization assay, and also degrade the IKZF2 in cellular assay (Table 1). Highly active compounds (TR-FRET>1.0 A.U. at 667 nM) in the TR-FRET dimerization assay included compounds 44, 52-54, 59, 61, 62, 121, 69, 70, 71, 74, 76, 126, 127, 129, 137 and 140. Inactive compounds (TR-FRET<0.1 A.U. at 667 nM) in the TR-FRET dimerization assay included compounds 64, 95, 112, 124, 107, 51, 48, and others. The compounds inactive in the dimerization assay also appeared to show low or no activity in IKZF2 cellular degradation assay.

TABLE 3

$DC_{50}$ values of inventive compounds.

| Compound | IKZF2 $DC_{50}$ (nM) | IKZF1 $DC_{50}$ (nM) | GSPT1 $DC_{50}$ (nM) |
|---|---|---|---|
| Lenalidomide | >1000 | 14 | >1000 |
| CC-885 | 80.7 | 0.56 | 0.084 |
| 49 | 7.2 | 1.9 | >1000 |
| 69 | 3.6 | 14 | >1000 |
| 62 | 29 | 26 | >1000 |
| 74 | 1.9 | 7.8 | >1000 |
| 71 | 1.9 | 2.1 | >1000 |
| 139 | 17 | 167 | >1000 |
| 142 | 16 | 16 | >1000 |
| 148 | 13 | 3.2 | >1000 |

TABLE 3-continued $DC_{50}$ values of inventive compounds.

| Compound | IKZF2 $DC_{50}$ (nM) | IKZF1 $DC_{50}$ (nM) | GSPT1 $DC_{50}$ (nM) |
|---|---|---|---|
| 78 | 2.2 | 1.9 | — |
| 125 | 24 | 1.7 | >1000 |

Inventive compounds in Table 3 were potent degrades of IKZF1 and IKZF2, compounds 71 and 74 were most potent against IKZF2, compound 139 achieved 10-fold degradation selectivity IKZF2/IKZF1, compound 74 achieved ~4-fold selectivity IKZF2/IKZF1, and compounds 49, 78, and 125 were most potent against IKZF1. None of the compounds tested showed degradation of GSPT1. The degradation assay was performed as described above. Specifically, compounds were in triplicate, 11 point dose response range 1 µM-2.5 µM using D300 (HP), normalizing DMSO across the plate to 0.5%. Degradation was measured after 5 h of compound treatment and the concentrations that lead to half degradation at 5 h ($DC_{50,5\ h}$) were calculated using the nonlinear fit variable slope model (GraphPad Software).

Example 123: Time-Resolved Fluorescence Energy Transfer Ratios in an IKFZ2-CRBN Dimerization Assay (TR-FRET)

Figure 5:
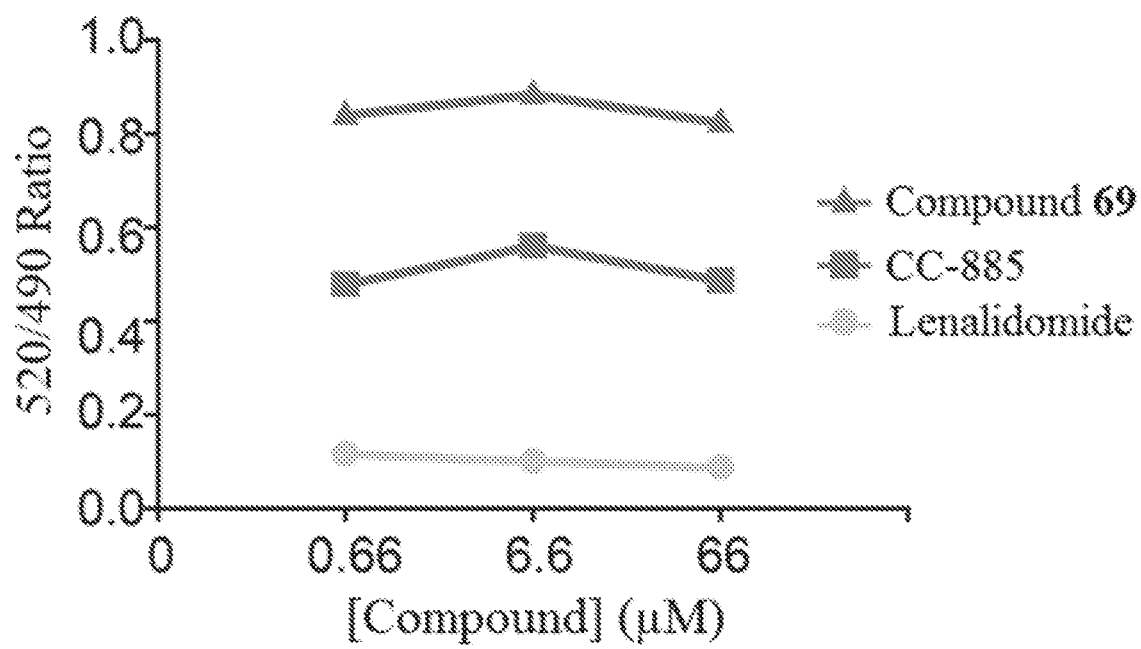
FIG. 5 is a graph that shows the time-resolved fluorescence energy transfer ratios of indicated compounds in an IKFZ2-CRBN dirmerization assay (TR-FRET).

BODIPY-labeled CRBN in complex with Damage Specific DNA Binding Protein 1 (DDB1) harboring an internal deletion of the flexible BPB propeller (DDB1AB-CRBN)

and in vitro biotinylated IKZF2 were treated with increasing concentrations of the indicated compounds in the presence of tracer amounts of Terbium-Streptavidin (Tb-SA). Compound-induced recruitment of IKZF2 to CRBN was quantified following the 520/490 TR-FRET ratio using a PHER-Astar® plate reader (BMG) utilizing two synchronized PMTs to reduce background. The results showed that compound 69 induced higher TR-FRET signals than CC-885 (positive control) or lenalidomide (negative control) (FIG. 5).

Example 124: Degradation in Crbn−/− Jurkat Cells

Figure 6:
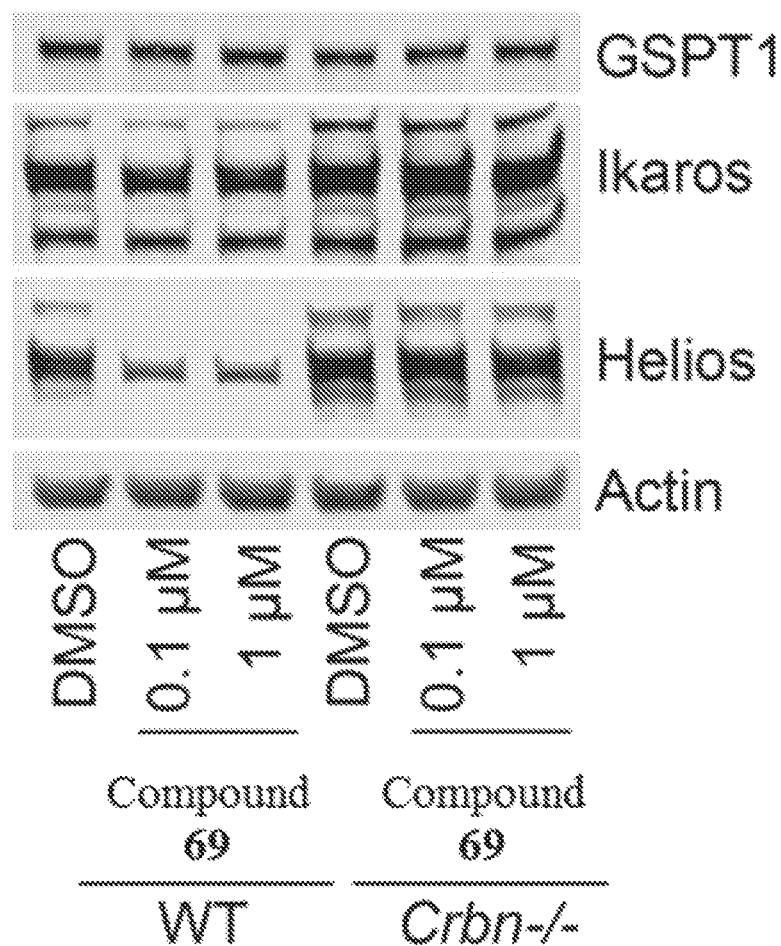
FIG. 6 is an immunoblot from wildtype and Crbn−/− Jurkat cells treated with compound 69 for 4 h.

Cells were lysed in M-PER buffer (Thermo Scientific) containing protease/phosphatase inhibitor cocktail (Roche). Protein concentration was measured using a BCA assay (Pierce™) Equivalent amounts of each sample were loaded on 4-12% Bis-Tris gels (Invitrogen™) transferred to nitrocellulose membranes, and immunoblotted with the indicated antibodies. IRDye®800-labeled goat anti-rabbit IgG and IRDye®680-labeled goat anti-mouse IgG (LI-COR®) secondary antibodies were purchased from LI-COR®, and membranes were detected on an Odyssey® detection system (LI-COR® Biosciences). Immunoblots for GSPT1, Ikaros, Helios, and Actin from wildtype or Crbn−/− Jurkat cells were treated with compound 69 for 4b at the indicated concentrations, which showed that compound 69 induced CRBN-dependent Helios degradation but did not affect the stability of GSPT1 or Ikaros (FIG. 6).

Example 125: Degradation in Jurkat Cells

Figure 7:
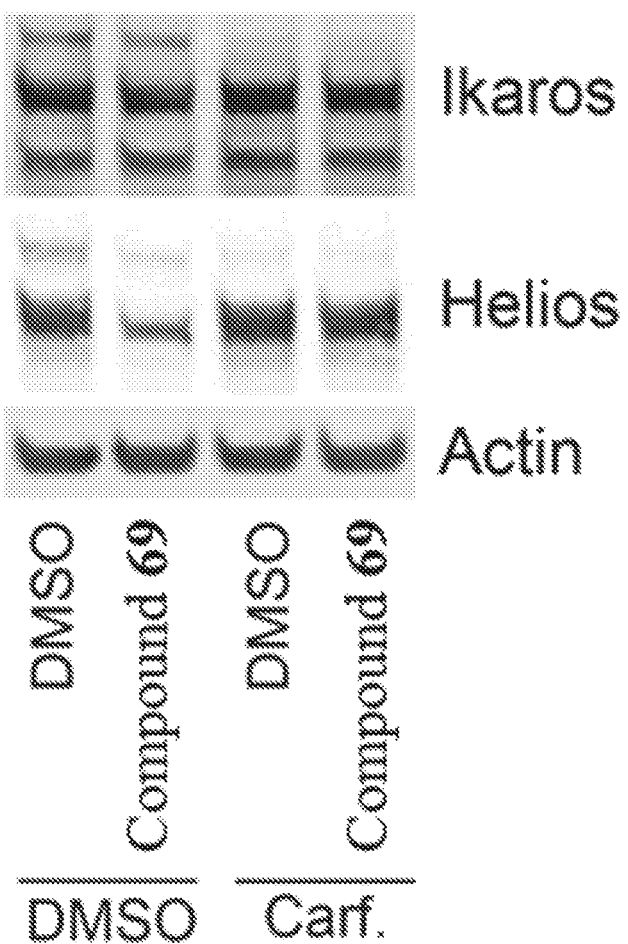
FIG. 7 is an imnmunoblot from Jurkat cells treated with 1 μM of compound 69 with or without 1 μM of carfilzomib (proteasome inhibitor) for 4 h.

Cells were lysed in M-PER buffer (Thermo Scientific) containing protease/phosphatase inhibitor cocktail (Roche). Protein concentration was measured using a BCA assay (Pierce™) Equivalent amounts of each sample were loaded on 4-12% Bis-Tris gels (Invitrogen™) transferred to nitrocellulose membranes, and immunoblotted with the indicated antibodies. IRDye®800-labeled goat anti-rabbit IgG and IRDye®680-labeled goat anti-mouse IgG (LI-COR®) secondary antibodies were purchased from LI-COR®, and membranes were detected on an Odyssey detection system (LI-COR® Biosciences). Immunoblot for Ikaros and Helios from Jurkat cells treated with 1 µM of compound 69 with or without 1 µM of carfilzomib (proteasome inhibitor) for 4 h, which showed that compound 69-induced Helios degradation is dependent on the proteasome (FIG. 7).

Example 126: Flow Cytometry of Ikaros and Helios

Figure 8A:
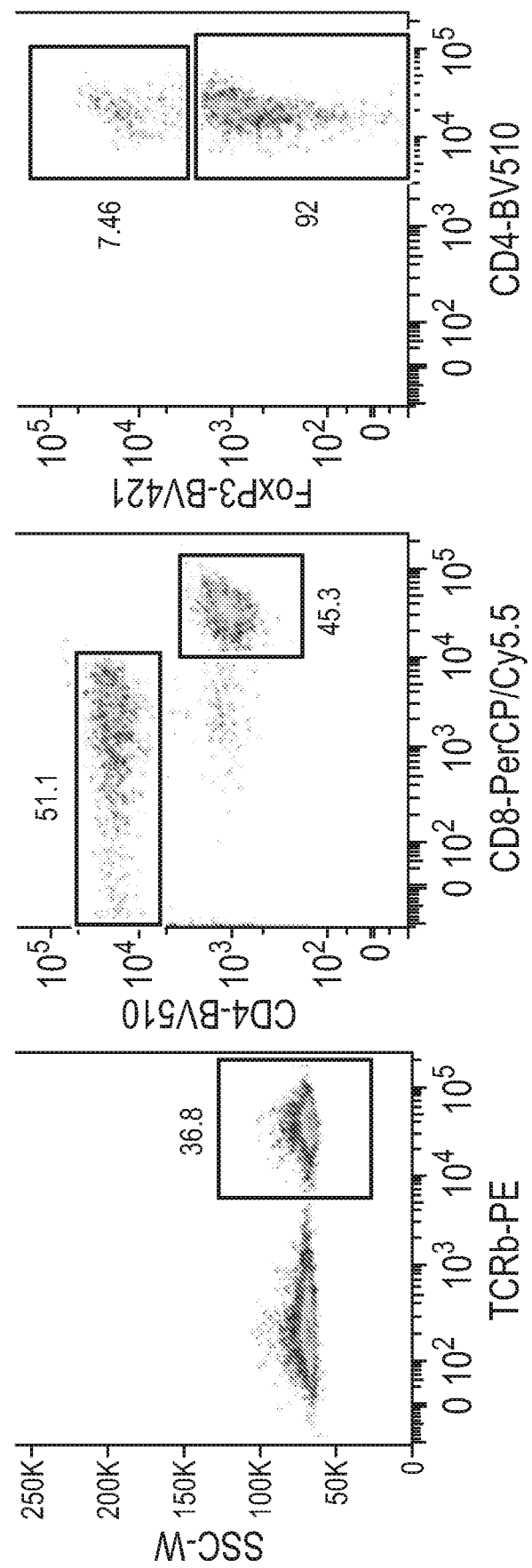
FIG. 8A-FIG. 8B are a series of graphs depicting levels of Ikaros and Helios that were assessed by flow cytometry.
Figure 8B:
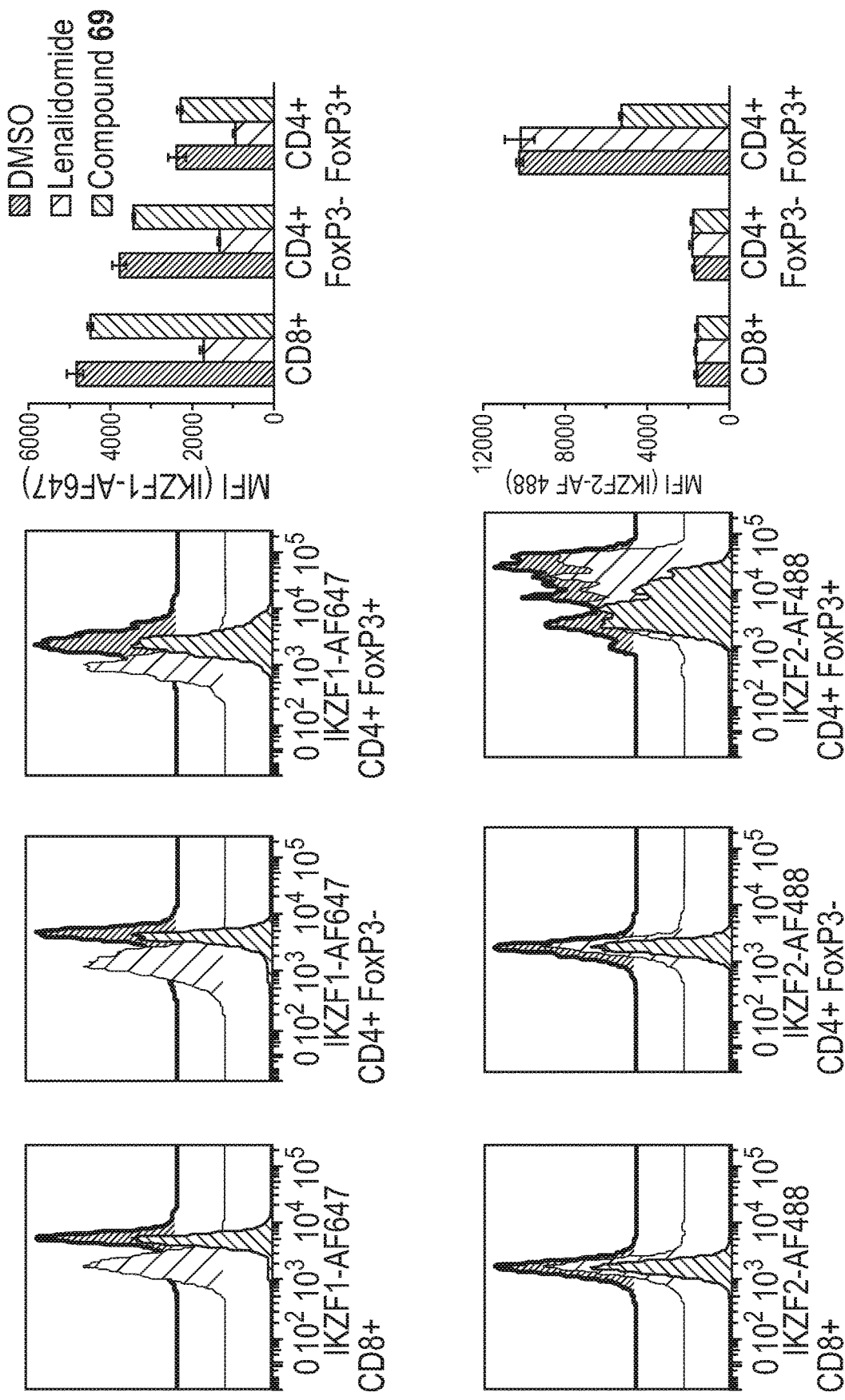

Splenocytes were fixed/permeabilized and stained with fluorochrome-coupled antibodies. FACS plots of murine splenocytes were stained for TCRβ, CD4, CD8, and FoxP3 (FIG. 8A). Ikaros and Helios of splenic T cell subpopulations from Crbn$^{I391V/I391V}$ mice were treated with 1 µM of indicated compounds for 16 h, demonstrating that compound 69 is capable of inducing degradation of Helios but not Ikaros in regulatory T cells (FIG. 8B).

Example 127: Increased Production of IFNγ

Figure 9A:
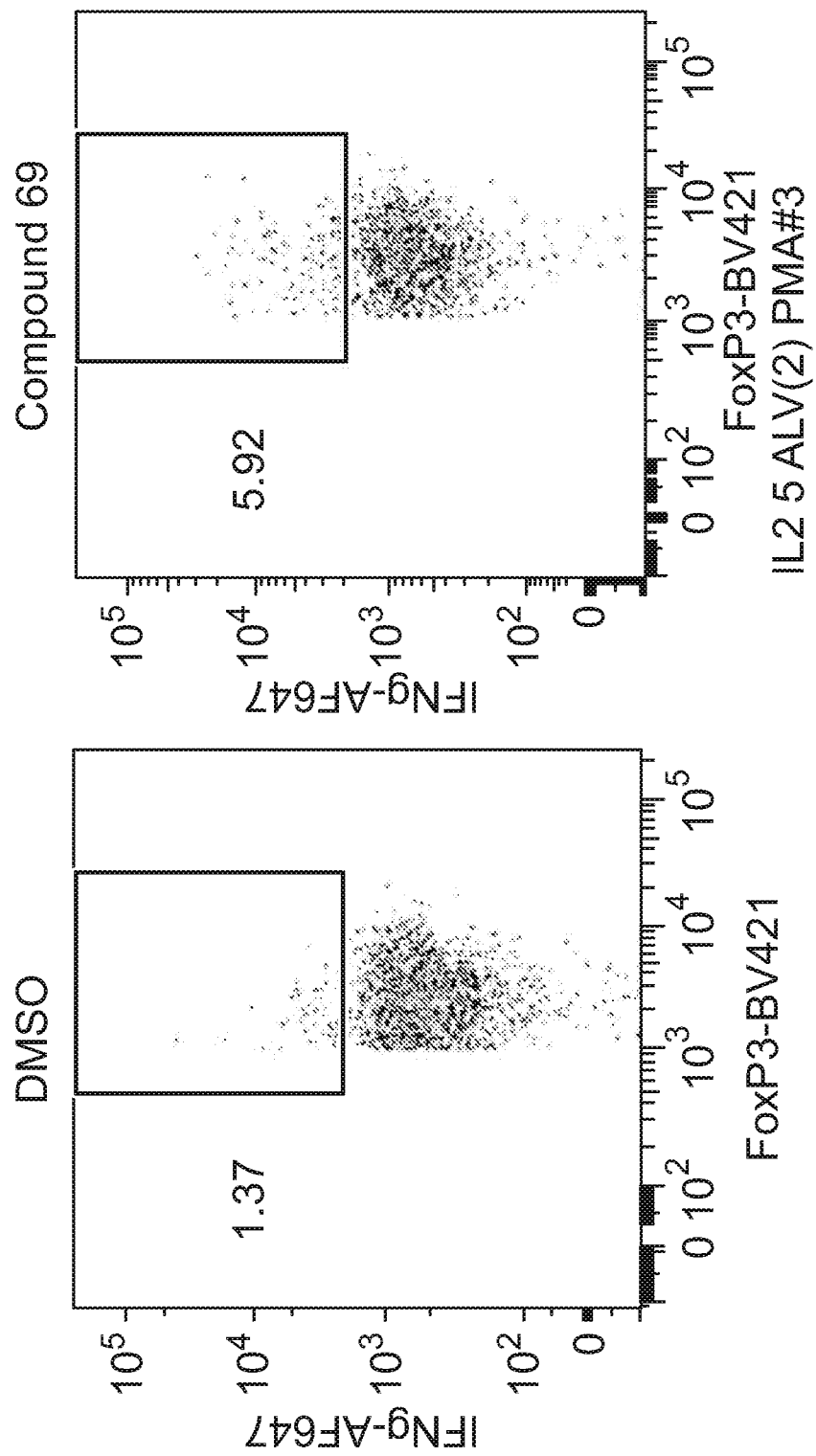
FIG. 9A-FIG. 9C are a series of graphs showing that Helios degradation in Tregs permits IFNγ production. Isolated Crbn$^{I391V/I391V}$ Tregs were treated with 2 μM of compound 69, 5 ng/mL IL-2, and 20 ng/mL IL-4 for 4 days and then restimulated with PMA/ionomycin for 5 h.
Figure 9B:
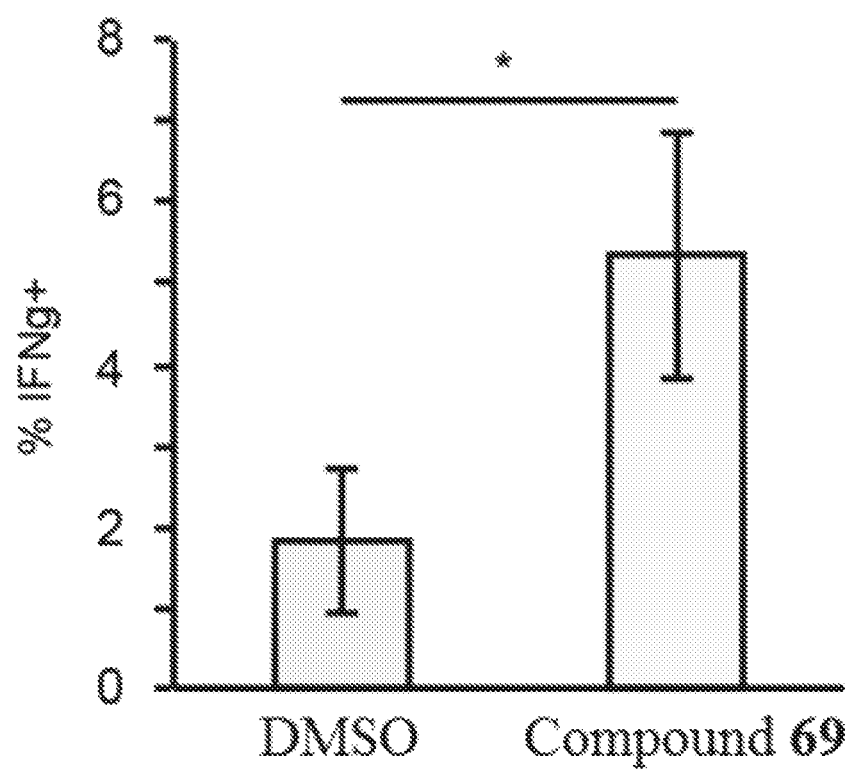
Figure 9C:
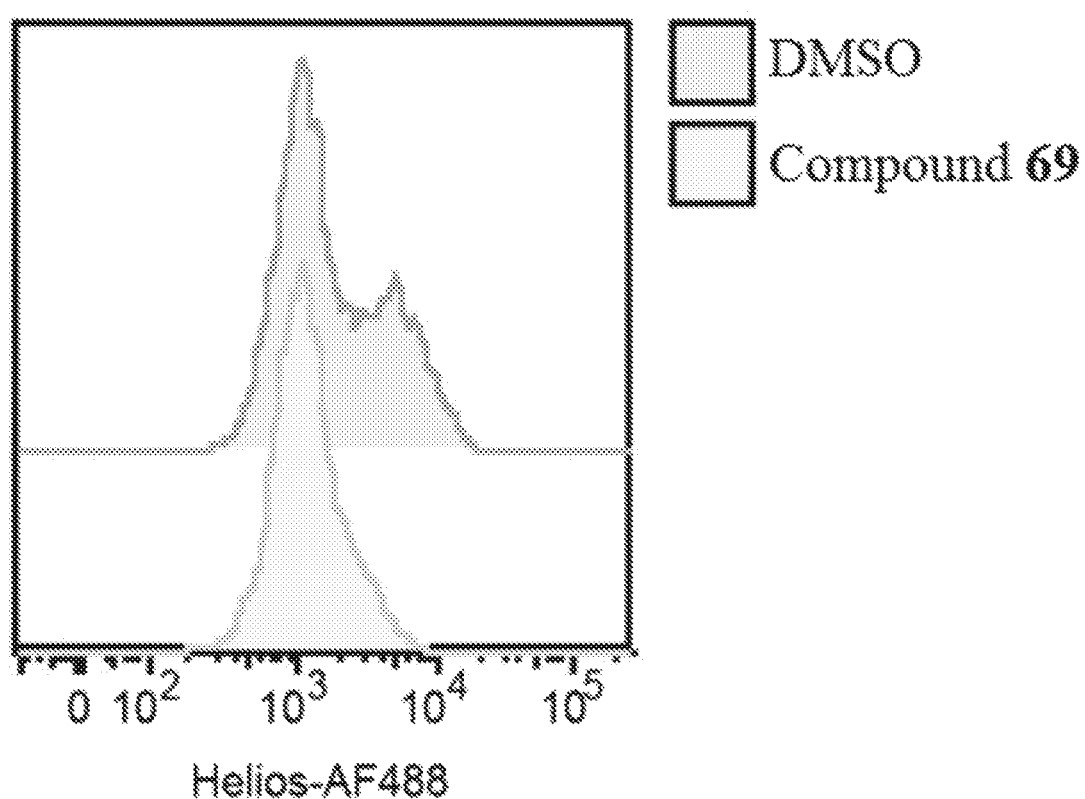

Foxp3+ regulatory T cells were isolated by sorting for CD4+ CD25+ T cells from Crbn$^{I391V/I391V}$ spleens, treated with 2 µM of compound 69, 5 ng/mL IL-2, and 20 ng/mL IL4 for 4 days and then restimulated with PMA/ionomycin for 5 h. Cells were then fixed/permeabilized and stained with fluorochrome-coupled antibodies. FIG. 9A shows the FACS plots for IFNγ. FIG. 9B is a bar graph showing the percent increase of IFNγ with treatment of compound 69. FIG. 9C shows levels of Helios in Tregs treated with DMSO or compound 69. These results demonstrate that compound 69 was able to induce degradation of Helios in Tregs, leading to increased production of IFNγ upon restimulation.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A compound represented by a structure of formula I:

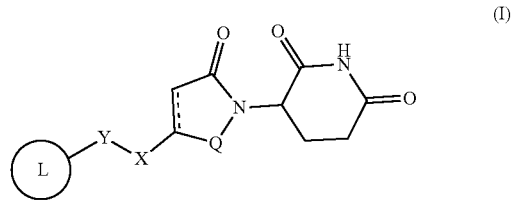

wherein:
Q represents CH$_2$ or C=O;
X represents NR, O, or S, wherein R is H or Me;
Y is absent or represents optionally substituted C1-C5 alkyl, optionally substituted phenyl, optionally substituted benzyl, optionally substituted pyridinyl, optionally substituted imidazolyl, optionally substituted pyrazolyl, optionally substituted triazolyl, optionally substituted tetrazolyl, optionally substituted thiazolyl, optionally substituted quinolinyl, optionally substituted indolyl, or optionally substituted indazolyl;

is absent or represents

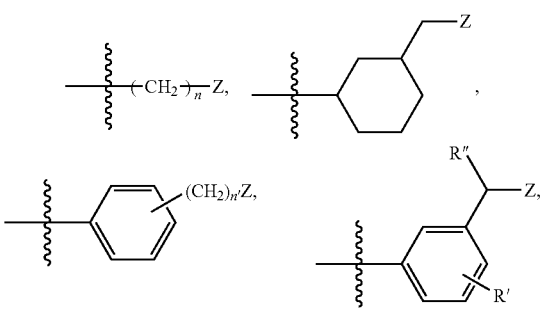

-continued

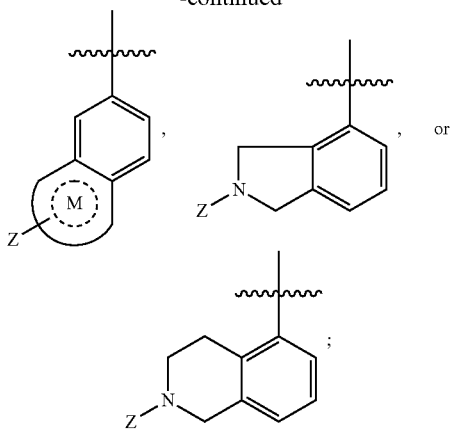

wherein n is 2 or 3; wherein n' is 0 or 1;
wherein R' is halo, optionally substituted C1-C2 alkyl, optionally substituted aryl, or optionally substituted heteroaryl; wherein R" represents optionally substituted C1-C2 alkyl; wherein Z represents

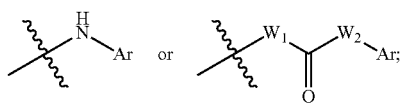

$W_1$ and $W_2$ are independently absent or independently represent CH, $CH_2$, O, O—$CH_2$, NH—$CH_2$ or optionally substituted amino;
M represents a 5- or 6-membered cyclic group; and
Ar represents

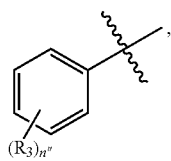

wherein each $R_3$ is independently alkyl, halo, trifluoromethyl, aryl, heteroaryl, or benzyl, and n" is 0, 1, or 2;
wherein

or Y is absent;
or a pharmaceutically acceptable salt or stereoisomer thereof,
wherein the optional substituent is independently alkyl, alkoxy, haloalkyl, alkenyl, alkynyl, carbocyclyl, heterocyclyl, aryl, heteroaryl, aralkyl, halo, hydroxyl, aryloxy, alkylthio, arylthio, cyano, carbonyl, carboxyl, amino, amido, thio, sulfinyl, sulfonyl, sulfinamide, sulfonamide, urea, carbamate, or an amino acid.

2. The compound of claim 1, wherein Q is C=O.
3. The compound of claim 1, wherein Q is $CH_2$.
4. The compound of claim 1, wherein X is NH or NMe.
5. The compound of claim 1, wherein X is O or S.
6. The compound of claim 1, wherein

is absent and Q is C=O, and the compound has a structure of formula Ia,

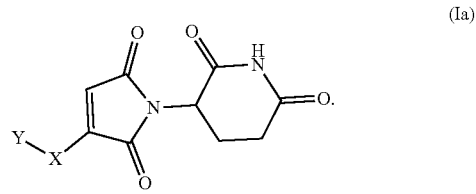

7. The compound of claim 6, wherein Y is optionally substituted pyridinyl, optionally substituted imidazolyl, optionally substituted pyrazolyl, optionally substituted triazolyl, optionally substituted tetrazolyl, optionally substituted thiazolyl, optionally substituted quinolinyl, optionally substituted indolyl, or optionally substituted indazolyl.

8. The compound of claim 6, wherein Y represents optionally substituted C1-C5 alkyl.

9. The compound of claim 6, wherein Y represents optionally substituted phenyl or optionally substituted benzyl.

10. The compound of claim 6, wherein Y represents phenyl, benzyl,

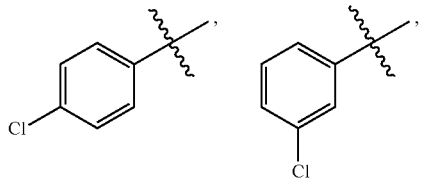

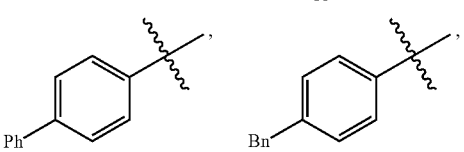

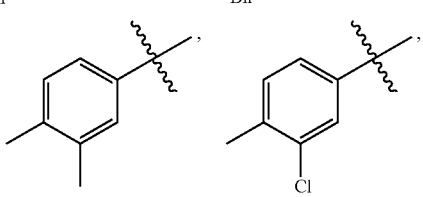

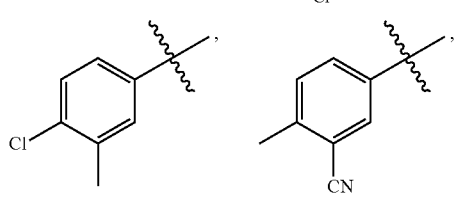

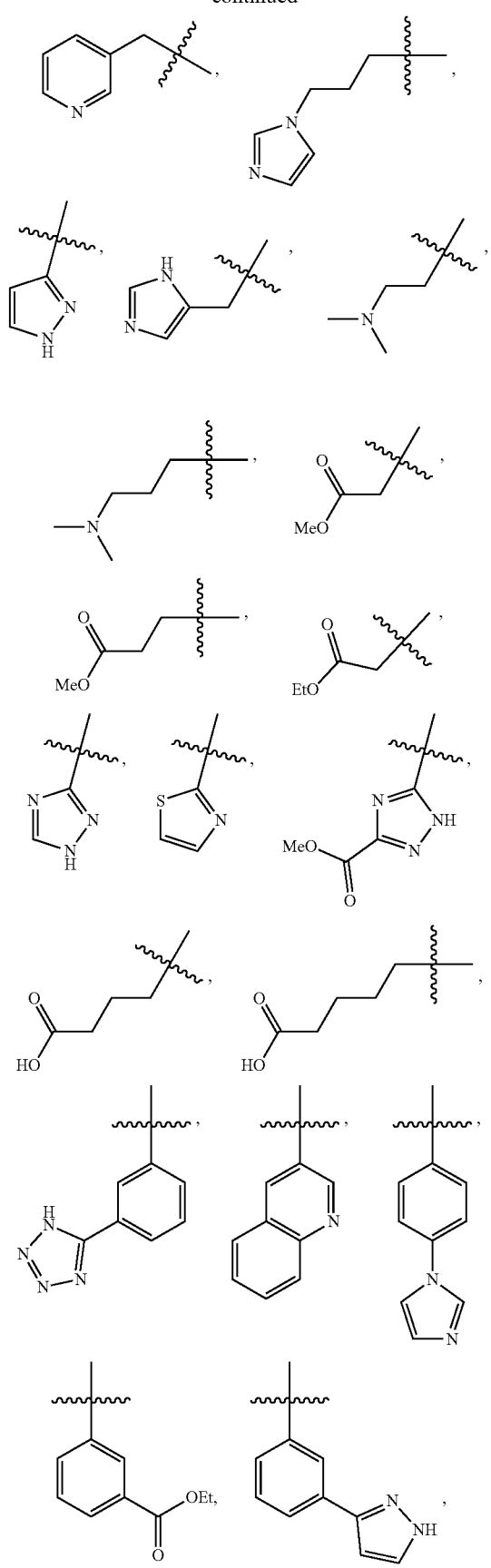

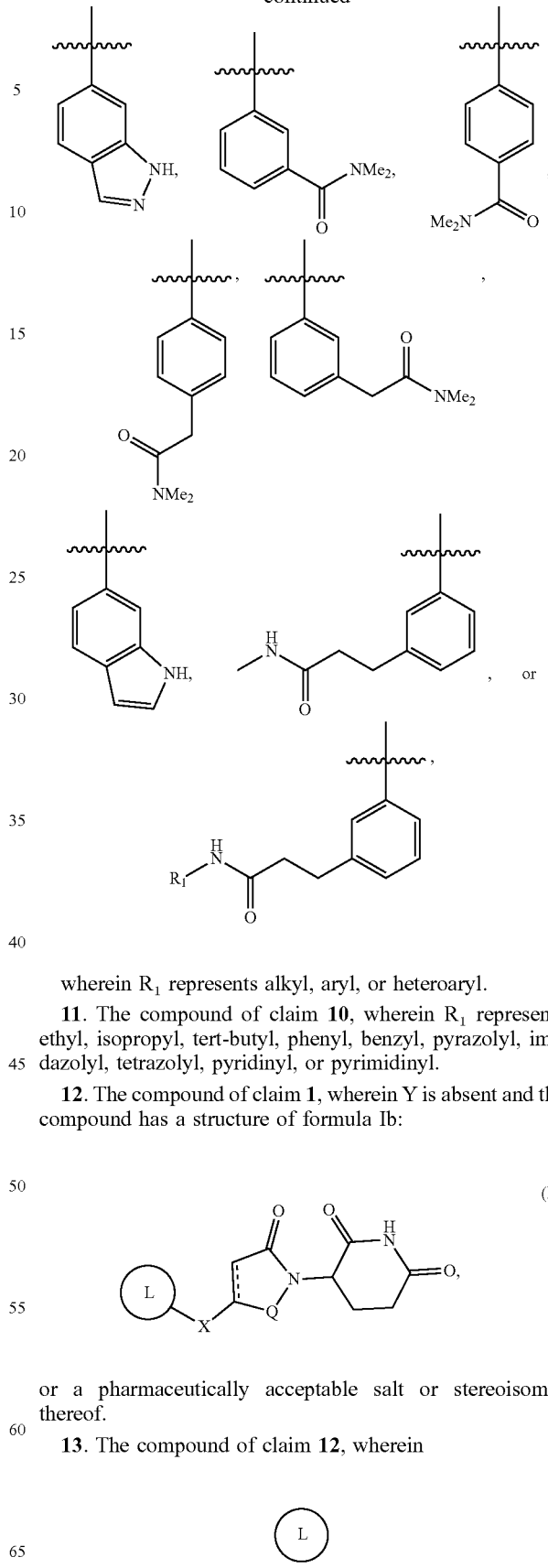

wherein $R_1$ represents alkyl, aryl, or heteroaryl.

11. The compound of claim 10, wherein $R_1$ represents ethyl, isopropyl, tert-butyl, phenyl, benzyl, pyrazolyl, imidazolyl, tetrazolyl, pyridinyl, or pyrimidinyl.

12. The compound of claim 1, wherein Y is absent and the compound has a structure of formula Ib:

(Ib)

or a pharmaceutically acceptable salt or stereoisomer thereof.

13. The compound of claim 12, wherein

is
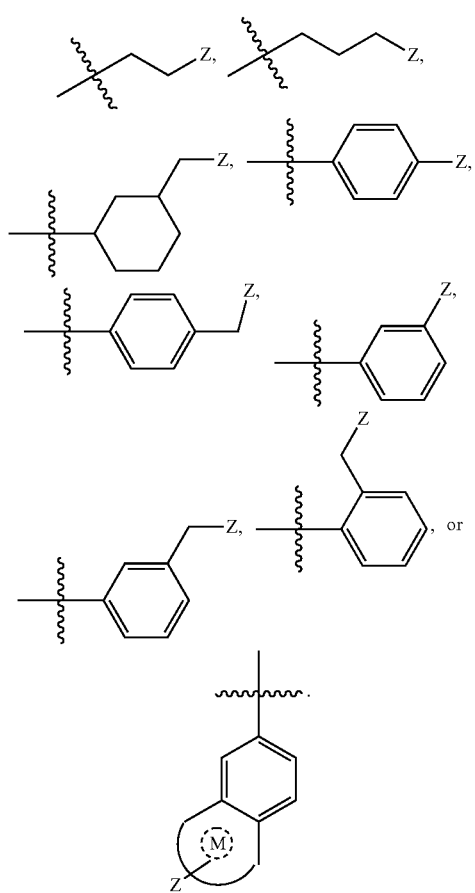
14. The compound of claim 12, wherein
represents an optionally substituted fused-5,6 or-6,6 ring system.
15. The compound of claim 14, wherein
is
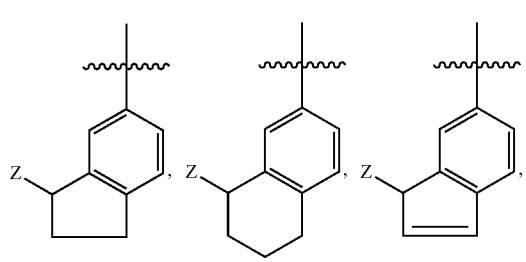
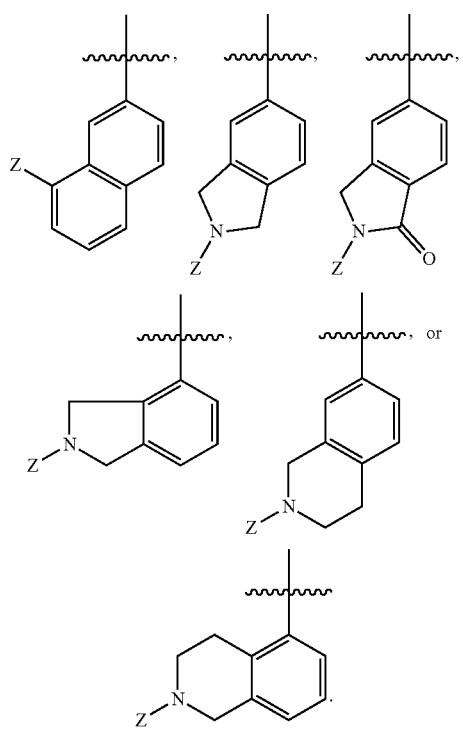
16. The compound of claim 15, wherein Z represents
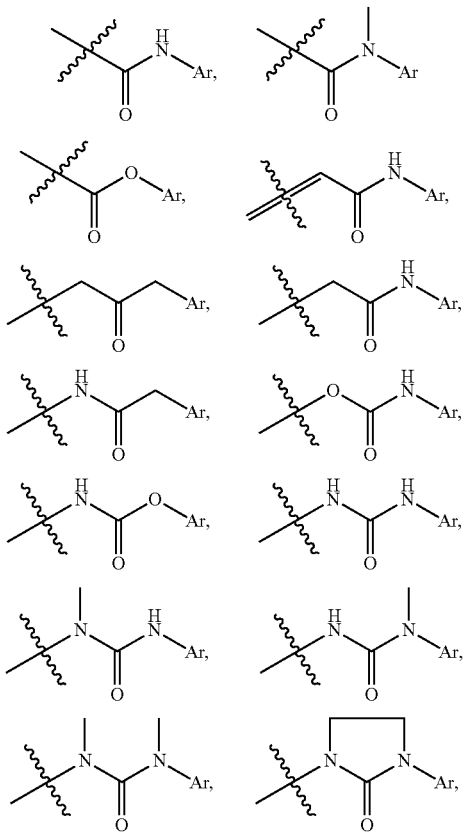

-continued
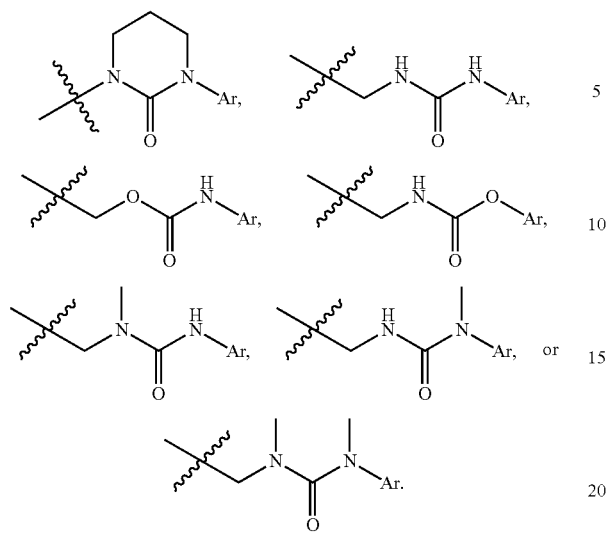
17. The compound of claim 16, wherein Ar represents
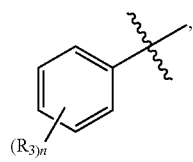
wherein R₃ represents alkyl, halo, aryl, or heteroaryl, and n" is 0, 1, or 2.
18. The compound of claim 17, wherein $R_3$ independently represents methyl, ethyl, isopropyl, tert-butyl, trifluoromethyl, chloro, or fluoro.
19. The compound of claim 17, wherein Ar represents
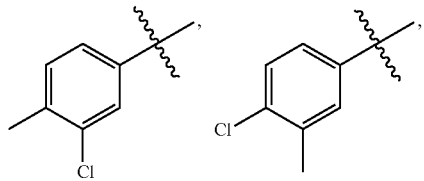
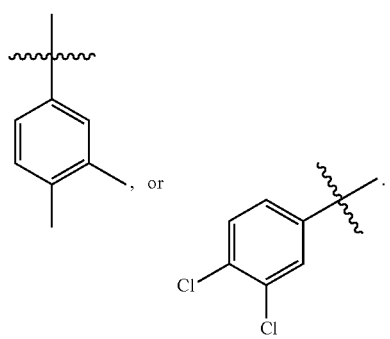
20. The compound of claim 1, which is:
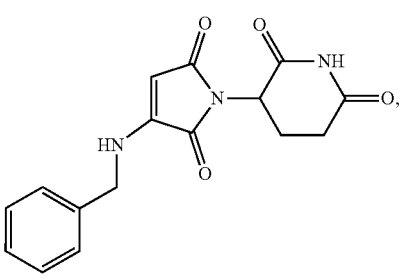
(1)
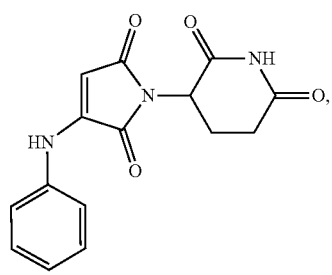
(2)
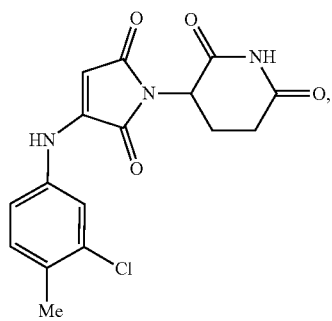
(3)
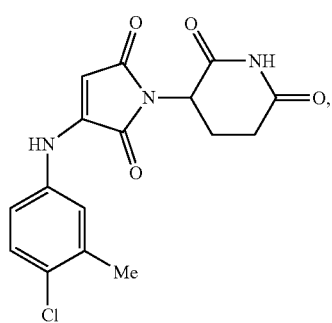
(4)
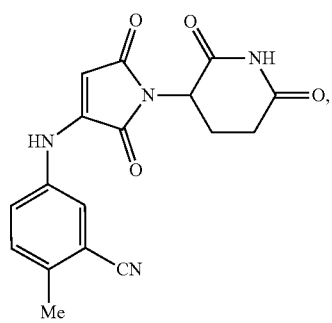
(5)

(6) 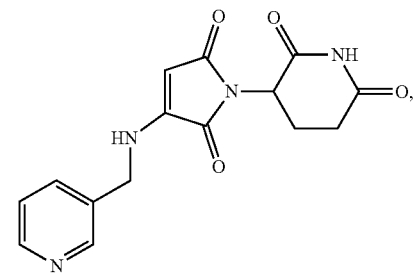
(7) 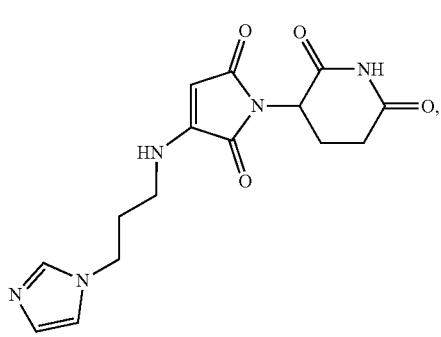
(8) 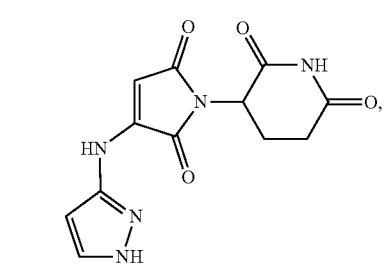
(9) 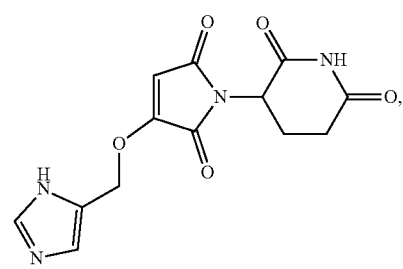
(10) 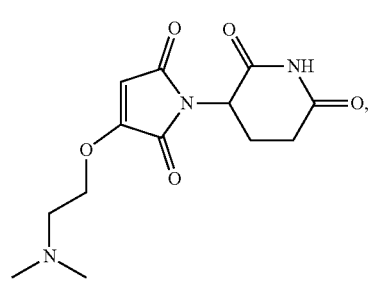
(11) 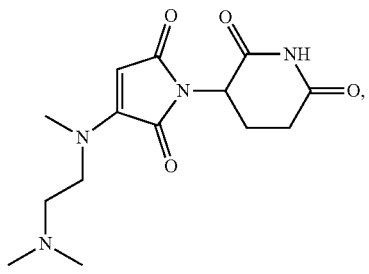
(12) 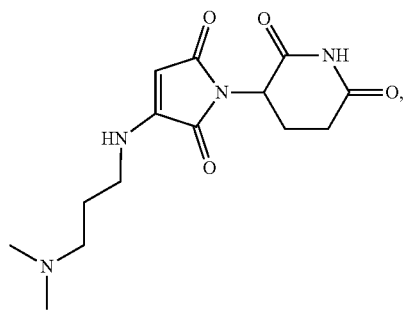
(13) 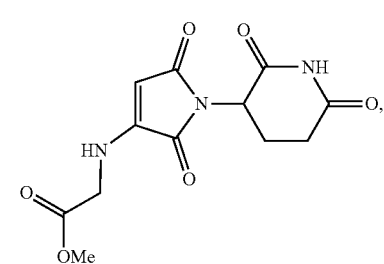
(14) 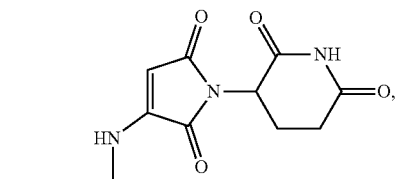
(15) 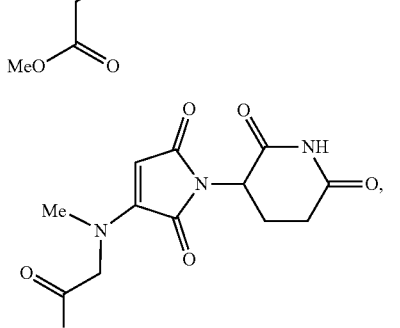
(16) 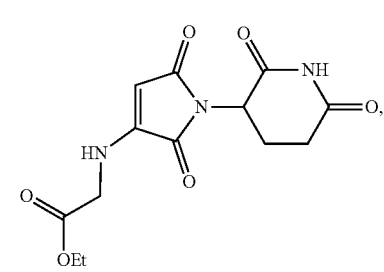

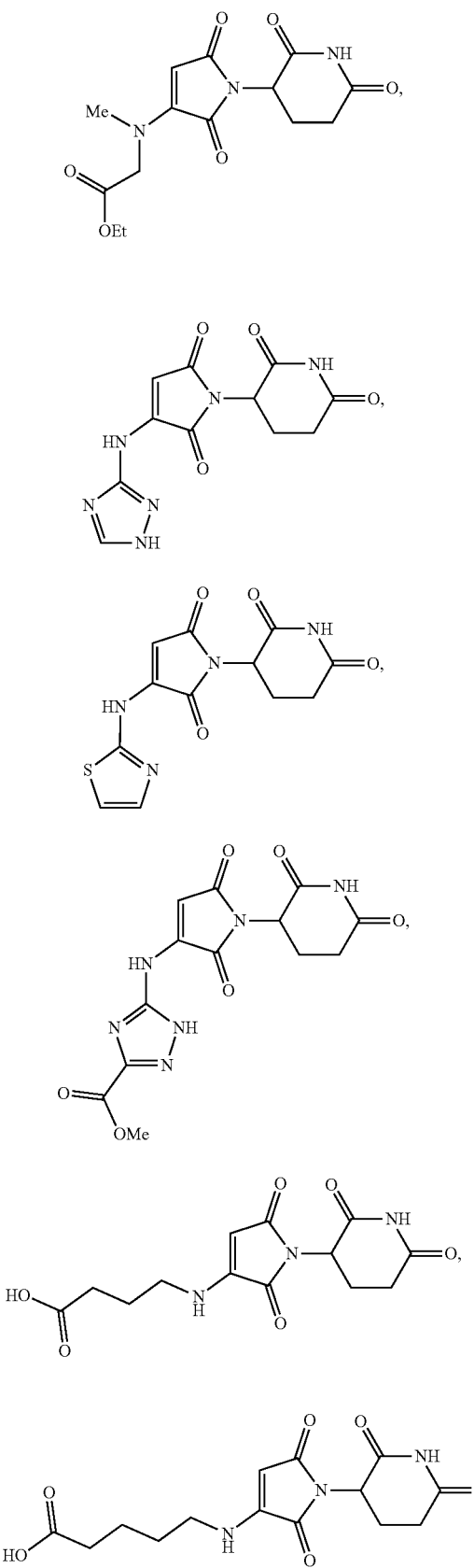
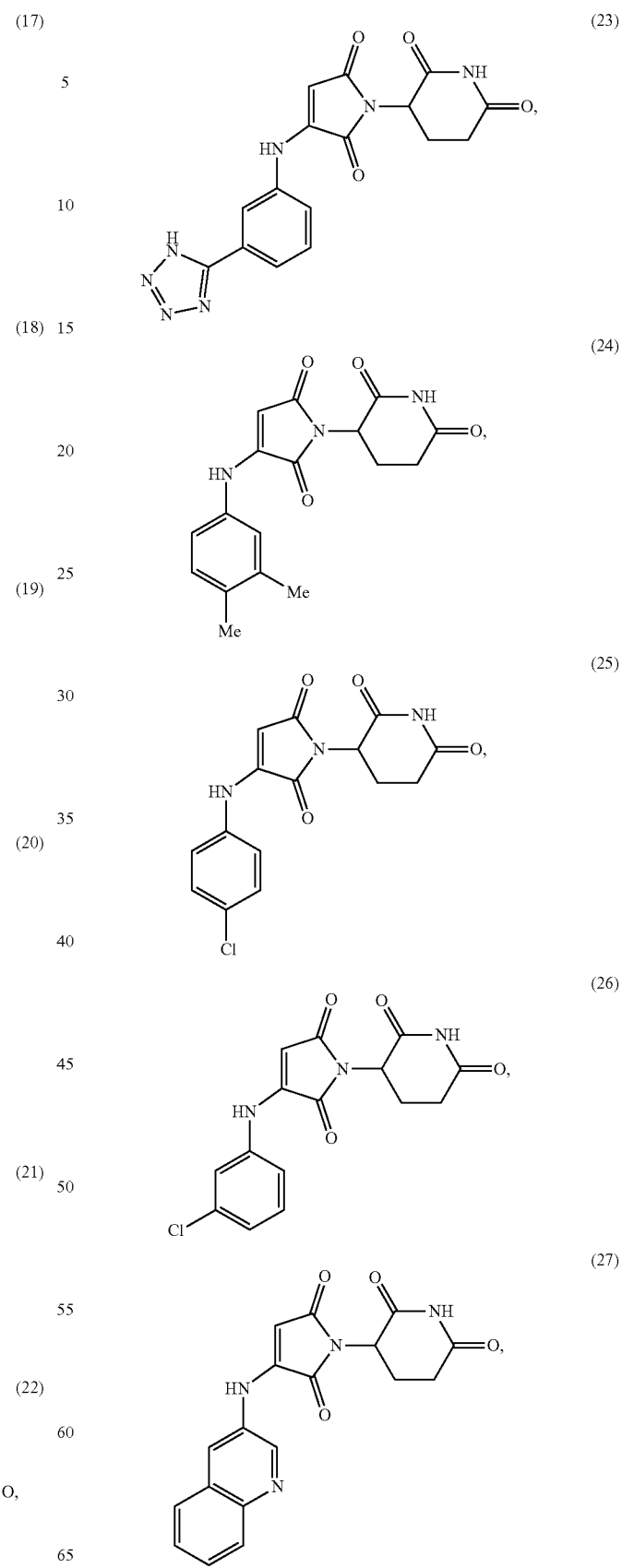

(28)
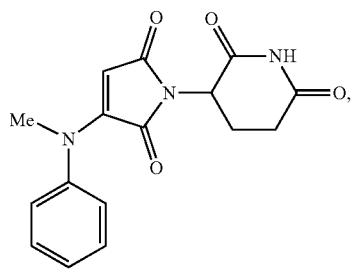
(29)
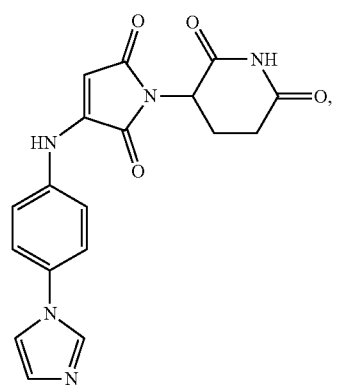
(30)
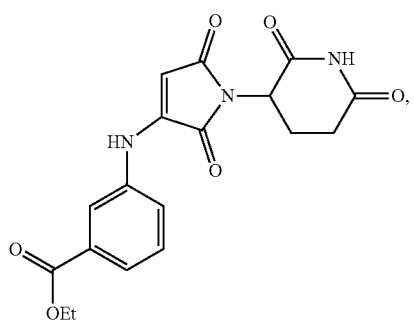
(31)
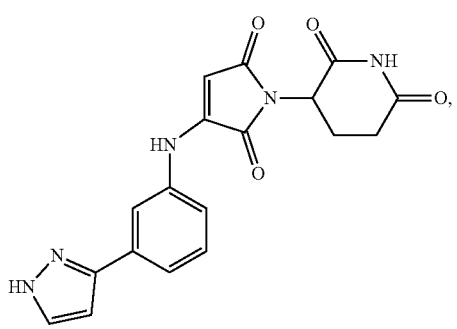
(32)
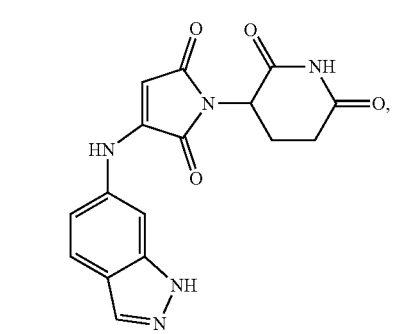
(33)
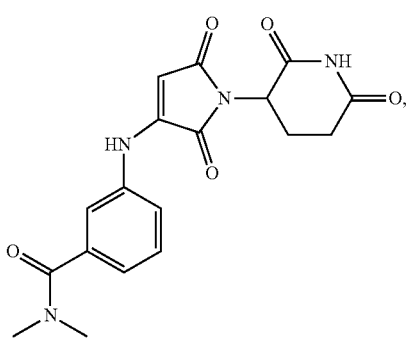
(34)
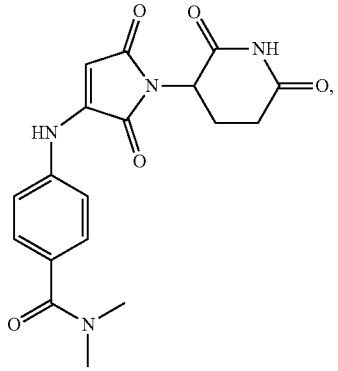
(35)
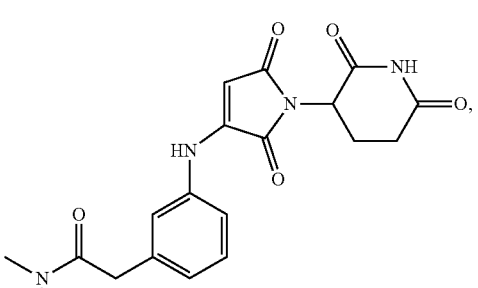
(36)
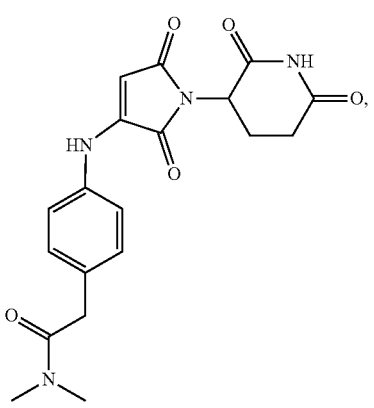

(37)
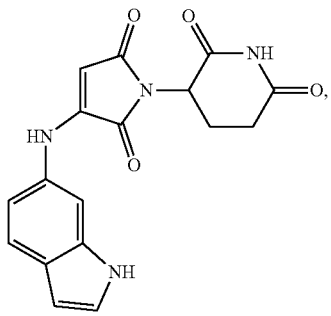
(38)
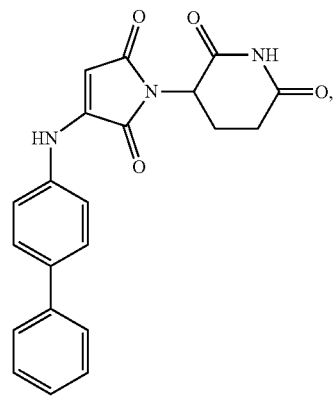
(39)
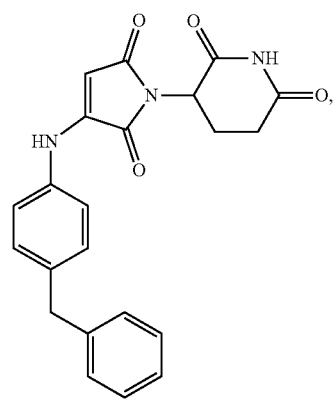
(40)
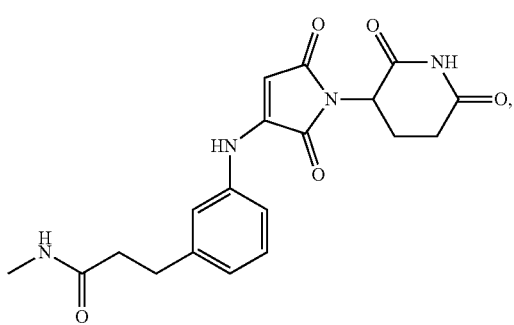
(41)
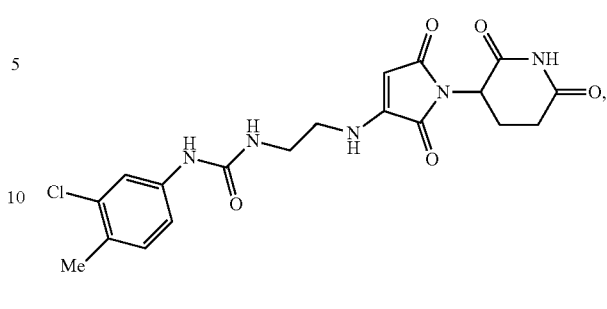
(42)
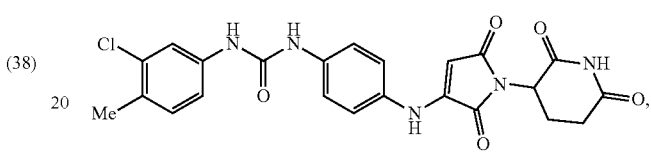
(43)
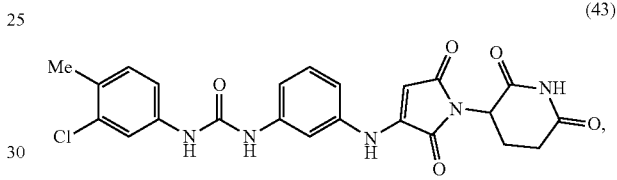
(44)
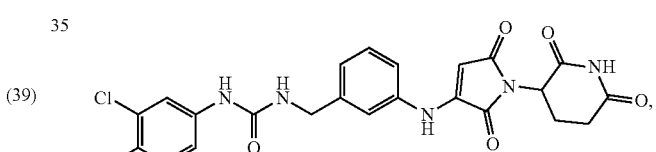
(45)
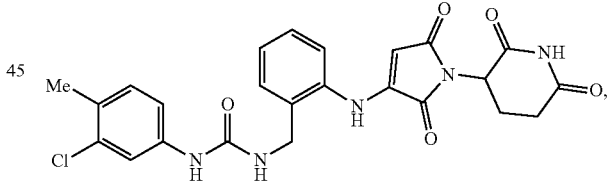
(46)
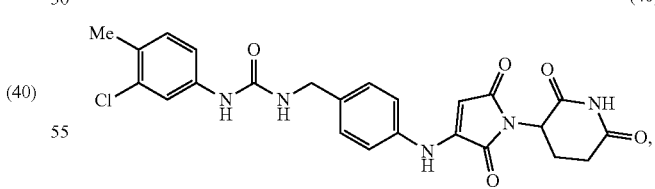
(47)
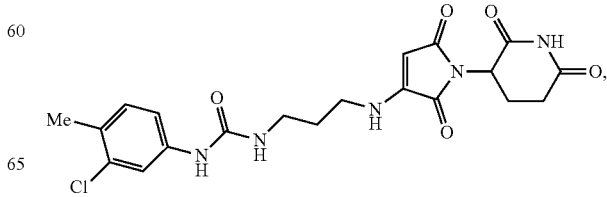

-continued
(48)
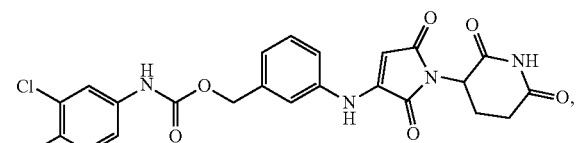
(49)
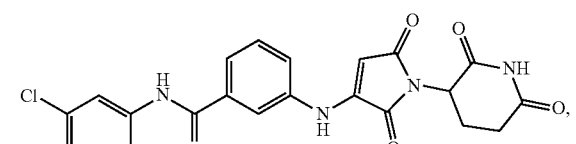
(50)
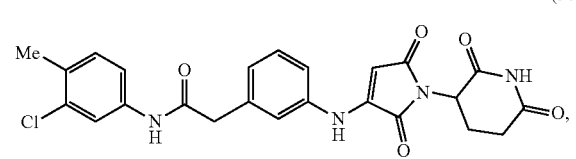
(51)
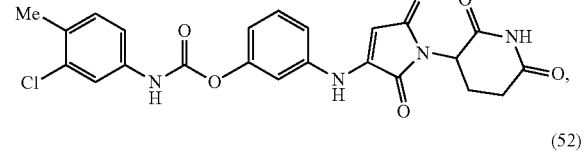
(52)
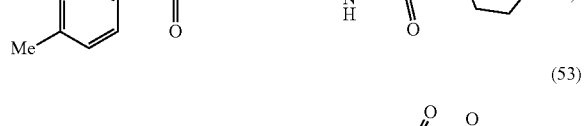
(53)
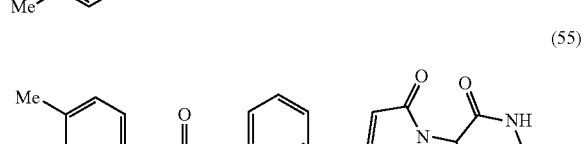
(55)
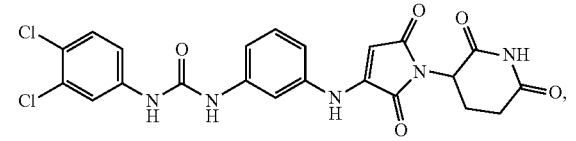
(56)
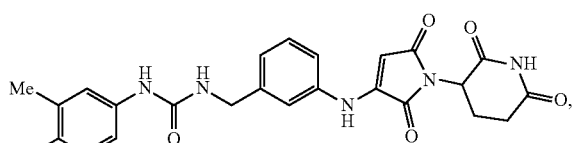
-continued
(58)
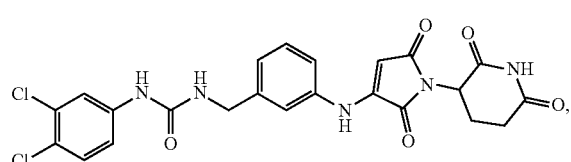
(59)
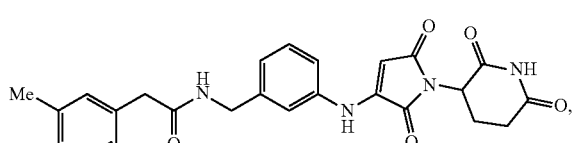
(60)
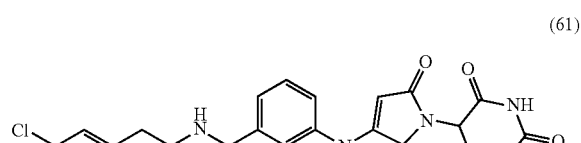
(61)
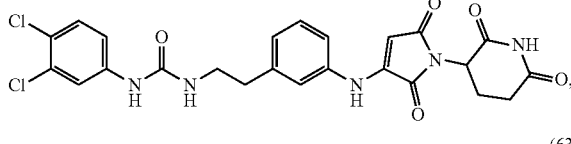
(62)
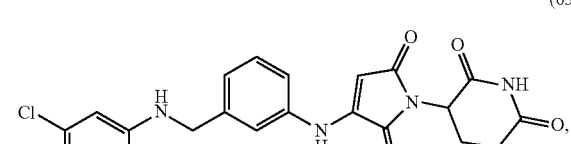
(63)
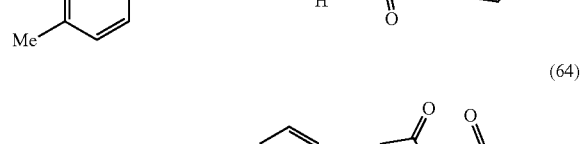
(64)
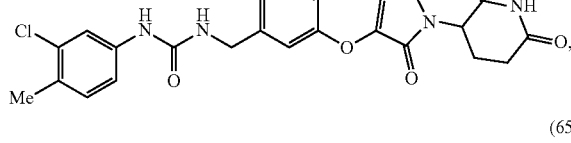
(65)
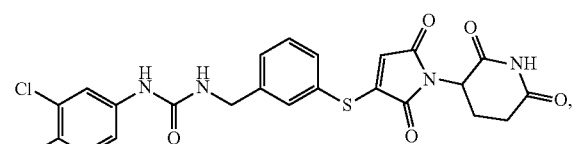

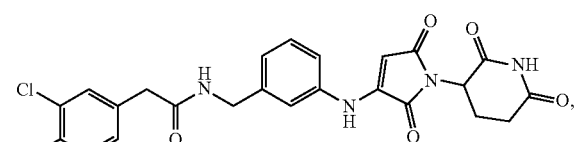
(66)
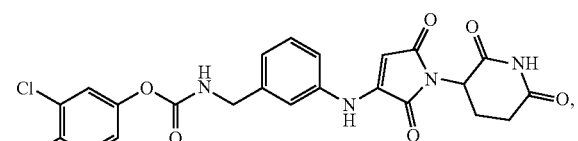
(67)
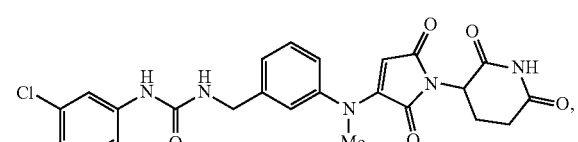
(68)
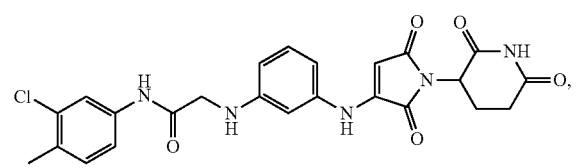
(78)
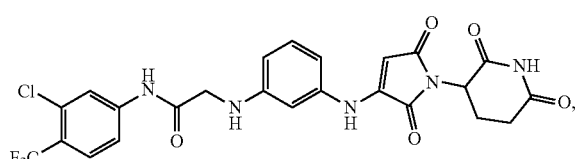
(79)
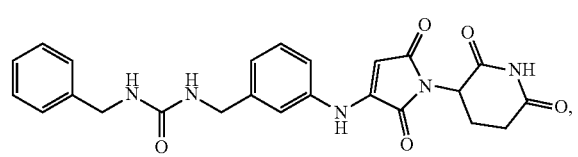
(81)
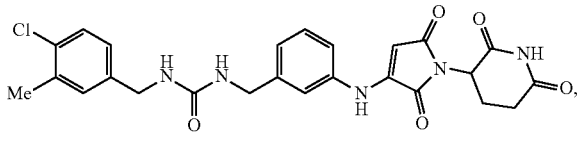
(82)
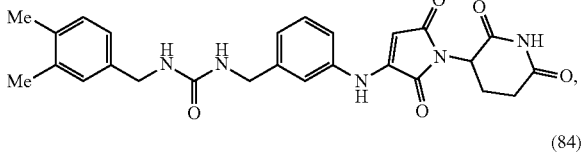
(83)
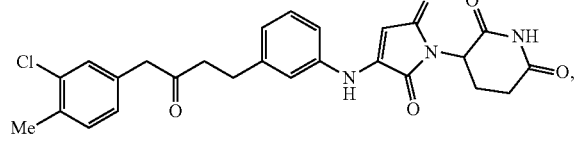
(84)
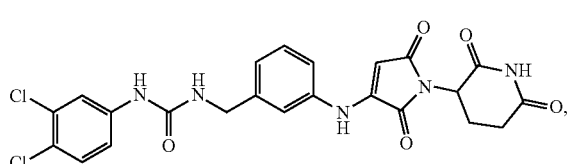
(85)
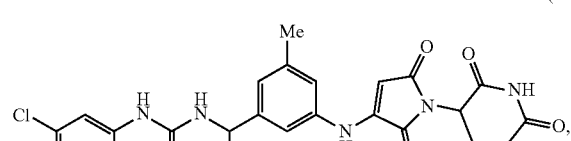
(88)
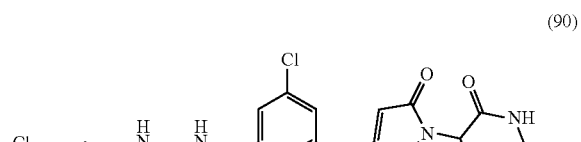
(90)
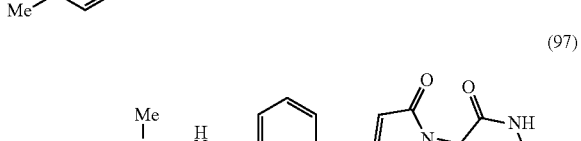
(97)
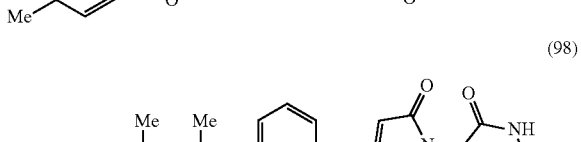
(98)
(99)
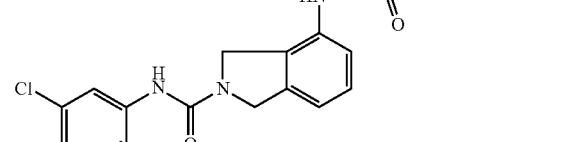
(100)
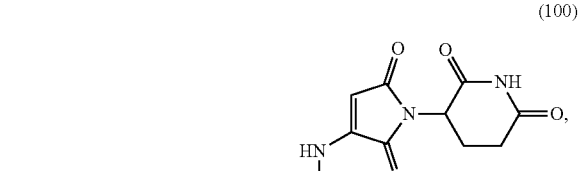
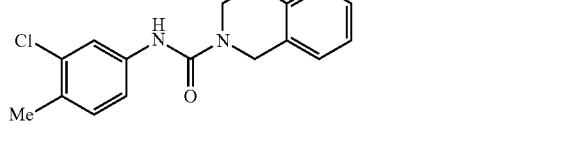

(101)
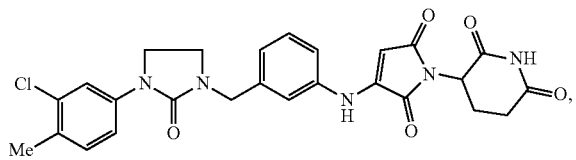
(102)
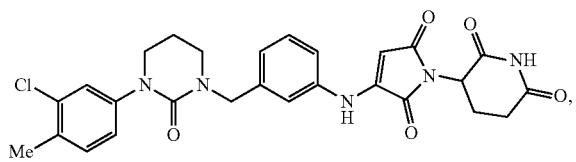
(103)
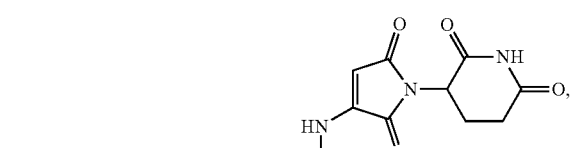
(104)
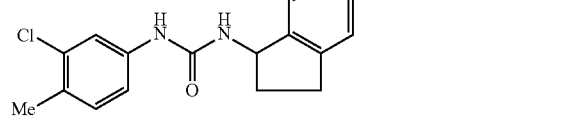
(105)
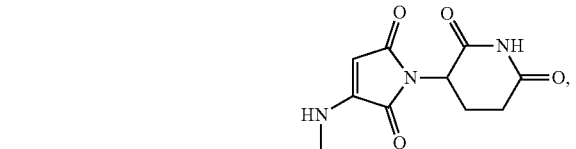
(106)
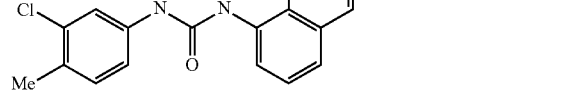
(107)
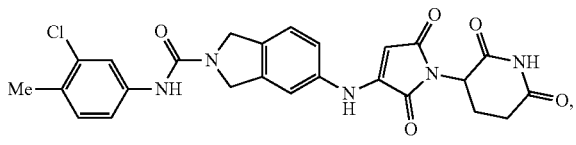
(108)
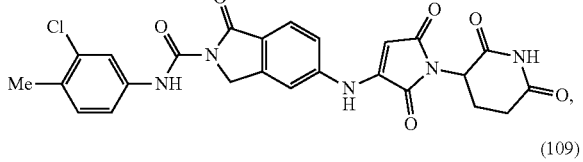
(109)
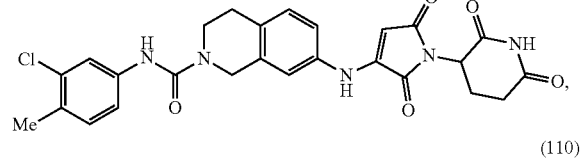
(110)
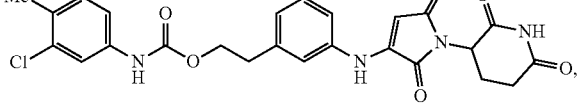
(113)
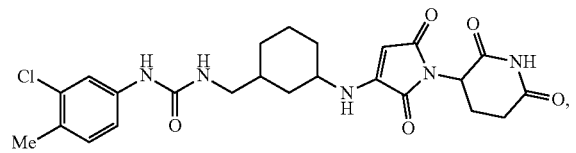
(114)
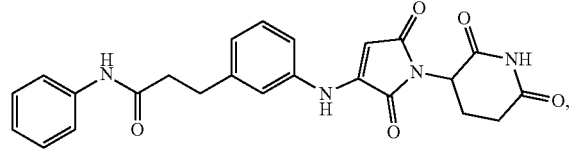
(115)
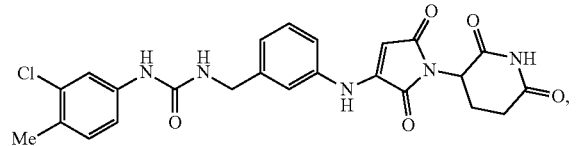
(116)
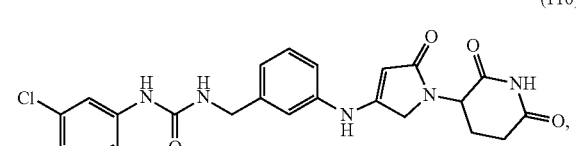
(117)
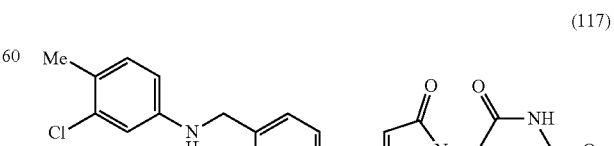

(118)
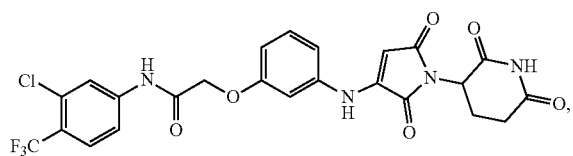
(127)
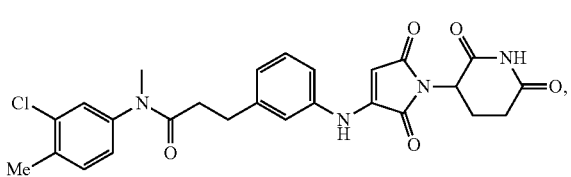
(119)
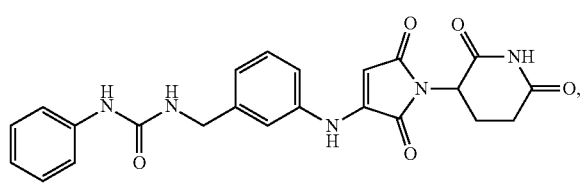
(128)
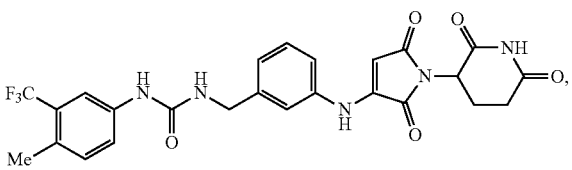
(121)
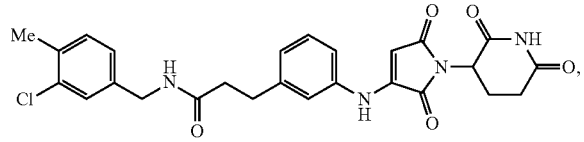
(129)
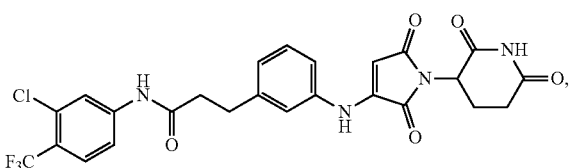
(122)
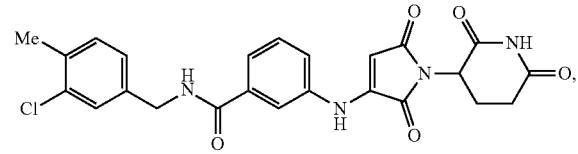
(130)
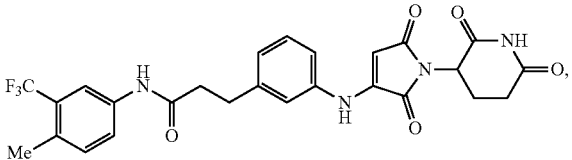
(123)
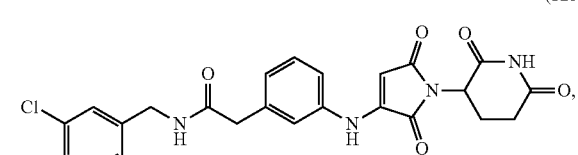
(148)
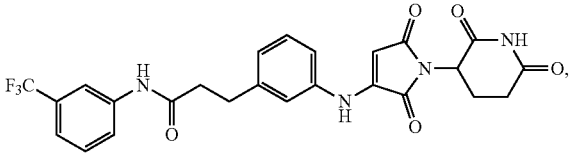
(124)
(149)
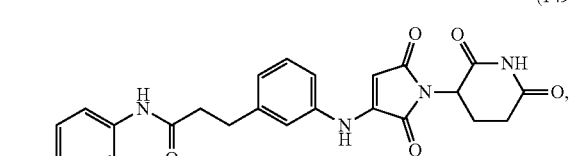
(125)
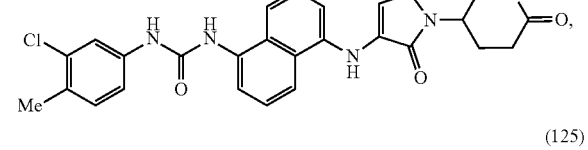
(150)
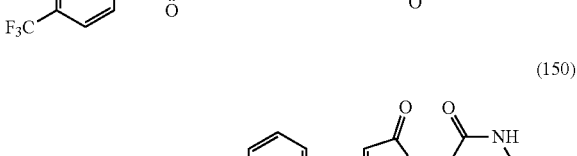
(126)
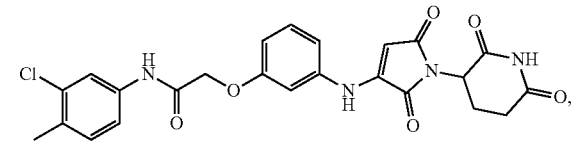
(151)
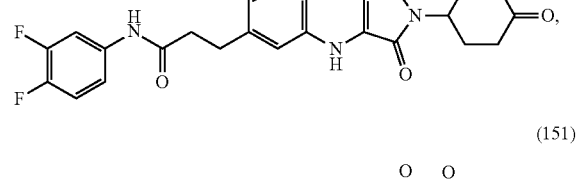

-continued (153)

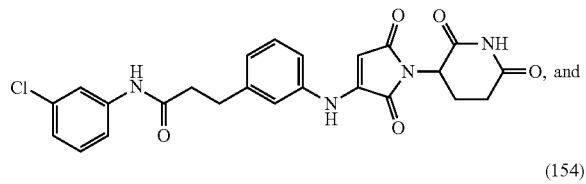

, and (154)

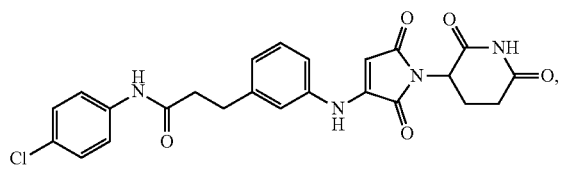

, or a pharmaceutically acceptable salt or stereoisomer thereof.

21. A pharmaceutical composition, comprising a therapeutically effective amount of the compound of claim 1, or pharmaceutically acceptable salt or stereoisomer thereof, and a pharmaceutically acceptable carrier.

22. A method of treating a disease or disorder that is characterized or mediated by dysfunctional activity of a protein that is a substrate for a complex between CRBN and the compound of claim 1, comprising administering to a subject in need thereof a therapeutically effective amount of the compound or pharmaceutically acceptable salt or stereoisomer of claim 1.

23. The method of claim 22, wherein the disease or disorder is mediated by dysfunctional IKZF2 (Helios) activity.

24. The method of claim 23, wherein the disease is cancer.

25. The method of claim 24, wherein the disease or disorder is leukemia, carcinoma, T cell leukemia, T cell lymphoma, Hodgkin's lymphoma, non-Hodgkin's lymphoma, myeloid leukemia, non-small cell lung cancer (NSCLC), melanoma, triple-negative breast cancer (TNBC), or nasopharyngeal cancer (NPC).

26. A method of treating a disease or disorder that is affected by a reduction of TXNIP protein levels, comprising administering to a subject in need thereof a therapeutically effective amount of the compound or pharmaceutically acceptable salt or stereoisomer claim 1.

27. A compound represented by a structure of formula II:

(II)

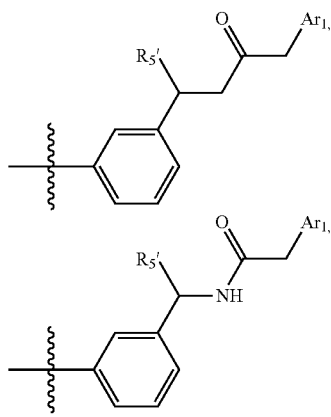

wherein:

$L_1$ represents

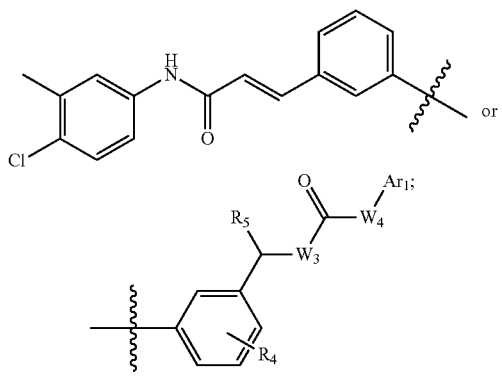

wherein $R_4$ is H or a substituent;

$R_5$ represents H, -Me, -Et,

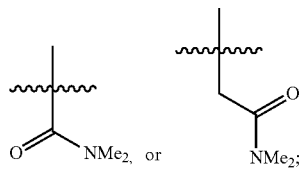 [SMILES: *C(=O)N(C)C ; *CC(=O)N(C)C]

$W_3$ and $W_4$ are independently absent or independently represent $CH_2$, NH, or NH—$CH_2$; and $Ar_1$ is optionally substituted aryl or heteroaryl;

or a pharmaceutically acceptable salt or stereoisomer thereof, wherein the optional substituent is independently alkyl, alkoxy, haloalkyl, alkenyl, alkynyl, carbocyclyl, heterocyclyl, aryl, heteroaryl, aralkyl, halo, hydroxyl, aryloxy, alkylthio, arylthio, cyano, carbonyl, carboxyl, amino, amido, thio, sulfinyl, sulfonyl, sulfonamide, sulfonamide, urea, carbamate, or an amino acid.

28. The compound of claim 27, wherein $L_1$ is

-continued
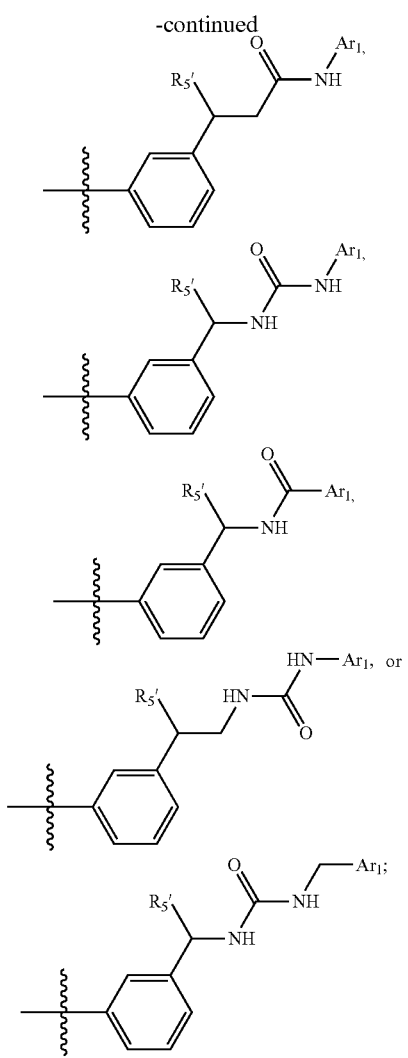
wherein $R_{5'}$ is H, Me, or Et.
29. The compound of claim 27, wherein $R_4$ is alkyl, halo, hydroxyl, amino, amido, substituted carbamate, or substituted carbamide.
30. The compound of claim 27, wherein $Ar_1$ is optionally substituted phenyl.
31. The compound of claim 27, which is:
(54)
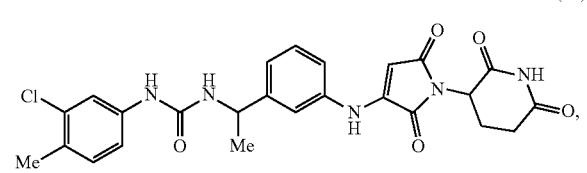
(57)
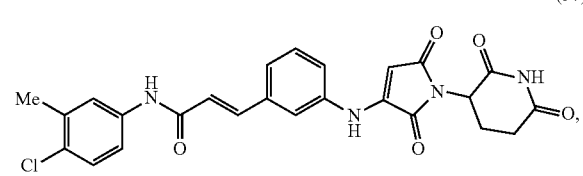
-continued
(70)
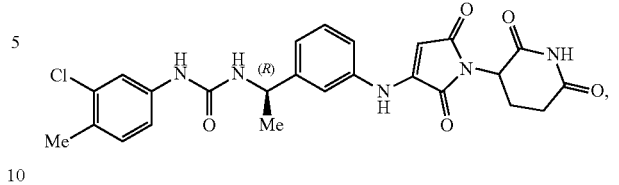
(71)
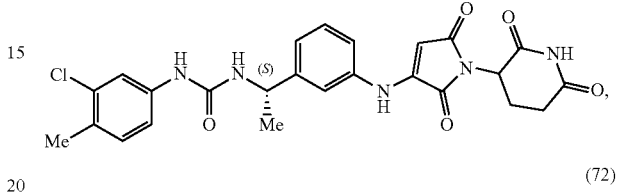
(72)
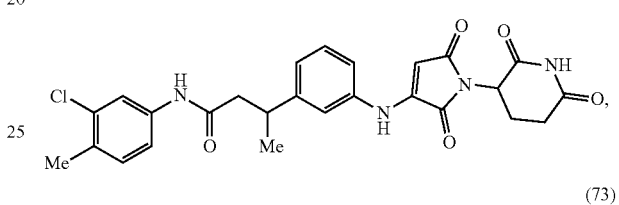
(73)
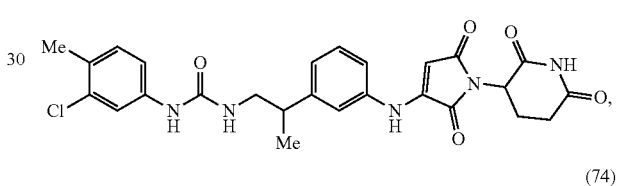
(74)
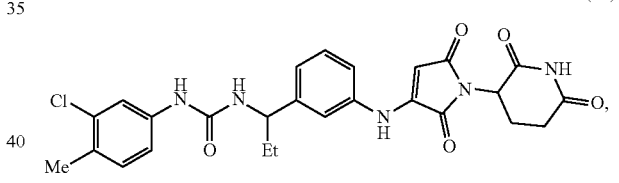
(75)
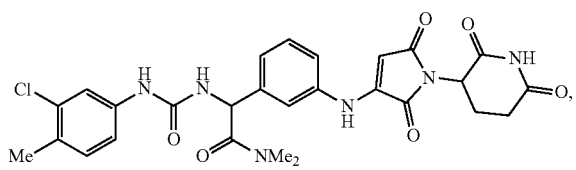
(76)
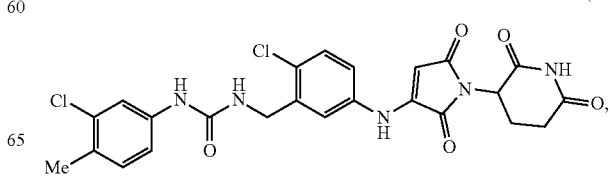
(77)

141
-continued
(80)
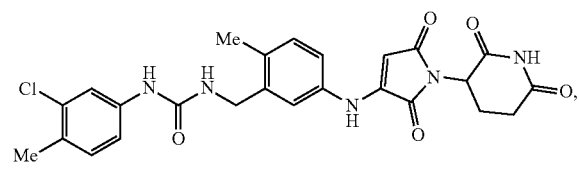
(86)
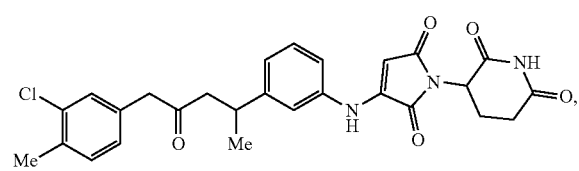
(87)
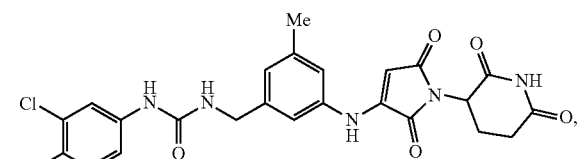
(89)
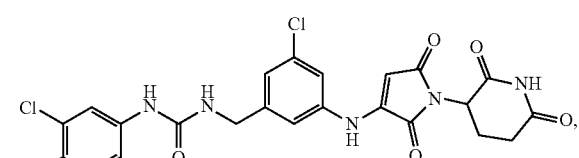
(91)
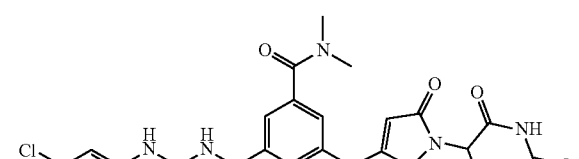
(92)
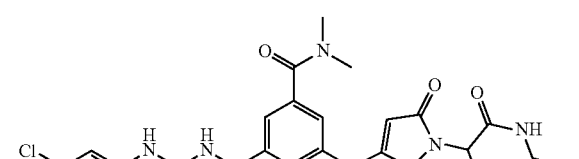
(93)
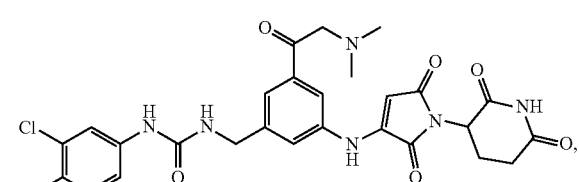
142
-continued
(94)
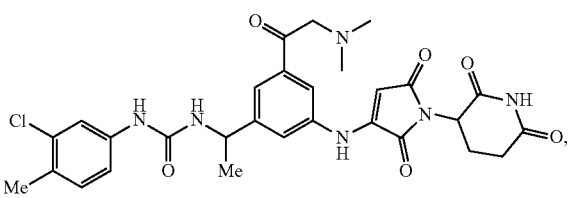
(95)
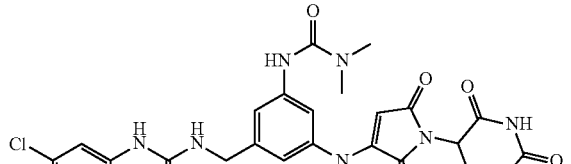
(96)
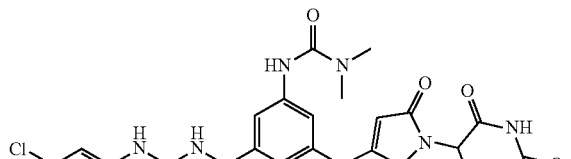
(111)
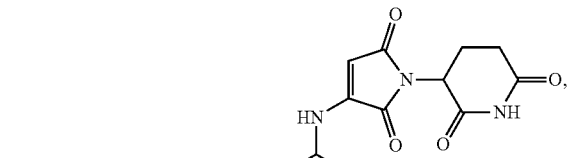
(112)
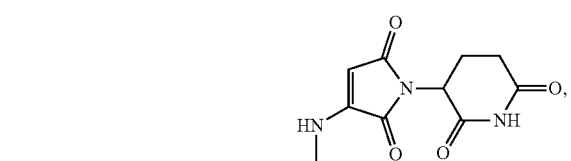
(120)
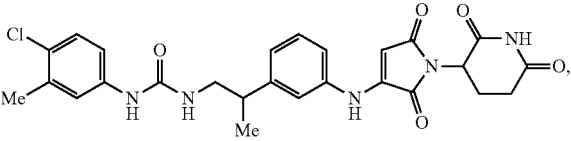

-continued
(131)
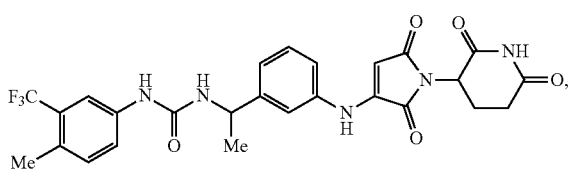
(132)
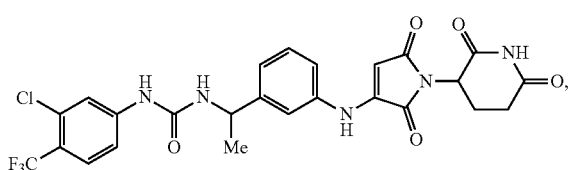
(134)
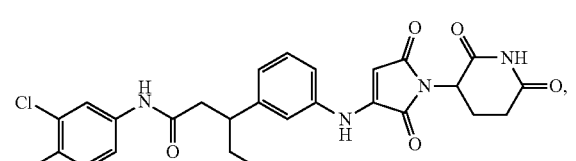
(135)
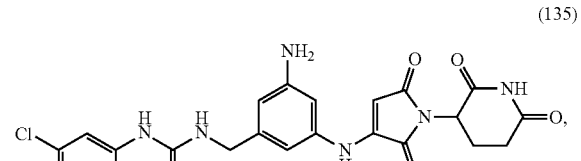
(137)
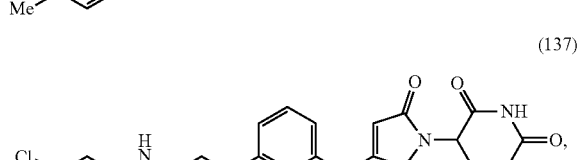
(138)
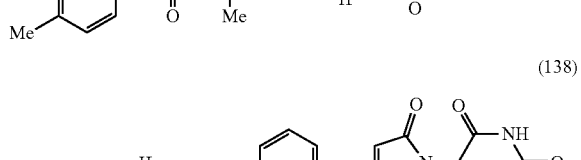
(140)
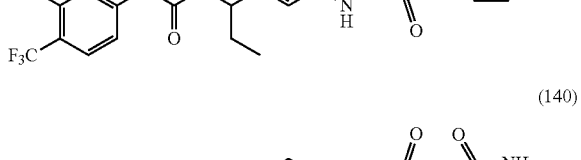
(141)
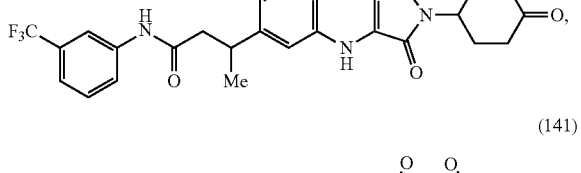
-continued
(142)
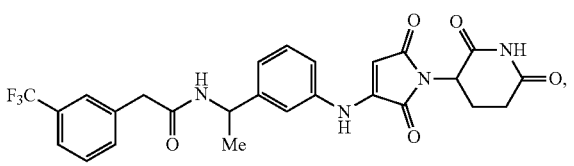
(143)
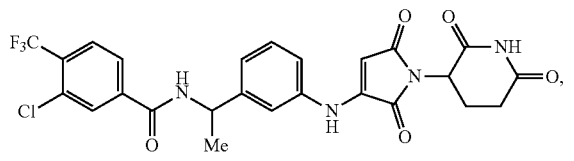
(144)
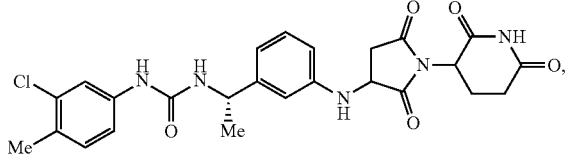
(146)
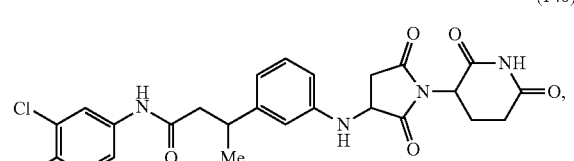
(147)
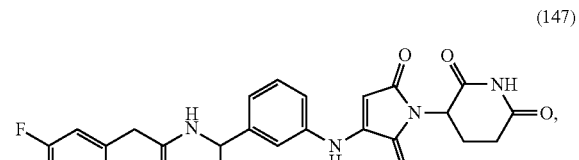
(152)
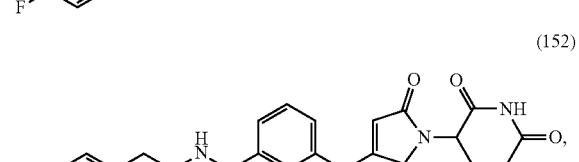
(155)
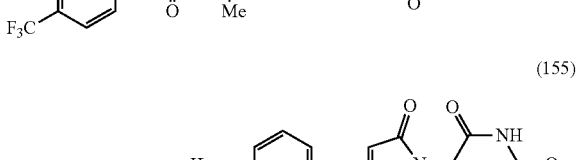
(156)
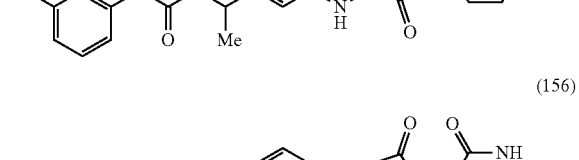

-continued (157)

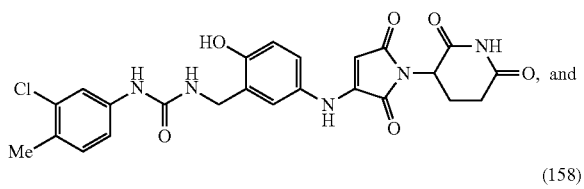

(158)

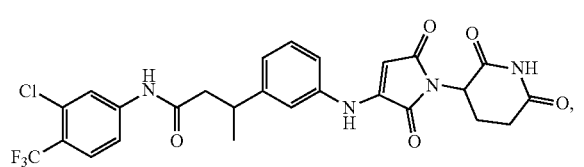

or a pharmaceutically acceptable salt or stereoisomer thereof.

32. A pharmaceutical composition, comprising a therapeutically effective amount of the compound or pharmaceutically acceptable salt or stereoisomer of claim 27, and a pharmaceutically acceptable carrier.

33. A method of treating a disease or disorder that is characterized or mediated by dysfunctional activity of activity of a protein that is a substrate for a complex between CRBN and the compound of claim 27, comprising administering to a subject in need thereof a therapeutically effective amount of the compound or pharmaceutically acceptable salt or stereoisomer of claim 27.

34. The method of claim 33, wherein the disease or disorder is mediated by dysfunctional IKZF2 (Helios) activity.

35. The method of claim 34, wherein the disease or disorder is cancer.

36. The method of claim 35, wherein the disease or disorder is leukemia, carcinoma, T cell leukemia, T cell lymphoma, Hodgkin's lymphoma, non-Hodgkin's lymphoma, myeloid leukemia, non-small cell lung cancer (NSCLC), melanoma, triple-negative breast cancer (TNBC), or nasopharyngeal cancer (NPC).

37. A method of treating a disease or disorder that is affected by a reduction of TXNIP protein levels, comprising administering to a subject in need thereof a therapeutically effective amount of the compound or pharmaceutically acceptable salt or stereoisomer of claim 27.

38. A compound represented by a structure of formula III:

(III)

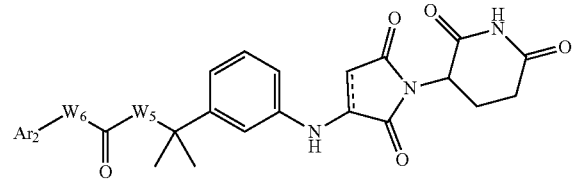

wherein
$W_5$ and $W_6$ each independently represents —CH$_2$— or —NH—, provided that one of $W_5$ and $W_6$ is —NH—; and
Ar$_2$ is optionally substituted aryl or heteroaryl;
or a pharmaceutically acceptable salt or stereoisomer thereof, wherein the optional substituent is independently alkyl, alkoxy, haloalkyl, alkenyl, alkynyl, carbocyclyl, heterocyclyl, aryl, heteroaryl, aralkyl, halo, hydroxyl, aryloxy, alkylthio, arylthio, cyano, carbonyl, carboxyl, amino, amido, thio, sulfinyl, sulfonyl, sulfinamide, sulfonamide, urea, carbamate, or an amino acid.

39. The compound of claim 38, wherein $W_5$ and $W_6$ are both —NH—.

40. The compound of claim 38, wherein Ar$_2$ is phenyl substituted with one or more groups selected from alkyl, halo, and haloalkyl.

41. The compound of claim 38, which is selected from the group consisting of:

(69)

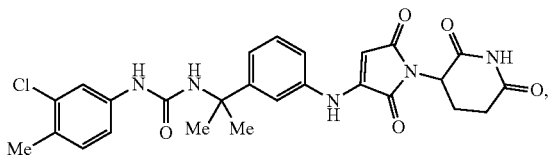

(136)

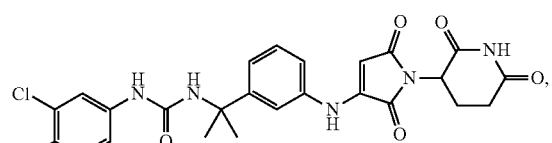

(139)

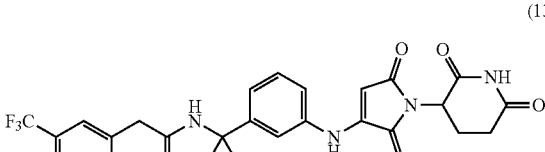

(145)

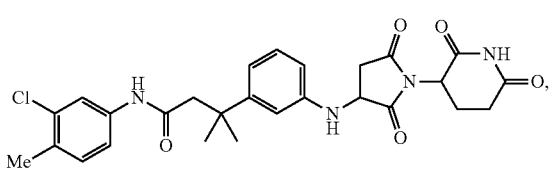

(159)

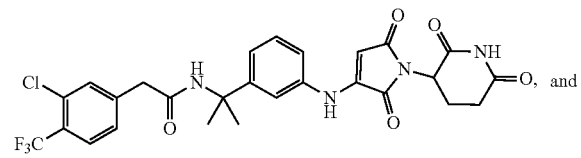

(160)

or a pharmaceutically acceptable salt or stereoisomer thereof.

42. A pharmaceutical composition, comprising a therapeutically effective amount of the compound or pharmaceutically acceptable salt or stereoisomer of claim 38, and a pharmaceutically acceptable carrier.

43. A method of treating a disease or disorder that is characterized or mediated by dysfunctional activity of activity of a protein that is a substrate for a complex between CRBN and the compound of claim 38, comprising administering to a subject in need thereof a therapeutically effective amount of the compound or pharmaceutically acceptable salt or stereoisomer of claim 38.

44. The method of claim 43, wherein the disease or disorder is mediated by dysfunctional IKZF2 (Helios) activity.

45. The method of claim 44, wherein the disease or disorder is cancer.

46. The method of claim 45, wherein the disease or disorder is leukemia, carcinoma, T cell leukemia, T cell lymphoma, Hodgkin's lymphoma, non-Hodgkin's lymphoma, myeloid leukemia, non-small cell lung cancer (NSCLC), melanoma, triple-negative breast cancer (TNBC), or nasopharyngeal cancer (NPC).

47. A method of treating a disease or disorder that is affected by the reduction of TXNIP protein levels, comprising administering to a subject in need thereof a therapeutically effective amount of the compound or pharmaceutically acceptable salt or stereoisomer of claim 38.

* * * * *

UNITED STATES PATENT AND TRADEMARK OFFICE
CERTIFICATE OF CORRECTION

PATENT NO. : 12,227,488 B2
APPLICATION NO. : 17/298823
DATED : February 18, 2025
INVENTOR(S) : Alyssa Verano et al.

Page 1 of 2

It is certified that error appears in the above-identified patent and that said Letters Patent is hereby corrected as shown below:

In the Claims

In Column 130, Lines 37-42:
Delete the following structure:

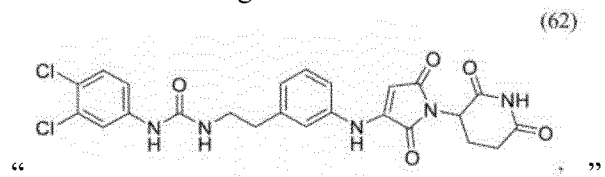

" , "

Replace with the following structure:

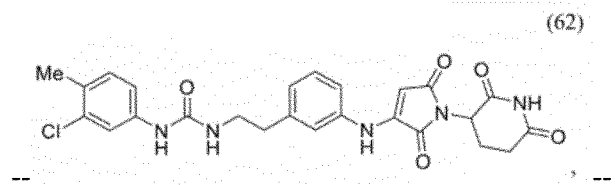

-- , --

In Column 142, Lines 60-65:
Delete the following structure:

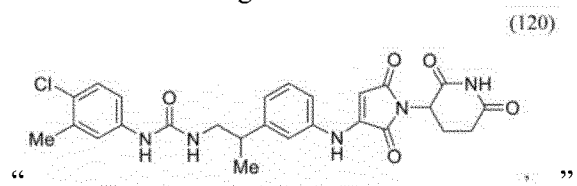

" , "

Replace with the following structure:

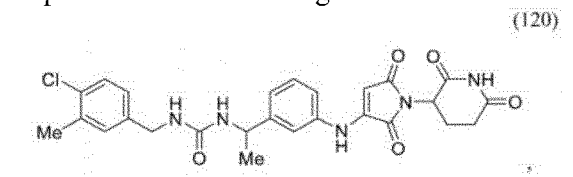

-- , --

Signed and Sealed this
Eighteenth Day of March, 2025

Coke Morgan Stewart
*Acting Director of the United States Patent and Trademark Office*

CERTIFICATE OF CORRECTION (continued)
U.S. Pat. No. 12,227,488 B2

Page 2 of 2

In Column 146, Lines 24-30:
Delete the following structure:

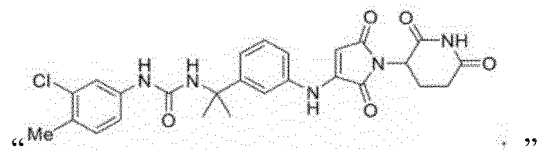

" , "

Replace with the following structure:

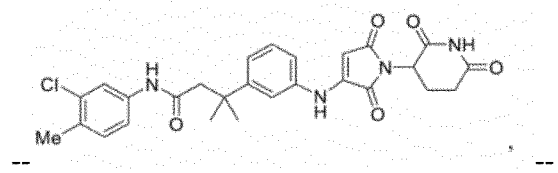

-- , --